US012673944B2

(12) United States Patent
Kim et al.

(10) Patent No.: US 12,673,944 B2
(45) Date of Patent: Jul. 7, 2026

(54) COMPOUNDS HAVING INHIBITORY ACTIVITY AGAINST GLUCOSYLCERAMIDE SYNTHASE OR PHARMACEUTICALLY ACCEPTABLE SALT THEREOF, PROCESSES FOR PREPARING THE SAME, AND PHARMACEUTICAL COMPOSITIONS COMPRISING THE SAME

(71) Applicants: YUHAN CORPORATION, Seoul (KR); GREEN CROSS CORPORATION, Yongin-si (KR)

(72) Inventors: Dong-Hoon Kim, Suwon-si (KR); Jae-Eun Joo, Yongin-si (KR); Eui-Chul Lee, Yongin-si (KR); Tae-Dong Han, Yongin-si (KR); Seung-Yub Shin, Osan-si (KR); Sool-Ki Kwon, Yongin-si (KR)

(73) Assignees: YUHAN CORPORATION, Seoul (KR); GREEN CROSS CORPORATION, Yongin-si (KR)

( * ) Notice: Subject to any disclaimer, the term of this patent is extended or adjusted under 35 U.S.C. 154(b) by 1035 days.

(21) Appl. No.: 17/755,858

(22) PCT Filed: Nov. 12, 2020

(86) PCT No.: PCT/KR2020/015871

§ 371 (c)(1),
(2) Date: May 10, 2022

(87) PCT Pub. No.: WO2021/096241

PCT Pub. Date: May 20, 2021

(65) Prior Publication Data

US 2023/0002380 A1 Jan. 5, 2023

(30) Foreign Application Priority Data

Nov. 15, 2019 (KR) ........................ 10-2019-0146684

(51) Int. Cl.

| | |
|---|---|
| ***C07D 453/02*** | (2006.01) |
| ***A61P 3/00*** | (2006.01) |
| ***C07D 471/08*** | (2006.01) |
| ***C07D 519/00*** | (2006.01) |

(52) U.S. Cl.

CPC .............. *C07D 453/02* (2013.01); *A61P 3/00* (2018.01); *C07D 471/08* (2013.01); *C07D 519/00* (2013.01)

(58) Field of Classification Search

CPC ............................ C07D 453/02; C07D 519/00

See application file for complete search history.

(56) References Cited

U.S. PATENT DOCUMENTS

| | | | |
|---|---|---|---|
| 5,998,429 | A | 12/1999 | Macor et al. |
| 6,054,464 | A | 4/2000 | Macor et al. |
| 8,003,617 | B2 | 8/2011 | Cheng et al. |
| 8,304,447 | B2 | 11/2012 | Siegel et al. |
| 8,389,517 | B2 | 3/2013 | Ibraghimov-Beskrovnaya et al. |
| 8,729,075 | B2 | 5/2014 | Ibraghimov-Beskrovnaya et al. |
| 8,940,776 | B2 | 1/2015 | Siegel et al. |
| 8,961,959 | B2 | 2/2015 | Larsen et al. |
| 9,126,993 | B2 | 9/2015 | Bourque et al. |
| 9,139,580 | B2 | 9/2015 | Bourque et al. |
| 9,481,671 | B2 | 11/2016 | Ibraghimov-Beskrovnaya et al. |

(Continued)

FOREIGN PATENT DOCUMENTS

| | | |
|---|---|---|
| WO | 97/30998 A1 | 8/1997 |
| WO | 2005/068426 A1 | 7/2005 |

(Continued)

OTHER PUBLICATIONS

Chen et al., "Abnormal transport along the lysosomal pathway in Mucolipidosis, type IV disease", Proc. Natl. Acad. Sci. USA, vol. 95, pp. 6373-6378, May 1998.

Goodman et al., "Ectopic dendrites occur only on cortical pyramidal cells containing elevated GM2 ganglioside in alpha-mannosidosis", Proc. Natl. Acad. Sci. USA, vol. 88, pp. 11330-11334, Dec. 1991.

Liu et al., "Uncoupling Ceramide Glycosylation by Transfection of Glucosylceramide Synthase Antisense Reverses Adriamycin Resistance", The Journal of Biological Chemistry, vol. 275, No. 10, Issue of Mar. 10, pp. 7138-7143, 2000.

(Continued)

*Primary Examiner* — Susanna Moore

(74) *Attorney, Agent, or Firm* — Vorys, Sater, Seymour and Pease LLP; Mih Suhn Koh

(57) ABSTRACT

Provided are a compound of Formula 1 having a chromane, isochromane, thiochromane, or tetrahydroquinoline moiety or pharmaceutically acceptable salt thereof, a process for the preparation thereof, a pharmaceutical composition comprising the same and a use thereof, wherein the compound having a chromane, isochromane, thiochromane, or tetrahydroquinoline moiety or pharmaceutically acceptable salt thereof has an inhibitory activity against glucosylceramide synthase (GCS), and therefore can be usefully applied for preventing or treating various diseases associated with GCS, such as Gaucher disease, Fabry disease, Tay-Sachs disease, Parkinson's disease, etc.:

<Formula 1>

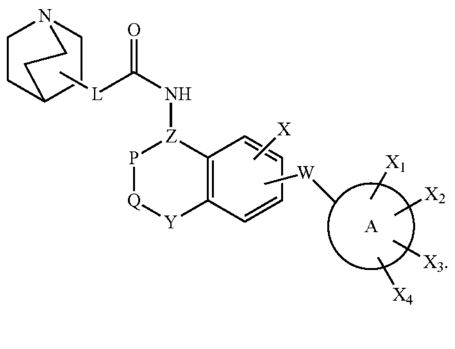

20 Claims, No Drawings

(56) References Cited

U.S. PATENT DOCUMENTS

| | | | |
|---|---|---|---|
| 9,532,976 | B2 | 1/2017 | Cheng et al. |
| 9,745,294 | B2 | 8/2017 | Siegel et al. |
| 10,227,323 | B2 | 3/2019 | Wang et al. |
| 11,008,316 | B2 | 5/2021 | Bourque et al. |
| 2004/0002513 | A1 | 1/2004 | Mazurov et al. |
| 2008/0161379 | A1 | 7/2008 | Cheng et al. |
| 2008/0234324 | A1 | 9/2008 | Orchard et al. |
| 2010/0256216 | A1 | 10/2010 | Siegel et al. |
| 2011/0166134 | A1 | 7/2011 | Ibraghimov-Beskrovnaya et al. |
| 2012/0022126 | A1 | 1/2012 | Cheng et al. |
| 2012/0322787 | A1 | 12/2012 | Siegel et al. |
| 2013/0095089 | A1 | 4/2013 | Larsen et al. |
| 2013/0225573 | A1 | 8/2013 | Ibraghimov-Beskrovnaya et al. |
| 2014/0255381 | A1 | 9/2014 | Bourque et al. |
| 2014/0336174 | A1 | 11/2014 | Ibraghimov-Beskrovnaya et al. |
| 2014/0371460 | A1 | 12/2014 | Bourque et al. |
| 2015/0190373 | A1 | 7/2015 | Cheng et al. |
| 2015/0210681 | A1 | 7/2015 | Bourque et al. |
| 2015/0225393 | A1 | 8/2015 | Siegel et al. |
| 2016/0207933 | A1 | 7/2016 | Bourque et al. |
| 2016/0229830 | A1 | 8/2016 | Wang et al. |
| 2017/0121385 | A1 | 5/2017 | Shah et al. |
| 2018/0065957 | A1 | 3/2018 | Bourque et al. |
| 2018/0093981 | A1 | 4/2018 | Siegel et al. |
| 2019/0263775 | A1 | 8/2019 | Wang et al. |
| 2020/0048266 | A1 | 2/2020 | Bourque et al. |
| 2022/0073508 | A1 | 3/2022 | Bourque et al. |

FOREIGN PATENT DOCUMENTS

| | | | |
|---|---|---|---|
| WO | 2006/053043 | A2 | 5/2006 |
| WO | 2008/105486 | A2 | 12/2008 |
| WO | 2009/117150 | A2 | 9/2009 |
| WO | 2010/014554 | A1 | 2/2010 |
| WO | 2010/091104 | A1 | 8/2010 |
| WO | 2010/091164 | A1 | 8/2010 |
| WO | 2012/129084 | A2 | 9/2012 |
| WO | 2013/059119 | A1 | 4/2013 |
| WO | 2014/043068 | A1 | 3/2014 |
| WO | 2017/075535 | A1 | 5/2017 |

OTHER PUBLICATIONS

Sardi et al., "Glucosylceramide synthase inhibition alleviates aberrations in synucleinopathy models", PNAS, Mar. 7, 2017, vol. 114, No. 10, pp. 2699-2704.

COMPOUNDS HAVING INHIBITORY ACTIVITY AGAINST GLUCOSYLCERAMIDE SYNTHASE OR PHARMACEUTICALLY ACCEPTABLE SALT THEREOF, PROCESSES FOR PREPARING THE SAME, AND PHARMACEUTICAL COMPOSITIONS COMPRISING THE SAME

TECHNICAL FIELD

The present invention relates to a novel compound having an inhibitory activity against glucosylceramide synthase (GCS), i.e., derivatives having a chromane, isochromane, thiochromane, or tetrahydroquinoline moiety or pharmaceutically acceptable salt thereof, a process for the preparation thereof, a pharmaceutical composition comprising the same and a use thereof.

BACKGROUND ART

Lysosomal storage disorders (LSDs) are the metabolic disorders that result from genetic lack or deficiency of certain enzymes in lysosomes. LSDs exhibit various pathological symptoms throughout the body, as the non-metabolized or non-degraded substrates are accumulated. Currently, about 50 types of LSDs are known and are largely classified into the diseases such as mucopolysaccaridose, oligosaccharidosis, and sphingolipidoses, depending on the substances accumulated.

Among the diseases, sphingolipidoses, which are a class of glycolipid storage disorders relating to sphingolipid metabolism, show pathologies due to the accumulation of various membrane glycosphingolipids (GSLs), such as glucosylceramide, trihexocylceramide, etc. For example, when the enzymes related to sphingolipid metabolism, such as beta-glucosidase, alpha-galactosidase, etc., do not have normal activity, the substrates thereof (e.g., glucosylceramide, trihexocylceramide, etc.) are accumulated, thereby exhibiting various pathologies, such as Gaucher disease, Fabry disease, etc.

There are known two types of therapies for the LSDs. The first method is to replace or supplement the insufficient or deficient metabolic enzymes. Although such an enzyme replacement therapy (ERT) is safe and effective, periodic intravenous administrations of the related enzyme(s) are required; the dose thereof should be adjusted according to the enzyme reaction(s); and the costs thereof are relatively high. Especially, since it is difficult to distribute the enzyme (s) toward the nervous system, the ERT does not show satisfactory efficacy in the treatment of symptoms related to the nervous system. In addition, there is also the problem that autoantibodies against the administered enzyme(s) are frequently generated.

The second method is a substrate reduction therapy (SRT) for inhibiting the syntheses of accumulated substrates. Glucosylceramide synthase (GCS) (also referred to as "UDP-glucose: ceramide glycosyltransferase", "UDP-glucose: N-acylsphingosine D-glucosyltransferase", or "EC 2.4.1.80"), which is an enzyme involved in sphingolipid metabolism, is involved in the reaction of ceramide with glucose to produce glucosylceramide. The resulting glucosylceramide is converted into various GSLs. Glucosylceramide synthase (GCS) inhibitors inhibit the activity of GCS, thereby reducing the production of glucosylceramide in the body and preventing abnormal accumulation of glycolipids, such as trihexocylceramide, GM1, and GM2, in cells or organs.

As such, GCS inhibitors inhibit the activity of GCS to prevent the accumulation of glycolipids and thus may be usefully applied to the treatment of lysosomal storage disorders, especially glycolipid storage disorders, such as GM1 gangliosidosis, Tay-Sachs disease, Sandhoff disease, Gaucher disease, Fabry disease, Niemann-Pick disease (types A and B), metachromatic leukodystrophy, Krabbe disease, etc. GCS inhibitors may be also used in the treatment of the secondary diseases associated with glycolipid storage, such as Niemann-Pick disease (type C), mucopolysaccharidosis, and mucolipidosis type IV (see, Chen C S, et al., Abnormal transport along the lysosomal pathway in mucolipidosis, type IV disease *Proc Natl Acad Sci USA.* 1998 May 26; 95(11):6373-8; and Goodman L A, et al., Ectopic dendrites occur only on cortical pyramidal cells containing elevated GM2 ganglioside in alpha-mannosidosis, *Proc Natl Acad Sci USA.* 1991 Dec. 15; 88(24):11330-4). In addition, it has been reported to be useful in the treatment of diseases associated with the accumulation of glycolipids, such as renal hypertrophy (e.g., diabetic kidney disease); hyperglycemia or hyperinsulinemia; cancers with abnormal glycolipid synthesis; infectious diseases caused by the organisms using cell-surface glycolipids as a receptor; infectious diseases where the synthesis of glucosylceramide is essential or important; diseases in which excessive glycolipid synthesis occurs (e.g., atherosclerosis, polycystic kidney disease, and renal hypertrophy); neurological disorders and/or damages associated with the replenishment and activity of macrophages (e.g., Alzheimer's disease, epilepsy, stroke, spinal cord diseases, Parkinson's disease, etc.); inflammatory diseases or disorders (e.g., rheumatoid arthritis, Crohn's disease, asthma, sepsis); and diabetes and obesity (see, WO 2006/053043). And, overexpression of GCS interferes with ceramide-induced apoptosis (see, Liu Y Y, et al., Uncoupling ceramide glycosylation by transfection of glucosylceramide synthase antisense reverses adriamycin resistance, *J Biol Chem.* 2000 Mar. 10; 275(10):7138-43). Therefore, GCS inhibitors may be useful for treating proliferative diseases, such as cancer, by inducing apoptosis in diseased cells.

Various studies have been conducted to develop GCS inhibitors. For example, various compounds having an inhibitory activity against GCS have been disclosed in WO 2005/068426, WO 2006/053043, WO 2008/150486, WO 2009/117150, WO 2010/014554, WO 2014/043068, etc.

DISCLOSURE

Technical Problem

The present inventors have found that a derivative having a 6,6-fused bicyclic moiety, i.e., a chromane, isochromane, thiochromane, or tetrahydroquinoline moiety, or pharmaceutically acceptable salt thereof has an excellent inhibitory activity against glucosylceramide synthase (GCS). Therefore, the derivative having a chromane, isochromane, thiochromane, or tetrahydroquinoline moiety or pharmaceutically acceptable salt thereof can be usefully applied for preventing or treating various diseases associated with GCS, such as Gaucher disease, Fabry disease, Tay-Sachs disease, Parkinson's disease, etc.

Therefore, the present invention provides the above derivative having a chromane, isochromane, thiochromane, or tetrahydroquinoline moiety or pharmaceutically acceptable salt thereof, a process for the preparation thereof, a pharmaceutical composition comprising the same, and a use thereof.

Technical Solution

According to an aspect of the present invention, there is provided a derivative having a chromane, isochromane, thiochromane, or tetrahydroquinoline moiety or pharmaceutically acceptable salt thereof.

According to another aspect of the present invention, there is provided a process for preparing said derivative having a chromane, isochromane, thiochromane, or tetrahydroquinoline moiety or pharmaceutically acceptable salt thereof.

According to still another aspect of the present invention, there is provided a pharmaceutical composition comprising said derivative having a chromane, isochromane, thiochromane, or tetrahydroquinoline moiety or pharmaceutically acceptable salt thereof as an active ingredient.

According to still another aspect of the present invention, there is provided a therapeutic method comprising administering said derivative having a chromane, isochromane, thiochromane, or tetrahydroquinoline moiety or pharmaceutically acceptable salt thereof.

According to still another aspect of the present invention, there is provided a use of said derivative having a chromane, isochromane, thiochromane, or tetrahydroquinoline moiety or pharmaceutically acceptable salt thereof for the manufacture of a medicament for inhibiting glucosylceramide synthase.

Advantageous Effects

It has been found by the present invention that the derivative having a 6,6-fused bicyclic moiety, i.e., a chromane, isochromane, thiochromane, or tetrahydroquinoline moiety, or pharmaceutically acceptable salt thereof has an excellent inhibitory activity against glucosylceramide synthase (GCS). Therefore, the compound or pharmaceutically acceptable salt thereof according to the present invention can be usefully applied for preventing or treating various diseases associated with GCS, such as Gaucher disease, Fabry disease, Tay-Sachs disease, Parkinson's disease, etc.

BEST MODE FOR CARRYING OUT THE INVENTION

As used herein, the term "alkyl" refers to a straight or branched aliphatic hydrocarbon radical. For example, the $C_1$-$C_6$ alkyl means a straight or branched aliphatic hydrocarbon having 1 to 6 carbon atoms, such as methyl, ethyl, propyl, n-butyl, n-pentyl, n-hexyl, isopropyl, isobutyl, sec-butyl, tert-butyl, neopentyl, and isopentyl.

The term "hydroxy" refers to the '—OH' group. The term "alkoxy" refers to a radical formed by substituting the hydrogen atom in the hydroxyl group with an alkyl. For example, the $C_1$-$C_6$ alkoxy includes methoxy, ethoxy, propoxy, n-butoxy, n-pentyloxy, isopropoxy, sec-butoxy, tert-butoxy, neopentyloxy, and isopentyloxy.

The term "halogen" refers to the fluoro, bromo, chloro, or iodo group.

The term "cycloalkyl" refers to a saturated aliphatic 3- to 10-membered ring, preferably 3- to 7-membered ring, unless otherwise defined. Typical cycloalkyl groups include cyclopropyl, cyclobutyl, cyclopentyl, cyclohexyl, and the like, but are not limited thereto.

The term "aryl" refers to an organic radical derived from an aromatic hydrocarbon, through removing one hydrogen atom therefrom, including mono or poly-fused ring systems such as 5- to 14-membered substituted or unsubstituted rings and a form in which a plurality of aryls are connected by a single bond. The "aryl" includes, for example, phenyl, naphthyl, biphenyl, terphenyl, anthryl, indenyl, fluorenyl, phenanthryl, triphenylenyl, pyrenyl, perylenyl, chrysenyl, naphthacenyl, fluoranthenyl, and the like, but are not limited thereto.

The term "heteroaryl" refers to a 5- to 12-membered aromatic radical having one to three heteroatoms selected from the group consisting of nitrogen (N) atom, oxygen (O) atom, and sulfur (S) atom, including a 5- or 6-membered monocyclic heteroaryl radical and a bicyclic heteroaryl radical formed by fusing the 5- or 6-membered monocyclic heteroaryl radical with a benzene or pyridine ring. And, the term "heterocycle" refers to a 3- to 12-membered mono- or poly-cyclic ring having one or more, preferably one to four, same or different heteroatoms selected from oxygen (O) atom, nitrogen (N) atom, and sulfur (S) atom, but not containing an aromatic ring. Non-limiting examples of heteroaryl or heterocyclic rings include oxetane, pyrrolidine, pyrrole, tetrahydrofuran, furan, tetrahydrothiophene, thiophene, imidazolidine, imidazole, pyrazolidine, pyrazole, pyrrolizine, oxazolidine, oxazole, isoxazolidine, isoxazole, thiazolidine, thiazole, isothiazolidine, isothiazole, dioxolane, dithiolane, oxadiazole, thiadiazole, dithiazole, tetrazole, oxatetrazole, thiatetrazole, piperidine, pyridine, pyrimidine, tetrahydropyran, pyran, thiane, thiopyran, piperazine, diazine, morpholine, oxazine, dioxane, indole, indoline, benzodioxole, benzothiophene, benzofuran, benzimidazole, bezoxazole, benzisoxazole, benzothiazole, benzothiadiazole, benzotriazole, quinoline, isoquinoline, purine, furopyridine, mono- or di-azabicycles (such as quinuclidine, diazabicycloheptane, monoazabicyclooctane, diazaspiroundecane, etc.), hexahydropyrrolopyrrole, pyrrolopyrrole, pyrrolopyridine, imidazopyridazine, dihydrobenzodioxine, dihydrobenzofuran, and the like, but are not limited thereto.

The term "amino" refers to the '—$NH_2$' group. The term "alkylamino" refers to an amino group substituted with mono- or di-alkyl. For example, the $C_1$-$C_6$ alkylamino group includes an amino group substituted with mono- or di-$C_1$-$C_6$ alkyl group.

The term "alkylthio" refers to the '—SR' group, in which R is an alkyl. The term "cyano" refers to the '—CN'.

The present invention provides a derivative having a 6,6-fused bicyclic moiety, i.e., a chromane, isochromane, thiochromane, or tetrahydroquinoline moiety or pharmaceutically acceptable salt thereof, that is a compound of Formula 1 or pharmaceutically acceptable salt thereof:

<Formula 1>

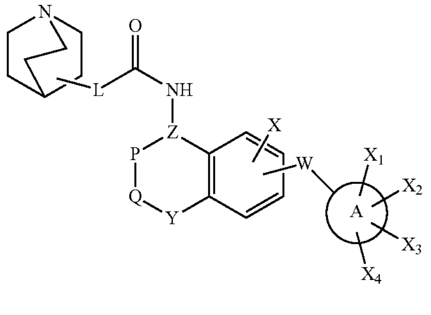

wherein,

L is —O—, —CO—, —$CR_1R_2$—, or —$NR_3$—,

X is hydrogen; halogen; $C_1$-$C_6$ alkyl; $C_1$-$C_6$ alkyl substituted with 1 to 3 halogens; $C_1$-$C_6$ alkyl having a nitrogen, oxygen, or sulfur atom; $C_1$-$C_6$ alkoxy; or $C_1$-$C_6$ alkoxy substituted with 1 to 3 halogens, Y is —$CR_4R_5$—; —$NR_3$—; —O—; or —S—, P is —$CR_4R_5$—, Q is —O— or —$CR_4R_5$—, Z is —$CR_6$—, $R_1$ and $R_2$ are, independently each other, hydrogen; halogen; $C_1$-$C_6$ alkyl; $C_1$-$C_6$ alkyl having a nitrogen, oxygen, or sulfur atom; $C_3$-$C_{10}$ cycloalkyl; 3- to 12-membered heterocyclic; or $C_1$-$C_6$ alkoxy; or $R_1$ and $R_2$ form $C_3$-$C_{10}$ cycloalkyl together with the carbon atom to which they are attached, $R_3$ is hydrogen; $C_1$-$C_6$ alkyl; $C_1$-$C_6$ alkyl having a nitrogen, oxygen, or sulfur atom; $C_3$-$C_{10}$ cycloalkyl; 3- to 12-membered heterocyclic; or $C_1$-$C_6$ alkoxy, $R_4$ and $R_5$ are, independently each other, hydrogen; halogen; $C_1$-$C_6$ alkyl; $C_1$-$C_6$ alkyl having a nitrogen, oxygen, or sulfur atom; $C_3$-$C_{10}$ cycloalkyl; 3- to 12-membered heterocyclic; or $C_1$-$C_6$ alkoxy; or $R_4$ and $R_5$ form $C_3$-$C_{10}$ cycloalkyl together with the carbon atom of P or Q to which they are attached, $R_6$ is hydrogen; $C_1$-$C_6$ alkyl; or $C_1$-$C_6$ alkyl having a nitrogen, oxygen, or sulfur atom W is a bond, —$CH_2$—, —O—, —NH—, —$CH_2CH_2$—, —CH═CH—, or —C≡C—, A ring is 6- to 12-membered aryl; 5- to 12-membered heteroaryl; $C_3$-$C_{10}$ cycloalkyl; or 3- to 12-membered heterocyclic, and $X_1$, $X_2$, $X_3$, and $X_4$ are, independently each other, hydrogen; cyano; halogen; $C_1$-$C_6$ alkyl; $C_1$-$C_6$ alkyl substituted with 1 to 3 halogens; $C_1$-$C_6$ alkyl substituted with cyano or $C_1$-$C_6$ alkoxy; $C_3$-$C_{10}$ cycloalkyl; $C_1$-$C_6$ alkenyl; 3- to 12-membered heterocyclic; $C_1$-$C_6$ alkoxy; $C_1$-$C_6$ alkoxy-$C_1$-$C_6$ alkoxy; $C_1$-$C_6$ alkoxy substituted with 1 to 3 halogens; $C_1$-$C_6$ alkoxy substituted with $C_3$-$C_{10}$ cycloalkyl or benzyl; $C_1$-$C_6$ alkylthio; amino; mono- or di-$C_1$-$C_6$ alkylamino; morpholinyl; pyrrolidinyl-sulfonyl; benzyl; hydroxy; or nitro.

In the compound of Formula 1 or pharmaceutically acceptable salt thereof according to the present invention, L may be —O—.

In the compound of Formula 1 or pharmaceutically acceptable salt thereof according to the present invention, X may be hydrogen; halogen; or $C_1$-$C_6$ alkoxy.

In the compound of Formula 1 or pharmaceutically acceptable salt thereof according to the present invention, $R_3$ may be $C_1$-$C_6$ alkyl; and $R_4$, $R_5$, and $R_6$ may be, independently each other, hydrogen or $C_1$-$C_6$ alkyl. In an embodiment, Y may be —O—, wherein the compound of Formula 1 may have a chromane moiety. In another embodiment, Q may be —O—, wherein the compound of Formula 1 may have an isochromane moiety. In still another embodiment, Y may be —S—, wherein the compound of Formula 1 may have a thiochromane moiety. In still another embodiment, Y may be —$NR_3$—, wherein the compound of Formula 1 may have a tetrahydroquinoline moiety.

In the compound of Formula 1 or pharmaceutically acceptable salt thereof according to the present invention, W may be a bond (i.e., the A ring is directly bound to the chromane, isochromane, thiochromane, or tetrahydroquinoline moiety), —$CH_2$—, or —CH═CH—.

In the compound of Formula 1 or pharmaceutically acceptable salt thereof according to the present invention, the A ring may be phenyl, biphenyl, thiophenyl, pyrazolyl, thiazolyl, naphthalenyl, benzothiadiazolyl, benzodioxolyl, 2,3-dihydrobenzodioxinyl, benzofuranyl, 2,3-dihydrobenzofuranyl, 1,3-dihydroisobenzofuranyl, 3,4-dihydro-1,4-benzoxazinyl, 3-oxo-3,4-dihydro-1,4-benzoxazinyl, benzothiophenyl, indolyl, indazolyl, isoquinolinyl, quinolinyl, 3,4-dihydro-benzodioxepinyl, benzo[c][1,2-5]oxadiazolyl, pyridinyl, 6-oxo-1,6-dihydropyridinyl, chromanyl, dibenzofuranyl, or pyrimidinyl.

In the compound of Formula 1 or pharmaceutically acceptable salt thereof according to the present invention, $X_1$, $X_2$, $X_3$, and $X_4$ may be, independently each other, hydrogen; cyano; halogen; $C_1$-$C_6$ alkyl; $C_1$-$C_6$ alkyl substituted with 1 to 3 halogens; $C_1$-$C_6$ alkyl substituted with cyano or $C_1$-$C_6$ alkoxy; $C_3$-$C_{10}$ cycloalkyl; $C_1$-$C_6$ alkenyl; $C_1$-$C_6$ alkoxy; $C_1$-$C_6$ alkoxy-$C_1$-$C_6$ alkoxy; $C_1$-$C_6$ alkoxy substituted with 1 to 3 halogens; $C_1$-$C_6$ alkoxy substituted with $C_3$-$C_{10}$ cycloalkyl or benzyl; morpholinyl; mono- or di-$C_1$-$C_6$ alkylamino; pyrrolidinyl-sulfonyl; benzyl; tetrahydropyranyl; $C_1$-$C_6$ alkylthio; or isoxazolyl.

In a preferred embodiment of the present invention,

L is —O—,

X is hydrogen; halogen; or $C_1$-$C_6$ alkoxy,

Y is —$CR_4R_5$—; —$NR_3$—; —O—; or —S—,

P is —$CR_4R_5$—,

Q is —O— or —$CR_4R_5$—,

Z is —$CR_6$—, $R_3$ is $C_1$-$C_6$ alkyl, $R_4$, $R_5$, and $R_6$ are, independently each other, hydrogen or $C_1$-$C_6$ alkyl, W is a bond, —$CH_2$—, -or —CH═CH—, A ring is phenyl, biphenyl, thiophenyl, pyrazolyl, thiazolyl, naphthalenyl, benzothiadiazolyl, benzodioxolyl, 2,3-dihydrobenzodioxinyl, benzofuranyl, 2,3-dihydrobenzofuranyl, 1,3-dihydroisobenzofuranyl, 3,4-dihydro-1,4-benzoxazinyl, 3-oxo-3,4-dihydro-1,4-benzoxazinyl, benzothiophenyl, indolyl, indazolyl, isoquinolinyl, quinolinyl, 3,4-dihydro-benzodioxepinyl, benzo[c][1,2-5]oxadiazolyl, pyridinyl, 6-oxo-1,6-dihydropyridinyl, chromanyl, dibenzofuranyl, or pyrimidinyl, and $X_1$, $X_2$, $X_3$, and $X_4$ is, independently each other, hydrogen; cyano; halogen; $C_1$-$C_6$ alkyl; $C_1$-$C_6$ alkyl substituted with 1 to 3 halogens; $C_1$-$C_6$ alkyl substituted with cyano or $C_1$-$C_6$ alkoxy; $C_3$-$C_{10}$ cycloalkyl; $C_1$-$C_6$ alkenyl; $C_1$-$C_6$ alkoxy; $C_1$-$C_6$ alkoxy-$C_1$-$C_6$ alkoxy; $C_1$-$C_6$ alkoxy substituted with 1 to 3 halogens; $C_1$-$C_6$ alkoxy substituted with $C_3$-$C_{10}$ cycloalkyl or benzyl; morpholinyl; mono- or di-$C_1$-$C_6$ alkylamino; pyrrolidinyl-sulfonyl; benzyl; tetrahydropyranyl; $C_1$-$C_6$ alkylthio; or isoxazolyl.

In the compound of Formula 1 or pharmaceutically acceptable salt, preferable compounds include a compound, including a pharmaceutically acceptable salt thereof, selected from the group consisting of:

(S)-quinuclidin-3-yl (7-(3-fluorophenyl)chroman-4-yl)carbamate;

(S)-quinuclidin-3-yl (7-(3-chlorophenyl)chroman-4-yl)carbamate;

(S)-quinuclidin-3-yl (7-(3-(trifluoromethyl)phenyl)chroman-4-yl)carbamate;

(S)-quinuclidin-3-yl (7-(3-(trifluoromethoxy)phenyl)chroman-4-yl)carbamate;

(S)-quinuclidin-3-yl (7-(2-(methoxymethoxy)phenyl)chroman-4-yl)carbamate;

(S)-quinuclidin-3-yl (7-(3-(methoxymethoxy)phenyl)chroman-4-yl)carbamate;

(S)-quinuclidin-3-yl (7-(2-(2-methoxyethoxy)phenyl)chroman-4-yl)carbamate;

(S)-quinuclidin-3-yl (7-(3-(2-methoxyethoxy)phenyl)chroman-4-yl)carbamate;
(S)-quinuclidin-3-yl (7-(2-fluorophenyl)chroman-4-yl)carbamate;
(S)-quinuclidin-3-yl (7-(2-chlorophenyl)chroman-4-yl)carbamate;
(S)-quinuclidin-3-yl (7-(2-(trifluoromethyl)phenyl)chroman-4-yl)carbamate;
(S)-quinuclidin-3-yl (7-(2-(trifluoromethoxy)phenyl)chroman-4-yl)carbamate;
(S)-quinuclidin-3-yl (7-(4-fluorophenyl)chroman-4-yl)carbamate;
(S)-quinuclidin-3-yl (7-(4-chlorophenyl)chroman-4-yl)carbamate;
(S)-quinuclidin-3-yl (7-(4-(trifluoromethyl)phenyl)chroman-4-yl)carbamate;
(S)-quinuclidin-3-yl (7-(4-(trifluoromethoxy)phenyl)chroman-4-yl)carbamate;
(S)-quinuclidin-3-yl (7-(2-methoxyphenyl)chroman-4-yl) carbamate;
(S)-quinuclidin-3-yl (7-(3-methoxyphenyl)chroman-4-yl) carbamate;
(S)-quinuclidin-3-yl (7-(4-methoxyphenyl)chroman-4-yl) carbamate;
(S)-quinuclidin-3-yl (7-(2-ethoxyphenyl)chroman-4-yl)carbamate;
(S)-quinuclidin-3-yl (7-(3-ethoxyphenyl)chroman-4-yl)carbamate;
(S)-quinuclidin-3-yl (7-(4-ethoxyphenyl)chroman-4-yl)carbamate;
(S)-quinuclidin-3-yl (7-(3-isopropylphenyl)chroman-4-yl) carbamate;
(S)-quinuclidin-3-yl (7-(4-isopropylphenyl)chroman-4-yl) carbamate;
(S)-quinuclidin-3-yl (7-(3-(tert-butyl)phenyl)chroman-4-yl) carbamate;
(S)-quinuclidin-3-yl (7-(4-(tert-butyl)phenyl)chroman-4-yl) carbamate;
(S)-quinuclidin-3-yl (7-(2,5-dichlorophenyl)chroman-4-yl) carbamate;
(S)-quinuclidin-3-yl (7-(3,4-dichlorophenyl)chroman-4-yl) carbamate;
(S)-quinuclidin-3-yl (7-(3,5-dichlorophenyl)chroman-4-yl) carbamate;
(S)-quinuclidin-3-yl (7-(2,3,4-trifluorophenyl)chroman-4-yl)carbamate;
(S)-quinuclidin-3-yl (7-(2,4,5-trifluorophenyl)chroman-4-yl)carbamate;
(S)-quinuclidin-3-yl (7-(4-(difluoromethoxy)phenyl)chroman-4-yl)carbamate;
(S)-quinuclidin-3-yl (7-(4-fluoro-3-(trifluoromethyl)phenyl)chroman-4-yl)carbamate;
(S)-quinuclidin-3-yl (7-(3-chloro-5-(trifluoromethyl)phenyl)chroman-4-yl)carbamate;
(S)-quinuclidin-3-yl (7-(4-cyclopropylphenyl)chroman-4-yl)carbamate;
(S)-quinuclidin-3-yl (7-(2,2-difluorobenzo[d][1,3]dioxol-5-yl)chroman-4-yl)carbamate;
(S)-quinuclidin-3-yl (7-(2,3-dihydrobenzo[b][1,4]dioxin-6-yl)chroman-4-yl)carbamate;
(S)-quinuclidin-3-yl (7-(2,3-dihydrofuran-5-yl)chroman-4-yl)carbamate;
(S)-quinuclidin-3-yl (7-(3-cyanophenyl)chroman-4-yl)carbamate;
(S)-quinuclidin-3-yl (7-(2-cyanophenyl)chroman-4-yl)carbamate;
(S)-quinuclidin-3-yl (7-(3-(dimethylamino)phenyl)chroman-4-yl)carbamate;
(S)-quinuclidin-3-yl (7-(benzo[b]thiophen-2-yl)chroman-4-yl)carbamate;
(S)-quinuclidin-3-yl (7-(benzofuran-3-yl)chroman-4-yl)carbamate;
(S)-quinuclidin-3-yl (7-(benzofuran-2-yl)chroman-4-yl)carbamate;
(S)-quinuclidin-3-yl (7-(1H-indol-6-yl)chroman-4-yl)carbamate;
(S)-quinuclidin-3-yl (7-(1H-indol-3-yl)chroman-4-yl)carbamate;
(S)-quinuclidin-3-yl (7-(1H-indol-7-yl)chroman-4-yl)carbamate;
(S)-quinuclidin-3-yl (7-(1H-indazol-4-yl)chroman-4-yl)carbamate;
(S)-quinuclidin-3-yl (7-(1H-indazol-7-yl)chroman-4-yl)carbamate;
(S)-quinuclidin-3-yl (7-(1-methyl-1H-indazol-6-yl)chroman-4-yl)carbamate;
(S)-quinuclidin-3-yl (7-(1-methyl-1H-indazol-4-yl)chroman-4-yl)carbamate;
(S)-quinuclidin-3-yl (7-(1-methyl-1H-indol-2-yl)chroman-4-yl)carbamate;
(S)-quinuclidin-3-yl (7-(isoquinolin-4-yl)chroman-4-yl)carbamate;
(S)-quinuclidin-3-yl (7-(isoquinolin-5-yl)chroman-4-yl)carbamate;
(S)-quinuclidin-3-yl (7-(quinolin-3-yl)chroman-4-yl)carbamate;
(S)-quinuclidin-3-yl (7-(quinolin-8-yl)chroman-4-yl)carbamate;
(S)-quinuclidin-3-yl (7-(isoquinolin-7-yl)chroman-4-yl)carbamate;
(S)-quinuclidin-3-yl (7-(3,4-dihydro-2H-benzo[b][1,4]dioxepin-7-yl)chroman-4-yl)carbamate;
(S)-quinuclidin-3-yl (7-([1,1'-biphenyl]-3-yl)chroman-4-yl) carbamate;
(S)-quinuclidin-3-yl (7-(3-(pyrrolidin-1-ylsulfonyl)phenyl) chroman-4-yl)carbamate;
(S)-quinuclidin-3-yl (7-(1,3-dihydroisobenzofuran-5-yl) chroman-4-yl)carbamate;
(S)-quinuclidin-3-yl (7-(benzo[c][1,2,5]thiadiazol-5-yl) chroman-4-yl)carbamate;
(S)-quinuclidin-3-yl (7-(4-methyl-3,4-dihydro-2H-benzo[b][1,4]oxazin-7-yl)chroman-4-yl)carbamate;
(S)-quinuclidin-3-yl (7-(thiophen-3-yl)chroman-4-yl)carbamate;
(S)-quinuclidin-3-yl (7-(2-chloro-5-methoxyphenyl)chroman-4-yl)carbamate;
(S)-quinuclidin-3-yl (7-(4-chloro-3-methoxyphenyl)chroman-4-yl)carbamate;
(S)-quinuclidin-3-yl (7-(2-chloro-3-methoxyphenyl)chroman-4-yl)carbamate;
(S)-quinuclidin-3-yl (7-(2-methoxypyridin-4-yl)chroman-4-yl)carbamate;
(S)-quinuclidin-3-yl (7-(3-(dimethylamino)-4-fluorophenyl) chroman-4-yl)carbamate;
(S)-quinuclidin-3-yl [6,7'-bichroman]-4'-ylcarbamate;
(S)-quinuclidin-3-yl (7-(6-methoxy-5-(trifluoromethyl)pyridin-3-yl)chroman-4-yl)carbamate;
(S)-quinuclidin-3-yl (7-(1-benzyl-1H-pyrazol-4-yl)chroman-4-yl)carbamate;
(S)-quinuclidin-3-yl (7-(4-(tetrahydro-2H-pyran-4-yl)phenyl)chroman-4-yl)carbamate;
(S)-quinuclidin-3-yl (7-(4-methyl-3-oxo-3,4-dihydro-2H-benzo[b][1,4]oxazin-6-yl)chroman-4-yl)carbamate;

(S)-quinuclidin-3-yl (7-(3-methyl-4-morpholinophenyl)chroman-4-yl)carbamate;
(S)-quinuclidin-3-yl (7-(3-chloro-4-morpholinophenyl)chroman-4-yl)carbamate;
(S)-quinuclidin-3-yl (7-(3-fluoro-4-morpholinophenyl)chroman-4-yl)carbamate;
(S)-quinuclidin-3-yl (7-(3-cyano-4-methylphenyl)chroman-4-yl)carbamate;
(S)-quinuclidin-3-yl (7-(5-methoxypyridin-3-yl)chroman-4-yl)carbamate;
(S)-quinuclidin-3-yl (7-(5-chloro-6-methoxypyridin-3-yl)chroman-4-yl)carbamate;
(S)-quinuclidin-3-yl (7-(6-(cyclopropylmethoxy)pyridin-3-yl)chroman-4-yl)carbamate;
(S)-quinuclidin-3-yl (7-(3-chloro-4-isopropoxyphenyl)chroman-4-yl)carbamate;
(S)-quinuclidin-3-yl (7-(4-methoxy-3-(trifluoromethyl)phenyl)chroman-4-yl)carbamate;
(S)-quinuclidin-3-yl (7-(2,6-dimethoxyphenyl)chroman-4-yl)carbamate;
(S)-quinuclidin-3-yl (6-(4-fluorophenyl)chroman-4-yl)carbamate;
(S)-quinuclidin-3-yl (6-(3-fluorophenyl)chroman-4-yl)carbamate;
(S)-quinuclidin-3-yl (6-(2-fluorophenyl)chroman-4-yl)carbamate;
(S)-quinuclidin-3-yl (6-(4-chlorophenyl)chroman-4-yl)carbamate;
(S)-quinuclidin-3-yl (6-(3-chlorophenyl)chroman-4-yl)carbamate;
(S)-quinuclidin-3-yl (6-(2-chlorophenyl)chroman-4-yl)carbamate;
(S)-quinuclidin-3-yl (6-(4-(trifluoromethyl)phenyl)chroman-4-yl)carbamate;
(S)-quinuclidin-3-yl (6-(3-(trifluoromethyl)phenyl)chroman-4-yl)carbamate;
(S)-quinuclidin-3-yl (6-(2-(trifluoromethyl)phenyl)chroman-4-yl)carbamate;
(S)-quinuclidin-3-yl (6-(4-(trifluoromethoxy)phenyl)chroman-4-yl)carbamate;
(S)-quinuclidin-3-yl (6-(3-(trifluoromethoxy)phenyl)chroman-4-yl)carbamate;
(S)-quinuclidin-3-yl (6-(2-(trifluoromethoxy)phenyl)chroman-4-yl)carbamate;
(S)-quinuclidin-3-yl (6-(4-(methylthio)phenyl)chroman-4-yl)carbamate;
(S)-quinuclidin-3-yl (6-(3-(methylthio)phenyl)chroman-4-yl)carbamate;
(S)-quinuclidin-3-yl (6-(p-tolyl)chroman-4-yl)carbamate;
(S)-quinuclidin-3-yl (6-(4-cyanophenyl)chroman-4-yl)carbamate;
(S)-quinuclidin-3-yl (6-(3-fluorophenyl)-3,3-dimethylchroman-4-yl)carbamate;
(S)-quinuclidin-3-yl (7-(3-fluorophenyl)-3,3-dimethylchroman-4-yl)carbamate;
(S)-quinuclidin-3-yl (7-(3-chlorophenyl)-3,3-dimethylchroman-4-yl)carbamate;
(S)-quinuclidin-3-yl (3,3-dimethyl-7-(3-(trifluoromethyl)phenyl)chroman-4-yl)carbamate;
(S)-quinuclidin-3-yl (3,3-dimethyl-7-(3-(trifluoromethoxy)phenyl)chroman-4-yl)carbamate;
(S)-quinuclidin-3-yl (7-(2-(methoxymethoxy)phenyl)-3,3-dimethylchroman-4-yl)carbamate;
(S)-quinuclidin-3-yl (7-(3-(methoxymethoxy)phenyl)-3,3-dimethylchroman-4-yl)carbamate;
(S)-quinuclidin-3-yl (7-(4-(methoxymethoxy)phenyl)-3,3-dimethylchroman-4-yl)carbamate;
(S)-quinuclidin-3-yl (7-(2-(2-methoxyethoxy)phenyl)-3,3-dimethylchroman-4-yl)carbamate;
(S)-quinuclidin-3-yl (7-(3-(2-methoxyethoxy)phenyl)-3,3-dimethylchroman-4-yl)carbamate;
(S)-quinuclidin-3-yl (7-(4-(2-methoxyethoxy)phenyl)-3,3-dimethylchroman-4-yl)carbamate;
(S)-quinuclidin-3-yl (7-(3-(difluoromethyl)phenyl)-3,3-dimethylchroman-4-yl)carbamate;
(S)-quinuclidin-3-yl (3,3-dimethyl-7-(8-methylquinolin-5-yl)chroman-4-yl)carbamate;
(S)-quinuclidin-3-yl (7-(3,5-dimethoxyphenyl)-3,3-dimethylchroman-4-yl)carbamate;
(S)-quinuclidin-3-yl (7-(4-methoxy-3-methylphenyl)-3,3-dimethylchroman-4-yl)carbamate;
(S)-quinuclidin-3-yl (7-(4-methoxy-2-methylphenyl)-3,3-dimethylchroman-4-yl)carbamate;
(S)-quinuclidin-3-yl (7-(3-chloro-4-methoxyphenyl)-3,3-dimethylchroman-4-yl)carbamate;
(S)-quinuclidin-3-yl (7-(3-fluoro-4-methoxyphenyl)-3,3-dimethylchroman-4-yl)carbamate;
(S)-quinuclidin-3-yl (7-(2-chloro-4-methoxyphenyl)-3,3-dimethylchroman-4-yl)carbamate;
(S)-quinuclidin-3-yl (7-(4-fluoro-2-methoxyphenyl)-3,3-dimethylchroman-4-yl)carbamate;
(S)-quinuclidin-3-yl (7-(2-chloro-6-methoxyphenyl)-3,3-dimethylchroman-4-yl)carbamate;
(S)-quinuclidin-3-yl (7-(2-fluoro-6-methoxyphenyl)-3,3-dimethylchroman-4-yl)carbamate;
(S)-quinuclidin-3-yl (7-(2,5-difluoro-4-methoxyphenyl)-3,3-dimethylchroman-4-yl)carbamate;
(S)-quinuclidin-3-yl (7-(4-ethoxy-3-fluorophenyl)-3,3-dimethylchroman-4-yl)carbamate;
(S)-quinuclidin-3-yl (7-(2,4-dimethoxyphenyl)-3,3-dimethylchroman-4-yl)carbamate;
(S)-quinuclidin-3-yl (7-(2,5-dimethoxyphenyl)-3,3-dimethylchroman-4-yl)carbamate;
(S)-quinuclidin-3-yl (7-(2,3-dimethoxyphenyl)-3,3-dimethylchroman-4-yl)carbamate;
(S)-quinuclidin-3-yl (7-(3,4-dimethoxyphenyl)-3,3-dimethylchroman-4-yl)carbamate;
(S)-quinuclidin-3-yl (7-(2,6-dimethoxypyridin-3-yl)-3,3-dimethylchroman-4-yl)carbamate;
(S)-quinuclidin-3-yl (3,3-dimethyl-7-(naphthalen-2-yl)chroman-4-yl)carbamate;
(S)-quinuclidin-3-yl (3,3-dimethyl-7-(naphthalen-1-yl)chroman-4-yl)carbamate;
(S)-quinuclidin-3-yl (3,3-dimethyl-7-(quinolin-6-yl)chroman-4-yl)carbamate;
(S)-quinuclidin-3-yl (7-(4-ethoxy-3,5-dimethylphenyl)-3,3-dimethylchroman-4-yl)carbamate;
(S)-quinuclidin-3-yl (7-(2,4-dichloro-5-ethoxyphenyl)-3,3-dimethylchroman-4-yl)carbamate;
(S)-quinuclidin-3-yl (7-(2-fluoro-5-isopropoxyphenyl)-3,3-dimethylchroman-4-yl)carbamate;
(S)-quinuclidin-3-yl (7-(3-fluoro-5-isopropoxyphenyl)-3,3-dimethylchroman-4-yl)carbamate;
(S)-quinuclidin-3-yl (7-(2-chloro-4-(trifluoromethyl)phenyl)-3,3-dimethylchroman-4-yl)carbamate;
(S)-quinuclidin-3-yl (7-(2-chloro-3-(trifluoromethyl)phenyl)-3,3-dimethylchroman-4-yl)carbamate;
(S)-quinuclidin-3-yl (7-(2-chloro-5-(trifluoromethyl)phenyl)-3,3-dimethylchroman-4-yl)carbamate;
(S)-quinuclidin-3-yl (7-(3,5-dimethyl-4-propoxyphenyl)-3,3-dimethylchroman-4-yl)carbamate;
(S)-quinuclidin-3-yl (7-(4-(tert-butoxymethyl)phenyl)-3,3-dimethylchroman-4-yl)carbamate;

(S)-quinuclidin-3-yl (7-(2-chloro-5-(trifluoromethoxy)phenyl)-3,3-dimethylchroman-4-yl)carbamate;
(S)-quinuclidin-3-yl (7-(2-butoxy-6-fluorophenyl)-3,3-dimethylchroman-4-yl)carbamate;
(S)-quinuclidin-3-yl (3,3-dimethyl-7-(6-(2,2,2-trifluoroethoxy)pyridin-3-yl)chroman-4-yl)carbamate;
(S)-quinuclidin-3-yl (7-(6-methoxynaphthalen-2-yl)-3,3-dimethylchroman-4-yl)carbamate;
(S)-quinuclidin-3-yl (7-(4-ethoxy-3-(trifluoromethyl)phenyl)-3,3-dimethylchroman-4-yl)carbamate;
(S)-quinuclidin-3-yl (7-(benzofuran-3-yl)-3,3-dimethylchroman-4-yl)carbamate;
(S)-quinuclidin-3-yl (7-(3-(dimethylamino)phenyl)-3,3-dimethylchroman-4-yl)carbamate;
(S)-quinuclidin-3-yl (7-(2,2-difluorobenzo[d][1,3]dioxol-5-yl)-3,3-dimethylchroman-4-yl)carbamate;
(S)-quinuclidin-3-yl (7-(2,5-dichlorophenyl)-3,3-dimethylchroman-4-yl)carbamate;
(S)-quinuclidin-3-yl (7-(3-isopropylphenyl)-3,3-dimethylchroman-4-yl)carbamate;
(S)-quinuclidin-3-yl (7-(3-(tert-butyl)phenyl)-3,3-dimethylchroman-4-yl)carbamate
(S)-quinuclidin-3-yl (7-(2-chloro-5-methoxyphenyl)-3,3-dimethylchroman-4-yl)carbamate;
(S)-quinuclidin-3-yl (7-([1,1'-biphenyl]-3-yl)-3,3-dimethylchroman-4-yl)carbamate;
(S)-quinuclidin-3-yl (7-(isoquinolin-4-yl)-3,3-dimethylchroman-4-yl)carbamate;
(S)-quinuclidin-3-yl (7-(2-fluorophenyl)-3,3-dimethylchroman-4-yl)carbamate;
(S)-quinuclidin-3-yl (3,3-dimethyl-7-(2-(trifluoromethoxy)phenyl)chroman-4-yl)carbamate;
(S)-quinuclidin-3-yl (7-(3-ethoxyphenyl)-3,3-dimethylchroman-4-yl)carbamate;
(S)-quinuclidin-3-yl (3,3-dimethyl-7-(1-methyl-1H-indazol-4-yl)chroman-4-yl)carbamate;
(S)-quinuclidin-3-yl (7-(isoquinolin-8-yl)-3,3-dimethylchroman-4-yl)carbamate;
(S)-quinuclidin-3-yl (7-(4-cyclopropylphenyl)-3,3-dimethylchroman-4-yl)carbamate;
(S)-quinuclidin-3-yl (7-(2-methoxyphenyl)-3,3-dimethylchroman-4-yl)carbamate;
(S)-quinuclidin-3-yl (3',3'-dimethyl-[6,7'-bichroman]-4'-yl) carbamate;
(S)-quinuclidin-3-yl (7-(3-chloro-5-(trifluoromethyl)phenyl)-3,3-dimethylchroman-4-yl)carbamate;
(S)-quinuclidin-3-yl (3,3-dimethyl-7-(quinolin-8-yl)chroman-4-yl)carbamate;
(S)-quinuclidin-3-yl (7-(3-methoxyphenyl)-3,3-dimethylchroman-4-yl)carbamate;
(S)-quinuclidin-3-yl (7-(3-chloro-4-isopropoxyphenyl)-3,3-dimethylchroman-4-yl)carbamate;
(S)-quinuclidin-3-yl (7-(2,6-dimethoxyphenyl)-3,3-dimethylchroman-4-yl)carbamate;
(S)-quinuclidin-3-yl (7-(2-chlorophenyl)-3,3-dimethylchroman-4-yl)carbamate;
(S)-quinuclidin-3-yl (7-(3-cyanophenyl)-3,3-dimethylchroman-4-yl)carbamate;
(S)-quinuclidin-3-yl (7-(3-(dimethylamino)-4-fluorophenyl)-3,3-dimethylchroman-4-yl)carbamate;
(S)-quinuclidin-3-yl (7-(2,3-dihydrobenzo[b][1,4]dioxin-6-yl)-3,3-dimethylchroman-4-yl)carbamate;
(S)-quinuclidin-3-yl (7-(1H-indol-7-yl)-3,3-dimethylchroman-4-yl)carbamate;
(S)-quinuclidin-3-yl (7-(4-isopropylphenyl)-3,3-dimethylchroman-4-yl)carbamate;
(S)-quinuclidin-3-yl (7-(4-fluoro-3-(trifluoromethyl)phenyl)-3,3-dimethylchroman-4-yl)carbamate;
(S)-quinuclidin-3-yl (7-(2-chloro-3-methoxyphenyl)-3,3-dimethylchroman-4-yl)carbamate;
(S)-quinuclidin-3-yl (7-(4-chloro-3-methoxyphenyl)-3,3-dimethylchroman-4-yl)carbamate;
(S)-quinuclidin-3-yl (7-(1H-indazol-7-yl)-3,3-dimethylchroman-4-yl)carbamate;
(S)-quinuclidin-3-yl (7-(3,5-dichlorophenyl)-3,3-dimethylchroman-4-yl)carbamate;
(S)-quinuclidin-3-yl (7-(1-benzyl-1H-pyrazol-4-yl)-3,3-dimethylchroman-4-yl)carbamate;
(S)-quinuclidin-3-yl (7-(2,3-dihydrobenzofuran-5-yl)-3,3-dimethylchroman-4-yl)carbamate;
(S)-quinuclidin-3-yl (7-(6-(cyclopropylmethoxy)pyridin-3-yl)-3,3-dimethylchroman-4-yl)carbamate;
(S)-quinuclidin-3-yl (7-(benzofuran-2-yl)-3,3-dimethylchroman-4-yl)carbamate;
(S)-quinuclidin-3-yl (3,3-dimethyl-7-(3-(pyrrolidin-1-ylsulfonyl)phenyl)chroman-4-yl)carbamate;
(S)-quinuclidin-3-yl (3,3-dimethyl-7-(2-(trifluoromethyl)phenyl)chroman-4-yl)carbamate;
(S)-quinuclidin-3-yl (7-(2-ethoxyphenyl)-3,3-dimethylchroman-4-yl)carbamate;
(S)-quinuclidin-3-yl (3,3-dimethyl-7-(thiophen-3-yl)chroman-4-yl)carbamate;
(S)-quinuclidin-3-yl (7-(4-methoxy-3-(trifluoromethyl)phenyl)-3,3-dimethylchroman-4-yl)carbamate;
(S)-quinuclidin-3-yl (7-(2-cyanophenyl)-3,3-dimethylchroman-4-yl)carbamate;
(S)-quinuclidin-3-yl (7-(3,4-dihydro-2H-benzo[b][1,4]dioxepin-7-yl)-3,3-dimethylchroman-4-yl)carbamate;
(S)-quinuclidin-3-yl (7-(benzo[c][1,2,5]thiadiazol-5-yl)-3,3-dimethylchroman-4-yl)carbamate;
(S)-quinuclidin-3-yl (7-(isoquinolin-4-yl)-3,3-dimethylchroman-4-yl)carbamate;
(S)-quinuclidin-3-yl (7-(4-(tert-butyl)phenyl)-3,3-dimethylchroman-4-yl)carbamate
(S)-quinuclidin-3-yl (3,3-dimethyl-7-(3-methyl-4-morpholinophenyl)chroman-4-yl)carbamate;
(S)-quinuclidin-3-yl (7-(3,4-dichlorophenyl)-3,3-dimethylchroman-4-yl)carbamate;
(S)-quinuclidin-3-yl (3,3-dimethyl-7-(1-methyl-1H-indazol-6-yl)chroman-4-yl)carbamate;
(S)-quinuclidin-3-yl (7-(1H-indol-6-yl)-3,3-dimethylchroman-4-yl)carbamate;
(S)-quinuclidin-3-yl (3,3-dimethyl-7-(4-methyl-3,4-dihydro-2H-benzo[b][1,4]oxazin-7-yl)chroman-4-yl)carbamate;
(S)-quinuclidin-3-yl (7-(3-cyano-4-methylphenyl)-3,3-dimethylchroman-4-yl)carbamate;
(S)-quinuclidin-3-yl (3,3-dimethyl-7-(2,4,5-trifluorophenyl)chroman-4-yl)carbamate;
(S)-quinuclidin-3-yl (3,3-dimethyl-7-(4-(trifluoromethoxy)phenyl)chroman-4-yl)carbamate;
(S)-quinuclidin-3-yl (3,3-dimethyl-7-(4-(tetrahydro-2H-pyran-4-yl)phenyl)chroman-4-yl)carbamate;
(S)-quinuclidin-3-yl (7-(2-methoxypyridin-4-yl)-3,3-dimethylchroman-4-yl)carbamate;
(S)-quinuclidin-3-yl (7-(3-fluoro-4-morpholinophenyl)-3,3-dimethylchroman-4-yl)carbamate;
(S)-quinuclidin-3-yl (7-(3-chloro-4-morpholinophenyl)-3,3-dimethylchroman-4-yl)carbamate;
(S)-quinuclidin-3-yl (7-(4-methoxyphenyl)-3,3-dimethylchroman-4-yl)carbamate;
(S)-quinuclidin-3-yl (7-(5-methoxypyridin-3-yl)-3,3-dimethylchroman-4-yl)carbamate;

(S)-quinuclidin-3-yl (7-(benzo[b]thiophen-2-yl)-3,3-dimethylchroman-4-yl)carbamate;
(S)-quinuclidin-3-yl (7-(4-ethoxyphenyl)-3,3-dimethylchroman-4-yl)carbamate;
(S)-quinuclidin-3-yl (7-(4-methoxy-3-(trifluoromethyl)phenyl)-3,3-dimethylchroman-4-yl)carbamate;
(S)-quinuclidin-3-yl (3,3-dimethyl-7-(4-(trifluoromethyl)phenyl)chroman-4-yl)carbamate;
(S)-quinuclidin-3-yl (7-(1H-indazol-4-yl)-3,3-dimethylchroman-4-yl)carbamate;
(S)-quinuclidin-3-yl (7-(4-chlorophenyl)-3,3-dimethylchroman-4-yl)carbamate;
(S)-quinuclidin-3-yl (7-(4-fluorophenyl)-3,3-dimethylchroman-4-yl)carbamate;
(S)-quinuclidin-3-yl (7-(5-chloro-6-methoxypyridin-3-yl)-3,3-dimethylchroman-4-yl)carbamate;
(S)-quinuclidin-3-yl (3,3-dimethyl-7-(4-methyl-3-oxo-3,4-dihydro-2H-benzo[b][1,4]oxazin-6-yl)chroman-4-yl)carbamate;
(S)-quinuclidin-3-yl (3,3-dimethyl-7-(2,3,4-trifluorophenyl)chroman-4-yl)carbamate;
(S)-quinuclidin-3-yl (7-(4-(difluoromethoxy)phenyl)-3,3-dimethylchroman-4-yl)carbamate;
(S)-quinuclidin-3-yl (3,3-dimethyl-7-(quinolin-5-yl)chroman-4-yl)carbamate;
(S)-quinuclidin-3-yl (7-(benzo[c][1,2,5]oxadiazol-5-yl)-3,3-dimethylchroman-4-yl)carbamate;
(S)-quinuclidin-3-yl (3,3-dimethyl-7-(5-methylpyridin-3-yl)chroman-4-yl)carbamate;
(S)-quinuclidin-3-yl (7-(2-fluoropyridin-3-yl)-3,3-dimethylchroman-4-yl)carbamate
(S)-quinuclidin-3-yl (7-(2-chloro-4-methylphenyl)-3,3-dimethylchroman-4-yl)carbamate;
(S)-quinuclidin-3-yl (7-(2-chloro-5-methylphenyl)-3,3-dimethylchroman-4-yl)carbamate;
(S)-quinuclidin-3-yl (7-(2-fluoro-4-methylphenyl)-3,3-dimethylchroman-4-yl)carbamate;
(S)-quinuclidin-3-yl (7-(3-chloro-4-methylphenyl)-3,3-dimethylchroman-4-yl)carbamate;
(S)-quinuclidin-3-yl (7-(4-fluoro-2-methylphenyl)-3,3-dimethylchroman-4-yl)carbamate;
(S)-quinuclidin-3-yl (7-(3-fluoro-4-methylphenyl)-3,3-dimethylchroman-4-yl)carbamate;
(S)-quinuclidin-3-yl (7-(4-fluoro-3-methylphenyl)-3,3-dimethylchroman-4-yl)carbamate;
(S)-quinuclidin-3-yl (7-(2,4-dichlorophenyl)-3,3-dimethylchroman-4-yl)carbamate;
(S)-quinuclidin-3-yl (7-(2-chloro-4-fluorophenyl)-3,3-dimethylchroman-4-yl)carbamate;
(S)-quinuclidin-3-yl (7-(2-chloro-5-fluorophenyl)-3,3-dimethylchroman-4-yl)carbamate;
(S)-quinuclidin-3-yl (7-(2,4-difluorophenyl)-3,3-dimethylchroman-4-yl)carbamate;
(S)-quinuclidin-3-yl (7-(2,5-difluorophenyl)-3,3-dimethylchroman-4-yl)carbamate;
(S)-quinuclidin-3-yl (7-(2,3-dichlorophenyl)-3,3-dimethylchroman-4-yl)carbamate;
(S)-quinuclidin-3-yl (7-(3-chloro-4-fluorophenyl)-3,3-dimethylchroman-4-yl)carbamate;
(S)-quinuclidin-3-yl (7-(2-chloro-3-fluorophenyl)-3,3-dimethylchroman-4-yl)carbamate;
(S)-quinuclidin-3-yl (7-(3,4-difluorophenyl)-3,3-dimethylchroman-4-yl)carbamate;
(S)-quinuclidin-3-yl (7-(2,3-difluorophenyl)-3,3-dimethylchroman-4-yl)carbamate;
(S)-quinuclidin-3-yl (7-(3,5-difluorophenyl)-3,3-dimethylchroman-4-yl)carbamate;
(S)-quinuclidin-3-yl (7-(6-methoxypyridin-3-yl)-3,3-dimethylchroman-4-yl)carbamate;
(S)-quinuclidin-3-yl (7-([1,1'-biphenyl]-4-yl)-3,3-dimethylchroman-4-yl)carbamate;
(S)-quinuclidin-3-yl (3,3-dimethyl-7-(thiazol-5-yl)chroman-4-yl)carbamate;
(S)-quinuclidin-3-yl (3,3-dimethyl-7-(3-vinylphenyl)chroman-4-yl)carbamate;
(S)-quinuclidin-3-yl (7-(2-methoxypyridin-3-yl)-3,3-dimethylchroman-4-yl)carbamate;
(S)-quinuclidin-3-yl (7-(6-methoxypyridin-2-yl)-3,3-dimethylchroman-4-yl)carbamate;
(S)-quinuclidin-3-yl (7-(4-cyanophenyl)-3,3-dimethylchroman-4-yl)carbamate;
(S)-quinuclidin-3-yl (7-(2-fluoro-6-methylpyridin-3-yl)-3,3-dimethylchroman-4-yl)carbamate;
(S)-quinuclidin-3-yl (7-(benzo[d][1,3]dioxol-5-yl)-3,3-dimethylchroman-4-yl)carbamate;
(S)-quinuclidin-3-yl (7-(6-cyclopropylpyridin-3-yl)-3,3-dimethylchroman-4-yl)carbamate;
(S)-quinuclidin-3-yl (7-(6-(dimethylamino)pyridin-3-yl)-3,3-dimethylchroman-4-yl)carbamate;
(S)-quinuclidin-3-yl (7-(5-fluoro-2-methoxyphenyl)-3,3-dimethylchroman-4-yl)carbamate;
(S)-quinuclidin-3-yl (7-(6-ethoxypyridin-3-yl)-3,3-dimethylchroman-4-yl)carbamate;
(S)-quinuclidin-3-yl (7-(6-methoxy-5-methylpyridin-3-yl)-3,3-dimethylchroman-4-yl)carbamate;
(S)-quinuclidin-3-yl (7-(4-methoxy-3,5-dimethylphenyl)-3,3-dimethylchroman-4-yl)carbamate;
(S)-quinuclidin-3-yl (7-(4-butylphenyl)-3,3-dimethylchroman-4-yl)carbamate;
(S)-quinuclidin-3-yl (7-(4-isobutylphenyl)-3,3-dimethylchroman-4-yl)carbamate;
(S)-quinuclidin-3-yl (7-(6-isopropoxypyridin-3-yl)-3,3-dimethylchroman-4-yl)carbamate;
(S)-quinuclidin-3-yl (7-(4-(isoxazol-3-yl)phenyl)-3,3-dimethylchroman-4-yl)carbamate;
(S)-quinuclidin-3-yl (7-(4-isobutoxyphenyl)-3,3-dimethylchroman-4-yl)carbamate;
(S)-quinuclidin-3-yl (7-(3-fluoro-4-isopropoxyphenyl)-3,3-dimethylchroman-4-yl)carbamate;
(S)-quinuclidin-3-yl (7-(2-fluoro-4-(trifluoromethyl)phenyl)-3,3-dimethylchroman-4-yl)carbamate;
(S)-quinuclidin-3-yl (7-(4-isopropoxy-3,5-dimethylphenyl)-3,3-dimethylchroman-4-yl)carbamate;
(S)-quinuclidin-3-yl (3,3-dimethyl-7-phenylchroman-4-yl)carbamate;
(S)-quinuclidin-3-yl (3,3-dimethyl-7-(pyridin-3-yl)chroman-4-yl)carbamate;
(S)-quinuclidin-3-yl (3,3-dimethyl-7-(pyridin-2-yl)chroman-4-yl)carbamate;
(S)-quinuclidin-3-yl (7-benzyl-3,3-dimethylchroman-4-yl)carbamate;
(S)-quinuclidin-3-yl (3,3-dimethyl-7-(m-tolyl)chroman-4-yl)carbamate;
(S)-quinuclidin-3-yl (3,3-dimethyl-7-(p-tolyl)chroman-4-yl)carbamate;
(S)-quinuclidin-3-yl (3,3-dimethyl-7-(o-tolyl)chroman-4-yl)carbamate;
(S)-quinuclidin-3-yl (3,3-dimethyl-7-((E)-2-(thiophen-3-yl)vinyl)chroman-4-yl)carbamate;
(S)-quinuclidin-3-yl (3,3-dimethyl-7-(4-vinylphenyl)chroman-4-yl)carbamate;
(S)-quinuclidin-3-yl (7-(4-ethylphenyl)-3,3-dimethylchroman-4-yl)carbamate;

(S)-quinuclidin-3-yl (3,3-dimethyl-7-(2-vinylphenyl)chroman-4-yl)carbamate;
(S)-quinuclidin-3-yl (7-(4-ethoxy-2-methylphenyl)-3,3-dimethylchroman-4-yl)carbamate;
(S)-quinuclidin-3-yl (7-(4-(benzyloxy)phenyl)-3,3-dimethylchroman-4-yl)carbamate;
(S)-quinuclidin-3-yl (7-(3-(benzyloxy)phenyl)-3,3-dimethylchroman-4-yl)carbamate;
(S)-quinuclidin-3-yl (7-(2,6-difluoropyridin-3-yl)-3,3-dimethylchroman-4-yl)carbamate;
(S)-quinuclidin-3-yl (7-(2-allylphenyl)-3,3-dimethylchroman-4-yl)carbamate;
(S)-quinuclidin-3-yl (7-(4-(cyanomethyl)phenyl)-3,3-dimethylchroman-4-yl)carbamate;
(S)-quinuclidin-3-yl (7-(3-(cyanomethyl)phenyl)-3,3-dimethylchroman-4-yl)carbamate;
(S)-quinuclidin-3-yl (7-((E)-2-([1,1'-diphenyl]-4-yl)vinyl)-3,3-dimethylchroman-4-yl)carbamate;
(S)-quinuclidin-3-yl (7-(2-cyclopropylpyrimidin-5-yl)-3,3-dimethylchroman-4-yl)carbamate;
(S)-quinuclidin-3-yl (3,3-dimethyl-7-((E)-4-(trifluoromethyl)styryl)chroman-4-yl)carbamate;
(S)-quinuclidin-3-yl (7-(2-chloro-3,5-dimethylphenyl)-3,3-dimethylchroman-4-yl)carbamate;
(S)-quinuclidin-3-yl (7-((E)-2,4-difluorostyryl)-3,3-dimethylchroman-4-yl)carbamate;
(S)-quinuclidin-3-yl (7-((E)-4-ethylstyryl)-3,3-dimethylchroman-4-yl)carbamate;
(S)-quinuclidin-3-yl (7-(6-ethoxynaphthalen-2-yl)-3,3-dimethylchroman-4-yl)carbamate;
(S)-quinuclidin-3-yl (7-((E)-3-fluorostyryl)-3,3-dimethylchroman-4-yl)carbamate;
(S)-quinuclidin-3-yl (7-(dibenzo[b,d]furan-4-yl)-3,3-dimethylchroman-4-yl)carbamate;
(S)-quinuclidin-3-yl (7-(4-cyano-3-fluorophenyl)-3,3-dimethylchroman-4-yl)carbamate;
(S)-quinuclidin-3-yl (7-(1-benzyl-6-oxo-1,6-dihydropyridin-3-yl)-3,3-dimethylchroman-4-yl)carbamate;
(S)-quinuclidin-3-yl (7-((E)-4-fluorostyryl)-3,3-dimethylchroman-4-yl)carbamate;
(S)-quinuclidin-3-yl (6-(3-fluorophenyl)-2,2-dimethylchroman-4-yl)carbamate;
(S)-quinuclidin-3-yl (2,2-dimethyl-7-(3-(trifluoromethyl)phenyl)chroman-4-yl)carbamate;
(S)-quinuclidin-3-yl (2,2-dimethyl-7-(3-(trifluoromethoxy)phenyl)chroman-4-yl)carbamate;
(S)-quinuclidin-3-yl (7-(3-chlorophenyl)-4-methylchroman-4-yl)carbamate;
(S)-quinuclidin-3-yl (7-(3-fluorophenyl)-4-methylchroman-4-yl)carbamate;
(S)-quinuclidin-3-yl (7-(3-methoxyphenyl)-4-methylchroman-4-yl)carbamate;
(S)-quinuclidin-3-yl (7-(3-isopropylphenyl)-4-methylchroman-4-yl)carbamate;
(S)-quinuclidin-3-yl (7-(2-chloro-5-methoxyphenyl)-4-methylchroman-4-yl)carbamate;
(S)-quinuclidin-3-yl (7-(4-ethoxyphenyl)-4-methylchroman-4-yl)carbamate;
(S)-quinuclidin-3-yl (7-(3-(dimethylamino)phenyl)-4-methylchroman-4-yl)carbamate;
(S)-quinuclidin-3-yl (7-(benzofuran-3-yl)-4-methylchroman-4-yl)carbamate;
(S)-quinuclidin-3-yl (4-methyl-7-(3-(trifluoromethyl)phenyl)chroman-4-yl)carbamate;
(S)-quinuclidin-3-yl (4-methyl-7-(3-(trifluoromethoxy)phenyl)chroman-4-yl)carbamate;
(S)-quinuclidin-3-yl (7-(2,2-difluorobenzo[d][1,3]dioxol-5-yl)-4-methylchroman-4-yl)carbamate;
(S)-quinuclidin-3-yl (7-(4-ethoxy-3,5-dimethylphenyl)-4-methylchroman-4-yl)carbamate;
(S)-quinuclidin-3-yl (7-(2-cyanophenyl)-4-methylchroman-4-yl)carbamate;
(S)-quinuclidin-3-yl (7-(3-(tert-butyl)phenyl)-4-methylchroman-4-yl)carbamate;
(S)-quinuclidin-3-yl (4-methyl-7-(4-methylthiophen-3-yl)chroman-4-yl)carbamate;
(S)-quinuclidin-3-yl (7-(3-(tert-butyl)phenyl)isochroman-4-yl)carbamate;
(S)-quinuclidin-3-yl (7-(3-isopropylphenyl)isochroman-4-yl)carbamate;
(S)-quinuclidin-3-yl (7-(3-(tert-butyl)phenyl)-1-methyl-1,2,3,4-tetrahydroquinolin-4-yl)carbamate;
(S)-quinuclidin-3-yl (7-(benzofuran-3-yl)-1-methyl-1,2,3,4-tetrahydroquinolin-4-yl)carbamate;
(S)-quinuclidin-3-yl (6-(4-chlorophenyl)thiochroman-4-yl)carbamate;
(S)-quinuclidin-3-yl (7-(3-fluorophenyl)thiochroman-4-yl)carbamate;
(S)-quinuclidin-3-yl (7-(3-chlorophenyl)thiochroman-4-yl)carbamate;
(S)-quinuclidin-3-yl (7-(3-(trifluoromethyl)phenyl)thiochroman-4-yl)carbamate;
(S)-quinuclidin-3-yl (7-(3-(trifluoromethoxy)phenyl)thiochroman-4-yl)carbamate;
(S)-quinuclidin-3-yl (7-(3-(methoxymethoxy)phenyl)thiochroman-4-yl)carbamate;
(S)-quinuclidin-3-yl (7-(3-(tert-butyl)phenyl)thiochroman-4-yl)carbamate;
(S)-quinuclidin-3-yl (7-(2,5-dichlorophenyl)thiochroman-4-yl)carbamate;
(S)-quinuclidin-3-yl (7-(3-ethoxyphenyl)thiochroman-4-yl)carbamate;
(S)-quinuclidin-3-yl (7-(3-(methylthio)phenyl)thiochroman-4-yl)carbamate;
(S)-quinuclidin-3-yl (7-(3-(dimethylamino)phenyl)thiochroman-4-yl)carbamate;
(S)-quinuclidin-3-yl (7-(2,2-difluorobenzo[d][1,3]dioxol-5-yl)thiochroman-4-yl)carbamate;
(S)-quinuclidin-3-yl (7-(benzofuran-3-yl)thiochroman-4-yl)carbamate;
(S)-quinuclidin-3-yl (3,3-dimethyl-6-(4-(trifluoromethyl)phenyl)thiochroman-4-yl)carbamate;
(S)-quinuclidin-3-yl (6-fluoro-7-(3-fluorophenyl)-3,3-dimethylchroman-4-yl)carbamate;
(S)-quinuclidin-3-yl (6-fluoro-7-(4-fluorophenyl)-3,3-dimethylchroman-4-yl)carbamate;
(S)-quinuclidin-3-yl (6-fluoro-7-(3-chlorophenyl)-3,3-dimethylchroman-4-yl)carbamate;
(S)-quinuclidin-3-yl (7-(3-ethylphenyl)-6-fluoro-3,3-dimethylchroman-4-yl)carbamate;
(S)-quinuclidin-3-yl (7-(4-ethylphenyl)-6-fluoro-3,3-dimethylchroman-4-yl)carbamate;
(S)-quinuclidin-3-yl (6-fluoro-7-(3-methoxyphenyl)-3,3-dimethylchroman-4-yl)carbamate;
(S)-quinuclidin-3-yl (6-fluoro-7-(4-methoxyphenyl)-3,3-dimethylchroman-4-yl)carbamate;
(S)-quinuclidin-3-yl (7-(4-ethoxyphenyl)-6-fluoro-3,3-dimethylchroman-4-yl)carbamate;
(S)-quinuclidin-3-yl (6-fluoro-3,3-dimethyl-7-(thiophen-3-yl)chroman-4-yl)carbamate;
(S)-quinuclidin-3-yl (6-fluoro-7-(3-isopropylphenyl)-3,3-dimethylchroman-4-yl)carbamate;

(S)-quinuclidin-3-yl (7-(2-chloro-5-methoxyphenyl)-6-fluoro-3,3-dimethylchroman-4-yl)carbamate;
(S)-quinuclidin-3-yl (6-fluoro-7-(2-fluoro-4-methoxyphenyl)-3,3-dimethylchroman-4-yl)carbamate;
(S)-quinuclidin-3-yl (6-fluoro-7-(4-methoxy-2-methylphenyl)-3,3-dimethylchroman-4-yl)carbamate;
(S)-quinuclidin-3-yl (7-(4-butylphenyl)-6-fluoro-3,3-dimethylchroman-4-yl)carbamate;
(S)-quinuclidin-3-yl (7-(3-chloro-4-isopropoxyphenyl)-6-fluoro-3,3-dimethylchroman-4-yl)carbamate;
(S)-quinuclidin-3-yl (7-(4-(tert-butyl)phenyl)-6-fluoro-3,3-dimethylchroman-4-yl)carbamate;
(S)-quinuclidin-3-yl (6-fluoro-7-(4-methoxy-3,5-dimethylphenyl)-3,3-dimethylchroman-4-yl)carbamate;
(S)-quinuclidin-3-yl (6-fluoro-7-(4-isobutoxyphenyl)-3,3-dimethylchroman-4-yl)carbamate;
(S)-quinuclidin-3-yl (6-fluoro-7-(6-isopropoxypyridin-3-yl)-3,3-dimethylchroman-4-yl)carbamate;
(S)-quinuclidin-3-yl (7-(3-fluorophenyl)-6-methoxy-3,3-dimethylchroman-4-yl)carbamate;
(S)-quinuclidin-3-yl (7-(4-fluorophenyl)-6-methoxy-3,3-dimethylchroman-4-yl)carbamate;
(S)-quinuclidin-3-yl (7-(3-chlorophenyl)-6-methoxy-3,3-dimethylchroman-4-yl)carbamate;
(S)-quinuclidin-3-yl (7-(3-ethylphenyl)-6-methoxy-3,3-dimethylchroman-4-yl)carbamate;
(S)-quinuclidin-3-yl (7-(4-ethylphenyl)-6-methoxy-3,3-dimethylchroman-4-yl)carbamate;
(S)-quinuclidin-3-yl (6-methoxy-7-(3-methoxyphenyl)-3,3-dimethylchroman-4-yl)carbamate;
(S)-quinuclidin-3-yl (6-methoxy-7-(4-methoxyphenyl)-3,3-dimethylchroman-4-yl)carbamate;
(S)-quinuclidin-3-yl (7-(4-ethoxyphenyl)-6-methoxy-3,3-dimethylchroman-4-yl)carbamate;
(S)-quinuclidin-3-yl (6-methoxy-3,3-dimethyl-7-(thiophen-3-yl)chroman-4-yl)carbamate;
(S)-quinuclidin-3-yl (7-(3-isopropylphenyl)-6-methoxy-3,3-dimethylchroman-4-yl)carbamate;
(S)-quinuclidin-3-yl (7-(2-chloro-5-methoxyphenyl)-6-methoxy-3,3-dimethylchroman-4-yl)carbamate;
(S)-quinuclidin-3-yl (7-(2-fluoro-4-methoxyphenyl)-6-methoxy-3,3-dimethylchroman-4-yl)carbamate;
(S)-quinuclidin-3-yl (6-methoxy-7-(4-methoxy-2-methylphenyl)-3,3-dimethylchroman-4-yl)carbamate;
(S)-quinuclidin-3-yl (7-(4-butylphenyl)-6-methoxy-3,3-dimethylchroman-4-yl)carbamate;
(S)-quinuclidin-3-yl (7-(3-chloro-4-isopropoxyphenyl)-6-methoxy-3,3-dimethylchroman-4-yl)carbamate;
(S)-quinuclidin-3-yl (7-(4-(tert-butyl)phenyl)-6-methoxy-3,3-dimethylchroman-4-yl)carbamate;
(S)-quinuclidin-3-yl (6-methoxy-7-(4-methoxy-3,5-dimethylphenyl)-3,3-dimethylchroman-4-yl)carbamate;
(S)-quinuclidin-3-yl (7-(4-isobutoxyphenyl)-6-methoxy-3,3-dimethylchroman-4-yl)carbamate; and
(S)-quinuclidin-3-yl (7-(6-isopropoxypyridin-3-yl)-6-methoxy-3,3-dimethylchroman-4-yl)carbamate.

The compound of Formula 1 or pharmaceutically acceptable salt thereof may be in the form of cis- or trans-geometrical isomer. The compound of Formula 1 or its pharmaceutically acceptable salt comprises both cis- and trans-geometrical isomers, unless otherwise indicated. The compound of Formula 1 or pharmaceutically acceptable salt thereof may also have substituents containing asymmetric atom and therefore be in the form of racemic mixture (RS) or in the form of an optical isomer, such as (R) or (S) isomer. The compound of Formula 1 or pharmaceutically acceptable salt thereof comprises both the racemic mixture (RS) and each optical isomer such as (R) or (S) isomer, unless otherwise indicated. In addition, the compound of Formula 1 or pharmaceutically acceptable salt thereof may have two or more chiral centers and therefore be in the form of one or more diastereomers or in the form of the mixture thereof. The compound of Formula 1 or pharmaceutically acceptable salt thereof comprises both each diastereomer and the mixture thereof, unless otherwise indicated.

The compound of Formula 1 of the present invention may be in a pharmaceutically acceptable salt form. The salt may be a conventional acid addition salt form, which includes e.g., salts derived from an inorganic acid such as hydrochloric acid, sulfuric acid, nitric acid, phosphoric acid, perchloric acid, or hydrobromic acid; and salts derived from an organic acid such as formic acid, acetic acid, propionic acid, oxalic acid, succinic acid, benzoic acid, citric acid, maleic acid, malonic acid, malic acid, tartaric acid, gluconic acid, lactic acid, gentisic acid, fumaric acid, lactobionic acid, salicylic acid, phthalic acid, embonic acid, aspartic acid, glutamic acid, or acetylsalicylic acid. And, the salt also includes, e.g., salts derived from an amino acid such as glycine, alanine, valine, isoleucine, serine, cysteine, cystine, aspartic acid, glutamine, lysine, arginine, tyrosine, or proline. In addition, the salt includes, e.g., salts derived from a sulfonic acid such as methanesulfonic acid, ethanesulfonic acid, benzenesulfonic acid, or toluenesulfonic acid.

The compound of Formula 1 or pharmaceutically acceptable salt thereof according the present invention may be prepared according to various methods.

For example, the compound of Formula 1a or pharmaceutically acceptable salt thereof according the present invention may be prepared by a process which comprises reacting a compound of Formula 2 or salt thereof with ethyl chloroformate to obtain a compound of Formula 3; coupling the compound of Formula 3 with a compound of Formula 4 to obtain a compound of Formula 5; reacting the compound of Formula 5 with a A-W-boronic acid substituted with $X_1$, $X_2$, $X_3$, or $X_4$ to obtain a compound of Formula 1a; and optionally converting the compound of Formula 1a to a pharmaceutically acceptable salt thereof, as shown in the following Reaction Scheme 1.

<Reaction Scheme 1>

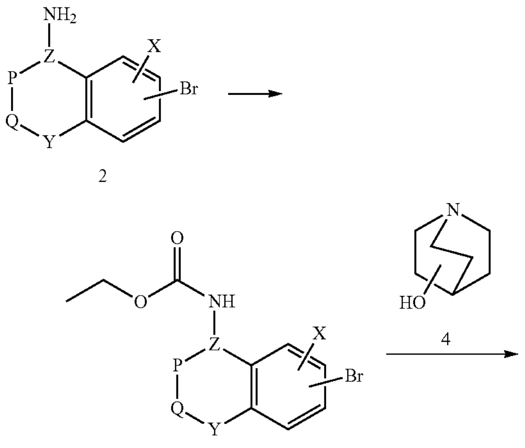

2

4

3

-continued

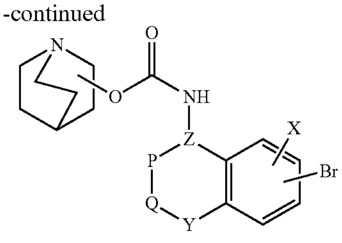

5

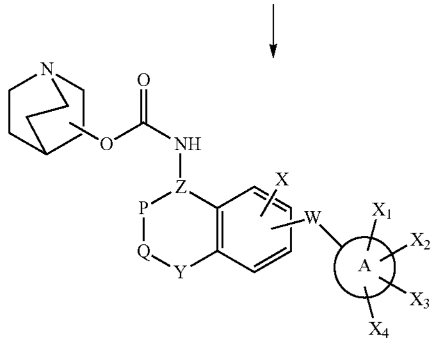

1a

In the Reaction Scheme 1, X, Y, P, Q, Z, W, A ring, $X_1$, $X_2$, $X_3$, and $X_4$ are the same as defined in the above.

The compound of Formula 2, which is commercially available or a known compound, may be synthesized according to literatures. The reaction between the compound of Formula 2 or salt thereof and ethyl chloroformate may be carried out in the presence of an organic base such as triethylamine, N,N-diisopropylethylamine, etc. or an inorganic base such as potassium carbonate, etc. The base may be used in an amount ranging from 1 to 1.5 equivalents based on 1 equivalent of the compound of Formula 2 or in an amount ranging from 3 to 5 equivalents based on 1 equivalent of the salt of the compound of Formula 2 (e.g., hydrochloride). The reaction may be carried out in a solvent such as dichloromethane or tetrahydrofuran preferably at 0° C. to room temperature.

The coupling between the compound of Formula 3 and the compound of Formula 4 (i.e., quinuclidinol) may be carried out through a condensation reaction including the removal of ethanol. The reaction may be carried out preferably in the presence of a base such as sodium hydride. In addition, the reaction may be carried out in a non-polar organic solvent such as toluene at 120° C. to 140° C.

The reaction between the compound of Formula 5 and the A-W-boronic acid substituted with $X_1$, $X_2$, $X_3$, or $X_4$ may be carried out according to the Suzuki reaction. Said Suzuki reaction may be carried out using a palladium catalyst, such as tetrakis(triphenylphosphine)palladium(0) ($Pd(PPh_3)_4$), palladium(II) acetate ($Pd(OAc)_2$), [1,1'-bis(diphenylphosphino)ferrocene]dichloropalladium(II) ($Pd(dppf)Cl_2$), etc. In addition, said Suzuki reaction may be carried out in the presence of an inorganic base such as cesium carbonate ($Cs_2CO_3$), sodium carbonate ($Na_2CO_3$), potassium carbonate ($K_2CO_3$), potassium phosphate ($K_3PO_4$), etc. Said Suzuki reaction may be carried out in a non-polar organic solvent such as toluene or a polar organic solvent such as 1,4-dioxane, tetrahydrofuran, acetonitrile, 1,2-dimethoxyethane, or N,N-dimethylformamide, at 50° C. to 150° C., preferably 80° C. to 120° C. Other reaction conditions including a reaction time may be determined according to known methods for the Suzuki reaction.

The conversion of the compound of Formula 1a to a pharmaceutically acceptable salt thereof may be carried out according to conventional methods. For example, a pharmaceutically acceptable salt of the compound of Formula 1a may be prepared by dissolving the compound of Formula 1a in a water-miscible solvent such as methanol, ethanol, acetone or 1,4-dioxane and then added a free acid or a free base thereto for the crystallization thereof.

In addition, the compound of Formula 1a or pharmaceutically acceptable salt thereof according the present invention may be prepared by a process which comprises reacting a compound of Formula 4 with bis(4-nitrophenyl) carbonate to obtain a compound of Formula 7; reacting the compound of Formula 7 with a compound of Formula 2 to obtain a compound of Formula 5; reacting the compound of Formula 5 with a A-W-boronic acid substituted with $X_1$, $X_2$, $X_3$, or $X_4$ to obtain a compound of Formula 1a; and optionally converting the compound of Formula 1a to a pharmaceutically acceptable salt thereof, as shown in the following Reaction Scheme 2.

<Reaction Scheme 2>

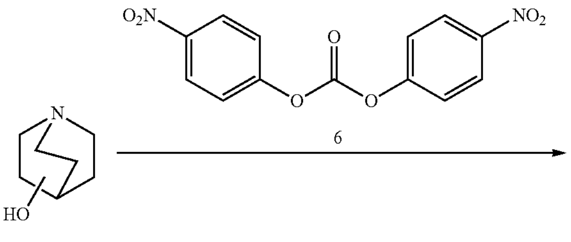

6

4

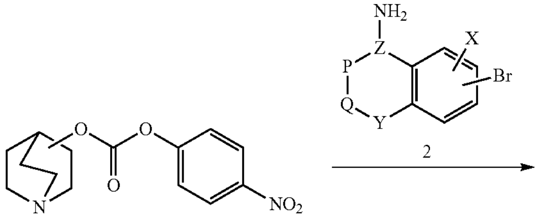

2

7

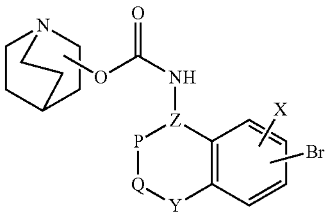

5

-continued

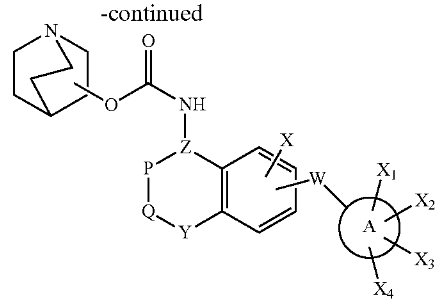

1a

In the Reaction Scheme 2, X, Y, P, Q, Z, W, A ring, $X_1$, $X_2$, $X_3$, and $X_4$ are the same as defined in the above.

The reaction between the compound of Formula 4 (i.e., quinuclidinol) and bis(4-nitrophenyl) carbonate may be carried out in a polar solvent such as N,N-dimethylformamide preferably at 0° C. to 25° C. The compound of Formula 7 may be also prepared by reacting the compound of Formula 4 with 4-nitrophenyl chloroformate, in the presence of a base such as triethylamine, in a solvent such as dichloromethane, acetonitrile, etc.

The reaction between the compound of Formula 7 and the compound of Formula 2 may be carried out in a solvent such as N,N-dimethylformamide, tetrahydrofuran or acetonitrile, in the presence of a base such as N,N-diisopropylethylamine or triethylamine, at 0° C. to 25° C.

The reaction between the compound of Formula 5 and the A-W-boronic acid substituted with $X_1$, $X_2$, $X_3$, or $X_4$ may be carried out according to the Suzuki reaction, as described in the above. In addition, the conversion of the compound of Formula 1a to a pharmaceutically acceptable salt thereof may be carried out according to conventional methods, as described in the above.

The compound having a chromane, isochromane, thiochromane, or tetrahydroquinoline moiety according to the present invention, i.e., the compound of Formula 1 or pharmaceutically acceptable salt thereof has an excellent inhibitory activity against glucosylceramide synthase (GCS), and therefore can be usefully applied for preventing or treating various diseases associated with GCS.

Therefore, the present invention includes, within its scope, a pharmaceutical composition for inhibiting glucosylceramide synthase (GCS), comprising a therapeutically effective amount of the compound of Formula 1 or pharmaceutically acceptable salt thereof as an active ingredient. In an embodiment, the present invention provides a pharmaceutical composition for preventing or treating the diseases associated with GCS, such as Gaucher disease, Fabry disease, Tay-Sachs disease, Parkinson's disease, etc., comprising a therapeutically effective amount of the compound of Formula 1 or pharmaceutically acceptable salt thereof as an active ingredient.

The pharmaceutical composition of the present invention may comprise a pharmaceutically acceptable carrier, such as diluents, disintegrants, sweeteners, lubricants, or flavoring agents. The pharmaceutical composition may be formulated to an oral dosage form such as tablets, capsules, powders, granules, suspensions, emulsions, or syrups; or a parenteral dosage form such as solutions for external use, suspensions for external use, emulsions for external use, gels (e.g., ointment), inhalations, nebulizations, injections. The dosage form may be various forms, e.g., dosage forms for single administration or for multiple administrations.

The pharmaceutical composition of the present invention may comprise, for example, a diluent (e.g., lactose, corn starch, etc); a lubricant (e.g., magnesium stearate); an emulsifying agent; a suspending agent; a stabilizer; and/or an isotonic agent. If necessary, the composition further comprises sweeteners and/or flavoring agents.

The composition of the present invention may be administered orally or parenterally, including inhalant, intravenous, intraperitoneal, subcutaneous, rectal and topical routes of administration. Therefore, the composition of the present invention may be formulated into various forms such as tablets, capsules, aqueous solutions or suspensions. In the case of tablets for oral administration, carriers such as lactose, corn starch, and lubricating agents, e.g. magnesium stearate, are conventionally used. In the case of capsules for oral administration, lactose and/or dried corn starch can be used as a diluent. When an aqueous suspension is required for oral administration, the active ingredient may be combined with emulsifying and/or suspending agents. If desired, certain sweetening and/or flavoring agents may be used. For intramuscular, intraperitoneal, subcutaneous and intravenous administration, sterile solutions of the active ingredient are usually prepared, and the pH of the solutions should be suitably adjusted and buffered. For intravenous administration, the total concentration of solutes should be controlled in order to render the preparation isotonic. The composition of the present invention may be in the form of an aqueous solution containing pharmaceutically acceptable carriers, e.g., saline having a pH level of 7.4. The solutions may be introduced into a patient's intramuscular blood-stream by local bolus injection.

The compound of Formula 1 or pharmaceutically acceptable salt thereof may be administered in a therapeutically effective amount ranging from about 0.0001 mg/kg to about 100 mg/kg per day to a subject patient. Of course, the dosage may be changed according to the patient's age, weight, susceptibility, symptom, or activity of the compound.

The present invention includes, within its scope, a method for inhibiting glucosylceramide synthase (GCS) in a mammal, comprising administering a therapeutically effective amount of the compound of Formula 1 or pharmaceutically acceptable salt thereof to the mammal in need thereof. In an embodiment, the present invention provides a method for treating the diseases associated with GCS, such as Gaucher disease, Fabry disease, Tay-Sachs disease, Parkinson's disease, etc., comprising administering a therapeutically effective amount of the compound of Formula 1 or pharmaceutically acceptable salt thereof to the mammal in need thereof.

The present invention also provides a use of the compound of Formula 1 or pharmaceutically acceptable salt thereof for the manufacture of a medicament for inhibiting glucosylceramide synthase (GCS) in a mammal. In an embodiment, the present invention provides a use of the compound of Formula 1 or pharmaceutically acceptable salt thereof for the manufacture of a medicament for preventing or treating the diseases associated with GCS, such as Gaucher disease, Fabry disease, Tay-Sachs disease, Parkinson's disease, etc.

The following examples and experimental examples are provided for illustration purposes only, and are not intended to limit the scope of the invention.

In the following examples, brine refers to a saturated aqueous sodium chloride solution. Unless otherwise indicated, all temperatures are in degrees Celsius (° C.). All reactions were carried out at room temperature unless otherwise indicated.

The analyses of the compounds prepared in the following Preparations and Examples were carried out as follows: Nuclear magnetic resonance (NMR) spectrum analysis was carried out using Bruker 400 MHz spectrometer and chemical shifts thereof were analyzed in ppm. Column chromatography was carried out on silica gel (Merck, 70-230 mesh). Each starting material is a known compound which was synthesized according to literatures or purchased commercially. All reactions and chromatographic fractions were analyzed by thin layer chromatography (TLC) on a 250 nm silica gel plate and visualized with ultraviolet or iodine ($I_2$) staining.

Preparation 1. (S)-quinuclidin-3-yl (7-bromochroman-4-yl)carbamate

Step 1. 7-bromo-3,4-dihydro-2H-chroman-4-amine

7-Bromochroman-4-one (10.0 g, 44.04 mmol) was dissolved in a mixed solvent of methanol (100 ml) and isopropanol (125 ml) and then ammonium acetate (67.9 g, 880.9 mmol) and sodium cyanoborohydride (13.84 g, 220.2 mmol) were added thereto at room temperature. The reaction mixture was stirred at room temperature for 4 hours and then refluxed under stirring at 80° C. for 12 hours. The reaction mixture was cooled to room temperature, concentrated under reduced pressure, basified to pH 8-9 with a 1N sodium hydroxide solution, and then extracted with ethyl acetate. The organic layer was dried over anhydrous magnesium sulfate and then filtered and concentrated under reduced pressure. The resulting residue was purified by column chromatography (dichloromethane/methanol=5/1, v/v) to give the titled compound as a pale yellow oil. (7.8 g, Yield: 77%)

Step 2. (S)-quinuclidin-3-yl (7-bromochroman-4-yl)carbamate (S)-(+)-3-Quinuclidinol (558 mg, 4.38 mmol) was dissolved in N,N-dimethylformamide (9 ml) at room temperature and then bis(4-nitrophenyl) carbonate (1.47 g, 4.82 mmol) was added thereto. The reaction mixture was stirred overnight. 7-Bromo-3,4-dihydro-2H-chroman-4-amine (1.0 g, 4.38 mmol) prepared in Step 1 was slowly added to the reaction mixture, which was then stirred at room temperature overnight. The reaction mixture was diluted with water and then extracted with ethyl acetate. The organic layer was washed with 10% ammonia, a saturated sodium bicarbonate solution, and brine, dried over anhydrous magnesium sulfate, and then filtered and concentrated under reduced pressure. The resulting residue was purified by column chromatography (ethyl acetate/(methanol/ammonia water=1/1)=9/1, v/v) to give the titled compound as a white solid. (1.23 g, Yield: 73%)

$^1$H-NMR (400 MHz, $CDCl_3$) δ 7.14 (t, 1H), 7.05-7.03 (m, 1H), 7.00 (s, 1H), 5.20-5.18 (m, 1H), 4.84-4.83 (m, 1H), 4.76-4.74 (m, 1H), 4.27-4.26 (m, 1H), 4.18-4.17 (m, 1H), 3.25-3.21 (m, 1H), 2.84-2.70 (m, 5H), 2.19-2.17 (m, 1H), 2.08-2.03 (m, 2H), 1.79-1.78 (m, 1H), 1.70-1.69 (m, 1H), 1.57-1.56 (m, 1H), 1.39-1.37 (m, 1H)

Preparation 2. (S)-quinuclidin-3-yl (6-bromochroman-4-yl)carbamate

Step 1. ethyl (6-bromochroman-4-yl)carbamate

6-Bromochroman-4-amine (3 g, 13.27 mmol) was dissolved in dichloromethane (100 mL) and then triethylamine (1.9 ml, 13.27 mmol) and ethyl chloroformate (1.4 ml, 1.46 mmol) were slowly added thereto. The reaction mixture was stirred at room temperature for 4 hours. Water was added to the reaction mixture, which was then extracted with dichloromethane. The organic layer was dried over anhydrous magnesium sulfate and then filtered and concentrated under reduced pressure. The resulting residue was purified by column chromatography (n-hexane/ethyl acetate=1/1, v/v) to give the titled compound as a white solid. (3.6 g, Yield: 90%)

Step 2. (S)-quinuclidin-3-yl (6-bromochroman-4-yl)carbamate (S)-(+)-3-Quinuclidinol (2.54 g, 20.0 mmol) was dissolved in toluene (33 ml) and then sodium hydride (239.9 mg, 1 mmol) was added thereto at 0° C. The reaction mixture was stirred for 15 minutes and then ethyl (6-bromochroman-4-yl)carbamate (3 g, 1 mmol) prepared in Step 1 was added thereto. The reaction mixture was refluxed under stirring at 140° C. for 20 hours and then cooled to room temperature. Brine was added to the reaction mixture, which was then extracted with ethyl acetate. The organic layer was washed with brine two times, dried over anhydrous magnesium sulfate, and then concentrated under reduced pressure. The resulting residue was purified by column chromatography (ethyl acetate/(methanol/ammonia water=1/1)=9/1, v/v) to give the titled compound as a white solid. (1.1 g, Yield: 29%)

$^1$H-NMR (400 MHz, $CDCl_3$) δ 7.37-7.24 (m, 2H), 6.74-6.69 (m, 1H), 4.80 (s, 1H), 4.23 (s, 2H), 3.27 (q, 1H), 2.88-2.65 (m, 4H), 2.17-1.90 (m, 4H), 1.84-1.76 (m, 1H), 1.71-1.60 (m, 1H), 1.56-1.46 (m, 1H)

Preparation 3. (S)-quinuclidin-3-yl (7-bromo-3,3-dimethylchroman-4-yl)carbamate

Step 1. 7-bromo-3,3-dimethylchroman-4-one

7-Bromochroman-4-one (20 g, 88.1 mmol) was dissolved in tetrahydrofuran (400 ml) and then iodomethane (37.5 g, 264.3 mmol) was slowly added thereto at −78° C. Potassium tert-butoxide (49.4 g, 440.4 mmol) was added to the reaction mixture, the temperature of which was slowly raised to room temperature, followed by stirring for 16 hours. Water was added to the reaction mixture, which was then extracted with diethyl ether. The organic layer was dried over anhydrous magnesium sulfate and then concentrated under reduced pressure. The resulting residue was purified by column chromatography (n-hexane/ethyl acetate=10/1, v/v) to give the titled compound as a white solid. (11.8 g, Yield: 52%)

$^1$H-NMR (400 MHz, $CDCl_3$) δ 7.76 (d, 1H), 7.17-7.15 (m, 2H), 4.15 (s, 2H), 1.20 (s, 6H)

Step 2. 7-bromo-3,3-dimethylchroman-4-amine

The titled compound was prepared in accordance with the same procedures as in Step 1 of Preparation 1, using 7-bromo-3,3-dimethylchroman-4-one prepared in Step 1.

$^1$H-NMR (400 MHz, $CDCl_3$) δ 7.25 (d, 1H), 7.04 (d, 1H), 6.97 (s, 1H), 3.97 (d, 1H), 3.75 (d, 1H), 3.55 (s, 1H), 0.96 (d, 6H)

Step 3. (S)-quinuclidin-3-yl (7-bromo-3,3-dimethylchroman-4-yl)carbamate

The titled compound was prepared in accordance with the same procedures as in Step 2 of Preparation 1, using 7-bromo-3,3-dimethylchroman-4-amine prepared in Step 2.

$^1$H-NMR (400 MHz, $CDCl_3$) δ 7.09-7.03 (m, 2H), 6.99 (s, 1H), 4.87 (t, 1H), 4.82-4.77 (m, 1H), 4.63 (d, 1H), 3.90-3.77 (m, 2H), 3.31-3.21 (m, 1H), 2.96-2.68 (m, 5H), 2.13-2.06 (m, 1H), 1.88-1.79 (m, 1H), 1.76-1.67 (m, 1H), 1.64-1.54 (m, 1H), 1.48-1.37 (m, 1H), 1.03 (d, 3H), 0.98 (d, 3H)

Preparation 4. (S)-quinuclidin-3-yl (6-bromo-3,3-dimethylchroman-4-yl)carbamate The titled compound was prepared in accordance with the same procedures as in Preparation 3, using 6-bromochroman-4-one as a starting material.

$^1$H-NMR (400 MHz, $CDCl_3$) δ 7.31-7.23 (m, 2H), 6.70 (d, 1H), 4.93-4.84 (m, 1H), 4.82-4.76 (m, 1H), 4.69-4.66 (m, 1H), 3.92-3.78 (m, 2H), 3.32-3.21 (m, 1H), 2.95-2.66 (m, 5H), 2.16-2.09 (m, 1H), 1.91-1.81 (m, 1H), 1.75-1.68 (m, 1H), 1.64-1.55 (m, 1H), 1.49-1.39 (m, 1H), 0.99 (d, 6H)

Preparation 5. (S)-quinuclidin-3-yl (7-bromo-2,2-dimethylchroman-4-yl)carbamate

Step 1. 7-bromo-2,2-dimethylchroman-4-one 1-(4-Bromo-2-hydroxyphenyl)ethan-1-one (5.0 g, 23.25 mmol) was dissolved in toluene (77 ml) and then acetone (8.6 ml, 116.25 mmol) and pyrrolidine (1.91 ml, 23.25 mmol) were slowly added. The reaction mixture was stirred at room temperature for 1 hour, refluxed under stirring for 24 hours, and then concentrated under reduced pressure. The resulting residue was diluted with ethyl acetate, washed with a 6N hydrochloric acid solution, a 2N sodium hydroxide solution, and brine, and then concentrated under reduced pressure to give the titled compound as a brown solid. (3.6 g, Yield: 60%) The product was used in subsequent reaction without further purification.

$^1$H-NMR (400 MHz, $CDCl_3$) δ 7.71 (d, 1H), 7.15-7.10 (m, 2H), 2.72 (s, 2H), 1.46 (s, 6H)

Step 2. 7-bromo-2,2-dimethyl-chroman-4-amine hydrochloride

7-Bromo-2,2-dimethylchroman-4-one (3.57 g, 13.99 mmol) prepared in Step 1 was dissolved in isopropanol (46.65 ml) and then ammonium acetate (21.57 g, 279.88 mmol) and sodium cyanoborohydride (4.4 g, 69.97 mmol) were added thereto at room temperature. The reaction mixture was stirred at room temperature for 4 hours and then refluxed under stirring at 80° C. for 22 hours. The reaction mixture was cooled to room temperature, concentrated under reduced pressure, basified to pH>12 with a 1N sodium hydroxide solution, and then extracted with dichloromethane. The organic layer was dried over anhydrous magnesium sulfate and then filtered and concentrated under reduced pressure. Ethyl acetate was added to the resulting residue and then a hydrochloric acid solution (4M) in 1,4-dioxane was added thereto. The mixture was stirred at room temperature for 1 hour. The resulting solid was filtered under reduced pressure, washed with ethyl acetate, and then dried to give the titled compound as a white solid. (3.43 g, Yield: 83.7%)

$^1$H-NMR (400 MHz, DMSO-$d_6$) δ 8.81 (brs, 3H), 7.63 (d, 1H), 7.16 (d, 1H), 7.02 (s, 1H), 4.47 (dd, 1H), 2.31 (dd, 1H), 1.80 (t, 1H), 1.41 (s, 3H), 1.21 (s, 3H)

Step 3. (S)-quinuclidin-3-yl (7-bromo-2,2-dimethyl-chroman-4-yl)carbamate (S)-(+)-3-Quinuclidinol (1.91 g, 15.04 mmol) was dissolved in N,N-dimethylformamide (27.34 ml) and then nitrophenyl chloroformate (3.03 g, 15.04 mmol) was added thereto at 25-30° C. under nitrogen atmosphere. The reaction mixture was stirred for over 3 hours at same temperature. 7-Bromo-2,2-dimethylchroman-4-amine hydrochloride (4 g, 13.67 mmol) prepared in Step 2 and N,N-diisopropylamine (5.89 ml, 34.18 mmol) were added to the reaction mixture, which was then stirred at the same temperature about for 4 hours. Water (250 ml) was added to the reaction mixture, which was then extracted with ethyl acetate. The extract was washed with brine, dried over anhydrous magnesium sulfate, and then filtered and concentrated under reduced pressure. The resulting residue was purified by column chromatography (ethyl acetate/(methanol/ammonia water=1/1)=9/1, v/v) to give the titled compound as a white solid. (620 mg, Yield: 11%)

$^1$H-NMR (400 MHz, $CDCl_3$) δ 7.14 (t, 1H), 7.00 (t, 1H), 6.95 (s, 1H), 5.11-5.01 (m, 1H), 4.97-4.87 (m, 1H), 4.83-4.74 (m, 1H), 3.32-3.19 (m, 1H), 2.91-2.66 (m, 5H), 2.26-2.16 (m, 1H), 2.13-2.01 (m, 1H), 1.90-1.79 (m, 1H), 1.76-1.66 (m, 2H), 1.64-1.54 (m, 1H), 1.48-1.37 (m, 4H), 1.30 (s, 3H)

Preparation 6. (S)-quinuclidin-3-yl (6-bromo-2,2-dimethylchroman-4-yl)carbamate The titled compound was prepared in accordance with the same procedures as in Step 3 of Preparation 5, using 6-bromo-2,2-dimethylchroman-4-amine as a starting material.

$^1$H-NMR (400 MHz, $CDCl_3$) δ 7.39 (d, 1H), 7.24 (d, 1H), 6.67 (d, 1H), 5.15-5.06 (m, 1H), 5.00-4.91 (m, 1H), 4.85-4.73 (m, 1H), 3.31-3.16 (m, 1H), 3.00-2.65 (m, 5H), 2.27-2.16 (m, 1H), 2.13-2.00 (m, 1H), 1.89-1.77 (m, 1H), 1.74-1.64 (m, 2H), 1.63-1.53 (m, 1H), 1.49-1.37 (m, 4H), 1.30 (s, 3H)

Preparation 7. (S)-quinuclidin-3-yl (7-bromo-4-methylchroman-4-yl)carbamate

Step 1. 7-bromo-4-methylchroman-4-ol

7-Bromochroman-4-one (5.0 g, 22.02 mmol) was dissolved in tetrahydrofuran (88 ml) and then a methylmagnesium bromide solution (3M) in ether (22.02 ml, 66.06 mmol) was slowly added thereto at −50° C. for 15 minutes. The temperature of the reaction mixture was raised to room temperature, followed by stirring for 20 hours. The reaction was quenched by adding a saturated ammonium chloride solution to the reaction mixture, which was then extracted with ethyl acetate. The organic layer was dried over anhydrous magnesium sulfate and then filtered and concentrated under reduced pressure. The resulting residue was purified by column chromatography (n-hexane/ethyl acetate=5/1, v/v) to give the titled compound as pale yellow oil. (4.87 g, Yield: 90%)

Step 2. 4-azido-7-bromo-4-methylchromane

7-Bromo-4-methylchroman-4-ol (2.0 g, 8.23 mmol) prepared in Step 1 was dissolved in dichloromethane (30 ml) and then sodium azide (0.87 ml, 24.68 mmol) was slowly added thereto. After the reaction mixture was cooled to 0° C., a solution obtained by dissolving trifluoroacetic acid (1.89 ml, 24.68 mmol) in dichloromethane (15 ml) was slowly added thereto for 20 minutes. The temperature of the reaction mixture was raised to room temperature, followed by stirring for 3 hours. The reaction was quenched by adding a saturated sodium bicarbonate solution to the reaction mixture, which was then extracted with dichloromethane. The organic layer was dried over anhydrous magnesium sulfate and then filtered and concentrated under reduced pressure to give the titled compound as a white solid. (2.21 g, Yield: 99.9%)

Step 3. 7-bromo-4-methylchroman-4-amine 4-azido-7-bromo-4-methylchromane (2.21 g, 8.23 mmol) prepared in Step 2 was dissolved in tetrahydrofuran (27.43 ml) and then water (0.3 ml, 16.46 mmol) and a solution of trimethylphosphine in tetrahydrofuran (9.05 ml, 9.05 mmol) were slowly added thereto. The reaction mixture was heated to 70° C. and then stirred for 1 hour. Water (1 ml) was additionally added to the reaction mixture, which was then stirred at the same temperature overnight. The reaction mixture was cooled to room temperature and then concentrated under reduced pressure. The resulting residue was purified by column chromatography (ethyl acetate/methanol=10/1, v/v) to give the titled compound as pale yellow oil. (1.71 g, Yield: 85%)

$^1$H-NMR (400 MHz, $CDCl_3$) δ 7.30 (d, 1H), 7.03 (d, 1H), 6.97 (s, 1H), 4.26-4.22 (m, 2H), 2.03-1.90 (m, 2H), 1.48 (s, 3H)

Step 4. (S)-quinuclidin-3-yl (7-bromo-4-methylchroman-4-yl)carbamate

The titled compound was prepared in accordance with the same procedures as in Step 2 of Preparation 1, using 7-bromo-4-methylchroman-4-amine prepared in Step 3.

$^1$H-NMR (400 MHz, $CDCl_3$) δ 7.22 (d, 1H), 7.03 (d, 1H), 6.99 (s, 1H), 5.15-5.01 (m, 1H), 4.68-4.58 (m, 1H), 4.30-4.14 (m, 2H), 3.24-3.09 (m, 1H), 2.89-2.55 (m, 6H), 2.00-1.86 (m, 2H), 1.82-1.61 (m, 5H), 1.56-1.46 (m, 1H), 1.41-1.29 (m, 1H)

Preparation 8. (S)-quinuclidin-3-yl (7-bromoisochroman-4-yl)carbamate

The titled compound was prepared in accordance with the same procedures as in Preparation 1, using 7-bromoisochroman-4-one as a starting material.

$^1$H-NMR (400 MHz, $CDCl_3$) δ 7.37 (t, 1H), 7.30 (t, 1H), 7.16 (s, 1H), 5.45 (t, 1H), 4.81-4.59 (m, 4H), 4.10-4.00 (m, 1H), 3.91-3.78 (m, 1H), 3.31-3.15 (m, 1H), 2.91-2.62 (m, 5H), 2.06-1.97 (m, 1H), 1.84-1.64 (m, 2H), 1.61-1.51 (m, 1H), 1.43-1.32 (m, 1H)

Preparation 9. (S)-quinuclidin-3-yl (7-bromo-1-methyl-1,2,3,4-tetrahydroquinolin-4-yl)carbamate Step 1. ethyl 7-bromo-1-methyl-4-oxo-1,4-dihydroquinolin-3-carboxylate Ethyl 7-bromo-4-oxo-1H-quinolin-3-carboxylate (15.75 g, 53.19 mmol) was dissolved in N,N-dimethylformamide (118.2 ml) and then potassium carbonate (18.36 g, 132.86 mmol) and iodomethane (16.55 ml, 265.87 mmol) were added thereto. The reaction mixture was heated to 90° C. and then stirred for 3 hours. The reaction mixture was concentrated under reduced pressure and then water was added thereto. The resulting residue was filtered under reduced pressure, washed with water, and then dried under reduced pressure to give the titled compound as a pale yellow solid. The product was used in subsequent reaction without further purification.

$^1$H-NMR (400 MHz, $CDCl_3$) δ 8.41 (s, 1H), 8.35 (d, 1H), 7.57 (s, 1H), 7.54 (dd, 1H), 4.38 (q, 2H), 3.85 (s, 3H), 1.40 (t, 3H)

Step 2. 7-bromo-1-methyl-4-oxo-1,4-dihydroquinolin-3-carboxylic acid

Ethyl 7-bromo-1-methyl-4-oxo-1,4-dihydroquinolin-3-carboxylate (17.22 g, 55.52 mmol) prepared in Step 1 was dissolved in methanol (100 ml) and then a solution of sodium hydroxide (11.1 g, 277.62 mmol) in water (200 ml) was slowly added thereto. The reaction was stirred at 90° C. for 3 hours, cooled to room temperature, and then concentrated under reduced pressure. To the resulting residue, were added water and a 10% citric acid solution. The resulting white solid was filtered under reduced pressure and then dried under reduced pressure to give the titled compound as a white solid. (11.73 g, Yield: 74%)

$^1$H-NMR (400 MHz, DMSO-$d_6$) δ 9.02 (s, 1H), 8.25 (d, 1H), 8.19 (s, 1H), 7.82 (d, 1H), 4.08 (s, 3H)

Step 3. 7-bromo-1-methyl-2,3-dihydroquinolin-4(1H)-one

7-Bromo-1-methyl-4-oxo-1,4-dihydroquinolin-3-carboxylic acid (11.73 g, 41.58 mmol) prepared in Step 2 was dissolved in methanol (415.82 ml) and then sodium borohydride (7.32 ml, 182.96 mmol) were slowly added thereto at room temperature. 4-Methylbenzenesulfonic acid hydrate (790.98 mg, 4.16 mmol) was added to the reaction mixture, which was then stirred at 65° C. for 1 hour. The reaction mixture was cooled to room temperature and then concentrated under reduced pressure. Ethyl acetate was added to the resulting residue. The organic layer was washed with a saturated sodium bicarbonate solution and water, dried over anhydrous magnesium sulfate, and then filtered and concentrated under reduced pressure to give the titled compound as a white solid. (5.74 g, Yield: 57%)

$^1$H-NMR (400 MHz, $CDCl_3$) δ 7.74 (d, 1H), 6.87-6.85 (m, 2H), 3.49 (t, 2H), 2.98 (s, 3H), 2.72 (t, 2H)

Step 4. 7-bromo-1-methyl-1,2,3,4-tetrahydroquinolin-4-amine

The titled compound was prepared in accordance with the same procedures as in Step 1 of Preparation 1, using 7-bromo-1-methyl-2,3-dihydroquinolin-4(1H)-one prepared in Step 3.

$^1$H-NMR (400 MHz, $CDCl_3$) δ 7.03 (d, 1H), 6.75 (d, 1H), 6.69 (s, 1H), 3.92 (t, 1H), 3.39-3.32 (m, 1H), 3.24-3.18 (m, 1H), 2.90 (s, 3H), 2.05-1.98 (m, 1H), 1.84-1.79 (m, 1H)

Step 5. (S)-quinuclidin-3-yl (7-bromo-1-methyl-1,2,3,4-tetrahydroquinolin-4-yl)carbamate The titled compound was prepared in accordance with the same procedures as in Step 2 of Preparation 1, using 7-bromo-1-methyl-1,2,3,4-tetrahydroquinolin-4-amine prepared in Step 4.

$^1$H-NMR (400 MHz, $CDCl_3$) δ 7.00 (d, 1H), 6.75 (t, 1H), 6.71 (s, 1H), 4.99-4.97 (m, 1H), 4.80-4.77 (m, 2H), 3.30-3.24 (m, 3H), 2.96-2.72 (m, 8H), 2.10-2.04 (m, 3H), 1.88-1.84 (m, 1H), 1.76-1.73 (m, 1H), 1.67-1.64 (m, 1H), 1.46-1.44 (m, 1H)

Preparation 10. (S)-quinuclidin-3-yl (6-bromothiochroman-4-yl)carbamate

The titled compound was prepared in accordance with the same procedures as in Preparation 2, using 6-bromothiochroman-4-amine as a starting material. The product was used in subsequent reaction without further purification.

Preparation 11. (S)-quinuclidin-3-yl (7-bromothiochroman-4-yl)carbamate

The titled compound was prepared in accordance with the same procedures as in Preparation 2, using 7-bromothiochroman-4-amine as a starting material. The product was used in subsequent reaction without further purification.

Preparation 12. (S)-quinuclidin-3-yl (6-bromo-3,3-dimethylthiochroman-4-yl)carbamate The titled compound was prepared in accordance with the same procedures as in Preparation 3, using 6-bromo-thiochroman-4-one as a starting material. The product was used in subsequent reaction without further purification.

Preparation 13. (S)-quinuclidin-3-yl (7-bromo-6-fluoro-3,3-dimethylchroman-4-yl)carbamate Step 1. 3-bromo-4-fluorophenyl 3-chloropropanoate 3-Bromo-4-fluorophenol (25.0 g, 130.89 mmol) was dissolved in dichloromethane (523.56 ml) and then aluminum (III) chloride (26.18 g, 196.34 mmol) was slowly added thereto at −50° C. 3-Chloropropionyl chloride (18.74 ml, 196.34 mmol) was slowly added to the reaction mixture, which was then stirred at room temperature overnight. The reaction was quenched by adding brine to the reaction mixture, which was then extracted with dichloromethane. The organic layer was dried over anhydrous magnesium sulfate and then concentrated under reduced pressure. The resulting residue was purified by column chromatography (n-hexane/ethyl acetate=1/1, v/v) to give the titled compound as pale yellow oil. (38 g, Yield: 100%)

$^1$H-NMR (400 MHz, $CDCl_3$) δ 7.36 (dd, 1H), 7.14 (t, 1H), 7.08-7.04 (m, 1H), 3.86 (t, 2H), 3.05 (t, 2H)

Step 2. 7-bromo-6-fluorochroman-4-one

To 3-bromo-4-fluorophenyl 3-chloropropanoate (38.0 g, 134.99 mmol) prepared in Step 1, was slowly added trifluoromethanesulfonic acid (75.08 ml, 850.41 mmol). The reaction mixture was stirred at 85° C. for 1 hour and then cooled to 0° C. Water (50 ml) was slowly added to the reaction mixture, which was then extracted with dichloromethane. The organic layer was dried over anhydrous magnesium sulfate and then concentrated under reduced pressure to give the titled compound as a brown solid. (19.31 g, Yield: 58%)

$^1$H-NMR (400 MHz, $CDCl_3$) δ 7.60 (d, 1H), 7.25 (d, 1H), 4.53 (t, 2H), 2.81 (t, 2H)

Step 3. 7-bromo-6-fluoro-3,3-dimethylchroman-4-one

The titled compound was prepared in accordance with the same procedures as in Step 1 of Preparation 3, using 7-bromo-6-fluorochroman-4-one prepared in Step 2.

$^1$H-NMR (400 MHz, $CDCl_3$) δ 7.59 (d, 1H), 7.24 (d, 1H), 4.14 (s, 2H), 1.20 (s, 6H)

Step 4. 7-bromo-6-fluoro-3,3-dimethylchroman-4-amine

The titled compound was prepared in accordance with the same procedures as in Step 1 of Preparation 1, using 7-bromo-6-fluoro-3,3-dimethylchroman-4-one prepared in Step 3.

$^1$H-NMR (400 MHz, $CDCl_3$) δ 7.21 (d, 1H), 6.97 (d, 1H), 3.93 (d, 1H), 3.73 (d, 1H), 3.53 (s, 1H), 1.28 (brs, 2H), 0.95 (d, 6H)

Step 5. (S)-quinuclidin-3-yl (7-bromo-6-fluoro-3,3-dimethylchroman-4-yl)carbamate The titled compound was prepared in accordance with the same procedures as in Step 2 of Preparation 1, using 7-bromo-6-fluoro-3,3-dimethylchroman-4-amine prepared in Step 4.

$^1$H-NMR (400 MHz, $CDCl_3$) δ 7.04-6.91 (m, 2H), 5.01 (t, 1H), 4.82-4.73 (m, 1H), 4.63 (d, 1H), 3.89-3.73 (m, 2H), 3.31-3.17 (m, 1H), 2.94-2.63 (m, 5H), 2.13-2.04 (m, 1H), 1.85-1.76 (m, 1H), 1.72-1.65 (m, 1H), 1.61-1.52 (m, 1H), 1.46-1.36 (m, 1H), 1.02 (d, 3H), 0.97 (d, 3H)

Preparation 14. (S)-quinuclidin-3-yl (7-bromo-6-methoxy-3,3-dimethylchroman-4-yl)carbamate Step 1. 3-(3-bromo-4-methoxyphenoxy)propionitrile 3-Bromo-4-methoxyphenol (25.0 g, 123.13 mmol) was dissolved in acrylonitrile (80.66 ml, 1231.3 mmol) and potassium carbonate (850.92 mg, 6.16 mmol) and tert-butanol (1.17 ml, 12.31 mmol) were slowly added thereto. The reaction mixture was refluxed under stirring for 8 hours. Potassium carbonate (850.92 mg, 6.16 mmol) was additionally added to the reaction mixture, which was then refluxed under stirring for 36 hours. The reaction mixture was cooled to room temperature and then concentrated under reduced pressure. The resulting residue was diluted with ethyl acetate and then washed with a 1N sodium hydroxide solution. The organic layer was extracted and then the aqueous layer was again extracted with water. The combined organic layer was dried over anhydrous magnesium sulfate and then concentrated under reduced pressure. The resulting residue was purified by column chromatography (n-hexane/ethyl acetate=10/1, v/v) to give the titled compound. (25.44 g, Yield: 80%) The product was used in subsequent reaction without further purification.

Step 2. 7-bromo-6-methoxychroman-4-one 3-(3-Bromo-4-methoxyphenoxy)propionitrile (25.44 g, 99.34 mmol) prepared in Step 1 was dissolved in trifluoroacetic acid (38.01 ml, 496.68 mmol) and then trifluoromethanesulfonic acid (13.15 ml, 149 mmol) was slowly added thereto at 0° C. The reaction mixture was stirred at 0° C. for 5 hours, stirred at room temperature for 24 hours, and then cooled to 0° C. Water (3.58 ml, 198.67 mmol) was slowly added at 0° C. to the reaction mixture, which was then stirred at room temperature for 5 hours. The reaction mixture was diluted with ethyl acetate and water and then the organic layer was extracted. The organic layer was washed with water, dried over anhydrous magnesium sulfate, and then concentrated under reduced pressure. The resulting residue was purified by column chromatography (n-hexane/ethyl acetate=1/1, v/v) to give the titled compound. (17.2 g, Yield: 67%)

$^1$H-NMR (400 MHz, $CDCl_3$) δ 7.33 (s, 1H), 7.26 (s, 1H), 4.50 (t, 2H), 3.89 (s, 3H), 2.79 (t, 2H)

Step 3. 7-bromo-6-methoxy-3,3-dimethylchroman-4-one

The titled compound was prepared in accordance with the same procedures as in Step 1 of Preparation 3, using 7-bromo-6-methoxychroman-4-one prepared in Step 2.

$^1$H-NMR (400 MHz, $CDCl_3$) δ 7.31 (s, 1H), 7.23 (s, 1H), 4.10 (s, 2H), 3.87 (s, 3H), 1.18 (s, 6H)

Step 4. 7-bromo-6-methoxy-3,3-dimethylchroman-4-amine

The titled compound was prepared in accordance with the same procedures as in Step 1 of Preparation 1, using 7-bromo-6-methoxy-3,3-dimethylchroman-4-one prepared in Step 3.

$^1$H-NMR (400 MHz, $CDCl_3$) δ 7.01 (s, 1H), 6.98 (s, 1H), 3.92-3.81 (m, 4H), 3.70 (d, 1H), 3.55 (s, 1H), 2.01 (brs, 2H), 0.95 (d, 6H)

Step 5. (S)-quinuclidin-3-yl (7-bromo-6-methoxy-3,3-dimethylchroman-4-yl)carbamate The titled compound was prepared in accordance with the same procedures as in Step 2 of Preparation 1, using 7-bromo-6-methoxy-3,3-dimethylchroman-4-amine prepared in Step 4.

$^1$H-NMR (400 MHz, $CDCl_3$) δ 7.03 (s, 1H), 6.71 (d, 1H), 4.95 (t, 1H), 4.80-4.74 (m, 1H), 4.59 (d, 1H), 3.87-3.70 (m, 5H), 3.30-3.18 (m, 1H), 2.91-2.66 (m, 5H), 2.11-2.04 (m, 1H), 1.85-1.76 (m, 1H), 1.73-1.65 (m, 1H), 1.61-1.51 (m, 1H), 1.45-1.34 (m, 1H), 1.02 (d, 3H), 0.98 (d, 3H)

Example 1. (S)-quinuclidin-3-yl (7-(3-fluorophenyl) chroman-4-yl)carbamate

To a mixture of (S)-quinuclidin-3-yl (7-bromochroman-4-yl)carbamate (50 mg, 0.13 mmol) prepared in Preparation 1, 3-fluorophenylboronic acid (28 mg, 0.2 mmol), potassium phosphate (82.8 mg, 0.39 mmol), and tetrakis(triphenylphosphine)palladium(0) (15 mg, 10 mol %), were slowly added 1,4-dioxane (1 ml) and water (0.5 ml). The reaction mixture was refluxed under stirring at 120° C. overnight and then cooled to room temperature. Water was added to the reaction mixture, which was then extracted with ethyl acetate. The organic layer was dried over anhydrous magnesium sulfate and then filtered and concentrated under reduced pressure. The resulting residue in the yellow liquid form was purified by silica gel column chromatography (ethyl acetate/(methanol/ammonia water=1/1)=9/1, v/v) to give the titled compound as a white solid. (45 mg, Yield: 85%)

$^1$H-NMR (400 MHz, $CDCl_3$) δ 7.39-7.32 (m, 3H), 7.23 (s, 1H), 7.15-7.11 (m, 1H), 7.06-7.02 (m, 2H), 5.08 (m, 1H), 4.94-4.92 (m, 1H), 4.79 (m, 1H), 4.31-4.30 (m, 1H), 4.24-4.22 (m, 1H), 3.28-3.24 (m, 1H), 2.88-2.69 (m, 5H), 2.25-2.23 (m, 1H), 2.13-2.03 (m, 2H), 1.81 (m, 1H), 1.71-1.68 (m, 1H), 1.59-1.57 (m, 1H), 1.40 (m, 1H)

Examples 2 to 84

The titled compounds of Examples 2 to 84 were prepared in accordance with the same procedures as in Example 1, using (S)-quinuclidin-3-yl (7-bromochroman-4-yl)carbamate prepared in Preparation 1; and the corresponding substituted-boronic acids, respectively.

Example 2. (S)-quinuclidin-3-yl (7-(3-chlorophenyl) chroman-4-yl)carbamate $^1$H-NMR (400 MHz, $CDCl_3$) δ 7.54 (s, 1H), 7.44-7.42 (d, 1H), 7.37-7.31 (m, 3H), 7.14-7.11 (m, 1H), 7.03 (d, 1H), 5.05 (m, 1H), 4.94-4.92 (m, 1H), 4.79 (m, 1H), 4.31-4.30 (m, 1H), 4.24-4.22 (m, 1H), 3.29-3.25 (m, 1H), 2.87-2.73 (m, 5H), 2.26-2.23 (m, 1H), 2.13-2.08 (m, 2H), 1.82-1.79 (m, 1H), 1.74-1.72 (m, 1H), 1.70-1.68 (m, 1H), 1.59-1.57 (m, 1H)

Example 3. (S)-quinuclidin-3-yl (7-(3-(trifluoromethyl)phenyl)chroman-4-yl)carbamate $^1$H-NMR (400 MHz, $CDCl_3$) δ 7.80 (s, 1H), 7.74-7.25 (d, 1H), 7.62-7.60 (d, 1H), 7.57-7.53 (t, 1H), 7.40-7.36 (t, 1H), 7.17-7.14 (t, 1H), 7.07 (s, 1H), 5.02-5.00 (m, 1H), 4.96-4.94 (m, 1H), 4.80 (m, 1H), 4.33-4.31 (m, 1H), 4.26-4.22 (m, 1H), 3.30-3.26 (m, 1H), 2.89-2.71 (m, 5H), 2.27-2.23 (m, 1H), 2.14-2.04 (m, 2H), 1.82-1.81 (m, 1H), 1.71-1.63 (m, 2H), 1.40 (m, 1H)

Example 4. (S)-quinuclidin-3-yl (7-(3-(trifluoromethoxy)phenyl)chroman-4-yl)carbamate $^1$H-NMR (400 MHz, $CDCl_3$) δ 7.49-7.42 (m, 2H), 7.39-7.34 (m, 2H), 7.21-7.19 (d, 1H), 7.15-7.11 (t, 1H), 7.04 (s, 1H), 5.09-5.07 (m, 1H), 4.94-4.93 (m, 1H), 4.79 (m, 1H), 4.32-4.30 (m, 1H), 4.25-4.22 (m, 1H), 3.28-3.24 (m, 1H), 2.88-2.69 (m, 5H), 2.26-2.24 (m, 1H), 2.13-2.08 (m, 2H), 1.83-1.71 (m, 1H), 1.71-1.68 (m, 1H), 1.60-1.57 (m, 1H), 1.40 (m, 1H)

Example 5. (S)-quinuclidin-3-yl (7-(2-(methoxymethoxy)phenyl)chroman-4-yl)carbamate $^1$H-NMR (400 MHz, $CDCl_3$) δ 7.31-7.27 (m, 2H), 7.22-7.20 (m, 2H), 7.18-7.05 (m, 2H), 7.00 (s, 1H), 5.23 (m, 1H), 5.13 (s, 2H), 4.92-4.91 (m, 1H), 4.77 (m, 1H), 4.28-4.19 (m, 2H), 3.43 (s, 3H), 3.25-3.22 (m, 1H), 2.83-2.71 (m, 5H), 2.25-2.21 (m, 1H), 2.12-2.04 (m, 2H), 1.81-1.80 (m, 1H), 1.70-1.69 (m, 1H), 1.59-1.57 (m, 1H), 1.39 (m, 1H)

Example 6. (S)-quinuclidin-3-yl (7-(3-(methoxymethoxy)phenyl)chroman-4-yl)carbamate $^1$H-NMR (400 MHz, $CDCl_3$) δ 7.35-7.29 (m, 2H), 7.27-7.14 (m, 3H), 7.05-7.01 (m, 2H), 5.31-5.22 (m, 1H), 5.21 (s, 2H), 4.90 (m, 1H), 4.76 (m, 1H), 4.28-4.19 (m, 2H), 3.49 (s, 3H), 3.24-3.21 (m, 1H), 2.83-2.70 (m, 5H), 2.24-2.22 (m, 1H), 2.21-2.07 (m, 2H), 1.79-1.78 (m, 1H), 1.69-1.68 (m, 1H), 1.58-1.56 (m, 1H), 1.39 (m, 1H)

Example 7. (S)-quinuclidin-3-yl (7-(2-(2-methoxyethoxy)phenyl)chroman-4-yl)carbamate $^1$H-NMR (400 MHz, $CDCl_3$) δ 7.32-7.27 (m, 3H), 7.18-7.16 (m, 1H), 7.06 (s, 1H), 7.05-6.99 (m, 2H), 5.11-5.09 (m, 1H), 4.92-4.91 (m, 1H), 4.78 (m, 1H), 4.29-4.27 (m, 1H), 4.22-4.18 (m, 1H), 4.13 (t, 2H), 3.70 (t, 2H), 3.39 (s, 3H), 3.28-3.25 (m, 1H), 2.87-2.73 (m, 5H), 2.25-2.22 (m, 1H), 2.12-2.04 (m, 2H), 1.81 (m, 1H), 1.70-1.69 (m, 1H), 1.61-1.59 (m, 1H), 1.45-1.36 (m, 1H)

Example 8. (S)-quinuclidin-3-yl (7-(3-(2-methoxyethoxy)phenyl)chroman-4-yl)carbamate $^1$H-NMR (400 MHz, $CDCl_3$) δ 7.33-7.27 (m, 2H), 7.15-7.13 (m, 3H), 7.04 (s, 1H), 6.92-6.89 (m, 1H), 5.30-5.29 (m, 1H), 4.91-4.89 (m, 1H), 4.77 (m, 1H), 4.29-4.28 (m, 1H), 4.22-4.19 (m, 1H), 4.16 (t, 2H), 3.77 (t, 2H), 3.46 (s, 3H), 3.24-3.21 (m, 1H), 2.83-2.70 (m, 5H), 2.28-2.21 (m, 1H), 2.10-2.02 (m, 2H), 1.80-1.79 (m, 1H), 1.68-1.67 (m, 1H), 1.58-1.56 (m, 1H), 1.49-1.31 (m, 1H)

Example 9. (S)-quinuclidin-3-yl (7-(2-fluorophenyl) chroman-4-yl)carbamate $^1$H-NMR (400 MHz, $CDCl_3$) δ 7.40 (m, 1H), 7.34-7.27 (m, 2H), 7.21-7.11 (m, 3H), 7.03 (s, 1H), 5.18-5.04 (m, 1H), 4.89-4.87 (m, 1H), 4.77 (m, 1H), 4.30-4.17 (m, 2H), 3.26-3.23 (m, 1H), 2.85-2.71 (m, 5H), 2.22-2.21 (m, 1H), 2.12-2.02 (m, 2H), 1.84-1.78 (m, 1H), 1.69-1.67 (m, 1H), 1.58-1.57 (m, 1H), 1.39 (m, 1H)

Example 10. (S)-quinuclidin-3-yl (7-(2-chlorophenyl)chroman-4-yl)carbamate $^1$H-NMR (400 MHz, $CDCl_3$) δ 7.46-7.44 (m, 1H), 7.32-7.24 (m, 3H), 7.18-7.16 (m, 1H), 7.00 (m, 1H), 6.91 (s, 1H), 5.41-5.16 (m, 1H), 4.88-4.86 (m, 1H), 4.77 (m, 1H), 4.29-4.16 (m, 2H), 3.24-3.21 (m, 1H), 2.83-2.69 (m, 5H), 2.22-2.01 (m, 3H), 1.80-1.77 (m, 1H), 1.68-1.66 (m, 1H), 1.57-1.56 (m, 1H), 1.38 (m, 1H)

Example 11. (S)-quinuclidin-3-yl (7-(2-(trifluoromethyl)phenyl)chroman-4-yl)carbamate $^1$H-NMR (400 MHz, $CDCl_3$) δ 7.74-7.22 (d, 1H), 7.56-7.52 (t, 1H), 7.47-7.44 (t, 1H), 7.30-7.26 (m, 2H), 6.89-6.83 (m, 1H), 6.80 (s, 1H), 5.45-5.18 (m, 1H), 4.93-4.76 (m, 2H), 4.29-4.20 (m, 2H), 3.24-3.21 (m, 1H), 2.82-2.68 (m, 5H), 2.25-2.24 (m, 1H), 2.23-2.03 (m, 2H), 1.81-1.79 (m, 1H), 1.68-1.67 (m, 1H), 1.58-1.55 (m, 1H), 1.38 (m, 1H)

Example 12. (S)-quinuclidin-3-yl (7-(2-(trifluoromethoxy)phenyl)chroman-4-yl)carbamate $^1$H-NMR (400 MHz, $CDCl_3$) δ 7.39-7.27 (m, 5H), 7.03-7.00 (m, 1H), 6.93 (s, 1H), 5.47-5.45 (d, 1H), 4.93-4.91 (m, 1H), 4.78-4.76 (m, 1H), 4.29-4.27 (m, 1H), 4.22-4.20 (m, 1H), 3.24-3.20 (m, 1H), 2.85-2.68 (m, 5H), 2.23 (m, 1H), 2.12-2.03 (m, 2H), 1.80-1.79 (m, 1H), 1.69-1.65 (m, 1H), 1.57-1.56 (m, 1H), 1.38 (m, 1H)

Example 13. (S)-quinuclidin-3-yl (7-(4-fluorophenyl)chroman-4-yl)carbamate $^1$H-NMR (400 MHz, $CDCl_3$) δ 7.51-7.48 (m, 2H), 7.31-7.25 (m, 2H), 7.12-7.08 (m, 2H), 7.00 (s, 1H), 5.30 (m, 1H), 4.95-4.80 (m, 1H), 4.76 (m, 1H), 4.29-4.18 (m, 2H), 3.22-3.20 (m, 1H), 2.82-2.69 (m, 5H), 2.27-2.20 (m, 1H), 2.10-2.02 (m, 2H), 1.80-1.77 (m, 1H), 1.68-1.66 (m, 1H), 1.57-1.55 (m, 1H), 1.38 (m, 1H)

Example 14. (S)-quinuclidin-3-yl (7-(4-chlorophenyl)chroman-4-yl)carbamate $^1$H-NMR (400 MHz, $CDCl_3$) δ 7.48-7.46 (m, 2H), 7.39-7.37 (m, 2H), 7.34-7.30 (m, 1H), 7.12-7.10 (m, 1H), 7.01 (s, 1H), 5.25-5.23 (m, 1H), 4.92-4.90 (m, 1H), 4.77 (m, 1H), 4.30-4.20 (m, 2H), 3.25-3.21 (m, 1H), 2.84-2.68 (m, 5H), 2.24-2.02 (m, 3H), 1.80-1.78 (m, 1H), 1.68-1.67 (m, 1H), 1.58-1.56 (m, 1H), 1.48-1.25 (m, 1H)

Example 15. (S)-quinuclidin-3-yl (7-(4-(trifluoromethyl)phenyl)chroman-4-yl)carbamate $^1$H-NMR (400 MHz, $CDCl_3$) δ 7.69-7.64 (m, 4H), 7.39-7.35 (t, 1H), 7.17-7.07 (m, 1H), 7.07 (s, 1H), 5.12-5.10 (m, 1H), 4.95-4.93 (m, 1H), 4.79 (m, 1H), 4.32-4.23 (m, 2H), 3.28-3.24 (m, 1H), 2.88-2.72 (m, 5H), 2.26-2.24 (m, 1H), 2.14-2.08 (m, 2H), 1.87-1.79 (m, 1H), 1.70-1.69 (m, 1H), 1.59-1.58 (m, 1H), 1.49-1.32 (m, 1H)

Example 16. (S)-quinuclidin-3-yl (7-(4-(trifluoromethoxy)phenyl)chroman-4-yl)carbamate $^1$H-NMR (400 MHz, $CDCl_3$) δ 7.56-7.54 (d, 2H), 7.33-7.31 (m, 1H), 7.27-7.25 (m, 2H), 7.17-7.10 (m, 1H), 7.02 (s, 1H), 5.29-5.27 (m, 1H), 4.96-4.81 (m, 1H), 4.76 (m, 1H), 4.30-4.19 (m, 2H), 3.23-3.21 (m, 1H), 2.83-2.69 (m, 5H), 2.21 (m, 1H), 2.11-2.02 (m, 2H), 1.79-1.77 (m, 1H), 1.70-1.66 (m, 1H), 1.59-1.55 (m, 1H), 1.38 (m, 1H)

Example 17. (S)-quinuclidin-3-yl (7-(2-methoxyphenyl)chroman-4-yl)carbamate $^1$H-NMR (400 MHz, $CDCl_3$) δ 7.34-7.27 (m, 3H), 7.11-7.08 (m, 1H), 7.04-6.84 (m, 3H), 5.12 (m, 1H), 4.92-4.89 (m, 1H), 4.78-4.77 (m, 1H), 4.30-4.18 (m, 2H), 3.82 (s, 3H), 3.27-3.24 (m, 1H), 2.86-2.69 (m, 5H), 2.25-2.22 (m, 1H), 2.12-2.02 (m, 2H), 1.86-1.79 (m, 1H), 1.69-1.68 (m, 1H), 1.59-1.57 (m, 1H), 1.39 (m, 1H)

Example 18. (S)-quinuclidin-3-yl (7-(3-methoxyphenyl)chroman-4-yl)carbamate $^1$H-NMR (400 MHz, $CDCl_3$) δ 7.36-7.32 (m, 2H), 7.31-7.27 (m, 1H), 7.19-7.14 (m, 2H), 7.09-7.06 (m, 2H), 5.06 (m, 1H), 4.95-4.82 (m, 1H), 4.78 (m, 1H), 4.30-4.20 (m, 2H), 3.86 (s, 3H), 3.27-3.26 (m, 1H), 2.86-2.72 (m, 5H), 2.23-2.22 (m, 1H), 2.12-2.02 (m, 2H), 1.80-1.69 (m, 2H), 1.59-1.57 (m, 1H), 1.39 (m, 1H)

Example 19. (S)-quinuclidin-3-yl (7-(4-methoxyphenyl)chroman-4-yl)carbamate $^1$H-NMR (400 MHz, $CDCl_3$) δ 7.51-7.49 (m, 2H), 7.33-7.29 (m, 1H), 7.13-7.10 (t, 1H), 7.02 (s, 1H), 6.98-6.95 (d, 2H), 5.08-5.06 (m, 1H), 4.92-4.91 (m, 1H), 4.79-4.78 (m, 1H), 4.30-4.29 (m, 1H), 4.23-4.21 (m, 1H), 3.85 (s, 3H), 3.28-3.24 (m, 1H), 2.86-2.69 (m, 5H), 2.25-2.22 (m, 1H), 2.12-2.05 (m, 2H), 1.82-1.77 (m, 1H), 1.71-1.67 (m, 1H), 1.60-1.57 (m, 1H), 1.39 (m, 1H)

Example 20. (S)-quinuclidin-3-yl (7-(2-ethoxyphenyl)chroman-4-yl)carbamate $^1$H-NMR (400 MHz, $CDCl_3$) δ 7.31-7.27 (m, 4H), 7.16-7.12 (m, 1H), 7.05 (s, 1H), 7.02-6.96 (m, 2H), 5.12-5.10 (m, 1H), 4.93-4.91 (m, 1H), 4.79-4.77 (m, 1H), 4.31-4.28 (m, 1H), 4.22-4.20 (m, 1H), 4.09-4.04 (m, 2H), 3.28-3.24 (m, 1H), 2.86-2.73 (m, 5H), 2.25-2.23 (m, 1H), 2.13-2.03 (m, 2H), 1.82-1.77 (m, 1H), 1.70-1.68 (m, 1H), 1.59-1.58 (m, 1H), 1.39-1.36 (m, 4H)

Example 21. (S)-quinuclidin-3-yl (7-(3-ethoxyphenyl)chroman-4-yl)carbamate $^1$H-NMR (400 MHz, $CDCl_3$) δ 7.35-7.31 (m, 2H), 7.17-7.12 (m, 2H), 7.08-7.06 (m, 2H), 6.90-6.87 (m, 1H), 5.06-5.02 (m, 1H), 4.93-4.92 (m, 1H), 4.78-4.77 (m, 1H), 4.31-4.20 (m, 2H), 4.10 (q, 2H), 3.27-3.24 (m, 1H), 2.86-2.72 (m, 5H), 2.25-2.22 (m, 1H), 2.13-2.02 (m, 2H), 1.80-1.69 (m, 2H), 1.59-1.57 (m, 1H), 1.46-1.42 (t, 3H), 1.40-1.36 (m, 1H)

Example 22. (S)-quinuclidin-3-yl (7-(4-ethoxyphenyl)chroman-4-yl)carbamate $^1$H-NMR (400 MHz, $CDCl_3$) δ 7.49-7.47 (d, 2H), 7.30-7.25 (m, 1H), 7.19-7.17 (m, 1H), 7.02 (s, 1H), 6.96-6.94 (m, 2H), 5.06-5.04 (m, 1H), 4.89-4.87 (m, 1H), 4.78-4.77 (m, 1H), 4.30-4.26 (m, 1H), 4.21-4.18 (m, 1H), 4.10-4.05 (m, 2H), 3.27-3.23 (m, 1H), 2.86-2.69 (m, 5H), 2.23-2.21 (m, 1H), 2.11-2.02 (m, 2H), 1.80-1.77 (m, 1H), 1.69-1.67 (m, 1H), 1.58-1.57 (m, 1H), 1.46-1.39 (m, 4H)

Example 23. (S)-quinuclidin-3-yl (7-(3-isopropylphenyl)chroman-4-yl)carbamate $^1$H-NMR (400 MHz, $CDCl_3$) δ 7.41 (s, 1H), 7.37-7.31 (m, 3H), 7.24-7.22 (m, 1H), 7.18-7.16 (m, 1H), 7.07 (s, 1H), 5.09-5.07 (m, 1H), 4.94-4.92 (m, 1H), 4.79-4.78 (m, 1H), 4.32-4.30 (m, 1H), 4.24-4.21 (m, 1H), 3.28-3.25 (m, 1H), 2.99-2.95 (m, 1H), 2.87-2.70 (m, 5H), 2.26-2.24 (m, 1H), 2.22-2.03 (m, 2H), 1.80-1.77 (m, 1H), 1.71-1.68 (m, 1H), 1.60-1.57 (m, 1H), 1.43-1.41 (m, 1H), 1.30 (d, 6H)

Example 24. (S)-quinuclidin-3-yl (7-(4-isopropylphenyl)chroman-4-yl)carbamate $^1$H-NMR (400 MHz, $CDCl_3$) δ 7.50-7.48 (d, 2H), 7.34-7.27 (m, 3H), 7.15 (t, 1H), 7.06 (s, 1H), 5.15-5.12 (m, 1H), 4.92-4.91 (m, 1H), 4.79-4.78 (m, 1H), 4.30-4.29 (m, 1H), 4.23-4.20 (m, 1H), 3.27-3.24 (m, 1H), 2.97-2.92 (m, 1H), 2.87-2.69 (m, 5H), 2.25-2.22 (m, 1H), 2.12-2.07 (m, 2H), 1.88-1.85 (m, 1H), 1.81-1.79 (m, 1H), 1.70-1.68 (m, 1H), 1.61-1.56 (m, 1H), 1.29 (d, 6H)

Example 25. (S)-quinuclidin-3-yl (7-(3-(tert-butyl)phenyl)chroman-4-yl)carbamate $^1$H-NMR (400 MHz, $CDCl_3$) δ 7.57 (s, 1H), 7.40-7.32 (m, 4H), 7.18-7.15 (m, 1H), 7.07 (s, 1H), 5.12-5.10 (m, 1H), 4.94-4.92 (m, 1H), 4.79-4.78 (m, 1H), 4.34-4.30 (m, 1H), 4.25-4.22 (m, 1H), 3.28-3.24 (m, 1H), 2.86-2.69 (m, 5H), 2.26-2.23 (m, 1H), 2.14-2.03 (m, 2H), 1.84-1.80 (m, 1H), 1.71-1.68 (m, 1H), 1.60-1.57 (m, 1H), 1.37-1.35 (m, 10H)

Example 26. (S)-quinuclidin-3-yl (7-(4-(tert-butyl)phenyl)chroman-4-yl)carbamate $^1$H-NMR (400 MHz, $CDCl_3$) δ 7.52-7.50 (d, 2H), 7.47-7.45 (d, 2H), 7.32 (t, 1H), 7.16 (t, 1H), 7.07 (s, 1H), 5.12-5.10 (m, 1H), 4.93-4.91 (m, 1H), 4.79-4.78 (m, 1H), 4.31-4.29 (m, 1H), 4.24-4.21 (m, 1H), 3.28-3.24 (m, 1H), 2.88-2.69 (m, 5H), 2.25-2.22 (m, 1H), 2.13-2.03 (m, 2H), 1.83-1.79 (m, 1H), 1.71-1.67 (m, 1H), 1.60-1.57 (m, 1H), 1.36-1.34 (m, 10H)

Example 27. (S)-quinuclidin-3-yl (7-(2,5-dichlorophenyl)chroman-4-yl)carbamate $^1$H-NMR (400 MHz, $CDCl_3$) δ 7.39-7.24 (m, 4H), 6.98-6.95 (m, 1H), 6.89 (s, 1H), 5.23-5.21 (m, 1H), 4.94-4.93 (m, 1H), 4.78-4.76 (m, 1H), 4.33-4.29 (m, 1H), 4.24-4.22 (m, 1H), 3.27-3.23 (m, 1H), 2.85-2.69 (m, 5H), 2.26-2.22 (m, 1H), 2.13-2.03 (m, 2H), 1.80-1.79 (m, 1H), 1.69-1.67 (m, 1H), 1.59-1.56 (m, 1H), 1.39-1.37 (m, 1H)

Example 28. (S)-quinuclidin-3-yl (7-(3,4-dichlorophenyl)chroman-4-yl)carbamate $^1$H-NMR (400 MHz, $CDCl_3$) δ 7.63 (s, 1H), 7.57-7.48 (m, 1H), 7.38-7.33 (m, 2H), 7.11-7.01 (m, 1H), 7.00 (s, 1H), 5.06-5.04 (m, 1H), 4.94-4.93 (m, 1H), 4.79-4.76 (m, 1H), 4.33-4.30 (m, 1H), 4.24-4.22 (m, 1H), 3.28-3.25 (m, 1H), 2.87-2.73 (m, 5H), 2.25-2.23 (m, 1H), 2.13-2.03 (m, 2H), 1.81-1.80 (m, 1H), 1.79-1.68 (m, 1H), 1.59-1.58 (m, 1H), 1.40-1.37 (m, 1H)

Example 29. (S)-quinuclidin-3-yl (7-(3,5-dichlorophenyl)chroman-4-yl)carbamate $^1$H-NMR (400 MHz, $CDCl_3$) δ 7.55 (s, 1H), 7.41-7.33 (m, 3H), 7.09-7.06 (m, 1H), 6.99 (s, 1H), 5.17-5.15 (m, 1H), 4.93-4.91 (m, 1H), 4.79-4.76 (m, 1H), 4.32-4.29 (m, 1H), 4.24-4.21 (m, 1H), 3.27-3.23 (m, 1H), 2.86-2.72 (m, 5H), 2.24-2.22 (m, 1H), 2.13-2.03 (m, 2H), 1.80-1.79 (m, 1H), 1.70-1.69 (m, 1H), 1.59-1.57 (m, 1H), 1.48-1.35 (m, 1H)

Example 30. (S)-quinuclidin-3-yl (7-(2,3,4-trifluorophenyl)chroman-4-yl)carbamate $^1$H-NMR (400 MHz, $CDCl_3$) δ 7.36 (t, 1H), 7.12-7.06 (m, 1H), 7.05-7.01 (m, 2H), 6.96 (s, 1H), 5.14-5.06 (m, 1H), 4.99-4.89 (m, 1H), 4.83-4.73 (m, 1H), 4.37-4.28 (m, 1H), 4.27-4.16 (m, 1H), 3.33-3.19 (m, 1H), 2.94-2.66 (m, 5H), 2.30-2.21 (m, 1H), 2.16-2.01 (m, 2H), 1.85-1.75 (m, 1H), 1.73-1.65 (m, 1H), 1.62-1.52 (m, 1H), 1.45-1.34 (m, 1H)

Example 31. (S)-quinuclidin-3-yl (7-(2,4,5-trifluorophenyl)chroman-4-yl)carbamate $^1$H-NMR (400 MHz, $CDCl_3$) δ 7.34 (t, 1H), 7.25-7.18 (m, 1H), 7.07-6.99 (m, 1H), 6.95 (s, 1H), 5.20-5.11 (m, 1H), 4.98-4.89 (m, 1H), 4.82-4.73 (m, 1H), 4.36-4.27 (m, 1H), 4.25-4.15 (m, 1H), 3.31-3.18 (m, 1H), 2.92-2.65 (m, 5H), 2.31-2.19 (m, 1H), 2.16-2.00 (m, 2H), 1.85-1.75 (m, 1H), 1.74-1.64 (m, 1H), 1.62-1.50 (m, 1H), 1.46-1.32 (m, 1H)

Example 32. (S)-quinuclidin-3-yl (7-(4-(difluoromethoxy)phenyl)chroman-4-yl)carbamate $^1$H-NMR (400 MHz, $CDCl_3$) δ 7.54 (d, 2H), 7.33 (t, 1H), 7.18 (d, 2H), 7.11 (t, 1H), 7.02 (s, 1H), 6.54 (t, 1H), 5.18-5.09 (m, 1H), 4.96-4.88 (m, 1H), 4.82-4.74 (m, 1H), 4.36-4.27 (m, 1H), 4.26-4.17 (m, 1H), 3.31-3.19 (m, 1H), 2.93-2.67 (m, 5H), 2.30-2.19 (m, 1H), 2.16-2.00 (m, 2H), 1.86-1.76 (m, 1H), 1.75-1.64 (m, 1H), 1.61-1.52 (m, 1H), 1.44-1.34 (m, 1H)

Example 33. (S)-quinuclidin-3-yl (7-(4-fluoro-3-(trifluoromethyl)phenyl)chroman-4-yl)carbamate $^1$H-NMR (400 MHz, $CDCl_3$) δ 7.75 (d, 1H), 7.73-7.67 (m, 1H), 7.36 (t, 1H), 7.28-7.23 (m, 1H), 7.09 (t, 1H), 7.00 (s, 1H), 5.16-5.06 (m, 1H), 5.00-4.89 (m, 1H), 4.83-4.73 (m, 1H), 4.37-4.29 (m, 1H), 4.26-4.17 (m, 1H), 3.32-3.20 (m, 1H), 2.94-2.65 (m, 5H), 2.32-2.20 (m, 1H), 2.16-2.00 (m, 2H), 1.85-1.77 (m, 1H), 1.76-1.65 (m, 1H), 1.63-1.53 (m, 1H), 1.48-1.34 (m, 1H)

Example 34. (S)-quinuclidin-3-yl (7-(3-chloro-5-(trifluoromethyl)phenyl)chroman-4-yl)carbamate $^1$H-NMR (400 MHz, $CDCl_3$) δ 7.69 (d, 2H), 7.58 (s, 1H), 7.44-7.35 (m, 1H), 7.15-7.09 (m, 1H), 7.03 (s, 1H), 5.15-5.06 (m, 1H), 4.99-4.89 (m, 1H), 4.84-4.75 (m, 1H), 4.38-4.28 (m, 1H), 4.26-4.17 (m, 1H), 3.33-3.21 (m, 1H), 2.95-2.67 (m, 5H), 2.33-2.21 (m, 1H), 2.18-2.00 (m, 2H), 1.86-1.76 (m, 1H), 1.73-1.65 (m, 1H), 1.62-1.53 (m, 1H), 1.47-1.35 (m, 1H)

Example 35. (S)-quinuclidin-3-yl (7-(4-cyclopropylphenyl)chroman-4-yl)carbamate $^1$H-NMR (400 MHz, $CDCl_3$) δ 7.45 (d, 2H), 7.34-7.29 (m, 1H), 7.14-7.12 (m, 3H), 7.04 (s, 1H), 5.09-5.02 (m, 1H), 4.96-4.89 (m, 1H), 4.83-4.74 (m, 1H), 4.35-4.27 (m, 1H), 4.25-4.14 (m, 1H), 3.31-3.21 (m, 1H), 2.93-2.67 (m, 5H), 2.31-2.20 (m, 1H), 2.17-2.00 (m, 2H), 1.97-1.89 (m, 1H), 1.86-1.76 (m, 1H), 1.74-1.64 (m, 1H), 1.63-1.52 (m, 1H), 1.45-1.34 (m, 1H), 1.04-0.95 (m, 2H), 0.77-0.70 (m, 2H)

Example 36. (S)-quinuclidin-3-yl (7-(2,2-difluorobenzo[d][1,3]dioxol-5-yl)chroman-4-yl)carbamate $^1$H-NMR (400 MHz, $CDCl_3$) δ 7.34 (t, 1H), 7.28-7.21 (m, 2H), 7.12-7.03 (m, 2H), 6.98 (s, 1H), 5.12-5.03 (m, 1H), 4.97-4.89 (m, 1H), 4.82-4.74 (m, 1H), 4.36-4.28 (m, 1H), 4.25-4.17 (m, 1H), 3.31-3.20 (m, 1H), 2.93-2.67 (m, 5H), 2.30-2.20 (m, 1H), 2.17-2.01 (m, 2H), 1.87-1.76 (m, 1H), 1.73-1.64 (m, 1H), 1.63-1.51 (m, 1H), 1.46-1.33 (m, 1H)

Example 37. (S)-quinuclidin-3-yl (7-(2,3-dihydrobenzo[b][1,4]dioxin-6-yl)chroman-4-yl)carbamate $^1$H-NMR (400 MHz, $CDCl_3$) δ 7.33-7.26 (m, 1H), 7.12-7.02 (m, 3H), 7.00 (s, 1H), 6.91 (d, 1H), 5.12-5.04 (m, 1H), 4.95-4.87 (m, 1H), 4.82-4.74 (m, 1H), 4.34-4.26 (m, 5H), 4.24-4.14 (m, 1H), 3.31-3.20 (m, 1H), 2.92-2.66 (m, 5H), 2.29-2.19 (m, 1H), 2.16-1.99 (m, 2H), 1.85-1.75 (m, 1H), 1.73-1.64 (m, 1H), 1.62-1.52 (m, 1H), 1.44-1.31 (m, 1H)

Example 38. (S)-quinuclidin-3-yl (7-(2,3-dihydrofuran-5-yl)chroman-4-yl)carbamate $^1$H-NMR (400 MHz, $CDCl_3$) δ 7.39 (s, 1H), 7.35-7.25 (m, 2H), 7.13-7.06 (m, 1H), 7.00 (s, 1H), 6.83 (d, 1H), 5.18-5.08 (m, 1H), 4.96-4.86 (m, 1H), 4.82-4.74 (m, 1H), 4.61 (t, 2H), 4.35-4.26 (m, 1H), 4.24-4.14 (m, 1H), 3.32-3.20 (m, 3H), 2.94-2.66 (m, 5H), 2.30-2.19 (m, 1H), 2.16-2.01 (m, 2H), 1.86-1.76 (m, 1H), 1.75-1.64 (m, 1H), 1.62-1.51 (m, 1H), 1.45-1.32 (m, 1H)

Example 39. (S)-quinuclidin-3-yl (7-(3-cyanophenyl)chroman-4-yl)carbamate $^1$H-NMR (400 MHz, $CDCl_3$) δ 7.81 (s, 1H), 7.76 (d, 1H), 7.62 (d, 1H), 7.52 (t, 1H), 7.37 (t, 1H), 7.13-7.07 (m, 1H), 7.01 (s, 1H), 5.26-5.18 (m, 1H), 4.96-4.89 (m, 1H), 4.82-4.74 (m, 1H), 4.36-4.28 (m, 1H), 4.26-4.18 (m, 1H), 3.30-3.18 (m, 1H), 2.91-2.65 (m, 5H), 2.31-2.20 (m, 1H), 2.18-2.05 (m, 2H), 1.86-1.75 (m, 1H), 1.72-1.65 (m, 1H), 1.62-1.51 (m, 1H), 1.46-1.34 (m, 1H)

Example 40. (S)-quinuclidin-3-yl (7-(2-cyanophenyl)chroman-4-yl)carbamate $^1$H-NMR (400 MHz, $CDCl_3$) δ 7.75 (d, 1H), 7.63 (t, 1H), 7.47 (t, 2H), 7.39 (t, 1H), 7.12 (d, 1H), 6.99 (s, 1H), 5.24-5.18 (m, 1H), 4.98-4.91 (m, 1H), 4.82-4.75 (m, 1H), 4.36-4.28 (m, 1H), 4.27-4.18 (m, 1H), 3.31-3.20 (m, 1H), 2.94-2.67 (m, 5H), 2.32-2.20 (m, 1H), 2.17-2.06 (m, 2H), 1.87-1.76 (m, 1H), 1.74-1.65 (m, 1H), 1.63-1.52 (m, 1H), 1.45-1.34 (m, 1H)

Example 41. (S)-quinuclidin-3-yl (7-(3-(dimethylamino)phenyl)chroman-4-yl)carbamate $^1$H-NMR (400 MHz, $CDCl_3$) δ 7.36-7.28 (m, 2H), 7.17 (t, 1H), 7.08 (s, 1H), 6.93-6.87 (m, 2H), 6.75 (d, 1H), 5.08-5.01 (m, 1H), 4.96-4.89 (m, 1H), 4.83-4.75 (m, 1H), 4.35-4.28 (m, 1H), 4.26-4.17 (m, 1H), 3.30-3.20 (m, 1H), 3.00 (s, 6H), 2.91-2.68 (m, 5H), 2.30-2.20 (m, 1H), 2.16-1.99 (m, 2H), 1.87-1.76 (m, 1H), 1.74-1.65 (m, 1H), 1.63-1.53 (m, 1H), 1.44-1.34 (m, 1H)

Example 42. (S)-quinuclidin-3-yl (7-(benzo[b]thiophen-2-yl)chroman-4-yl)carbamate $^1$H-NMR (400 MHz, $CDCl_3$) δ 7.82 (d, 1H), 7.77 (d, 1H), 7.52 (s, 1H), 7.38-7.25 (m, 4H), 7.19 (s, 1H), 5.15-5.08 (m, 1H), 4.95-4.87 (m, 1H), 4.82-4.73 (m, 1H), 4.36-4.28 (m, 1H), 4.25-4.17 (m, 1H), 3.32-3.20 (m, 1H), 2.94-2.66 (m, 5H), 2.31-2.20 (m, 1H), 2.15-2.00 (m, 2H), 1.89-1.77 (m, 1H), 1.75-1.65 (m, 1H), 1.63-1.53 (m, 1H), 1.46-1.34 (m, 1H)

Example 43. (S)-quinuclidin-3-yl (7-(benzofuran-3-yl)chroman-4-yl)carbamate $^1$H-NMR (400 MHz, $CDCl_3$) δ 7.83 (d, 1H), 7.78 (s, 1H), 7.55 (d, 1H), 7.40-7.29 (m, 3H), 7.21 (t, 1H), 7.14 (s, 1H), 5.12-5.09 (m, 1H), 4.98-4.91 (m, 1H), 4.83-4.76 (m, 1H), 4.37-4.30 (m, 1H), 4.27-4.19 (m, 1H), 3.32-3.21 (m, 1H), 2.94-2.68 (m, 5H), 2.32-2.21 (m, 1H), 2.18-2.02 (m, 2H), 1.90-1.77 (m, 1H), 1.74-1.66 (m, 1H), 1.63-1.53 (m, 1H), 1.46-1.35 (m, 1H)

Example 44. (S)-quinuclidin-3-yl (7-(benzofuran-2-yl)chroman-4-yl)carbamate $^1$H-NMR (400 MHz, $CDCl_3$) δ 7.58 (d, 1H), 7.51 (d, 1H), 7.44-7.39 (m, 1H), 7.36-7.20 (m, 4H), 7.00 (s, 1H), 5.20-5.12 (m, 1H), 4.96-4.88 (m, 1H), 4.82-4.75 (m, 1H), 4.35-4.28 (m, 1H), 4.26-4.18 (m, 1H), 3.31-3.20 (m, 1H), 2.93-2.67 (m, 5H), 2.31-2.20 (m, 1H), 2.15-2.01 (m, 2H), 1.86-1.77 (m, 1H), 1.73-1.65 (m, 1H), 1.62-1.53 (m, 1H), 1.45-1.34 (m, 1H)

Example 45. (S)-quinuclidin-3-yl (7-(1H-indol-6-yl)chroman-4-yl)carbamate $^1$H-NMR (400 MHz, $CDCl_3$) δ 8.65 (d, 1H), 7.68 (d, 1H), 7.55 (s, 1H), 7.37-7.30 (m, 2H), 7.25-7.19 (m, 2H), 7.13 (s, 1H), 6.57 (s, 1H), 5.24 (d, 1H), 4.96-4.88 (m, 1H), 4.83-4.76 (m, 1H), 4.34-4.26 (m, 1H), 4.24-4.16 (m, 1H), 3.31-3.20 (m, 1H), 2.93-2.66 (m, 5H), 2.29-2.19 (m, 1H), 2.14-2.03 (m, 2H), 1.88-1.77 (m, 1H), 1.73-1.66 (m, 1H), 1.63-1.53 (m, 1H), 1.46-1.35 (m, 1H)

Example 46. (S)-quinuclidin-3-yl (7-(1H-indol-3-yl)chroman-4-yl)carbamate $^1$H-NMR (400 MHz, $CDCl_3$) δ 8.67 (d, 1H), 7.68 (d, 1H), 7.55 (s, 1H), 7.36-7.30 (m, 2H), 7.25-7.19 (m, 2H), 7.12 (s, 1H), 6.56 (s, 1H), 5.24 (d, 1H), 4.96-4.88 (m, 1H), 4.83-4.76

(m, 1H), 4.33-4.26 (m, 1H), 4.24-4.16 (m, 1H), 3.32-3.19 (m, 1H), 2.92-2.67 (m, 5H), 2.28-2.19 (m, 1H), 2.15-2.02 (m, 2H), 1.88-1.77 (m, 1H), 1.74-1.66 (m, 1H), 1.62-1.54 (m, 1H), 1.45-1.35 (m, 1H)

Example 47. (S)-quinuclidin-3-yl (7-(1H-indol-7-yl) chroman-4-yl)carbamate $^1$H-NMR (400 MHz, $CDCl_3$) δ 8.70 (d, 1H), 7.64 (t, 1H), 7.40 (t, 1H), 7.24-7.17 (m, 4H), 7.13 (s, 1H), 6.62 (s, 1H), 5.32 (d, 1H), 4.99-4.92 (m, 1H), 4.83-4.73 (m, 1H), 4.36-4.29 (m, 1H), 4.27-4.18 (m, 1H), 3.27-3.15 (m, 1H), 2.90-2.61 (m, 5H), 2.32-2.21 (m, 1H), 2.18-2.02 (m, 2H), 1.86-1.76 (m, 1H), 1.74-1.65 (m, 1H), 1.61-1.52 (m, 1H), 1.46-1.35 (m, 1H)

Example 48. (S)-quinuclidin-3-yl (7-(1H-indazol-4-yl)chroman-4-yl)carbamate $^1$H-NMR (400 MHz, $CDCl_3$) δ 8.21 (s, 1H), 7.50-7.37 (m, 3H), 7.29-7.24 (m, 2H), 7.21 (d, 1H), 7.17 (s, 1H), 5.38-5.29 (m, 1H), 5.02-4.93 (m, 1H), 4.85-4.76 (m, 1H), 4.38-4.30 (m, 1H), 4.28-4.20 (m, 1H), 3.34-3.22 (m, 1H), 2.93-2.70 (m, 5H), 2.33-2.22 (m, 1H), 2.19-2.02 (m, 2H), 1.88-1.79 (m, 1H), 1.74-1.66 (m, 1H), 1.63-1.55 (m, 1H), 1.46-1.35 (m, 1H)

Example 49. (S)-quinuclidin-3-yl (7-(1H-indazol-7-yl)chroman-4-yl)carbamate $^1$H-NMR (400 MHz, $CDCl_3$) δ 8.11 (s, 1H), 7.74 (d, 1H), 7.45-7.33 (m, 2H), 7.25-7.18 (m, 3H), 7.13 (s, 1H), 5.71-5.56 (m, 1H), 5.03-4.93 (m, 1H), 4.80-4.72 (m, 1H), 4.36-4.19 (m, 2H), 3.20-3.07 (m, 1H), 2.89-2.67 (m, 4H), 2.55 (dd, 1H), 2.31-2.19 (m, 1H), 2.15-2.00 (m, 2H), 1.84-1.74 (m, 1H), 1.72-1.64 (m, 1H), 1.61-1.50 (m, 1H), 1.46-1.33 (m, 1H)

Example 50. (S)-quinuclidin-3-yl (7-(1-methyl-1H-indazol-6-yl)chroman-4-yl)carbamate $^1$H-NMR (400 MHz, $CDCl_3$) δ 7.98 (s, 1H), 7.76 (d, 1H), 7.52 (s, 1H), 7.36 (d, 2H), 7.23 (t, 1H), 7.14 (s, 1H), 5.25-5.16 (m, 1H), 4.98-4.90 (m, 1H), 4.82-4.75 (m, 1H), 4.37-4.29 (m, 1H), 4.27-4.19 (m, 1H), 4.10 (s, 3H), 3.31-3.19 (m, 1H), 2.93-2.67 (m, 5H), 2.32-2.22 (m, 1H), 2.17-2.00 (m, 2H), 1.87-1.77 (m, 1H), 1.74-1.65 (m, 1H), 1.62-1.53 (m, 1H), 1.46-1.34 (m, 1H)

Example 51. (S)-quinuclidin-3-yl (7-(1-methyl-1H-indazol-4-yl)chroman-4-yl)carbamate $^1$H-NMR (400 MHz, $CDCl_3$) δ 8.11 (s, 1H), 7.48-7.36 (m, 3H), 7.29-7.23 (m, 1H), 7.22-7.14 (m, 1H), 5.43-5.28 (m, 1H), 5.02-4.92 (m, 1H), 4.84-4.74 (m, 1H), 4.38-4.30 (m, 1H), 4.28-4.20 (m, 1H), 4.10 (s, 3H), 3.32-3.21 (m, 1H), 2.90-2.67 (m, 5H), 2.34-2.23 (m, 1H), 2.19-2.01 (m, 2H), 1.85-1.76 (m, 1H), 1.73-1.65 (m, 1H), 1.62-1.53 (m, 1H), 1.44-1.34 (m, 1H)

Example 52. (S)-quinuclidin-3-yl (7-(1-methyl-1H-indol-2-yl)chroman-4-yl)carbamate $^1$H-NMR (400 MHz, $CDCl_3$) δ 7.63 (d, 1H), 7.40-7.33 (m, 2H), 7.28-7.22 (m, 1H), 7.14 (t, 1H), 7.08 (t, 1H), 6.99 (s, 1H), 6.55 (s, 1H), 5.18-5.12 (m, 1H), 4.99-4.92 (m, 1H), 4.83-4.75 (m, 1H), 4.37-4.30 (m, 1H), 4.27-4.21 (m, 1H), 3.76 (s, 3H), 3.32-3.21 (m, 1H), 2.93-2.68 (m, 5H), 2.33-2.23 (m, 1H), 2.18-2.01 (m, 2H), 1.86-1.77 (m, 1H), 1.74-1.66 (m, 1H), 1.63-1.54 (m, 1H), 1.45-1.36 (m, 1H)

Example 53. (S)-quinuclidin-3-yl (7-(isoquinolin-4-yl)chroman-4-yl)carbamate $^1$H-NMR (400 MHz, $CDCl_3$) δ 9.22 (s, 1H), 8.19 (s, 1H), 8.01 (d, 1H), 7.91 (d, 1H), 7.69-7.58 (m, 2H), 7.42 (t, 1H), 7.04 (t, 1H), 6.97 (s, 1H), 6.15-6.03 (m, 1H), 5.04-4.95 (m, 1H), 4.85-4.77 (m, 1H), 4.37-4.30 (m, 1H), 4.28-4.21 (m, 1H), 3.33-3.21 (m, 1H), 2.92-2.68 (m, 5H), 2.33-2.22 (m, 2H), 2.20-2.12 (m, 1H), 1.90-1.79 (m, 1H), 1.75-1.66 (m, 1H), 1.64-1.54 (m, 1H), 1.47-1.35 (m, 1H)

Example 54. (S)-quinuclidin-3-yl (7-(isoquinolin-5-yl)chroman-4-yl)carbamate $^1$H-NMR (400 MHz, $CDCl_3$) δ 9.29 (s, 1H), 8.41 (d, 1H), 7.98 (d, 1H), 7.74 (d, 1H), 7.68-7.61 (m, 2H), 7.42 (t, 1H), 7.03 (t, 1H), 6.96 (s, 1H), 5.43-5.34 (m, 1H), 5.04-4.96 (m, 1H), 4.85-4.77 (m, 1H), 4.39-4.32 (m, 1H), 4.30-4.22 (m, 1H), 3.34-3.23 (m, 1H), 2.94-2.69 (m, 5H), 2.36-2.26 (m, 1H), 2.22-2.13 (m, 1H), 2.10-2.04 (m, 1H), 1.89-1.79 (m, 1H), 1.76-1.67 (m, 1H), 1.64-1.56 (m, 1H), 1.46-1.36 (m, 1H)

Example 55. (S)-quinuclidin-3-yl (7-(quinolin-3-yl) chroman-4-yl)carbamate $^1$H-NMR (400 MHz, $CDCl_3$) δ 9.05 (s, 1H), 8.26 (s, 1H), 8.14 (d, 1H), 7.87 (d, 1H), 7.72 (t, 1H), 7.58 (t, 1H), 7.43 (t, 1H), 7.29-7.23 (m, 1H), 7.16 (s, 1H), 5.46-5.37 (m, 1H), 5.01-4.92 (m, 1H), 4.85-4.76 (m, 1H), 4.37-4.30 (m, 1H), 4.27-4.19 (m, 1H), 3.33-3.20 (m, 1H), 2.94-2.68 (m, 5H), 2.32-2.22 (m, 1H), 2.18-2.03 (m, 2H), 1.86-1.77 (m, 1H), 1.74-1.66 (m, 1H), 1.63-1.54 (m, 1H), 1.46-1.34 (m, 1H)

Example 56. (S)-quinuclidin-3-yl (7-(quinolin-8-yl) chroman-4-yl)carbamate $^1$H-NMR (400 MHz, $CDCl_3$) δ 8.95 (d, 1H), 8.20 (d, 1H), 7.83 (d, 1H), 7.70 (d, 1H), 7.59 (t, 1H), 7.44-7.35 (m, 2H), 7.30-7.24 (m, 1H), 7.16 (s, 1H), 5.23-5.16 (m, 1H), 5.00-4.91 (m, 1H), 4.83-4.74 (m, 1H), 4.37-4.29 (m, 1H), 4.26-4.17 (m, 1H), 3.32-3.20 (m, 1H), 2.93-2.67 (m, 5H), 2.32-2.22 (m, 1H), 2.17-2.02 (m, 2H), 1.88-1.78 (m, 1H), 1.74-1.66 (m, 1H), 1.62-1.54 (m, 1H), 1.45-1.35 (m, 1H)

Example 57. (S)-quinuclidin-3-yl (7-(isoquinolin-7-yl)chroman-4-yl)carbamate $^1$H-NMR (400 MHz, $CDCl_3$) δ 9.24 (s, 1H), 8.52 (d, 1H), 8.11 (s, 1H), 7.95-7.87 (m, 2H), 7.67 (d, 1H), 7.40 (t, 1H), 7.30-7.24 (m, 1H), 7.18 (d, 1H), 5.34-5.26 (m, 1H), 5.01-4.92 (m, 1H), 4.85-4.75 (m, 1H), 4.38-4.30 (m, 1H), 4.28-4.19 (m, 1H), 3.33-3.20 (m, 1H), 2.94-2.66 (m, 5H), 2.34-2.22 (m, 1H), 2.19-2.02 (m, 2H), 1.87-1.77 (m, 1H), 1.75-1.66 (m, 1H), 1.64-1.54 (m, 1H), 1.47-1.36 (m, 1H)

Example 58. (S)-quinuclidin-3-yl (7-(3,4-dihydro-2H-benzo[b][1,4]dioxepin-7-yl)chroman-4-yl)carbamate $^1$H-NMR (400 MHz, $CDCl_3$) δ 7.33-7.25 (m, 1H), 7.18 (s, 1H), 7.15-7.07 (m, 2H), 7.03-6.98 (m, 2H), 5.14-5.06 (m, 1H), 4.94-4.87 (m, 1H), 4.82-4.74 (m, 1H), 4.34-4.15 (m, 6H), 3.31-3.20 (m, 1H), 2.92-2.66 (m, 5H), 2.29-2.18 (m, 3H), 2.15-1.98 (m, 2H), 1.85-1.76 (m, 1H), 1.73-1.65 (m, 1H), 1.62-1.53 (m, 1H), 1.45-1.33 (m, 1H)

Example 59. (S)-quinuclidin-3-yl (7-([1,1'-biphenyl]-3-yl)chroman-4-yl)carbamate $^{1}$H-NMR (400 MHz, $CDCl_3$) δ 7.78 (s, 1H), 7.64 (d, 2H), 7.60-7.44 (m, 5H), 7.39-7.34 (m, 2H), 7.21 (t, 1H), 7.13 (s, 1H), 5.22-5.14 (m, 1H), 4.97-4.90 (m, 1H), 4.83-4.75 (m, 1H), 4.36-4.29 (m, 1H), 4.28-4.18 (m, 1H), 3.32-3.21 (m, 1H), 2.94-2.67 (m, 5H), 2.31-2.21 (m, 1H), 2.16-2.06 (m, 2H), 1.86-1.78 (m, 1H), 1.75-1.66 (m, 1H), 1.63-1.53 (m, 1H), 1.45-1.30 (m, 1H)

Example 60. (S)-quinuclidin-3-yl (7-(3-(pyrrolidin-1-ylsulfonyl)phenyl)chroman-4-yl)carbamate $^{1}$H-NMR (400 MHz, $CDCl_3$) δ 8.00 (s, 1H), 7.82-7.73 (m, 2H), 7.58 (t, 1H), 7.37 (t, 1H), 7.19-7.13 (m, 1H), 7.07 (s, 1H), 5.20-5.09 (m, 1H), 4.98-4.89 (m, 1H), 4.82-4.73 (m, 1H), 4.37-4.29 (m, 1H), 4.27-4.17 (m, 1H), 3.33-3.20 (m, 5H), 2.92-2.66 (m, 5H), 2.32-2.21 (m, 1H), 2.17-2.01 (m, 2H), 1.86-1.66 (m, 1H), 1.62-1.53 (m, 1H), 1.44-1.35 (m, 1H)

Example 61. (S)-quinuclidin-3-yl (7-(1,3-dihydroisobenzofuran-5-yl)chroman-4-yl)carbamate $^{1}$H-NMR (400 MHz, $CDCl_3$) δ 7.46 (d, 1H), 7.41 (s, 1H), 7.36-7.26 (m, 2H), 7.13 (t, 1H), 7.04 (s, 1H), 5.20-5.09 (m, 5H), 4.97-4.89 (m, 1H), 4.82-4.75 (m, 1H), 4.35-4.28 (m, 1H), 4.25-4.17 (m, 1H), 3.31-3.21 (m, 1H), 2.92-2.67 (m, 5H), 2.30-2.20 (m, 1H), 2.16-2.01 (m, 2H), 1.85-1.77 (m, 1H), 1.74-1.65 (m, 1H), 1.62-1.54 (m, 1H), 1.45-1.34 (m, 1H)

Example 62. (S)-quinuclidin-3-yl (7-(benzo[c][1,2,5]thiadiazol-5-yl)chroman-4-yl)carbamate $^{1}$H-NMR (400 MHz, $CDCl_3$) δ 8.14 (s, 1H), 8.05 (d, 1H), 7.84 (d, 1H), 7.41 (t, 1H), 7.29-7.23 (m, 1H), 7.17 (s, 1H), 5.15-5.09 (m, 1H), 5.00-4.93 (m, 1H), 4.83-4.76 (m, 1H), 4.38-4.31 (m, 1H), 4.29-4.21 (m, 1H), 3.33-3.22 (m, 1H), 2.94-2.68 (m, 5H), 2.33-2.23 (m, 1H), 2.19-2.02 (m, 2H), 1.86-1.76 (m, 1H), 1.73-1.65 (m, 1H), 1.64-1.53 (m, 1H), 1.46-1.35 (m, 1H)

Example 63. (S)-quinuclidin-3-yl (7-(4-methyl-3,4-dihydro-2H-benzo[b][1,4]oxazin-7-yl)chroman-4-yl) carbamate $^{1}$H-NMR (400 MHz, $CDCl_3$) δ 7.30-7.23 (m, 1H), 7.14-7.05 (m, 2H), 7.02-7.00 (m, 2H), 6.71 (d, 1H), 5.13-5.06 (m, 1H), 4.92-4.86 (m, 1H), 4.81-4.73 (m, 1H), 4.35-4.25 (m, 3H), 4.23-4.14 (m, 1H), 3.34-3.19 (m, 3H), 2.92 (s, 3H), 2.89-2.67 (m, 5H), 2.28-2.17 (m, 1H), 2.14-2.00 (m, 2H), 1.86-1.77 (m, 1H), 1.73-1.65 (m, 1H), 1.61-1.53 (m, 1H), 1.43-1.34 (m, 1H)

Example 64. (S)-quinuclidin-3-yl (7-(thiophen-3-yl) chroman-4-yl)carbamate $^{1}$H-NMR (400 MHz, $CDCl_3$) δ 7.43 (s, 1H), 7.40-7.34 (m, 2H), 7.32-7.25 (m, 1H), 7.16 (t, 1H), 7.07 (s, 1H), 5.12-5.04 (m, 1H), 4.94-4.87 (m, 1H), 4.82-4.74 (m, 1H), 4.34-4.27 (m, 1H), 4.24-4.17 (m, 1H), 3.31-3.21 (m, 1H), 2.91-2.67 (m, 5H), 2.29-2.19 (m, 1H), 2.14-2.01 (m, 2H), 1.90-1.77 (m, 1H), 1.73-1.66 (m, 1H), 1.63-1.53 (m, 1H), 1.45-1.35 (m, 1H)

Example 65. (S)-quinuclidin-3-yl (7-(2-chloro-5-methoxyphenyl)chroman-4-yl)carbamate $^{1}$H-NMR (400 MHz, $CDCl_3$) δ 7.36-7.30 (m, 2H), 7.03-6.98 (m, 1H), 6.91 (s, 1H), 6.85-6.80 (m, 2H), 5.32-5.25 (m, 1H), 4.96-4.89 (m, 1H), 4.81-4.73 (m, 1H), 4.35-4.27 (m, 1H), 4.25-4.16 (m, 1H), 3.80 (s, 3H), 3.30-3.19 (m, 1H), 2.90-2.66 (m, 5H), 2.30-2.20 (m, 1H), 2.16-2.00 (m, 2H), 1.85-1.77 (m, 1H), 1.74-1.64 (m, 1H), 1.62-1.52 (m, 1H), 1.44-1.33 (m, 1H)

Example 66. (S)-quinuclidin-3-yl (7-(4-chloro-3-methoxyphenyl)chroman-4-yl)carbamate $^{1}$H-NMR (400 MHz, $CDCl_3$) δ 7.41-7.38 (m, 1H), 7.36-7.32 (m, 1H), 7.16-7.06 (m, 3H), 7.03 (s, 1H), 5.19-5.10 (m, 1H), 4.97-4.88 (m, 1H), 4.81-4.74 (m, 1H), 4.35-4.29 (m, 1H), 4.26-4.18 (m, 1H), 3.95 (s, 3H), 3.31-3.20 (m, 1H), 2.92-2.67 (m, 5H), 2.29-2.20 (m, 1H), 2.15-2.05 (m, 2H), 1.86-1.76 (m, 1H), 1.73-1.65 (m, 1H), 1.62-1.53 (m, 1H), 1.44-1.34 (m, 1H)

Example 67. (S)-quinuclidin-3-yl (7-(2-chloro-3-methoxyphenyl)chroman-4-yl)carbamate $^{1}$H-NMR (400 MHz, $CDCl_3$) δ 7.32 (t, 1H), 7.28-7.23 (m, 1H), 7.01-6.97 (m, 1H), 6.96-6.89 (m, 3H), 5.26-5.20 (m, 1H), 4.97-4.89 (m, 1H), 4.81-4.73 (m, 1H), 4.35-4.27 (m, 1H), 4.25-4.16 (m, 1H), 3.94 (s, 3H), 3.31-3.19 (m, 1H), 2.91-2.66 (m, 5H), 2.31-2.20 (m, 1H), 2.16-1.99 (m, 2H), 1.85-1.75 (m, 1H), 1.74-1.65 (m, 1H), 1.62-1.53 (m, 1H), 1.43-1.34 (m, 1H)

Example 68. (S)-quinuclidin-3-yl (7-(2-methoxypyridin-4-yl)chroman-4-yl)carbamate $^{1}$H-NMR (400 MHz, $CDCl_3$) δ 8.20 (d, 1H), 7.37 (t, 1H), 7.16 (t, 1H), 7.08-7.05 (m, 2H), 6.91 (s, 1H), 5.10-5.04 (m, 1H), 4.97-4.90 (m, 1H), 4.82-4.74 (m, 1H), 4.35-4.29 (m, 1H), 4.26-4.18 (m, 1H), 3.98 (s, 3H), 3.33-3.20 (m, 1H), 2.94-2.68 (m, 5H), 2.31-2.21 (m, 1H), 2.16-2.01 (m, 2H), 1.86-1.76 (m, 1H), 1.73-1.65 (m, 1H), 1.62-1.52 (m, 1H), 1.44-1.35 (m, 1H)

Example 69. (S)-quinuclidin-3-yl (7-(3-(dimethylamino)-4-fluorophenyl)chroman-4-yl)carbamate $^{1}$H-NMR (400 MHz, $CDCl_3$) δ 7.32 (t, 1H), 7.11 (dd, 1H), 7.07-6.99 (m, 4H), 5.11-5.05 (m, 1H), 4.95-4.89 (m, 1H), 4.82-4.74 (m, 1H), 4.35-4.28 (m, 1H), 4.25-4.17 (m, 1H), 3.32-3.20 (m, 1H), 2.89 (s, 6H), 2.87-2.66 (m, 5H), 2.30-2.20 (m, 1H), 2.15-2.02 (m, 2H), 1.85-1.76 (m, 1H), 1.74-1.66 (m, 1H), 1.62-1.54 (m, 1H), 1.44-1.35 (m, 1H)

Example 70. (S)-quinuclidin-3-yl [6,7'-bichroman]-4'-ylcarbamate $^{1}$H-NMR (400 MHz, $CDCl_3$) δ 7.33-7.23 (m, 3H), 7.10 (t, 1H), 7.00 (s, 1H), 6.85 (d, 1H), 5.10-5.03 (m, 1H), 4.94-4.87 (m, 1H), 4.82-4.73 (m, 1H), 4.34-4.27 (m, 1H), 4.25-4.15 (m, 3H), 3.32-3.21 (m, 1H), 2.93-2.67 (m, 7H), 2.29-2.19

(m, 1H), 2.15-2.00 (m, 4H), 1.85-1.77 (m, 1H), 1.73-1.66 (m, 1H), 1.62-1.53 (m, 1H), 1.44-1.35 (m, 1H)

Example 71. (S)-quinuclidin-3-yl (7-(6-methoxy-5-(trifluoromethyl)pyridin-3-yl)chroman-4-yl)carbamate $^1$H-NMR (400 MHz, $CDCl_3$) δ 8.49 (s, 1H), 8.01 (s, 1H), 7.37 (t, 1H), 7.11-7.05 (m, 1H), 6.99 (s, 1H), 5.12-5.05 (m, 1H), 4.97-4.90 (m, 1H), 4.83-4.73 (m, 1H), 4.36-4.29 (m, 1H), 4.27-4.19 (m, 1H), 4.08 (s, 3H), 3.31-3.20 (m, 1H), 2.92-2.68 (m, 5H), 2.30-2.21 (m, 1H), 2.16-2.01 (m, 2H), 1.85-1.77 (m, 1H), 1.74-1.66 (m, 1H), 1.62-1.53 (m, 1H), 1.46-1.33 (m, 1H)

Example 72. (S)-quinuclidin-3-yl (7-(1-benzyl-1H-pyrazol-4-yl)chroman-4-yl)carbamate $^1$H-NMR (400 MHz, $CDCl_3$) δ 7.78 (s, 1H), 7.58 (s, 1H), 7.39-7.31 (m, 3H), 7.29-7.19 (m, 1H), 6.92 (s, 1H), 5.32 (s, 3H), 5.10-5.03 (m, 1H), 4.90-4.83 (m, 1H), 4.80-4.73 (m, 1H), 4.30-4.23 (m, 1H), 4.21-4.13 (m, 1H), 3.30-3.20 (m, 1H), 2.92-2.66 (m, 5H), 2.26-2.16 (m, 1H), 2.12-2.01 (m, 2H), 1.82-1.75 (m, 1H), 1.73-1.64 (m, 1H), 1.61-1.53 (m, 1H), 1.44-1.34 (m, 1H)

Example 73. (S)-quinuclidin-3-yl (7-(4-(tetrahydro-2H-pyran-4-yl)phenyl)chroman-4-yl)carbamate $^1$H-NMR (400 MHz, $CDCl_3$) δ 7.55-7.49 (m, 2H), 7.36-7.26 (m, 3H), 7.18-7.12 (m, 1H), 7.06 (s, 1H), 5.13-5.07 (m, 1H), 4.95-4.89 (m, 1H), 4.81-4.76 (m, 1H), 4.35-4.28 (m, 1H), 4.14-4.07 (m, 2H), 3.60-3.51 (m, 2H), 3.31-3.21 (m, 1H), 2.92-2.67 (m, 6H), 2.31-2.19 (m, 1H), 2.15-2.00 (m, 2H), 1.91-1.78 (m, 5H), 1.73-1.65 (m, 1H), 1.62-1.52 (m, 1H), 1.47-1.34 (m, 1H)

Example 74. (S)-quinuclidin-3-yl (7-(4-methyl-3-oxo-3,4-dihydro-2H-benzo[b][1,4]oxazin-6-yl)chroman-4-yl)carbamate $^1$H-NMR (400 MHz, $CDCl_3$) δ 7.34 (t, 1H), 7.19 (d, 1H), 7.13-7.08 (m, 2H), 7.05-6.99 (m, 2H), 5.10-5.04 (m, 1H), 4.97-4.90 (m, 1H), 4.82-4.75 (m, 1H), 4.65 (s, 2H), 4.36-4.29 (m, 1H), 4.27-4.18 (m, 1H), 3.41 (s, 3H), 3.32-3.21 (m, 1H), 2.92-2.68 (m, 5H), 2.31-2.20 (m, 1H), 2.16-2.01 (m, 2H), 1.86-1.75 (m, 1H), 1.72-1.65 (m, 1H), 1.63-1.53 (m, 1H), 1.46-1.35 (m, 1H)

Example 75. (S)-quinuclidin-3-yl (7-(3-methyl-4-morpholinophenyl)chroman-4-yl)carbamate $^1$H-NMR (400 MHz, $CDCl_3$) δ 7.41-7.35 (m, 2H), 7.31 (t, 1H), 7.16-7.10 (m, 1H), 7.09-7.00 (m, 2H), 5.15-5.07 (m, 1H), 4.95-4.87 (m, 1H), 4.82-4.74 (m, 1H), 4.35-4.27 (m, 1H), 4.25-4.15 (m, 1H), 3.90-3.81 (m, 4H), 3.33-3.20 (m, 1H), 2.98-2.92 (m, 4H), 2.90-2.68 (m, 5H), 2.37 (s, 3H), 2.31-2.19 (m, 1H), 2.16-1.99 (m, 2H), 1.86-1.77 (m, 1H), 1.74-1.65 (m, 1H), 1.63-1.52 (m, 1H), 1.44-1.34 (m, 1H)

Example 76. (S)-quinuclidin-3-yl (7-(3-chloro-4-morpholinophenyl)chroman-4-yl)carbamate $^1$H-NMR (400 MHz, $CDCl_3$) δ 7.58 (s, 1H), 7.42 (d, 1H), 7.32 (t, 1H), 7.13-7.05 (m, 2H), 7.00 (s, 1H), 5.17-5.10 (m, 1H), 4.95-4.88 (m, 1H), 4.82-4.74 (m, 1H), 4.34-4.27 (m, 1H), 4.24-4.17 (m, 1H), 3.94-3.83 (m, 4H), 3.31-3.20 (m, 1H), 3.14-3.04 (m, 4H), 2.91-2.67 (m, 5H), 2.29-2.19 (m, 1H), 2.15-2.00 (m, 2H), 1.85-1.76 (m, 1H), 1.73-1.65 (m, 1H), 1.62-1.53 (m, 1H), 1.44-1.34 (m, 1H)

Example 77. (S)-quinuclidin-3-yl (7-(3-fluoro-4-morpholinophenyl)chroman-4-yl)carbamate $^1$H-NMR (400 MHz, $CDCl_3$) δ 7.35-7.22 (m, 3H), 7.10 (t, 1H), 7.02-6.94 (m, 2H), 5.10-5.07 (m, 1H), 4.95-4.88 (m, 1H), 4.81-4.74 (m, 1H), 4.34-4.27 (m, 1H), 4.24-4.16 (m, 1H), 3.92-3.84 (m, 4H), 3.32-3.21 (m, 1H), 3.16-3.08 (m, 4H), 2.91-2.66 (m, 5H), 2.29-2.20 (m, 1H), 2.14-2.00 (m, 2H), 1.84-1.76 (m, 1H), 1.73-1.65 (m, 1H), 1.61-1.52 (m, 1H), 1.44-1.34 (m, 1H)

Example 78. (S)-quinuclidin-3-yl (7-(3-cyano-4-methylphenyl)chroman-4-yl)carbamate $^1$H-NMR (400 MHz, $CDCl_3$) δ 7.76 (s, 1H), 7.65 (d, 1H), 7.38-7.34 (m, 2H), 7.12-7.07 (m, 1H), 7.00 (s, 1H), 5.15-5.08 (m, 1H), 4.97-4.89 (m, 1H), 4.82-4.74 (m, 1H), 4.36-4.29 (m, 1H), 4.26-4.18 (m, 1H), 3.30-3.21 (m, 1H), 2.91-2.67 (m, 5H), 2.58 (s, 3H), 2.31-2.21 (m, 1H), 2.16-2.01 (m, 2H), 1.85-1.77 (m, 1H), 1.74-1.65 (m, 1H), 1.62-1.53 (m, 1H), 1.45-1.34 (m, 1H)

Example 79. (S)-quinuclidin-3-yl (7-(5-methoxypyridin-3-yl)chroman-4-yl)carbamate $^1$H-NMR (400 MHz, $CDCl_3$) δ 8.35 (d, 1H), 8.28 (s, 1H), 7.37 (t, 1H), 7.31 (s, 1H), 7.16-7.09 (m, 1H), 7.03 (s, 1H), 5.40-5.24 (m, 1H), 4.98-4.89 (m, 1H), 4.84-4.74 (m, 1H), 4.38-4.29 (m, 1H), 4.26-4.18 (m, 1H), 3.91 (s, 3H), 3.34-3.20 (m, 1H), 2.94-2.67 (m, 5H), 2.31-2.20 (m, 1H), 2.17-2.02 (m, 2H), 1.85-1.77 (m, 1H), 1.73-1.66 (m, 1H), 1.62-1.54 (m, 1H), 1.45-1.35 (m, 1H)

Example 80. (S)-quinuclidin-3-yl (7-(5-chloro-6-methoxypyridin-3-yl)chroman-4-yl)carbamate $^1$H-NMR (400 MHz, $CDCl_3$) δ 8.24 (s, 1H), 7.82 (s, 1H), 7.36-7.33 (m, 1H), 7.10-7.02 (m, 1H), 6.97 (s, 1H), 5.12-5.05 (m, 1H), 4.97-4.88 (m, 1H), 4.82-4.74 (m, 1H), 4.35-4.28 (m, 1H), 4.26-4.18 (m, 1H), 4.06 (s, 3H), 3.32-3.20 (m, 1H), 2.93-2.68 (m, 5H), 2.30-2.21 (m, 1H), 2.15-2.01 (m, 2H), 1.88-1.77 (m, 1H), 1.73-1.66 (m, 1H), 1.63-1.54 (m, 1H), 1.46-1.34 (m, 1H)

Example 81. (S)-quinuclidin-3-yl (7-(6-(cyclopropylmethoxy)pyridin-3-yl)chroman-4-yl)carbamate $^1$H-NMR (400 MHz, $CDCl_3$) δ 8.32 (s, 1H), 7.75 (d, 1H), 7.33 (t, 1H), 7.08 (t, 1H), 6.98 (s, 1H), 6.83 (d, 1H), 5.15-5.06 (m, 1H), 4.97-4.87 (m, 1H), 4.81-4.74 (m, 1H), 4.35-4.27 (m, 1H), 4.25-4.19 (m, 1H), 4.17 (d, 2H), 3.31-3.20 (m, 1H), 2.93-2.67 (m, 5H), 2.30-2.20 (m, 1H), 2.15-2.00 (m, 2H), 1.83-1.75 (m, 1H), 1.73-1.65 (m, 1H), 1.62-1.53 (m, 1H), 1.45-1.36 (m, 1H), 1.34-1.25 (m, 1H), 0.68-0.59 (m, 2H), 0.41-0.35 (m, 2H)

Example 82. (S)-quinuclidin-3-yl (7-(3-chloro-4-isopropoxyphenyl)chroman-4-yl)carbamate $^1$H-NMR (400 MHz, $CDCl_3$) δ 7.57 (s, 1H), 7.38 (d, 1H), 7.31 (t, 1H), 7.09 (t, 1H), 7.02-6.97 (m, 2H), 5.10-5.03 (m, 1H), 4.95-4.88 (m, 1H), 4.82-4.75 (m, 1H), 4.65-4.54 (m, 1H), 4.35-4.27 (m, 1H), 4.25-4.16 (m, 1H), 3.32-3.21 (m, 1H), 2.95-2.68 (m, 5H), 2.31-2.19 (m, 1H), 2.16-1.99 (m, 2H), 1.87-1.76 (m, 1H), 1.74-1.66 (m, 1H), 1.63-1.54 (m, 1H), 1.47-1.34 (m, 7H)

Example 83. (S)-quinuclidin-3-yl (7-(4-methoxy-3-(trifluoromethyl)phenyl)chroman-4-yl)carbamate $^1$H-NMR (400 MHz, $CDCl_3$) δ 7.75 (s, 1H), 7.68 (d, 1H), 7.33 (t, 1H), 7.13-7.04 (m, 2H), 7.01 (s, 1H), 5.18-5.09 (m, 1H), 4.97-4.88 (m, 1H), 4.83-4.74 (m, 1H), 4.35-4.28 (m, 1H), 4.25-4.17 (m, 1H), 3.94 (s, 3H), 3.31-3.20 (m, 1H), 2.91-2.66 (m, 5H), 2.30-2.20 (m, 1H), 2.15-2.01 (m, 2H), 1.85-1.77 (m, 1H), 1.74-1.65 (m, 1H), 1.62-1.54 (m, 1H), 1.44-1.36 (m, 1H)

Example 84. (S)-quinuclidin-3-yl (7-(2,6-dimethoxyphenyl)chroman-4-yl)carbamate $^1$H-NMR (400 MHz, $CDCl_3$) δ 7.32-7.25 (m, 2H), 6.94-6.90 (m, 1H), 6.85 (s, 1H), 6.68-6.61 (m, 2H), 5.28-5.20 (m, 1H), 4.94-4.87 (m, 1H), 4.81-4.73 (m, 1H), 4.33-4.25 (m, 1H), 4.21-4.14 (m, 1H), 3.75 (s, 6H), 3.31-3.19 (m, 1H), 2.92-2.67 (m, 5H), 2.29-2.20 (m, 1H), 2.15-2.00 (m, 2H), 1.85-1.77 (m, 1H), 1.73-1.65 (m, 1H), 1.61-1.53 (m, 1H), 1.43-1.34 (m, 1H)

Examples 85 to 100

The titled compounds of Examples 85 to 100 were prepared in accordance with the same procedures as in Example 1, using (S)-quinuclidin-3-yl (6-bromochroman-4-yl)carbamate prepared in Preparation 2; and the corresponding substituted-boronic acids, respectively.

Example 85. (S)-quinuclidin-3-yl (6-(4-fluorophenyl)chroman-4-yl)carbamate $^1$H-NMR (400 MHz, $CD_3OD$) δ 7.54-7.51 (m, 2H), 7.44 (d, 1H), 7.40-7.37 (m, 1H), 7.15-7.10 (m, 1H), 6.85 (d, 1H), 4.77 (s, 1H), 4.26 (s, 2H), 3.31-3.21 (m, 2H), 2.83-2.70 (m, 5H), 2.23-2.12 (m, 1H), 2.11-2.03 (m, 2H), 1.97-1.85 (m, 1H), 1.80-1.74 (m, 1H), 1.69-1.59 (m, 1H), 1.50-1.46 (m, 1H)

Example 86. (S)-quinuclidin-3-yl (6-(3-fluorophenyl)chroman-4-yl)carbamate $^1$H-NMR (400 MHz, $CD_3OD$) δ 7.51-7.36 (m, 4H), 7.27 (t, 1H), 7.01 (t, 1H), 6.87 (d, 1H), 4.78 (s, 1H), 4.28 (s, 2H), 3.33-3.21 (m, 2H), 2.84-2.71 (m, 5H), 2.23-2.14 (m, 1H), 2.13-2.04 (m, 1H), 1.98-1.87 (m, 1H), 1.82-1.72 (m, 1H), 1.70-1.61 (m, 1H), 1.53-1.47 (m, 1H)

Example 87. (S)-quinuclidin-3-yl (6-(2-fluorophenyl)chroman-4-yl)carbamate $^1$H-NMR (400 MHz, $CD_3OD$) δ 7.44-7.41 (m, 2H), 7.35-7.28 (m, 2H), 7.21 (t, 1H), 7.14 (t, 1H), 6.86 (d, 1H), 4.75 (s, 1H), 4.27 (s, 2H), 3.32-3.21 (m, 2H), 2.83-2.72 (m, 5H), 2.23-2.13 (m, 1H), 2.10-2.02 (m, 2H), 1.96-1.86 (m, 1H), 1.80-1.70 (m, 1H), 1.67-1.56 (m, 1H), 1.51-1.37 (m, 1H)

Example 88. (S)-quinuclidin-3-yl (6-(4-chlorophenyl)chroman-4-yl)carbamate $^1$H-NMR (400 MHz, $CD_3OD$) δ 7.53-7.50 (m, 3H), 7.40 (t, 3H), 6.86 (d, 1H), 4.77 (s, 1H), 4.27 (s, 2H), 3.32-3.21 (m, 2H), 2.82-2.70 (m, 5H), 2.22-2.12 (m, 1H), 2.11-2.03 (m, 1H), 1.97-1.86 (m, 1H), 1.82-1.70 (m, 1H), 1.68-1.60 (m, 1H), 1.52-1.43 (m, 1H)

Example 89. (S)-quinuclidin-3-yl (6-(3-chlorophenyl)chroman-4-yl)carbamate $^1$H-NMR (400 MHz, $CD_3OD$) δ 7.54-7.36 (m, 5H), 7.28 (d, 1H), 6.87 (d, 1H), 4.78 (s, 1H), 4.27 (s, 2H), 3.32-3.23 (m, 2H), 2.84-2.73 (m, 5H), 2.20-2.03 (m, 3H), 1.98-1.87 (m, 1H), 1.81-1.71 (m, 1H), 1.69-1.58 (m, 1H), 1.54-1.42 (m, 1H)

Example 90. (S)-quinuclidin-3-yl (6-(2-chlorophenyl)chroman-4-yl)carbamate $^1$H-NMR (400 MHz, $CD_3OD$) δ 7.46 (d, 1H), 7.32-7.29 (m, 4H), 7.22 (d, 1H), 6.84 (d, 1H), 4.74 (s, 1H), 4.27 (s, 2H), 3.32-3.21 (m, 2H), 2.82-2.69 (m, 5H), 2.47-2.14 (m, 1H), 2.11-1.99 (m, 2H), 1.96-1.84 (m, 1H), 1.80-1.68 (m, 1H), 1.67-1.57 (m, 1H), 1.50-1.37 (m, 1H)

Example 91. (S)-quinuclidin-3-yl (6-(4-(trifluoromethyl)phenyl)chroman-4-yl)carbamate $^1$H-NMR (400 MHz, $CD_3OD$) δ 7.73-7.70 (m, 4H), 7.56 (d, 1H), 6.90 (d, 1H), 4.78 (s, 1H), 4.28 (s, 2H), 3.32-3.23 (m, 2H), 2.83-2.70 (m, 5H), 2.24-2.13 (m, 1H), 2.11-2.03 (m, 2H), 1.97-1.89 (m, 1H), 1.82-1.71 (m, 1H), 1.70-1.57 (m, 1H), 1.54-1.40 (m, 1H)

Example 92. (S)-quinuclidin-3-yl (6-(3-(trifluoromethyl)phenyl)chroman-4-yl)carbamate $^1$H-NMR (400 MHz, $CD_3OD$) δ 7.79 (d, 2H), 7.58-7.46 (m, 4H), 6.90 (d, 1H), 4.78 (s, 1H), 4.27 (s, 2H), 3.32-3.23 (m, 2H), 2.83-2.75 (m, 5H), 2.25-2.14 (m, 1H), 2.12-2.03 (m, 2H), 1.97-1.85 (m, 1H), 1.81-1.69 (m, 1H), 1.68-1.55 (m, 1H), 1.53-1.39 (m, 1H)

Example 93. (S)-quinuclidin-3-yl (6-(2-(trifluoromethyl)phenyl)chroman-4-yl)carbamate $^1$H-NMR (400 MHz, $CD_3OD$) δ 7.75 (d, 1H), 7.61 (t, 1H), 7.51 (t, 1H), 7.32 (d, 1H), 7.18 (d, 1H), 7.10 (d, 1H), 6.82 (d, 1H), 4.72 (s, 1H), 4.28 (s, 2H), 3.32-3.20 (m, 2H), 2.82-2.69 (m, 5H), 2.25-2.13 (m, 1H), 2.12-2.01 (m, 2H), 1.97-1.83 (m, 1H), 1.80-1.68 (m, 1H), 1.68-1.55 (m, 1H), 1.50-1.43 (m, 1H)

Example 94. (S)-quinuclidin-3-yl (6-(4-(trifluoromethoxy)phenyl)chroman-4-yl)carbamate $^1$H-NMR (400 MHz, $CD_3OD$) δ 7.62 (t, 1H), 7.49 (d, 1H), 7.42 (d, 1H), 7.30 (d, 2H), 6.87 (d, 1H), 4.77 (s, 1H), 4.27 (s, 2H), 3.32-3.22 (m, 2H), 2.84-2.70 (m, 5H), 2.24-2.13 (m, 1H), 2.11-2.02 (m, 2H), 1.97-1.84 (m, 1H), 1.81-1.70 (m, 1H), 1.69-1.55 (m, 1H), 1.52-1.40 (m, 1H)

Example 95. (S)-quinuclidin-3-yl (6-(3-(trifluoromethoxy)phenyl)chroman-4-yl)carbamate $^1$H-NMR (400 MHz, $CD_3OD$) δ 7.55-7.41 (m, 5H), 7.20 (d, 1H), 6.88 (d, 1H), 4.78 (s, 1H), 4.27 (s, 2H), 3.32-3.23 (m, 2H), 2.84-2.73 (m, 5H), 2.25-2.14 (m, 3H), 2.13-2.03 (m, 2H), 1.98-1.87 (m, 1H), 1.81-1.70 (m, 1H), 1.69-1.58 (m, 1H), 1.52-1.41 (m, 1H)

Example 96. (S)-quinuclidin-3-yl (6-(2-(trifluoromethoxy)phenyl)chroman-4-yl)carbamate

$^1$H-NMR (400 MHz, $CD_3OD$) δ 7.44-7.34 (m, 5H), 7.27 (d, 1H), 6.86 (d, 1H), 4.75 (s, 1H), 4.28 (s, 2H), 3.32-3.23 (m, 2H), 2.84-2.70 (m, 5H), 2.25-2.13 (m, 1H), 2.10-2.02 (m, 2H), 1.97-1.85 (m, 1H), 1.81-1.69 (m, 1H), 1.68-1.56 (m, 1H), 1.52-1.39 (m, 1H)

Example 97. (S)-quinuclidin-3-yl (6-(4-(methylthio) phenyl)chroman-4-yl)carbamate

$^1$H-NMR (400 MHz, $CD_3OD$) δ 7.46 (d, 2H), 7.40 (d, 2H), 7.29 (d, 2H), 6.84 (d, 1H), 4.77 (s, 1H), 4.26 (s, 2H), 3.32-3.20 (m, 2H), 2.83-2.73 (m, 5H), 2.49 (s, 3H), 2.22-2.13 (m, 1H), 2.12-2.03 (m, 2H), 1.97-1.87 (m, 1H), 1.82-1.70 (m, 1H), 1.70-1.57 (m, 1H), 1.52-1.41 (m, 1H)

Example 98. (S)-quinuclidin-3-yl (6-(3-(methylthio) phenyl)chroman-4-yl)carbamate

$^1$H-NMR (400 MHz, $CD_3OD$) δ 7.46 (d, 1H), 7.40 (d, 2H), 7.35-7.25 (m, 2H), 7.19 (d, 1H), 6.85 (d, 1H), 4.78 (s, 1H), 4.25 (s, 2H), 3.32-3.20 (m, 2H), 2.85-2.73 (m, 5H), 2.51 (s, 3H), 2.23-2.03 (m, 3H), 1.97-1.83 (m, 1H), 1.82-1.71 (m, 1H), 1.68-1.58 (m, 1H), 1.53-1.41 (m, 1H)

Example 99. (S)-quinuclidin-3-yl (6-(p-tolyl)chroman-4-yl)carbamate

$^1$H-NMR (400 MHz, $CD_3OD$) δ 7.46-7.38 (m, 4H), 7.20 (d, 2H), 6.86 (d, 1H), 4.77 (s, 1H), 4.25 (s, 2H), 3.32-3.20 (m, 2H), 2.83-2.70 (m, 5H), 2.35 (s, 3H), 2.23-2.13 (m, 1H), 2.12-2.03 (m, 2H), 1.98-1.86 (m, 1H), 1.81-1.70 (m, 1H), 1.69-1.56 (m, 1H), 1.52-1.39 (m, 1H)

Example 100. (S)-quinuclidin-3-yl (6-(4-cyanophenyl)chroman-4-yl)carbamate

$^1$H-NMR (400 MHz, $CD_3OD$) δ 7.77-7.66 (m, 4H), 7.57 (d, 1H), 7.50 (d, 1H), 6.90 (d, 1H), 4.77 (s, 1H), 4.25 (s, 2H), 3.32-3.23 (m, 2H), 2.85-2.74 (m, 5H), 2.22-2.13 (m, 1H), 2.11-2.03 (m, 2H), 1.97-1.85 (m, 1H), 1.82-1.69 (m, 1H), 1.69-1.58 (m, 1H), 1.52-1.41 (m, 1H)

Example 101. (S)-quinuclidin-3-yl (6-(3-fluorophenyl)-3,3-dimethylchroman-4-yl)carbamate The titled compound was prepared in accordance with the same procedures as in Example 1, using (S)-quinuclidin-3-yl (6-bromo-3,3-dimethylchroman-4-yl)carbamate prepared in Preparation 4 and 4-fluorophenylboronic acid.

$^1$H-NMR (400 MHz, $CDCl_3$) δ 7.41-7.30 (m, 3H), 7.29-7.27 (d, 1H), 7.20-7.18 (d, 1H), 7.00-6.96 (t, 1H), 6.90-6.87 (d, 1H), 5.01-4.99 (m, 1H), 4.80-4.72 (m, 2H), 3.92-3.83 (m, 2H), 3.27-3.21 (m, 1H), 2.87-2.71 (m, 5H), 2.26 (m, 1H), 1.80 (m, 1H), 1.71-1.67 (m, 1H), 1.58-1.57 (m, 1H), 1.40 (m, 1H), 1.06 (s, 3H), 1.02 (s, 3H)

Examples 102 to 293

The titled compounds of Examples 102 to 293 were prepared in accordance with the same procedures as in Example 1, using (S)-quinuclidin-3-yl (7-bromo-3,3-dimethylchroman-4-yl)carbamate prepared in Preparation 3; and the corresponding substituted-boronic acids, respectively.

Example 102. (S)-quinuclidin-3-yl (7-(3-fluorophenyl)-3,3-dimethylchroman-4-yl)carbamate

$^1$H-NMR (400 MHz, $CDCl_3$) δ 7.41-7.33 (m, 2H), 7.30-7.25 (m, 2H), 7.17-7.12 (t, 1H), 7.06-7.04 (m, 2H), 4.92-4.84 (m, 2H), 4.74-4.71 (m, 1H), 3.93-3.77 (m, 2H), 3.30 (m, 1H), 2.92-2.80 (m, 5H), 2.15 (m, 1H), 1.87 (m, 1H), 1.75-1.74 (m, 1H), 1.64 (m, 1H), 1.49-1.45 (m, 1H), 1.07 (d, 3H), 1.01 (d, 3H)

Example 103. (S)-quinuclidin-3-yl (7-(3-chlorophenyl)-3,3-dimethylchroman-4-yl)carbamate

$^1$H-NMR (400 MHz, $CDCl_3$) δ 7.55 (s, 1H), 7.45-7.43 (m, 1H), 7.38-7.25 (m, 3H), 7.15-7.13 (m, 1H), 7.03 (s, 1H), 4.91 (m, 1H), 4.81-4.79 (m, 1H), 4.74-4.72 (m, 1H), 3.91-3.86 (m, 2H), 3.35-3.21 (m, 1H), 2.91-2.72 (m, 5H), 2.11-2.05 (m, 1H), 1.90-1.81 (m, 1H), 1.71-1.70 (m, 1H), 1.70-1.54 (m, 1H), 1.49-1.35 (m, 1H), 1.07 (d, 3H), 1.03 (d, 3H)

Example 104. (S)-quinuclidin-3-yl (3,3-dimethyl-7-(3-(trifluoromethyl)phenyl)chroman-4-yl)carbamate

$^1$H-NMR (400 MHz, $CDCl_3$) δ 7.81 (s, 1H), 7.75-7.73 (d, 1H), 7.62-7.53 (m, 2H), 7.34-7.27 (m, 1H), 7.19-7.15 (t, 1H), 7.06 (s, 1H), 4.83-4.74 (m, 3H), 3.96-3.85 (m, 2H), 3.29-3.26 (m, 1H), 2.90-2.73 (m, 5H), 2.10 (m, 1H), 1.84 (m, 1H), 1.76-1.70 (m, 1H), 1.63-1.60 (m, 1H), 1.43-1.42 (m, 1H), 1.27 (d, 3H), 1.08 (d, 3H)

Example 105. (S)-quinuclidin-3-yl (3,3-dimethyl-7-(3-(trifluoromethoxy)phenyl)chroman-4-yl)carbamate

$^1$H-NMR (400 MHz, $CDCl_3$) δ 7.50-7.40 (m, 4H), 7.32-7.28 (m, 1H), 7.21-7.12 (m, 1H), 7.04 (s, 1H), 4.92-4.90 (m, 1H), 4.81-4.80 (m, 1H), 4.75-4.72 (m, 1H), 3.94-3.84 (m, 2H), 3.28-3.26 (m, 1H), 2.89-2.75 (m, 5H), 2.11-2.08 (m, 1H), 1.83 (m, 1H), 1.71-1.68 (m, 1H), 1.59 (m, 1H), 1.42 (m, 1H), 1.08 (d, 3H), 1.03 (d, 3H)

Example 106. (S)-quinuclidin-3-yl (7-(2-(methoxymethoxy)phenyl)-3,3-dimethylchroman-4-yl)carbamate

$^1$H-NMR (400 MHz, $CDCl_3$) δ 7.32-7.21 (m, 4H), 7.18-7.05 (m, 2H), 7.00 (s, 1H), 5.14 (s, 2H), 4.83-4.79 (m, 2H), 4.73-4.71 (m, 1H), 3.90-3.82 (m, 2H), 3.27 (s, 3H), 3.28-3.27 (m, 1H), 2.87-2.72 (m, 5H), 2.10-2.02 (m, 1H), 1.83-1.82 (m, 1H), 1.71-1.69 (m, 1H), 1.60 (m, 1H), 1.43 (m, 1H), 1.07-0.99 (m, 6H)

Example 107. (S)-quinuclidin-3-yl (7-(3-(methoxymethoxy)phenyl)-3,3-dimethylchroman-4-yl)carbamate

$^1$H-NMR (400 MHz, $CDCl_3$) δ 7.33-7.31 (m, 1H), 7.27-7.15 (m, 5H), 7.04-7.01 (m, 1H), 5.21 (s, 2H), 4.96-4.94 (m, 1H), 4.79-4.78 (m, 1H), 4.72-4.66 (m, 1H), 3.89-3.81 (m, 2H), 3.50 (s, 3H), 3.30-3.19 (m, 1H), 2.86-2.72 (m, 5H), 2.10-2.08 (m, 1H), 1.82-1.81 (m, 1H), 1.70-1.68 (m, 1H), 1.58-1.57 (m, 1H), 1.55-1.35 (m, 1H), 1.06-0.98 (m, 6H)

Example 108. (S)-quinuclidin-3-yl (7-(4-(methoxymethoxy)phenyl)-3,3-dimethylchroman-4-yl)carbamate

$^1$H-NMR (400 MHz, $CDCl_3$) δ 7.50-7.48 (m, 2H), 7.21-7.14 (s, 1H), 7.12-7.08 (m, 3H), 7.01 (s, 1H), 5.21 (s, 2H), 4.85-4.81 (m, 2H), 4.72-4.69 (m, 1H), 3.92-3.82 (m, 2H), 3.51 (s, 3H), 3.28-3.26 (m, 1H), 2.91-2.71 (m, 5H), 2.10-2.08 (m, 1H), 1.81 (m, 1H), 1.71-1.69 (m, 1H), 1.60-1.59 (m, 1H), 1.42 (m, 1H), 1.07-0.99 (m, 6H)

Example 109. (S)-quinuclidin-3-yl (7-(2-(2-methoxyethoxy)phenyl)-3,3-dimethylchroman-4-yl) carbamate $^{1}$H-NMR (400 MHz, $CDCl_3$) δ 7.30-7.27 (m, 2H), 7.22-7.15 (m, 3H), 7.04-6.92 (m, 2H), 5.10-4.95 (m, 1H), 4.78-4.77 (m, 1H), 4.70-4.65 (t, 1H), 4.12-4.10 (m, 2H), 3.87-3.80 (m, 2H), 3.70-3.68 (m, 2H), 3.37 (s, 3H), 3.30-3.16 (m, 1H), 2.87-2.71 (m, 5H), 2.09-2.07 (m, 1H), 1.82 (m, 1H), 1.58 (m, 1H), 1.39 (m, 1H), 1.06-0.97 (m, 6H)

Example 110. (S)-quinuclidin-3-yl (7-(3-(2-methoxyethoxy)phenyl)-3,3-dimethylchroman-4-yl) carbamate $^{1}$H-NMR (400 MHz, $CDCl_3$) δ 7.35-7.23 (m, 2H), 7.16-7.13 (m, 3H), 7.04 (s, 1H), 6.93-6.91 (d, 1H), 4.85-4.79 (m, 2H), 4.73-4.70 (m, 1H), 4.19-4.16 (m, 2H), 3.90-3.82 (m, 2H), 3.79-3.77 (m, 2H), 3.47 (s, 3H), 3.27 (m, 1H), 2.90-2.72 (m, 5H), 2.10-2.08 (m, 1H), 1.83 (m, 1H), 1.71-1.69 (m, 1H), 1.60-1.58 (m, 1H), 1.50-1.35 (m, 1H), 1.07-0.97 (m, 6H)

Example 111. (S)-quinuclidin-3-yl (7-(4-(2-methoxyethoxy)phenyl)-3,3-dimethylchroman-4-yl) carbamate $^{1}$H-NMR (400 MHz, $CDCl_3$) δ 7.49-7.47 (m, 1H), 7.27-7.17 (m, 3H), 7.00-6.91 (m, 2H), 6.82-6.80 (d, 1H), 4.96-4.82 (m, 1H), 4.79-4.77 (m, 1H), 4.71-4.66 (m, 1H), 4.17-4.14 (m, 2H), 3.88-3.76 (m, 4H), 3.46 (s, 3H), 3.32-3.20 (m, 1H), 2.88-2.70 (m, 5H), 2.07-2.04 (m, 1H), 1.82-1.81 (m, 1H), 1.70-1.69 (m, 1H), 1.58-1.57 (m, 1H), 1.48-1.32 (m, 1H), 1.06-0.97 (m, 6H)

Example 112. (S)-quinuclidin-3-yl (7-(3-(difluoromethyl)phenyl)-3,3-dimethylchroman-4-yl)carbamate $^{1}$H-NMR (400 MHz, $CDCl_3$) δ 7.71-7.64 (m, 2H), 7.55-7.46 (m, 2H), 7.35-7.22 (m, 1H), 7.20-7.13 (m, 1H), 7.06 (s, 1H), 6.70 (t, 1H), 4.91-4.78 (m, 2H), 4.76-4.69 (m, 1H), 3.96-3.82 (m, 2H), 3.35-3.23 (m, 1H), 2.96-2.70 (m, 5H), 2.14-2.07 (m, 1H), 1.87-1.79 (m, 1H), 1.76-1.68 (m, 1H), 1.64-1.55 (m, 1H), 1.48-1.38 (m, 1H), 1.07 (d, 3H), 1.03 (d, 3H)

Example 113. (S)-quinuclidin-3-yl (3,3-dimethyl-7-(8-methylquinolin-5-yl)chroman-4-yl)carbamate $^{1}$H-NMR (400 MHz, $CDCl_3$) δ 8.95 (d, 1H), 8.27 (d, 1H), 7.60 (d, 1H), 7.41-7.29 (m, 3H), 7.01 (t, 1H), 6.92 (s, 1H), 4.98-4.89 (m, 1H), 4.86-4.75 (m, 2H), 3.99-3.83 (m, 2H), 3.34-3.23 (m, 1H), 2.96-2.68 (m, 8H), 2.17-2.07 (m, 1H), 1.90-1.81 (m, 1H), 1.77-1.67 (m, 1H), 1.64-1.55 (m, 1H), 1.48-1.38 (m, 1H), 1.10 (d, 3H), 1.07 (d, 3H)

Example 114. (S)-quinuclidin-3-yl (7-(3,5-dimethoxyphenyl)-3,3-dimethylchroman-4-yl)carbamate $^{1}$H-NMR (400 MHz, $CDCl_3$) δ 7.29-7.21 (m, 1H), 7.14 (t, 1H), 7.04 (s, 1H), 6.72-6.68 (m, 2H), 6.46 (s, 1H), 4.90-4.84 (m, 1H), 4.82-4.77 (m, 1H), 4.75-4.68 (d, 1H), 3.95-3.78 (m, 8H), 3.32-3.23 (m, 1H), 2.94-2.69 (m, 5H), 2.14-2.06 (m, 1H), 1.85-1.78 (m, 1H), 1.76-1.66 (m, 1H), 1.63-1.54 (m, 1H), 1.47-1.36 (m, 1H), 1.07 (d, 3H), 1.03 (d, 3H)

Example 115. (S)-quinuclidin-3-yl (7-(4-methoxy-3-methylphenyl)-3,3-dimethylchroman-4-yl)carbamate $^{1}$H-NMR (400 MHz, $CDCl_3$) δ 7.39-7.34 (m, 2H), 7.28-7.19 (m, 1H), 7.12 (t, 1H), 7.01 (s, 1H), 6.87 (d, 1H), 5.00-4.91 (m, 1H), 4.82-4.76 (m, 1H), 4.68 (d, 1H), 3.93-3.80 (m, 5H), 3.32-3.21 (m, 1H), 2.94-2.68 (m, 5H), 2.27 (s, 3H), 2.14-2.06 (m, 1H), 1.87-1.78 (m, 1H), 1.75-1.66 (m, 1H), 1.62-1.54 (m, 1H), 1.46-1.37 (m, 1H), 1.06 (d, 3H), 1.02 (d, 3H)

Example 116. (S)-quinuclidin-3-yl (7-(4-methoxy-2-methylphenyl)-3,3-dimethylchroman-4-yl)carbamate $^{1}$H-NMR (400 MHz, $CDCl_3$) δ 7.20 (d, 1H), 7.13 (d, 1H), 6.87 (d, 1H), 6.83-6.75 (m, 3H), 4.94-4.85 (m, 1H), 4.83-4.77 (m, 1H), 4.73 (d, 1H), 3.95-3.80 (m, 5H), 3.34-3.23 (m, 1H), 2.96-2.69 (m, 5H), 2.27 (s, 3H), 2.14-2.06 (m, 1H), 1.90-1.80 (m, 1H), 1.75-1.66 (m, 1H), 1.63-1.54 (m, 1H), 1.48-1.38 (m, 1H), 1.07 (d, 3H), 1.03 (d, 3H)

Example 117. (S)-quinuclidin-3-yl (7-(3-chloro-4-methoxyphenyl)-3,3-dimethylchroman-4-yl)carbamate $^{1}$H-NMR (400 MHz, $CDCl_3$) δ 7.58 (s, 1H), 7.42 (d, 1H), 7.26-7.20 (m, 1H), 7.09 (t, 1H), 7.00-6.95 (m, 2H), 4.94-4.86 (m, 1H), 4.82-4.77 (m, 1H), 4.69 (d, 1H), 3.94 (s, 3H), 3.92-3.80 (m, 2H), 3.33-3.20 (m, 1H), 2.95-2.67 (m, 5H), 2.14-2.06 (m, 1H), 1.89-1.78 (m, 1H), 1.75-1.67 (m, 1H), 1.63-1.53 (m, 1H), 1.46-1.36 (m, 1H), 1.06 (d, 3H), 1.02 (d, 3H)

Example 118. (S)-quinuclidin-3-yl (7-(3-fluoro-4-methoxyphenyl)-3,3-dimethylchroman-4-yl)carbamate $^{1}$H-NMR (400 MHz, $CDCl_3$) δ 7.33-7.20 (m, 3H), 7.09 (t, 1H), 7.04-6.96 (m, 2H), 4.90 (t, 1H), 4.83-4.76 (m, 1H), 4.70 (d, 1H), 3.92 (s, 3H), 3.91-3.79 (m, 2H), 3.31-3.22 (m, 1H), 2.96-2.67 (m, 5H), 2.13-2.06 (m, 1H), 1.87-1.79 (m, 1H), 1.74-1.66 (m, 1H), 1.62-1.55 (m, 1H), 1.46-1.37 (m, 1H), 1.06 (d, 3H), 1.02 (d, 3H)

Example 119. (S)-quinuclidin-3-yl (7-(2-chloro-4-methoxyphenyl)-3,3-dimethylchroman-4-yl)carbamate $^{1}$H-NMR (400 MHz, $CDCl_3$) δ 7.30-7.28 (m, 2H), 7.04-6.95 (m, 2H), 6.91-6.82 (m, 2H), 5.02 (t, 1H), 4.82-4.76 (m, 1H), 4.72 (d, 1H), 3.95-3.78 (m, 5H), 3.32-3.19 (m, 1H), 2.93-2.67 (m, 5H), 2.13-2.06 (m, 1H), 1.88-1.78 (m, 1H), 1.74-1.65 (m, 1H), 1.62-1.53 (m, 1H), 1.47-1.35 (m, 1H), 1.07 (d, 3H), 1.03 (d, 3H)

Example 120. (S)-quinuclidin-3-yl (7-(4-fluoro-2-methoxyphenyl)-3,3-dimethylchroman-4-yl)carbamate $^{1}$H-NMR (400 MHz, $CDCl_3$) δ 7.28-7.19 (m, 2H), 7.05 (t, 1H), 6.95 (s, 1H), 6.75-6.66 (m, 2H), 4.87 (t, 1H), 4.82-4.76 (m, 1H), 4.70 (d, 1H), 3.93-3.87 (m, 5H), 3.85-3.76 (m, 4H), 3.33-3.22 (m, 1H), 2.93-2.68 (m, 5H), 2.12-2.06 (m, 1H), 1.88-1.78 (m, 1H), 1.75-1.66 (m, 1H), 1.62-1.54 (m, 1H), 1.46-1.37 (m, 1H), 1.07 (d, 3H), 1.03 (d, 3H)

Example 121. (S)-quinuclidin-3-yl (7-(2-chloro-6-methoxyphenyl)-3,3-dimethylchroman-4-yl)carbamate $^1$H-NMR (400 MHz, $CDCl_3$) δ 7.70-7.62 (m, 1H), 7.49-7.42 (m, 1H), 7.24-7.00 (m, 2H), 6.96-6.89 (m, 1H), 6.84-6.79 (m, 1H), 4.93-4.84 (m, 1H), 4.81-4.62 (m, 2H), 3.95-3.73 (m, 5H), 3.30-3.20 (m, 1H), 2.92-2.66 (m, 5H), 2.14-2.04 (m, 1H), 1.88-1.77 (m, 1H), 1.74-1.65 (m, 1H), 1.61-1.54 (m, 1H), 1.45-1.36 (m, 1H), 1.04 (d, 3H), 0.99 (d, 3H)

Example 122. (S)-quinuclidin-3-yl (7-(2-fluoro-6-methoxyphenyl)-3,3-dimethylchroman-4-yl)carbamate $^1$H-NMR (400 MHz, $CDCl_3$) δ 7.71-7.63 (m, 1H), 7.58-7.52 (m, 1H), 7.50-7.42 (m, 1H), 7.25-7.16 (m, 1H), 7.02-6.88 (m, 1H), 6.84-6.74 (m, 1H) 4.91-4.84 (m, 1H), 4.82-4.76 (m, 1H), 4.70 (d, 1H), 3.94-3.79 (m, 5H), 3.33-3.22 (m, 1H), 2.95-2.68 (m, 5H), 2.12-2.05 (m, 1H), 1.88-1.78 (m, 1H), 1.75-1.66 (m, 1H), 1.63-1.53 (m, 1H), 1.47-1.36 (m, 1H), 1.08 (d, 3H), 1.04 (d, 3H)

Example 123. (S)-quinuclidin-3-yl (7-(2,5-difluoro-4-methoxyphenyl)-3,3-dimethylchroman-4-yl)carbamate $^1$H-NMR (400 MHz, $CDCl_3$) δ 7.29-7.21 (m, 1H), 7.14 (dd, 1H), 7.05 (t, 1H), 6.95 (s, 1H), 6.76 (dd, 1H) 5.01 (t, 1H), 4.82-4.75 (m, 1H), 4.69 (d, 1H), 3.94-3.79 (m, 5H), 3.30-3.20 (m, 1H), 2.91-2.66 (m, 5H), 2.13-2.05 (m, 1H), 1.86-1.77 (m, 1H), 1.74-1.65 (m, 1H), 1.61-1.53 (m, 1H), 1.46-1.36 (m, 1H), 1.05 (d, 3H), 1.01 (d, 3H)

Example 124. (S)-quinuclidin-3-yl (7-(4-ethoxy-3-fluorophenyl)-3,3-dimethylchroman-4-yl)carbamate $^1$H-NMR (400 MHz, $CDCl_3$) δ 7.33-7.19 (m, 3H), 7.09 (t, 1H), 7.02-7.95 (m, 2H), 4.95 (t, 1H), 4.82-4.75 (m, 1H), 4.69 (d, 1H), 4.14 (q, 2H), 3.93-3.79 (m, 2H), 3.31-3.20 (m, 1H), 2.93-2.68 (m, 5H), 2.12-2.06 (m, 1H), 1.88-1.77 (m, 1H), 1.74-1.65 (m, 1H), 1.62-1.53 (m, 1H), 1.46 (t, 3H), 1.42-1.35 (m, 1H), 1.05 (d, 3H), 1.01 (d, 3H)

Example 125. (S)-quinuclidin-3-yl (7-(2,4-dimethoxyphenyl)-3,3-dimethylchroman-4-yl)carbamate $^1$H-NMR (400 MHz, $CDCl_3$) δ 7.25-7.17 (m, 2H), 7.08 (t, 1H), 6.98 (s, 1H), 6.59-6.52 (m, 2H), 4.95 (t, 1H), 4.82-4.75 (m, 1H), 4.68 (d, 1H), 3.91-3.76 (m, 8H), 3.32-3.20 (m, 1H), 2.95-2.67 (m, 5H), 2.13-2.06 (m, 1H), 1.88-1.78 (m, 1H), 1.74-1.65 (m, 1H), 1.62-1.53 (m, 1H), 1.45-1.36 (m, 1H), 1.06 (d, 3H), 1.02 (d, 3H)

Example 126. (S)-quinuclidin-3-yl (7-(2,5-dimethoxyphenyl)-3,3-dimethylchroman-4-yl)carbamate $^1$H-NMR (400 MHz, $CDCl_3$) δ 7.29-7.20 (m, 1H), 7.12 (t, 1H), 7.01 (s, 1H), 6.93-6.82 (m, 3H), 4.85-4.77 (m, 2H), 4.70 (d, 1H), 3.93-3.80 (m, 2H), 3.78 (s, 3H), 3.77 (s, 3H), 3.32-3.23 (m, 1H), 2.94-2.69 (m, 5H), 2.13-2.06 (m, 1H), 1.88-1.79 (m, 1H), 1.74-1.67 (m, 1H), 1.62-1.55 (m, 1H), 1.46-1.37 (m, 1H), 1.07 (d, 3H), 1.04 (d, 3H)

Example 127. (S)-quinuclidin-3-yl (7-(2,3-dimethoxyphenyl)-3,3-dimethylchroman-4-yl)carbamate $^1$H-NMR (400 MHz, $CDCl_3$) δ 7.28-7.19 (m, 1H), 7.15-7.05 (m, 2H), 7.00 (s, 1H), 6.93-6.89 (m, 2H), 5.02-4.93 (m, 1H), 4.83-4.76 (m, 1H), 4.71 (d, 1H), 3.95-3.87 (m, 4H), 3.86-3.79 (m, 1H), 3.63 (d, 3H), 3.32-3.22 (m, 1H), 2.94-2.67 (m, 5H), 2.13-2.06 (m, 1H), 1.89-1.79 (m, 1H), 1.74-1.66 (m, 1H), 1.62-1.54 (m, 1H), 1.46-1.36 (m, 1H), 1.07 (d, 3H), 1.03 (d, 3H)

Example 128. (S)-quinuclidin-3-yl (7-(3,4-dimethoxyphenyl)-3,3-dimethylchroman-4-yl)carbamate $^1$H-NMR (400 MHz, $CDCl_3$) δ 7.29-7.21 (m, 1H), 7.16-7.12 (m, 2H), 7.08 (s, 1H), 7.02 (s, 1H), 6.93 (d, 1H), 4.85-4.77 (m, 2H), 4.71 (d, 1H), 3.96-3.89 (m, 7H), 3.87-3.81 (m, 1H), 3.34-3.23 (m, 1H), 2.95-2.69 (m, 5H), 2.13-2.05 (m, 1H), 1.89-1.80 (m, 1H), 1.75-1.67 (m, 1H), 1.63-1.55 (m, 1H), 1.46-1.38 (m, 1H), 1.07 (d, 3H), 1.03 (d, 3H)

Example 129. (S)-quinuclidin-3-yl (7-(2,6-dimethoxypyridin-3-yl)-3,3-dimethylchroman-4-yl)carbamate $^1$H-NMR (400 MHz, $CDCl_3$) δ 7.55 (dd, 1H), 7.22 (dd, 1H), 7.11 (t, 1H), 7.01 (s, 1H), 6.38 (d, 1H), 4.88 (t, 1H), 4.86-4.78 (m, 1H), 4.69 (d, 1H), 3.96 (d, 6H), 3.88 (dd, 1H), 3.82 (dd, 1H), 3.32-3.22 (m, 1H), 2.93-2.67 (m, 5H), 2.12-2.05 (m, 1H), 1.88-1.78 (m, 1H), 1.75-1.66 (m, 1H), 1.61-1.53 (m, 1H), 1.46-1.36 (m, 1H), 1.06 (d, 3H), 1.02 (d, 3H)

Example 130. (S)-quinuclidin-3-yl (3,3-dimethyl-7-(naphthalen-2-yl)chroman-4-yl)carbamate $^1$H-NMR (400 MHz, $CDCl_3$) δ 8.02 (s, 1H), 7.94-7.84 (m, 3H), 7.71 (d, 1H), 7.54-7.45 (m, 2H), 7.36-7.28 (m, 2H), 7.19 (s, 1H), 4.93 (t, 1H), 4.86-4.78 (m, 1H), 4.74 (d, 1H), 3.94 (dd, 1H), 3.88 (dd, 1H), 3.34-3.22 (m, 1H), 2.97-2.68 (m, 5H), 2.16-2.07 (m, 1H), 1.91-1.80 (m, 1H), 1.76-1.67 (m, 1H), 1.65-1.55 (m, 1H), 1.48-1.30 (m, 1H), 1.09 (d, 3H), 1.05 (d, 3H)

Example 131. (S)-quinuclidin-3-yl (3,3-dimethyl-7-(naphthalen-1-yl)chroman-4-yl)carbamate $^1$H-NMR (400 MHz, $CDCl_3$) δ 7.95-7.89 (m, 2H), 7.86 (d, 1H), 7.53-7.40 (m, 4H), 7.32 (dd, 1H), 7.07 (t, 1H), 6.98 (s, 1H), 4.93 (t, 1H), 4.85-4.76 (m, 2H), 3.96 (dd, 1H), 3.89 (dd, 1H), 3.35-3.23 (m, 1H), 2.96-2.71 (m, 5H), 2.16-2.08 (m, 1H), 1.91-1.82 (m, 1H), 1.77-1.67 (m, 1H), 1.64-1.54 (m, 1H), 1.48-1.38 (m, 1H), 1.11 (d, 3H), 1.08 (d, 3H)

Example 132. (S)-quinuclidin-3-yl (3,3-dimethyl-7-(quinolin-6-yl)chroman-4-yl)carbamate $^1$H-NMR (400 MHz, $CDCl_3$) δ 8.89 (d, 1H), 8.19 (d, 1H), 8.15 (d, 1H), 8.00-7.89 (m, 2H), 7.17 (s, 1H), 5.01 (t, 1H), 4.85-4.78 (m, 1H), 4.74 (d, 1H), 3.93 (dd, 1H), 3.87 (dd, 1H), 3.35-3.21 (m, 1H), 2.97-2.67 (m, 5H), 2.17-2.07 (m, 1H), 1.89-1.79 (m, 1H), 1.75-1.67 (m, 1H), 1.63-1.55 (m, 1H), 1.47-1.36 (m, 1H), 1.08 (d, 3H), 1.04 (d, 3H)

Example 133. (S)-quinuclidin-3-yl (7-(4-ethoxy-3,5-dimethylphenyl)-3,3-dimethylchroman-4-yl)carbamate $^1$H-NMR (400 MHz, $CDCl_3$) δ 7.26-7.18 (m, 3H), 7.11 (t, 1H), 7.00 (s, 1H), 4.86 (t, 1H), 4.83-4.77 (m, 1H), 4.70 (d, 1H), 3.90-3.80 (m, 4H), 3.33-3.23 (m, 1H), 2.95-2.69 (m, 5H), 2.32 (s, 6H), 2.13-2.06 (m, 1H), 1.86-1.79 (m, 1H), 1.76-1.67 (m, 1H), 1.63-1.55 (m, 1H), 1.48-1.37 (m, 4H), 1.06 (d, 3H), 1.02 (d, 3H)

Example 134. (S)-quinuclidin-3-yl (7-(2,4-dichloro-5-ethoxyphenyl)-3,3-dimethylchroman-4-yl)carbamate $^1$H-NMR (400 MHz, $CDCl_3$) δ 7.45 (s, 1H), 7.30-7.22 (m, 1H), 7.03-6.95 (m, 1H), 6.89-6.82 (m, 2H), 4.99 (t, 1H), 4.84-4.76 (m, 1H), 4.72 (d, 1H), 4.11-4.06 (m, 2H), 3.95-3.81 (m, 2H), 3.32-3.19 (m, 1H), 2.93-2.67 (m, 5H), 2.13-2.06 (m, 1H), 1.88-1.78 (m, 1H), 1.74-1.66 (m, 1H), 1.63-1.54 (m, 1H), 1.50-1.37 (m, 4H), 1.07 (d, 3H), 1.03 (d, 3H)

Example 135. (S)-quinuclidin-3-yl (7-(2-fluoro-5-isopropoxyphenyl)-3,3-dimethylchroman-4-yl)carbamate $^1$H-NMR (400 MHz, $CDCl_3$) δ 7.26 (dd, 1H), 7.11 (t, 1H), 7.06-6.98 (m, 2H), 6.95-6.89 (m, 1H), 6.85-6.77 (m, 1H), 4.96 (t, 1H), 4.82-4.76 (m, 1H), 4.71 (d, 1H), 4.53-4.44 (m, 1H), 3.90 (dd, 1H), 3.83 (dd, 1H), 3.31-3.20 (m, 1H), 2.93-2.67 (m, 5H), 2.13-2.05 (m, 1H), 1.87-1.78 (m, 1H), 1.74-1.65 (m, 1H), 1.62-1.54 (m, 1H), 1.45-1.37 (m, 1H), 1.33 (d, 6H), 1.06 (d, 3H), 1.02 (d, 3H)

Example 136. (S)-quinuclidin-3-yl (7-(3-fluoro-5-isopropoxyphenyl)-3,3-dimethylchroman-4-yl)carbamate $^1$H-NMR (400 MHz, $CDCl_3$) δ 7.26 (dd, 1H), 7.11 (t, 1H), 7.01 (s, 1H), 6.86 (s, 1H), 6.82 (d, 1H), 6.57 (d, 1H), 4.89 (t, 1H), 4.83-4.77 (m, 1H), 4.72 (d, 1H), 4.60-4.52 (m, 1H), 3.91 (dd, 1H), 3.84 (dd, 1H), 3.33-3.22 (m, 1H), 2.94-2.69 (m, 5H), 2.14-2.06 (m, 1H), 1.88-1.79 (m, 1H), 1.75-1.67 (m, 1H), 1.63-1.55 (m, 1H), 1.47-1.39 (m, 1H), 1.36 (d, 6H), 1.06 (d, 3H), 1.02 (d, 3H)

Example 137. (S)-quinuclidin-3-yl (7-(2-chloro-4-(trifluoromethyl)phenyl)-3,3-dimethylchroman-4-yl)carbamate $^1$H-NMR (400 MHz, $CDCl_3$) δ 7.73 (s, 1H), 7.56 (d, 1H), 7.44 (d, 1H), 7.34-7.24 (m, 1H), 6.99 (t, 1H), 6.89 (s, 1H), 4.96 (t, 1H), 4.84-4.78 (m, 1H), 4.74 (d, 1H), 3.93 (dd, 1H), 3.86 (dd, 1H), 3.32-3.22 (m, 1H), 2.95-2.67 (m, 5H), 2.14-2.06 (m, 1H), 1.89-1.79 (m, 1H), 1.75-1.67 (m, 1H), 1.63-1.55 (m, 1H), 1.47-1.37 (m, 1H), 1.08 (d, 3H), 1.04 (d, 3H)

Example 138. (S)-quinuclidin-3-yl (7-(2-chloro-3-(trifluoromethyl)phenyl)-3,3-dimethylchroman-4-yl)carbamate $^1$H-NMR (400 MHz, $CDCl_3$) δ 7.70 (d, 1H), 7.48 (d, 1H), 7.40 (t, 1H), 7.28 (dd, 1H), 6.98-6.92 (m, 1H), 6.84 (s, 1H), 5.00 (t, 1H), 4.83-4.78 (m, 1H), 4.74 (d, 1H), 3.92 (dd, 1H), 3.85 (dd, 1H), 3.32-3.20 (m, 1H), 2.95-2.67 (m, 5H), 2.13-2.06 (m, 1H), 1.87-1.79 (m, 1H), 1.75-1.65 (m, 1H), 1.63-1.53 (m, 1H), 1.47-1.36 (m, 1H), 1.08 (d, 3H), 1.04 (d, 3H)

Example 139. (S)-quinuclidin-3-yl (7-(2-chloro-5-(trifluoromethyl)phenyl)-3,3-dimethylchroman-4-yl)carbamate $^1$H-NMR (400 MHz, $CDCl_3$) δ 7.63-7.49 (m, 3H), 7.35-7.24 (m, 1H), 7.00 (t, 1H), 6.89 (s, 1H), 5.08-4.92 (m, 1H), 4.84-4.77 (m, 1H), 4.73 (d, 1H), 3.98-3.81 (m, 2H), 3.34-3.18 (m, 1H), 2.96-2.64 (m, 5H), 2.13-2.06 (m, 1H), 1.88-1.78 (m, 1H), 1.74-1.66 (m, 1H), 1.62-1.54 (m, 1H), 1.46-1.36 (m, 1H), 1.11 (d, 3H), 0.96 (d, 3H)

Example 140. (S)-quinuclidin-3-yl (7-(3,5-dimethyl-4-propoxyphenyl)-3,3-dimethylchroman-4-yl)carbamate $^1$H-NMR (400 MHz, $CDCl_3$) δ 7.26-7.18 (m, 3H), 7.11 (t, 1H), 7.00 (s, 1H), 4.84-4.77 (m, 2H), 4.70 (d, 1H), 3.94-3.81 (m, 2H), 3.76 (t, 2H), 3.33-3.23 (m, 1H), 2.95-2.69 (m, 5H), 2.32 (s, 6H), 2.13-2.05 (m, 1H), 1.90-1.81 (m, 3H), 1.77-1.69 (m, 1H), 1.63-1.54 (m, 1H), 1.47-1.37 (m, 1H), 1.09 (t, 3H), 1.06 (d, 3H), 1.02 (d, 3H)

Example 141. (S)-quinuclidin-3-yl (7-(4-(tert-butoxymethyl)phenyl)-3,3-dimethylchroman-4-yl)carbamate $^1$H-NMR (400 MHz, $CDCl_3$) δ 7.53 (d, 2H), 7.40 (d, 2H), 7.30-7.22 (m, 1H), 7.15 (t, 1H), 7.04 (s, 1H), 4.89-4.77 (m, 2H), 4.71 (d, 1H), 4.48 (s, 1H), 3.91 (dd, 1H), 3.84 (dd, 1H), 3.33-3.23 (m, 1H), 2.94-2.69 (m, 5H), 2.14-2.05 (m, 1H), 1.89-1.78 (m, 1H), 1.75-1.67 (m, 1H), 1.64-1.54 (m, 1H), 1.48-1.37 (m, 1H), 1.32 (s, 9H), 1.07 (d, 3H), 1.03 (d, 3H)

Example 142. (S)-quinuclidin-3-yl (7-(2-chloro-5-(trifluoromethoxy)phenyl)-3,3-dimethylchroman-4-yl)carbamate $^1$H-NMR (400 MHz, $CDCl_3$) δ 7.47 (d, 1H), 7.27 (dd, 1H), 7.19 (s, 1H), 7.14 (d, 1H), 7.00 (dd, 1H), 6.89 (s, 1H), 5.02 (t, 1H), 4.84-4.77 (m, 1H), 4.74 (d, 1H), 3.97-3.80 (m, 2H), 3.34-3.20 (m, 1H), 2.95-2.67 (m, 5H), 2.15-2.01 (m, 1H), 1.89-1.78 (m, 1H), 1.75-1.66 (m, 1H), 1.63-1.53 (m, 1H), 1.47-1.36 (m, 1H), 1.07 (d, 3H), 1.03 (d, 3H)

Example 143. (S)-quinuclidin-3-yl (7-(2-butoxy-6-fluorophenyl)-3,3-dimethylchroman-4-yl)carbamate $^1$H-NMR (400 MHz, $CDCl_3$) δ 7.70-7.60 (m, 1H), 7.49-7.41 (m, 1H), 7.33-7.14 (m, 2H), 7.01-6.87 (m, 1H), 6.83-6.71 (m, 1H), 5.19-4.91 (m, 1H), 4.83-4.75 (m, 1H), 4.74-4.64 (m, 1H), 4.00-3.78 (m, 4H), 3.31-3.20 (m, 1H), 2.93-2.66 (m, 5H), 2.12-2.05 (m, 1H), 1.88-1.76 (m, 1H), 1.73-1.63 (m, 3H), 1.61-1.52 (m, 1H), 1.45-1.31 (m, 3H), 1.10-0.84 (m, 9H)

Example 144. (S)-quinuclidin-3-yl (3,3-dimethyl-7-(6-(2,2,2-trifluoroethoxy)pyridin-3-yl)chroman-4-yl)carbamate $^1$H-NMR (400 MHz, $CDCl_3$) δ 8.33 (s, 1H), 7.82 (d, 1H), 7.29 (dd, 1H), 7.09 (t, 1H), 6.98 (s, 1H), 6.92 (d, 1H), 4.90-4.68 (m, 5H), 3.92 (dd, 1H), 3.85 (dd, 1H), 3.34-3.22 (m, 1H), 2.95-2.69 (m, 5H), 2.13-2.06 (m, 1H), 1.88-1.79 (m, 1H), 1.74-1.66 (m, 1H), 1.64-1.54 (m, 1H), 1.48-1.38 (m, 1H), 1.07 (d, 3H), 1.03 (d, 3H)

Example 145. (S)-quinuclidin-3-yl (7-(6-methoxynaphthalen-2-yl)-3,3-dimethylchroman-4-yl)carbamate $^1$H-NMR (400 MHz, $CDCl_3$) δ 7.95 (s, 1H), 7.81-7.75 (m, 2H), 7.68 (d, 1H), 7.34-7.26 (m, 2H), 7.21-7.12 (m, 3H), 4.96 (t, 1H), 4.85-4.78 (m, 1H), 4.74 (d, 1H), 3.98-3.90 (m, 4H), 3.86 (dd, 1H), 3.34-3.21 (m, 1H), 2.95-2.68 (m, 5H), 2.16-2.06 (m, 1H), 1.90-1.80 (m, 1H), 1.75-1.67 (m, 1H), 1.64-1.55 (m, 1H), 1.48-1.38 (m, 1H), 1.08 (d, 3H), 1.04 (d, 3H)

Example 146. (S)-quinuclidin-3-yl (7-(4-ethoxy-3-(trifluoromethyl)phenyl)-3,3-dimethylchroman-4-yl) carbamate $^1$H-NMR (400 MHz, $CDCl_3$) δ 7.76 (s, 1H), 7.66 (d, 1H), 7.27 (dd, 1H), 7.11 (t, 1H), 7.04 (d, 1H), 7.00 (s, 1H), 4.89-4.77 (m, 2H), 4.72 (d, 1H), 4.17 (q, 2H), 3.92 (dd, 1H), 3.85 (dd, 1H), 3.34-3.22 (m, 1H), 2.96-2.69 (m, 5H), 2.14-2.05 (m, 1H), 1.88-1.79 (m, 1H), 1.76-1.68 (m, 1H), 1.63-1.54 (m, 1H), 1.47 (t, 3H), 1.43-1.36 (m, 1H), 1.07 (d, 3H), 1.03 (d, 3H)

Example 147. (S)-quinuclidin-3-yl (7-(benzofuran-3-yl)-3,3-dimethylchroman-4-yl)carbamate $^1$H-NMR (400 MHz, $CDCl_3$) δ 7.84 (d, 1H), 7.78 (s, 1H), 7.54 (d, 1H), 7.39-7.27 (m, 3H), 7.21 (t, 1H), 7.12 (s, 1H), 4.94 (t, 1H), 4.85-4.78 (m, 1H), 4.73 (d, 1H), 3.94-3.84 (m, 2H), 3.35-3.21 (m, 1H), 2.96-2.68 (m, 5H), 2.14-2.06 (m, 1H), 1.90-1.79 (m, 1H), 1.75-1.66 (m, 1H), 1.64-1.55 (m, 1H), 1.47-1.38 (m, 1H), 1.08 (d, 3H), 1.04 (d, 3H)

Example 148. (S)-quinuclidin-3-yl (7-(3-(dimethylamino)phenyl)-3,3-dimethylchroman-4-yl)carbamate $^1$H-NMR (400 MHz, $CDCl_3$) δ 7.33-7.22 (m, 2H), 7.17 (t, 1H), 7.06 (s, 1H), 6.94-6.86 (m, 2H), 6.74 (d, 1H), 4.94 (t, 1H), 4.83-4.77 (m, 1H), 4.71 (d, 1H), 3.92-3.82 (m, 2H), 3.31-3.22 (m, 1H), 2.99 (s, 6H), 2.91-2.68 (m, 5H), 2.13-2.06 (m, 1H), 1.88-1.79 (m, 1H), 1.74-1.66 (m, 1H), 1.62-1.54 (m, 1H), 1.46-1.37 (m, 1H), 1.07 (d, 3H), 1.03 (d, 3H)

Example 149. (S)-quinuclidin-3-yl (7-(2,2-difluorobenzo[d][1,3]dioxol-5-yl)-3,3-dimethylchroman-4-yl)carbamate $^1$H-NMR (400 MHz, $CDCl_3$) δ 7.31-7.21 (m, 3H), 7.12-7.03 (m, 2H), 6.96 (s, 1H), 4.91 (t, 1H), 4.83-4.76 (m, 1H), 4.72 (d, 1H), 3.93-3.83 (m, 2H), 3.33-3.20 (m, 1H), 2.95-2.67 (m, 5H), 2.14-2.06 (m, 1H), 1.88-1.78 (m, 1H), 1.75-1.66 (m, 1H), 1.63-1.53 (m, 1H), 1.46-1.36 (m, 1H), 1.06 (d, 3H), 1.02 (d, 3H)

Example 150. (S)-quinuclidin-3-yl (7-(2,5-dichlorophenyl)-3,3-dimethylchroman-4-yl)carbamate $^1$H-NMR (400 MHz, $CDCl_3$) δ 7.37 (d, 1H), 7.31 (s, 1H), 729-7.21 (m, 2H), 6.97 (t, 1H), 6.87 (s, 1H), 5.05 (t, 1H), 4.83-4.77 (m, 1H), 4.73 (d, 1H), 3.93-3.82 (m, 2H), 3.33-3.18 (m, 1H), 2.94-2.66 (m, 5H), 2.14-2.05 (m, 1H), 1.88-1.77 (m, 1H), 1.75-1.64 (m, 1H), 1.62-1.53 (m, 1H), 1.46-1.35 (m, 1H), 1.06 (d, 3H), 1.02 (d, 3H)

Example 151. (S)-quinuclidin-3-yl (7-(3-isopropylphenyl)-3,3-dimethylchroman-4-yl)carbamate $^1$H-NMR (400 MHz, $CDCl_3$) δ 7.41 (s, 1H), 7.40-7.33 (m, 2H), 7.30-7.21 (m, 2H), 7.17 (t, 1H), 7.06 (s, 1H), 4.91 (t, 1H), 4.83-4.77 (m, 1H), 4.72 (d, 1H), 3.93-3.83 (m, 2H), 3.34-3.22 (m, 1H), 3.00-2.93 (m, 1H), 2.91-2.70 (m, 5H), 2.14-2.07 (m, 1H), 1.89-1.79 (m, 1H), 1.75-1.67 (m, 1H), 1.63-1.54 (m, 1H), 1.48-1.38 (m, 1H), 1.30 (d, 6H), 1.07 (d, 3H), 1.03 (d, 3H)

Example 152. (S)-quinuclidin-3-yl (7-(3-(tert-butyl)phenyl)-3,3-dimethylchroman-4-yl)carbamate $^1$H-NMR (400 MHz, $CDCl_3$) δ 7.58 (s, 1H), 7.42-7.34 (m, 3H), 7.27 (dd, 1H), 7.15 (t, 1H), 7.06 (s, 1H), 4.93 (t, 1H), 4.84-4.77 (m, 1H), 4.72 (d, 1H), 3.93-3.83 (m, 2H), 3.35-3.21 (m, 1H), 2.94-2.67 (m, 5H), 2.14-2.07 (m, 1H), 1.88-1.78 (m, 1H), 1.76-1.66 (m, 1H), 1.63-1.54 (m, 1H), 1.47-1.40 (m, 1H), 1.37 (s, 9H), 1.07 (d, 3H), 1.03 (d, 3H)

Example 153. (S)-quinuclidin-3-yl (7-(2-chloro-5-methoxyphenyl)-3,3-dimethylchroman-4-yl)carbamate $^1$H-NMR (400 MHz, $CDCl_3$) δ 7.34 (d, 1H), 7.29-7.21 (m, 1H), 7.01 (t, 1H), 6.90 (s, 1H), 6.87-6.78 (m, 2H), 5.06 (t, 1H), 4.83-4.75 (m, 1H), 4.72 (d, 1H), 3.94-3.82 (m, 2H), 3.79 (s, 3H), 3.31-3.20 (m, 1H), 2.92-2.65 (m, 5H), 2.14-2.06 (m, 1H), 1.88-1.78 (m, 1H), 1.75-1.66 (m, 1H), 1.62-1.53 (m, 1H), 1.46-1.36 (m, 1H), 1.07 (d, 3H), 1.03 (d, 3H)

Example 154. (S)-quinuclidin-3-yl (7-([1,1'-biphenyl]-3-yl)-3,3-dimethylchroman-4-yl)carbamate $^1$H-NMR (400 MHz, $CDCl_3$) δ 7.79 (s, 1H), 7.65-7.63 (m, 2H), 7.59-7.43 (m, 5H), 7.37 (t, 1H), 7.33-7.19 (m, 2H), 7.12 (s, 1H), 4.99 (t, 1H), 4.85-4.78 (m, 1H), 4.73 (d, 1H), 3.94-3.83 (m, 2H), 3.35-3.21 (m, 1H), 2.95-2.69 (m, 5H), 2.16-2.07 (m, 1H), 1.90-1.79 (m, 1H), 1.76-1.66 (m, 1H), 1.63-1.54 (m, 1H), 1.47-1.37 (m, 1H), 1.08 (d, 3H), 1.04 (d, 3H)

Example 155. (S)-quinuclidin-3-yl (7-(isoquinolin-4-yl)-3,3-dimethylchroman-4-yl)carbamate $^1$H-NMR (400 MHz, $CDCl_3$) δ 9.22 (s, 1H), 8.30 (s, 1H), 8.02 (d, 1H), 7.93 (d, 1H), 7.70-7.58 (m, 2H), 7.35 (dd, 1H), 7.05 (t, 1H), 6.96 (s, 1H), 5.59 (t, 1H), 4.86-4.72 (m, 2H), 3.96-3.87 (m, 2H), 3.34-3.22 (m, 1H), 2.95-2.67 (m, 5H), 2.16-2.08 (m, 1H), 1.90-1.79 (m, 1H), 1.76-1.67 (m, 1H), 1.63-1.55 (m, 1H), 1.47-1.37 (m, 1H), 1.11 (d, 3H), 1.06 (d, 3H)

Example 156. (S)-quinuclidin-3-yl (7-(2-fluorophenyl)-3,3-dimethylchroman-4-yl)carbamate $^1$H-NMR (400 MHz, $CDCl_3$) δ 7.41 (t, 1H), 7.34-7.25 (m, 2H), 7.22-7.09 (m, 3H), 7.02 (s, 1H), 4.90 (t, 1H), 4.83-4.7 (m, 1H), 4.72 (d, 1H), 3.93-3.82 (m, 2H), 3.35-3.20 (m, 1H), 2.95-2.67 (m, 5H), 2.14-2.06 (m, 1H), 1.88-1.78 (m, 1H), 1.75-1.66 (m, 1H), 1.63-1.54 (m, 1H), 1.48-1.37 (m, 1H), 1.07 (d, 3H), 1.03 (d, 3H)

Example 157. (S)-quinuclidin-3-yl (3,3-dimethyl-7-(2-(trifluoromethoxy)phenyl)chroman-4-yl)carbamate $^1$H-NMR (400 MHz, $CDCl_3$) δ 7.43-7.30 (m, 4H), 7.28-7.20 (m, 1H), 7.02 (t, 1H), 6.92 (s, 1H), 5.06 (t, 1H), 4.84-4.77 (m, 1H), 4.73 (d, 1H), 3.93-3.82 (m, 2H), 3.32-3.19 (m, 1H), 2.95-2.67 (m, 5H), 2.19-2.06 (m, 1H), 1.90-

1.79 (m, 1H), 1.76-1.66 (m, 1H), 1.63-1.53 (m, 1H), 1.47-1.36 (m, 1H), 1.06 (d, 3H), 1.02 (d, 3H)

Example 158. (S)-quinuclidin-3-yl (7-(3-ethoxyphenyl)-3,3-dimethylchroman-4-yl)carbamate $^1$H-NMR (400 MHz, $CDCl_3$) δ 7.32 (t, 1H), 7.28-7.22 (m, 1H), 7.19-7.11 (m, 2H), 7.09 (s, 1H), 7.04 (s, 1H), 6.88 (dd, 1H), 4.95 (t, 1H), 4.83-4.77 (m, 1H), 4.71 (d, 1H), 4.08 (q, 2H), 3.92-3.82 (m, 2H), 3.30-3.20 (m, 1H), 2.94-2.66 (m, 5H), 2.16-2.06 (m, 1H), 1.89-1.79 (m, 1H), 1.75-1.66 (m, 1H), 1.63-1.53 (m, 1H), 1.48-1.36 (m, 4H), 1.06 (d, 3H), 1.02 (d, 3H)

Example 159. (S)-quinuclidin-3-yl (3,3-dimethyl-7-(1-methyl-1H-indazol-4-yl)chroman-4-yl)carbamate $^1$H-NMR (400 MHz, $CDCl_3$) δ 8.12 (s, 1H), 7.44 (t, 1H), 7.39-7.30 (m, 2H), 7.29-7.23 (m, 1H), 7.20 (d, 1H), 7.15 (s, 1H), 5.22 (dd, 1H), 4.85-4.79 (m, 1H), 4.75 (d, 1H), 4.05 (s, 3H), 3.97-3.83 (m, 2H), 3.34-3.21 (m, 1H), 2.92-2.66 (m, 5H), 2.15-2.05 (m, 1H), 1.87-1.79 (m, 1H), 1.74-1.66 (m, 1H), 1.62-1.54 (m, 1H), 1.46-1.37 (m, 1H), 1.09 (d, 3H), 1.05 (d, 3H)

Example 160. (S)-quinuclidin-3-yl (7-(isoquinolin-8-yl)-3,3-dimethylchroman-4-yl)carbamate $^1$H-NMR (400 MHz, $CDCl_3$) δ 9.32 (d, 1H), 8.45-8.36 (m, 1H), 7.81 (d, 1H), 7.75-7.64 (m, 2H), 7.49 (dd, 1H), 7.34 (t, 1H), 7.05 (dd, 1H), 6.98 (d, 1H), 6.04-5.87 (m, 1H), 4.90-4.71 (m, 2H), 3.98-3.82 (m, 2H), 3.33-3.18 (m, 1H), 2.93-2.65 (m, 5H), 2.21-2.06 (m, 1H), 1.91-1.77 (m, 1H), 1.75-1.66 (m, 1H), 1.62-1.55 (m, 1H), 1.45-1.36 (m, 1H), 1.10-1.06 (m, 6H)

Example 161. (S)-quinuclidin-3-yl (7-(4-cyclopropylphenyl)-3,3-dimethylchroman-4-yl)carbamate $^1$H-NMR (400 MHz, $CDCl_3$) δ 7.46 (d, 2H), 7.29-7.21 (m, 1H), 7.18-7.09 (m, 3H), 7.03 (s, 1H), 4.96 (t, 1H), 4.83-4.75 (m, 1H), 4.70 (d, 1H), 3.91-3.81 (m, 2H), 3.33-3.20 (m, 1H), 2.94-2.68 (m, 5H), 2.13-2.06 (m, 1H), 1.98-1.89 (m, 1H), 1.87-1.78 (m, 1H), 1.75-1.65 (m, 1H), 1.63-1.54 (m, 1H), 1.47-1.36 (m, 1H), 1.10-0.94 (m, 8H), 0.75-0.71 (m, 2H)

Example 162. (S)-quinuclidin-3-yl (7-(2-methoxyphenyl)-3,3-dimethylchroman-4-yl)carbamate $^1$H-NMR (400 MHz, $CDCl_3$) δ 7.35 (m, 3H), 7.11 (t, 1H), 7.05-6.95 (m, 3H), 4.94-4.86 (m, 1H), 4.83-4.76 (m, 1H), 4.71-4.69 (d, 1H), 3.93-3.87 (m, 1H), 3.85-3.77 (m, 4H), 3.32-3.21 (m, 1H), 2.94-2.68 (m, 5H), 2.13-2.06 (m, 1H), 1.88-1.79 (m, 1H), 1.75-1.66 (m, 1H), 1.63-1.54 (m, 1H), 1.47-1.37 (m, 1H), 1.07 (d, 3H), 1.03 (d, 3H)

Example 163. (S)-quinuclidin-3-yl (3',3'-dimethyl-[6,7'-bichroman]-4'-yl)carbamate $^1$H-NMR (400 MHz, $CDCl_3$) δ 7.32-7.18 (m, 3H), 7.10 (t, 1H), 6.99 (s, 1H), 6.84 (d, 1H), 4.89 (t, 1H), 4.83-4.76 (m, 1H), 4.69 (d, 1H), 4.21 (t, 2H), 3.91-3.81 (m, 2H), 3.32-3.20 (m, 1H), 2.94-2.67 (m, 7H), 2.13-2.00 (m, 3H), 1.88-1.78 (m, 1H), 1.74-1.66 (m, 1H), 1.63-1.54 (m, 1H), 1.46-1.36 (m, 1H), 1.06 (d, 3H), 1.02 (d, 3H)

Example 164. (S)-quinuclidin-3-yl (7-(3-chloro-5-(trifluoromethyl)phenyl)-3,3-dimethylchroman-4-yl) carbamate $^1$H-NMR (400 MHz, $CDCl_3$) δ 7.72-7.65 (m, 2H), 7.57 (s, 1H), 7.38-7.29 (m, 1H), 7.12 (t, 1H), 7.02 (s, 1H), 4.92 (t, 1H), 4.84-4.78 (m, 1H), 4.74 (d, 1H), 3.98-3.81 (m, 2H), 3.34-3.22 (m, 1H), 2.94-2.69 (m, 5H), 2.15-2.07 (m, 1H), 1.88-1.79 (m, 1H), 1.75-1.67 (m, 1H), 1.63-1.54 (m, 1H), 1.48-1.38 (m, 1H), 1.07 (d, 3H), 1.02 (d, 3H)

Example 165. (S)-quinuclidin-3-yl (3,3-dimethyl-7-(quinolin-8-yl)chroman-4-yl)carbamate $^1$H-NMR (400 MHz, $CDCl_3$) δ 8.98-8.93 (m, 1H), 8.21 (d, 1H), 7.84 (d, 1H), 7.72 (d, 1H), 7.59 (t, 1H), 7.42 (dd, 1H), 7.10-7.02 (m, 2H), 6.99 (s, 1H), 4.92-4.72 (m, 2H), 4.63 (d, 1H), 3.95-3.75 (m, 2H), 3.33-3.20 (m, 1H), 2.95-2.67 (m, 5H), 2.13-2.04 (m, 1H), 1.87-1.77 (m, 1H), 1.74-1.66 (m, 1H), 1.62-1.54 (m, 1H), 1.46-1.36 (m, 1H), 1.02 (d, 3H), 0.98 (d, 3H)

Example 166. (S)-quinuclidin-3-yl (7-(3-methoxyphenyl)-3,3-dimethylchroman-4-yl)carbamate $^1$H-NMR (400 MHz, $CDCl_3$) δ 7.34 (t, 1H), 7.27 (t, 1H), 7.19-7.13 (m, 2H), 7.09 (s, 1H), 7.05 (s, 1H), 6.90 (dd, 1H), 4.89-4.77 (m, 2H), 4.72 (d, 1H), 3.95-3.80 (m, 5H), 3.34-3.23 (m, 1H), 2.95-2.68 (m, 5H), 2.15-2.05 (m, 1H), 1.90-1.79 (m, 1H), 1.74-1.67 (m, 1H), 1.63-1.54 (m, 1H), 1.47-1.38 (m, 1H), 1.07 (d, 3H), 1.03 (d, 3H)

Example 167. (S)-quinuclidin-3-yl (7-(3-chloro-4-isopropoxyphenyl)-3,3-dimethylchroman-4-yl)carbamate $^1$H-NMR (400 MHz, $CDCl_3$) δ 7.58 (s, 1H), 7.38 (d, 1H), 7.24 (dd, 1H), 7.09 (t, 1H), 7.02-6.95 (m, 2H), 4.89-4.77 (m, 2H), 4.71 (d, 1H), 4.62-4.56 (m, 1H), 3.92-3.82 (m, 2H), 3.33-3.23 (m, 1H), 2.95-2.67 (m, 5H), 2.14-2.04 (m, 1H), 1.89-1.81 (m, 1H), 1.76-1.67 (m, 1H), 1.63-1.54 (m, 1H), 1.47-1.36 (m, 7H), 1.06 (d, 3H), 1.02 (d, 3H)

Example 168. (S)-quinuclidin-3-yl (7-(2,6-dimethoxyphenyl)-3,3-dimethylchroman-4-yl)carbamate $^1$H-NMR (400 MHz, $CDCl_3$) δ 7.31-7.28 (m, 2H), 6.92 (t, 1H), 6.83 (s, 1H), 6.67-6.61 (m, 2H), 4.89 (t, 1H), 4.82-4.76 (m, 1H), 4.71 (d, 1H), 3.91-3.79 (m, 2H), 3.74 (s, 6H), 3.34-3.22 (m, 1H), 2.93-2.69 (m, 5H), 2.13-2.06 (m, 1H), 1.89-1.83 (m, 1H), 1.75-1.66 (m, 1H), 1.63-1.54 (m, 1H), 1.46-1.37 (m, 1H), 1.08 (d, 3H), 1.04 (d, 3H)

Example 169. (S)-quinuclidin-3-yl (7-(2-chlorophenyl)-3,3-dimethylchroman-4-yl)carbamate $^1$H-NMR (400 MHz, $CDCl_3$) δ 7.47-7.45 (m, 1H), 7.35-7.22 (m, 4H), 7.01 (t, 1H), 6.91 (s, 1H), 4.91 (t, 1H), 4.84-4.77 (m, 1H), 4.74 (d, 1H), 3.94-3.83 (m, 2H), 3.33-3.23 (m, 1H), 2.96-2.69 (m, 5H), 2.13-2.06 (m, 1H), 1.90-1.81 (m, 1H), 1.74-1.66 (m, 1H), 1.64-1.55 (m, 1H), 1.46-1.37 (m, 1H), 1.08 (d, 3H), 1.04 (d, 3H)

Example 170. (S)-quinuclidin-3-yl (7-(3-cyanophenyl)-3,3-dimethylchroman-4-yl)carbamate $^1$H-NMR (400 MHz, $CDCl_3$) δ 7.83 (s, 1H), 7.78 (d, 1H), 7.63 (d, 1H), 7.53 (t, 1H), 7.33-7.27 (m, 1H), 7.10 (dd, 1H), 7.01 (s, 1H), 4.93-4.78 (m, 2H), 4.74 (d, 1H), 3.95-3.84 (m, 2H), 3.34-3.23 (m, 1H), 2.95-2.69 (m, 5H), 2.14-2.06 (m, 1H), 1.88-1.80 (m, 1H), 1.74-1.66 (m, 1H), 1.63-1.55 (m, 1H), 1.48-1.38 (m, 1H), 1.07 (d, 3H), 1.03 (d, 3H)

Example 171. (S)-quinuclidin-3-yl (7-(3-(dimethylamino)-4-fluorophenyl)-3,3-dimethylchroman-4-yl) carbamate $^1$H-NMR (400 MHz, $CDCl_3$) δ 7.30-7.21 (m, 1H), 7.15-7.02 (m, 4H), 7.00 (s, 1H), 4.8-4.78 (m, 2H), 4.72 (d, 1H), 3.93-3.83 (m, 2H), 3.33-3.23 (m, 1H), 2.94-2.85 (m, 8H), 2.83-2.70 (m, 3H), 2.14-2.06 (m, 1H), 1.89-1.80 (m, 1H), 1.74-1.66 (m, 1H), 1.64-1.55 (m, 1H), 1.48-1.37 (m, 1H), 1.07 (d, 3H), 1.03 (d, 3H)

Example 172. (S)-quinuclidin-3-yl (7-(2,3-dihydrobenzo[b][1,4]dioxin-6-yl)-3,3-dimethylchroman-4-yl)carbamate $^1$H-NMR (400 MHz, $CDCl_3$) δ 7.26-7.19 (m, 1H), 7.13-7.03 (m, 3H), 6.99 (s, 1H), 6.91 (d, 1H), 4.86-4.77 (m, 2H), 4.70 (d, 1H), 4.29 (s, 4H), 3.92-3.81 (m, 2H), 3.33-3.23 (m, 1H), 2.95-2.68 (m, 5H), 2.14-2.06 (m, 1H), 1.90-1.79 (m, 1H), 1.77-1.67 (m, 1H), 1.64-1.55 (m, 1H), 1.48-1.37 (m, 1H), 1.06 (d, 3H), 1.02 (d, 3H)

Example 173. (S)-quinuclidin-3-yl (7-(1H-indol-7-yl)-3,3-dimethylchroman-4-yl)carbamate $^1$H-NMR (400 MHz, $CDCl_3$) δ 8.75 (brs, 1H), 7.69-7.61 (m, 1H), 7.37-7.15 (m, 5H), 7.11 (s, 1H), 6.61 (s, 1H), 5.18-5.05 (m, 1H), 4.85-4.65 (m, 2H), 3.96-3.80 (m, 2H), 3.30-3.16 (m, 1H), 2.92-2.64 (m, 5H), 2.15-2.07 (m, 1H), 1.87-1.78 (m, 1H), 1.75-1.65 (m, 1H), 1.63-1.54 (m, 1H), 1.48-1.37 (m, 1H), 1.09 (d, 3H), 1.05 (d, 3H)

Example 174. (S)-quinuclidin-3-yl (7-(4-isopropylphenyl)-3,3-dimethylchroman-4-yl)carbamate $^1$H-NMR (400 MHz, $CDCl_3$) δ 7.50 (m, 2H), 7.32-7.23 (m, 3H), 7.15 (t, 1H), 7.04 (s, 1H), 4.86 (t, 1H), 4.83-4.78 (m, 1H), 4.72 (d, 1H), 3.93-3.82 (m, 2H), 3.34-3.23 (m, 1H), 3.00-2.69 (m, 6H), 2.14-2.06 (m, 1H), 1.88-1.79 (m, 1H), 1.75-1.67 (m, 1H), 1.63-1.55 (m, 1H), 1.46-1.37 (m, 1H), 1.29 (d, 6H), 1.07 (d, 3H), 1.03 (d, 3H)

Example 175. (S)-quinuclidin-3-yl (7-(4-fluoro-3-(trifluoromethyl)phenyl)-3,3-dimethylchroman-4-yl) carbamate $^1$H-NMR (400 MHz, $CDCl_3$) δ 7.76 (d, 1H), 7.73-7.67 (m, 1H), 7.33-7.21 (m, 2H), 7.01 (t, 1H), 6.99 (s, 1H), 4.88 (t, 1H), 4.83-4.77 (m, 1H), 4.73 (d, 1H), 3.94-3.84 (m, 2H), 3.35-3.22 (m, 1H), 2.96-2.67 (m, 5H), 2.14-2.05 (m, 1H), 1.88-1.79 (m, 1H), 1.76-1.67 (m, 1H), 1.63-1.54 (m, 1H), 1.47-1.38 (m, 1H), 1.07 (d, 3H), 1.03 (d, 3H)

Example 176. (S)-quinuclidin-3-yl (7-(2-chloro-3-methoxyphenyl)-3,3-dimethylchroman-4-yl)carbamate $^1$H-NMR (400 MHz, $CDCl_3$) δ 7.30-7.21 (m, 2H), 7.00 (t, 1H), 6.97-6.91 (m, 2H), 6.89 (s, 1H), 4.97-4.89 (m, 1H), 4.83-4.77 (m, 1H), 4.73 (d, 1H), 3.98-3.82 (m, 5H), 3.33-3.21 (m, 1H), 2.94-2.68 (m, 5H), 2.12-2.06 (m, 1H), 1.89-1.80 (m, 1H), 1.75-1.65 (m, 1H), 1.53-1.53 (m, 1H), 1.47-1.37 (m, 1H), 1.07 (d, 3H), 1.04 (d, 3H)

Example 177. (S)-quinuclidin-3-yl (7-(4-chloro-3-methoxyphenyl)-3,3-dimethylchroman-4-yl)carbamate $^1$H-NMR (400 MHz, $CDCl_3$) δ 7.40 (d, 1H), 7.30-7.25 (m, 1H), 7.18-7.06 (m, 3H), 7.02 (s, 1H), 4.89-4.78 (m, 2H), 4.73 (d, 1H), 3.99-3.84 (m, 5H), 3.35-3.23 (m, 1H), 2.95-2.70 (m, 5H), 2.14-2.06 (m, 1H), 1.89-1.79 (m, 1H), 1.74-1.66 (m, 1H), 1.63-1.55 (m, 1H), 1.47-1.38 (m, 1H), 1.07 (d, 3H), 1.03 (d, 3H)

Example 178. (S)-quinuclidin-3-yl (7-(1H-indazol-7-yl)-3,3-dimethylchroman-4-yl)carbamate $^1$H-NMR (400 MHz, $CDCl_3$) δ 8.10 (s, 1H), 7.73 (d, 1H), 7.39-7.31 (m, 2H), 7.25-7.16 (m, 2H), 7.09 (s, 1H), 5.43 (dd, 1H), 4.83-4.71 (m, 2H), 3.96-3.82 (m, 2H), 3.22-3.00 (m, 1H), 2.89-2.48 (m, 5H), 2.17-2.06 (m, 1H), 1.85-1.77 (m, 1H), 1.73-1.65 (m, 1H), 1.61-1.51 (m, 1H), 1.46-1.36 (m, 1H), 1.08 (d, 3H), 1.04 (d, 3H)

Example 179. (S)-quinuclidin-3-yl (7-(3,5-dichlorophenyl)-3,3-dimethylchroman-4-yl)carbamate $^1$H-NMR (400 MHz, $CDCl_3$) δ 7.50-7.38 (m, 2H), 7.34-7.25 (m, 2H), 7.12-7.04 (m, 1H), 6.98 (s, 1H), 4.91-4.78 (m, 2H), 4.74 (t, 1H), 3.97-3.82 (m, 2H), 3.35-3.20 (m, 1H), 2.96-2.67 (m, 5H), 2.15-2.07 (m, 1H), 1.89-1.79 (m, 1H), 1.77-1.67 (m, 1H), 1.64-1.55 (m, 1H), 1.49-1.37 (m, 1H), 1.08-1.01 (m, 6H)

Example 180. (S)-quinuclidin-3-yl (7-(1-benzyl-1H-pyrazol-4-yl)-3,3-dimethylchroman-4-yl)carbamate $^1$H-NMR (400 MHz, $CDCl_3$) δ 7.78 (s, 1H), 7.58 (s, 1H), 7.40-7.30 (m, 3H), 7.28-7.22 (m, 2H), 7.16 (dd, 1H), 7.02 (t, 1H), 6.91 (s, 1H), 5.33 (s, 2H), 4.85-4.75 (m, 2H), 4.66 (d, 1H), 3.89-3.79 (m, 2H), 3.33-3.21 (m, 1H), 2.94-2.69 (m, 5H), 2.14-2.04 (m, 1H), 1.87-1.77 (m, 1H), 1.74-1.66 (m, 1H), 1.62-1.54 (m, 1H), 1.46-1.36 (m, 1H), 1.04 (d, 3H), 1.00 (d, 3H)

Example 181. (S)-quinuclidin-3-yl (7-(2,3-dihydrobenzofuran-5-yl)-3,3-dimethylchroman-4-yl)carbamate $^1$H-NMR (400 MHz, $CDCl_3$) δ 7.40 (s, 1H), 7.32 (d, 1H), 7.26-7.19 (m, 1H), 7.10 (t, 1H), 6.98 (s, 1H), 6.83 (d, 1H), 4.90-4.7 (m, 2H), 4.70 (d, 1H), 4.61 (t, 2H), 3.92-3.81 (m, 2H), 3.33-3.21 (m, 3H), 2.95-2.69 (m, 5H), 2.13-2.05 (m, 1H), 1.89-1.81 (m, 1H), 1.74-1.66 (m, 1H), 1.63-1.55 (m, 1H), 1.48-1.37 (m, 1H), 1.06 (d, 3H), 1.02 (d, 3H)

Example 182. (S)-quinuclidin-3-yl (7-(6-(cyclopropylmethoxy)pyridin-3-yl)-3,3-dimethylchroman-4-yl)carbamate $^1$H-NMR (400 MHz, $CDCl_3$) δ 8.33 (s, 1H), 7.75 (d, 1H), 7.32-7.22 (m, 1H), 7.09 (t, 1H), 6.98 (s, 1H), 6.83 (d, 1H), 4.88-4.77 (m, 2H), 4.72 (d, 1H), 4.17 (d, 2H), 3.93-3.83 (m, 2H), 3.36-3.23 (m, 1H), 2.95-2.68 (m, 5H), 2.13-2.06 (m, 1H), 1.88-1.80 (m, 1H), 1.74-1.66 (m, 1H), 1.63-1.54 (m, 1H), 1.47-1.38 (m, 1H), 1.36-1.25 (m, 1H), 1.07 (d, 3H), 1.03 (d, 3H), 0.68-0.59 (m, 2H), 0.41-0.32 (m, 2H)

Example 183. (S)-quinuclidin-3-yl (7-(benzofuran-2-yl)-3,3-dimethylchroman-4-yl)carbamate $^1$H-NMR (400 MHz, $CDCl_3$) δ 7.58 (d, 1H), 7.51 (d, 1H), 7.43 (t, 1H), 7.34-7.20 (m, 4H), 7.00 (s, 1H), 4.87 (t, 1H), 4.83-4.78 (m, 1H), 4.72 (d, 1H), 3.95-3.84 (m, 2H), 3.34-3.23 (m, 1H), 2.95-2.69 (m, 5H), 2.14-2.07 (m, 1H), 1.90-1.82 (m, 1H), 1.75-1.67 (m, 1H), 1.64-1.55 (m, 1H), 1.48-1.38 (m, 1H), 1.07 (d, 3H), 1.03 (d, 3H)

Example 184. (S)-quinuclidin-3-yl (3,3-dimethyl-7-(3-(pyrrolidin-1-ylsulfonyl)phenyl)chroman-4-yl) carbamate $^1$H-NMR (400 MHz, $CDCl_3$) δ 8.01 (s, 1H), 7.80-7.76 (m, 2H), 7.58 (t, 1H), 7.35-7.25 (m, 1H), 7.17 (t, 1H), 7.07 (s, 1H), 4.88 (t, 1H), 4.83-4.78 (m, 1H), 4.74 (d, 1H), 3.95-3.85 (m, 2H), 3.32-3.22 (m, 5H), 2.93-2.69 (m, 5H), 2.14-2.06 (m, 1H), 1.89-1.67 (m, 6H), 1.63-1.56 (m, 1H), 1.48-1.38 (m, 1H), 1.07 (d, 3H), 1.03 (d, 3H)

Example 185. (S)-quinuclidin-3-yl (3,3-dimethyl-7-(2-(trifluoromethyl)phenyl)chroman-4-yl)carbamate $^1$H-NMR (400 MHz, $CDCl_3$) δ 7.72 (d, 1H), 7.54 (t, 1H), 7.45 (t, 1H), 7.31 (d, 1H), 7.21 (dd, 1H), 6.88 (t, 1H), 6.78 (s, 1H), 5.17 (t, 1H), 4.83-4.76 (m, 1H), 4.74 (d, 1H), 3.92-3.82 (m, 2H), 3.30-3.19 (m, 1H), 2.93-2.67 (m, 5H), 2.12-2.05 (m, 1H), 1.89-1.79 (m, 1H), 1.75-1.65 (m, 1H), 1.62-1.54 (m, 1H), 1.46-1.36 (m, 1H), 1.06 (d, 3H), 1.02 (d, 3H)

Example 186. (S)-quinuclidin-3-yl (7-(2-ethoxyphenyl)-3,3-dimethylchroman-4-yl)carbamate $^1$H-NMR (400 MHz, $CDCl_3$) δ 7.35-7.27 (m, 2H), 7.22 (t, 1H), 7.19-7.13 (m, 1H), 7.05-6.94 (m, 3H), 4.93 (t, 1H), 4.83-4.77 (m, 1H), 4.71 (d, 1H), 4.09-4.04 (q, 2H), 3.91-3.80 (m, 2H), 3.36-3.21 (m, 1H), 2.94-2.70 (m, 5H), 2.14-2.06 (m, 1H), 1.88-1.79 (m, 1H), 1.75-1.66 (m, 1H), 1.63-1.53 (m, 1H), 1.46-1.36 (m, 4H), 1.07 (d, 3H), 1.03 (d, 3H)

Example 187. (S)-quinuclidin-3-yl (3,3-dimethyl-7-(thiophen-3-yl)chroman-4-yl)carbamate $^1$H-NMR (400 MHz, $CDCl_3$) δ 7.44 (s, 1H), 7.40-7.34 (m, 2H), 7.26-7.15 (m, 2H), 7.06 (s, 1H), 4.89-4.77 (m, 2H), 4.70 (d, 1H), 3.92-3.82 (m, 2H), 3.35-3.20 (m, 1H), 2.94-2.69 (m, 5H), 2.14-2.05 (m, 1H), 1.89-1.83 (m, 1H), 1.81-1.75 (m, 1H), 1.66-1.55 (m, 1H), 1.48-1.37 (m, 1H), 1.06 (d, 3H), 1.02 (d, 3H)

Example 188. (S)-quinuclidin-3-yl (7-(4-methoxy-3-(trifluoromethyl)phenyl)-3,3-dimethylchroman-4-yl)carbamate $^1$H-NMR (400 MHz, $CDCl_3$) δ 7.76 (s, 1H), 7.68 (d, 1H), 7.32-7.22 (m, 1H), 7.15-7.04 (m, 2H), 7.00 (s, 1H), 4.87-4.77 (m, 1H), 4.72 (d, 1H), 3.98-3.83 (m, 5H), 3.35-3.23 (m, 1H), 2.94-2.70 (m, 5H), 2.14-2.06 (m, 1H), 1.89-1.79 (m, 1H), 1.74-1.68 (m, 1H), 1.64-1.54 (m, 1H), 1.47-1.36 (m, 1H), 1.07 (d, 3H), 1.03 (d, 3H)

Example 189. (S)-quinuclidin-3-yl (7-(2-cyanophenyl)-3,3-dimethylchroman-4-yl)carbamate $^1$H-NMR (400 MHz, $CDCl_3$) δ 7.75 (d, 1H), 7.63 (t, 1H), 7.51-7.41 (m, 2H), 7.36-7.28 (m, 1H), 7.13 (d, 1H), 6.98 (s, 1H), 5.08-4.99 (m, 1H), 4.83-4.77 (m, 1H), 4.74 (d, 1H), 3.94-3.84 (m, 2H), 3.32-3.22 (m, 1H), 2.92-2.68 (m, 5H), 2.14-2.06 (m, 1H), 1.90-1.80 (m, 1H), 1.76-1.67 (m, 1H), 1.62-1.54 (m, 1H), 1.46-1.37 (m, 1H), 1.07 (d, 3H), 1.03 (d, 3H)

Example 190. (S)-quinuclidin-3-yl (7-(3,4-dihydro-2H-benzo[b][1,4]dioxepin-7-yl)-3,3-dimethylchroman-4-yl)carbamate $^1$H-NMR (400 MHz, $CDCl_3$) δ 7.29-7.17 (m, 2H), 7.16-7.06 (m, 2H), 7.03-6.95 (m, 2H), 4.91 (t, 1H), 4.83-4.75 (m, 1H), 4.70 (d, 1H), 4.30-4.20 (m, 4H), 3.91-3.81 (m, 2H), 3.31-3.21 (m, 1H), 2.93-2.67 (m, 5H), 2.23-2.20 (m, 2H), 2.23-2.20 (m, 2H), 2.13-2.06 (m, 1H), 1.88-1.79 (m, 1H), 1.74-1.66 (m, 1H), 1.62-1.54 (m, 1H), 1.46-1.37 (m, 1H), 1.06 (d, 3H), 1.01 (d, 3H)

Example 191. (S)-quinuclidin-3-yl (7-(benzo[c][1,2,5]thiadiazol-5-yl)-3,3-dimethylchroman-4-yl)carbamate $^1$H-NMR (400 MHz, $CDCl_3$) δ 8.11 (s, 1H), 8.02 (d, 1H), 7.83 (d, 1H), 7.35-7.30 (m, 1H), 7.27-7.24 (m, 1H), 7.14 (s, 1H), 5.06 (t, 1H), 4.84-4.78 (m, 1H), 4.74 (d, 1H), 3.95-3.85 (m, 2H), 3.33-3.21 (m, 1H), 2.93-2.68 (m, 5H), 2.16-2.06 (m, 1H), 1.88-1.79 (m, 1H), 1.74-1.66 (m, 1H), 1.62-1.54 (m, 1H), 1.47-1.37 (m, 1H), 1.07 (d, 3H), 1.03 (d, 3H)

Example 192. (S)-quinuclidin-3-yl (7-(isoquinolin-4-yl)-3,3-dimethylchroman-4-yl)carbamate $^1$H-NMR (400 MHz, $CDCl_3$) δ 9.03 (s, 1H), 8.25 (s, 1H), 8.13 (d, 1H), 7.86 (d, 1H), 7.71 (t, 1H), 7.57 (t, 1H), 7.35 (dd, 1H), 7.28-7.24 (m, 1H), 7.14 (s, 1H), 5.38-5.35 (m, 1H), 4.86-4.79 (m, 1H), 4.75 (d, 1H), 3.93-3.84 (m, 2H), 3.32-3.22 (m, 1H), 2.93-2.67 (m, 5H), 2.15-2.07 (m, 1H), 1.87-1.77 (m, 1H), 1.74-1.65 (m, 1H), 1.63-1.54 (m, 1H), 1.45-1.35 (m, 1H), 1.08 (d, 3H), 1.03 (d, 3H)

Example 193. (S)-quinuclidin-3-yl (7-(4-(tert-butyl) phenyl)-3,3-dimethylchroman-4-yl)carbamate $^1$H-NMR (400 MHz, $CDCl_3$) δ 7.52-7.50 (m, 2H), 7.46-7.44 (m, 2H), 7.30-7.22 (m, 1H), 7.16 (t, 1H), 7.05 (s, 1H), 4.98 (t, 1H), 4.83-4.76 (m, 1H), 4.71 (d, 1H), 3.92-3.82 (m, 2H), 3.32-3.21 (m, 1H), 2.95-2.67 (m, 5H), 2.13-2.06 (m, 1H), 1.88-1.78 (m, 1H), 1.75-1.66 (m, 1H), 1.63-1.55 (m, 1H), 1.47-1.38 (m, 1H), 1.36 (s, 9H), 1.07 (d, 3H), 1.03 (d, 3H)

Example 194. (S)-quinuclidin-3-yl (3,3-dimethyl-7-(3-methyl-4-morpholinophenyl)chroman-4-yl)carbamate $^1$H-NMR (400 MHz, $CDCl_3$) δ 7.43-7.34 (m, 2H), 7.28-7.19 (m, 1H), 7.12 (t, 1H), 7.07-6.99 (m, 2H), 5.03 (t, 1H), 4.83-4.75 (m, 1H), 4.70 (d, 1H), 3.87-3.85 (m, 6H), 3.33-3.20 (m, 1H), 2.94-2.92 (m, 4H), 2.90-2.66 (m, 5H), 2.36 (s, 3H), 2.14-2.05 (m, 1H), 1.88-1.78 (m, 1H), 1.75-1.65 (m, 1H), 1.62-1.53 (m, 1H), 1.46-1.36 (m, 1H), 1.06 (d, 3H), 1.02 (d, 3H)

Example 195. (S)-quinuclidin-3-yl (7-(3,4-dichlorophenyl)-3,3-dimethylchroman-4-yl)carbamate $^1$H-NMR (400 MHz, $CDCl_3$) δ 7.65-7.60 (m, 1H), 7.54-7.44 (m, 2H), 7.40-7.34 (m, 1H), 7.31-7.21 (m, 1H), 6.98 (s, 1H), 4.96 (t, 1H), 4.83-4.76 (m, 1H), 4.72 (d, 1H), 3.93-3.82 (m, 2H), 3.32-3.21 (m, 1H), 2.92-2.68 (m, 5H), 2.13-2.05 (m, 1H), 1.88-1.78 (m, 1H), 1.74-1.66 (m, 1H), 1.62-1.54 (m, 1H), 1.45-1.37 (m, 1H), 1.06 (d, 3H), 1.02 (d, 3H)

Example 196. (S)-quinuclidin-3-yl (3,3-dimethyl-7-(1-methyl-1H-indazol-6-yl)chroman-4-yl)carbamate $^1$H-NMR (400 MHz, $CDCl_3$) δ 7.97 (s, 1H), 7.75 (d, 1H), 7.52 (s, 1H), 7.36 (d, 1H), 7.32-7.21 (m, 2H), 7.12 (s, 1H), 5.05 (t, 1H), 4.84-4.78 (m, 1H), 4.73 (d, 1H), 4.09 (s, 2H), 3.94-3.84 (m, 2H), 3.35-3.20 (m, 1H), 2096-2.67 (m, 5H), 2.15-2.06 (m, 1H), 1.89-1.78 (m, 1H), 1.75-1.65 (m, 1H), 1.64-1.55 (m, 1H), 1.45-1.36 (m, 1H), 1.07 (d, 3H), 1.03 (d, 3H)

Example 197. (S)-quinuclidin-3-yl (7-(1H-indol-6-yl)-3,3-dimethylchroman-4-yl)carbamate $^1$H-NMR (400 MHz, $CDCl_3$) δ 8.57 (d, 1H), 7.68 (d, 1H), 7.57 (s, 1H), 7.35 (d, 1H), 7.30-7.21 (m, 3H), 7.12 (s, 1H), 6.57 (s, 1H), 4.93 (t, 1H), 4.84-4.78 (m, 1H), 4.73 (d, 1H), 3.92-3.82 (m, 2H), 3.34-3.24 (m, 1H), 2.95-2.71 (m, 5H), 2.16-2.08 (m, 1H), 1.91-1.80 (m, 1H), 1.76-1.67 (m, 1H), 1.64-1.55 (m, 1H), 1.48-1.38 (m, 1H), 1.07 (d, 3H), 1.03 (d, 3H)

Example 198. (S)-quinuclidin-3-yl (3,3-dimethyl-7-(4-methyl-3,4-dihydro-2H-benzo[b][1,4]oxazin-7-yl)chroman-4-yl)carbamate $^1$H-NMR (400 MHz, $CDCl_3$) δ 7.20 (dd, 1H), 7.12-7.07 (m, 2H), 7.02 (s, 1H), 6.99 (s, 1H), 6.71 (d, 1H), 4.95 (t, 1H), 4.82-4.76 (m, 1H), 4.68 (d, 1H), 4.32 (t, 2H), 3.90-3.79 (m, 2H), 3.30-3.20 (m, 3H), 2.91 (s, 3H), 2.89-2.68 (m, 5H), 2.12-2.06 (m, 1H), 1.87-1.77 (m, 1H), 1.74-1.66 (m, 1H), 1.62-1.54 (m, 1H), 1.45-1.35 (m, 1H), 1.05 (d, 3H), 1.01 (d, 3H)

Example 199. (S)-quinuclidin-3-yl (7-(3-cyano-4-methylphenyl)-3,3-dimethylchroman-4-yl)carbamate $^1$H-NMR (400 MHz, $CDCl_3$) δ 7.75 (s, 1H), 7.64 (d, 1H), 7.35 (d, 1H), 7.28 (dd, 1H), 7.08 (t, 1H), 6.98 (s, 1H), 5.03 (t, 1H), 4.82-4.75 (m, 1H), 4.71 (d, 1H), 3.92-3.82 (m, 2H), 3.29-3.19 (m, 1H), 2.92-2.65 (m, 5H). 2.56 (s, 3H), 2.12-2.05 (m, 1H), 1.89-1.77 (m, 1H), 1.72-1.65 (m, 1H), 1.62-1.53 (m, 1H), 1.46-1.36 (m, 1H), 1.05 (d, 3H), 1.01 (d, 3H)

Example 200. (S)-quinuclidin-3-yl (3,3-dimethyl-7-(2,4,5-trifluorophenyl)chroman-4-yl)carbamate $^1$H-NMR (400 MHz, $CDCl_3$) δ 7.30-7.20 (m, 2H), 7.07-6.97 (m, 2H), 6.94 (s, 1H), 4.95 (t, 1H), 4.83-4.77 (m, 1H), 4.72 (d, 1H), 3.93-3.82 (m, 2H), 3.33-3.20 (m, 1H), 2.94-2.68 (m, 5H), 2.13-2.06 (m, 1H), 1.88-1.78 (m, 1H), 1.75-1.66 (m, 1H), 1.62-1.54 (m, 1H), 1.46-1.37 (m, 1H), 1.06 (d, 3H), 1.02 (d, 3H)

Example 201. (S)-quinuclidin-3-yl (3,3-dimethyl-7-(4-(trifluoromethoxy)phenyl)chroman-4-yl)carbamate $^1$H-NMR (400 MHz, $CDCl_3$) δ 7.61-7.52 (m, 2H), 7.31-7.22 (m, 3H), 7.12 (t, 1H), 7.01 (s, 1H), 4.96 (t, 1H), 4.84-4.76 (m, 1H), 4.72 (d, 1H), 3.93-3.83 (m, 2H), 3.32-3.20 (m, 1H), 2.93-2.68 (m, 5H), 2.13-2.06 (m, 1H), 1.87-1.78 (m, 1H), 1.74-1.66 (m, 1H), 1.62-1.54 (m, 1H), 1.47-1.36 (m, 1H), 1.07 (d, 3H), 1.02 (d, 3H)

Example 202. (S)-quinuclidin-3-yl (3,3-dimethyl-7-(4-(tetrahydro-2H-pyran-4-yl)phenyl)chroman-4-yl)carbamate $^1$H-NMR (400 MHz, $CDCl_3$) δ 7.52-7.50 (m, 2H), 7.31-7.22 (m, 3H), 7.15 (t, 1H), 7.04 (s, 1H), 4.97 (t, 1H), 4.85-4.76 (m, 1H), 4.71 (d, 1H), 4.15-4.05 (m, 2H), 3.92-3.82 (m, 2H), 3.60-3.49 (m, 2H), 3.34-3.21 (m, 1H), 2.93-2.68 (m, 6H), 2.16-2.06 (m, 1H), 1.91-1.77 (m, 5H), 1.75-1.67 (m, 1H), 1.63-1.55 (m, 1H), 1.46-1.37 (m, 1H), 1.06 (d, 3H), 1.02 (d, 3H)

Example 203. (S)-quinuclidin-3-yl (7-(2-methoxypyridin-4-yl)-3,3-dimethylchroman-4-yl)carbamate $^1$H-NMR (400 MHz, $CDCl_3$) δ 8.17 (d, 1H), 7.28 (dd, 1H), 7.16 (t, 1H), 7.08-7.02 (m, 2H), 6.90 (s, 1H), 5.04 (t, 1H), 4.83-4.75 (m, 1H), 4.71 (d, 1H), 3.96 (s, 3H), 3.93-3.81 (m, 2H), 3.31-3.18 (m, 1H), 2.91-2.06 (m, 5H), 2.13-2.03 (m, 1H), 1.86-1.76 (m, 1H), 1.73-1.64 (m, 1H), 1.60-1.52 (m, 1H), 1.45-1.36 (m, 1H), 1.05 (d, 3H), 1.01 (d, 3H)

Example 204. (S)-quinuclidin-3-yl (7-(3-fluoro-4-morpholinophenyl)-3,3-dimethylchroman-4-yl)carbamate $^1$H-NMR (400 MHz, $CDCl_3$) δ 7.30-7.19 (m, 3H), 7.09 (t, 1H), 7.01-6.91 (m, 2H), 5.05 (t, 1H), 4.82-4.74 (m, 1H), 4.69 (d, 1H), 3.92-3.79 (m, 6H), 3.29-3.19 (m, 1H), 3.15-3.06 (m, 4H), 2.91-2.64 (m, 5H), 2.11-2.05 (m, 1H), 1.85-1.77 (m, 1H), 1.73-1.65 (m, 1H), 1.61-1.53 (m, 1H), 1.44-1.35 (m, 1H), 1.05 (d, 3H), 1.01 (d, 3H)

Example 205. (S)-quinuclidin-3-yl (7-(3-chloro-4-morpholinophenyl)-3,3-dimethylchroman-4-yl)carbamate $^1$H-NMR (400 MHz, $CDCl_3$) δ 7.58 (s, 1H), 7.42 (d, 1H), 7.29-7.20 (m, 1H), 7.11-7.06 (m, 2H), 6.98 (s, 1H), 4.97 (t, 1H), 4.83-4.76 (m, 1H), 4.70 (d, 1H), 3.95-3.80 (m, 6H), 3.32-3.20 (m, 1H), 3.14-3.02 (m, 4H), 2.94-2.68 (m, 5H), 2.12-2.06 (m, 1H), 1.87-1.77 (m, 1H), 1.74-1.66 (m, 1H), 1.62-1.53 (m, 1H), 1.45-1.37 (m, 1H), 1.06 (d, 3H), 1.01 (d, 3H)

Example 206. (S)-quinuclidin-3-yl (7-(4-methoxyphenyl)-3,3-dimethylchroman-4-yl)carbamate $^1$H-NMR (400 MHz, $CDCl_3$) δ 7.50 (d, 2H), 7.28-7.19 (m, 1H), 7.12 (t, 1H), 7.00 (s, 1H), 6.95 (d, 2H), 5.03 (t, 1H), 4.82-4.76 (m, 1H), 4.69 (d, 1H), 3.93-3.79 (m, 5H), 3.30-3.20 (m, 1H), 2.92-2.68 (m, 5H), 2.13-2.05 (m, 1H), 1.87-1.77 (m, 1H), 1.74-1.65 (m, 1H), 1.62-1.54 (m, 1H), 1.45-1.36 (m, 1H), 1.06 (d, 3H), 1.01 (d, 3H)

Example 207. (S)-quinuclidin-3-yl (7-(5-methoxypyridin-3-yl)-3,3-dimethylchroman-4-yl)carbamate $^1$H-NMR (400 MHz, $CDCl_3$) δ 8.43 (s, 1H), 8.23 (s, 1H), 7.33-7.24 (m, 2H), 7.10 (t, 1H), 7.00 (s, 1H), 5.32 (t, 1H), 4.83-4.75 (m, 1H), 4.71 (d, 1H), 3.95-3.82 (m, 5H), 3.31-3.18 (m, 1H), 2.91-2.65 (m, 5H), 2.13-2.05 (m, 1H), 1.86-

1.77 (m, 1H), 1.73-1.65 (m, 1H), 1.62-1.53 (m, 1H), 1.44-1.36 (m, 1H), 1.05 (d, 3H), 1.01 (d, 3H)

Example 208. (S)-quinuclidin-3-yl (7-(benzo[b]thiophen-2-yl)-3,3-dimethylchroman-4-yl)carbamate $^1$H-NMR (400 MHz, $CDCl_3$) δ 7.82 (d, 1H), 7.77 (d, 1H), 7.52 (s, 1H), 7.38-7.22 (m, 4H), 7.12 (s, 1H), 4.88-4.77 (m, 2H), 4.72 (d, 1H), 3.94-3.84 (m, 2H), 3.35-3.20 (m, 1H), 2.95-2.69 (m, 5H), 2.14-2.06 (m, 1H), 1.90-1.80 (m, 1H), 1.76-1.67 (m, 1H), 1.64-1.55 (m, 1H), 1.47-1.38 (m, 1H), 1.07 (d, 3H), 1.03 (d, 3H)

Example 209. (S)-quinuclidin-3-yl (7-(4-ethoxyphenyl)-3,3-dimethylchroman-4-yl)carbamate $^1$H-NMR (400 MHz, $CDCl_3$) δ 7.49 (d, 2H), 7.29-7.19 (m, 1H), 7.12 (t, 1H), 7.01 (s, 1H), 6.95 (d, 2H), 4.89 (t, 1H), 4.83-4.77 (m, 1H), 4.70 (d, 1H), 4.07 (q, 2H), 3.92-3.81 (m, 2H), 3.35-3.20 (m, 1H), 2.95-2.69 (m, 5H), 2.12-2.04 (m, 1H), 1.88-1.79 (m, 1H), 1.74-1.66 (m, 1H), 1.63-1.54 (m, 1H), 1.45-1.34 (m, 4H), 1.06 (d, 3H), 1.02 (d, 3H)

Example 210. (S)-quinuclidin-3-yl (7-(4-methoxy-3-(trifluoromethyl)phenyl)-3,3-dimethylchroman-4-yl)carbamate $^1$H-NMR (400 MHz, $CDCl_3$) δ 8.49 (s, 1H), 8.01 (s, 1H), 7.30 (t, 1H), 7.08 (t, 1H), 6.97 (s, 1H), 4.89 (t, 1H), 4.83-4.77 (m, 1H), 4.73 (d, 1H), 4.08 (s, 3H), 3.94-3.84 (m, 2H), 3.34-3.23 (m, 1H), 2.94-2.69 (m, 5H), 2.14-2.05 (m, 1H), 1.89-1.78 (m, 1H), 1.75-1.67 (m, 1H), 1.63-1.53 (m, 1H), 1.46-1.36 (m, 1H), 1.07 (d, 3H), 1.02 (d, 3H)

Example 211. (S)-quinuclidin-3-yl (3,3-dimethyl-7-(4-(trifluoromethyl)phenyl)chroman-4-yl)carbamate $^1$H-NMR (400 MHz, $CDCl_3$) δ 7.72-7.60 (m, 4H), 7.32-7.27 (m, 1H), 7.16 (t, 1H), 7.05 (s, 1H), 4.99 (t, 1H), 4.84-4.76 (m, 1H), 4.73 (d, 1H), 3.94-3.84 (m, 2H), 3.32-3.21 (m, 1H), 2.93-2.68 (m, 5H), 2.14-2.04 (m, 1H), 1.88-1.79 (m, 1H), 1.75-1.66 (m, 1H), 1.62-1.54 (m, 1H), 1.46-1.37 (m, 1H), 1.07 (d, 3H), 1.03 (d, 3H)

Example 212. (S)-quinuclidin-3-yl (7-(1H-indazol-4-yl)-3,3-dimethylchroman-4-yl)carbamate $^1$H-NMR (400 MHz, $CDCl_3$) δ 8.22 (s, 1H), 7.49-7.40 (m, 2H), 7.33 (t, 1H), 7.29-7.24 (m, 1H), 7.21 (d, 1H), 7.16 (s, 1H), 5.18 (d, 1H), 4.87-4.80 (m, 1H), 4.76 (d, 1H), 3.94-3.86 (m, 2H), 3.38-3.24 (m, 1H), 2.96-2.70 (m, 5H), 2.16-2.09 (m, 1H), 1.91-1.81 (m, 1H), 1.77-1.68 (m, 1H), 1.65-1.57 (m, 1H), 1.48-1.39 (m, 1H), 1.09 (d, 3H), 1.05 (d, 3H)

Example 213. (S)-quinuclidin-3-yl (7-(4-chlorophenyl)-3,3-dimethylchroman-4-yl)carbamate $^1$H-NMR (400 MHz, $CDCl_3$) δ 7.47 (d, 2H), 7.37 (d, 2H), 7.26 (dd, 1H), 7.11 (t, 1H), 7.00 (s, 1H), 4.99 (t, 1H), 4.84-4.75 (m, 1H), 4.71 (d, 1H), 3.92-3.82 (m, 2H), 3.31-3.20 (m, 1H), 2.92-2.68 (m, 5H), 2.12-2.06 (m, 1H), 1.86-1.78 (m, 1H), 1.74-1.66 (m, 1H), 1.61-1.54 (m, 1H), 1.46-1.36 (m, 1H), 1.06 (d, 3H), 1.02 (d, 3H)

Example 214. (S)-quinuclidin-3-yl (7-(4-fluorophenyl)-3,3-dimethylchroman-4-yl)carbamate $^1$H-NMR (400 MHz, $CDCl_3$) δ 7.56-7.47 (m, 2H), 7.29-7.23 (m, 1H), 7.15-7.06 (m, 3H), 7.00 (s, 1H), 4.88 (t, 1H), 4.83-4.78 (m, 1H), 4.71 (d, 1H), 3.93-3.82 (m, 2H), 3.35-3.22 (m, 1H), 2.96-2.68 (m, 5H), 2.14-2.06 (m, 1H), 1.87-1.79 (m, 1H), 1.75-1.67 (m, 1H), 1.62-1.55 (m, 1H), 1.46-1.38 (m, 1H), 1.07 (d, 3H), 1.03 (d, 3H)

Example 215. (S)-quinuclidin-3-yl (7-(5-chloro-6-methoxypyridin-3-yl)-3,3-dimethylchroman-4-yl)carbamate $^1$H-NMR (400 MHz, $CDCl_3$) δ 8.31-8.23 (m, 1H), 7.84-7.75 (m, 1H), 7.34-7.24 (m, 1H), 7.16-7.03 (m, 1H), 6.94 (s, 1H), 4.88-4.77 (m, 2H), 4.73 (d, 1H), 4.02 (s, 3H), 3.95-3.82 (m, 2H), 3.34-3.23 (m, 1H), 2.93-2.69 (m, 5H), 2.13-2.06 (m, 1H), 1.89-1.78 (m, 1H), 1.75-1.67 (m, 1H), 1.62-1.55 (m, 1H), 1.45-1.37 (m, 1H), 1.07 (d, 3H), 1.02 (d, 3H)

Example 216. (S)-quinuclidin-3-yl (3,3-dimethyl-7-(4-methyl-3-oxo-3,4-dihydro-2H-benzo[b][1,4]oxazin-6-yl)chroman-4-yl)carbamate $^1$H-NMR (400 MHz, $CDCl_3$) δ 7.41-7.22 (m, 2H), 7.17 (s, 1H), 7.12 (t, 1H), 7.09-7.07 (m, 2H), 4.99 (t, 1H), 4.83-4.76 (m, 1H), 4.70 (d, 1H), 4.61 (s, 2H), 3.92-3.83 (m, 2H), 3.37 (s, 3H), 3.31-3.22 (m, 1H), 2.93-2.68 (m, 5H), 2.13-2.06 (m, 1H), 1.87-1.79 (m, 1H), 1.75-1.66 (m, 1H), 1.62-1.54 (m, 1H), 1.46-1.36 (m, 1H), 1.06 (d, 3H), 1.02 (d, 3H)

Example 217. (S)-quinuclidin-3-yl (3,3-dimethyl-7-(2,3,4-trifluorophenyl)chroman-4-yl)carbamate $^1$H-NMR (400 MHz, $CDCl_3$) δ 7.31-7.25 (m, 1H), 7.16-7.09 (m, 1H), 7.08-6.98 (m, 2H), 6.95 (s, 1H), 4.94 (t, 1H), 4.83-4.76 (m, 1H), 4.73 (d, 1H), 3.93-3.83 (m, 2H), 3.32-3.21 (m, 1H), 2.94-2.67 (m, 5H), 2.13-2.06 (m, 1H), 1.90-1.78 (m, 1H), 1.74-1.67 (m, 1H), 1.63-1.53 (m, 1H), 1.46-1.37 (m, 1H), 1.07 (d, 3H), 1.03 (d, 3H)

Example 218. (S)-quinuclidin-3-yl (7-(4-(difluoromethoxy)phenyl)-3,3-dimethylchroman-4-yl)carbamate $^1$H-NMR (400 MHz, $CDCl_3$) δ 7.56 (d, 2H), 7.27 (dd, 1H), 7.18 (d, 2H), 7.11 (t, 1H), 7.00 (s, 1H), 6.54 (t, 1H), 4.95 (t, 1H), 4.83-4.76 (m, 1H), 4.71 (d, 1H), 3.92-3.82 (m, 2H), 3.32-3.20 (m, 1H), 2.93-2.68 (m, 5H), 2.12-2.05 (m, 1H), 1.87-1.78 (m, 1H), 1.74-1.66 (m, 1H), 1.62-1.53 (m, 1H), 1.45-1.36 (m, 1H), 1.06 (d, 3H), 1.02 (d, 3H)

Example 219. (S)-quinuclidin-3-yl (3,3-dimethyl-7-(quinolin-5-yl)chroman-4-yl)carbamate $^1$H-NMR (400 MHz, $CDCl_3$) δ 8.91 (d, 1H), 8.28 (d, 1H), 8.11 (d, 1H), 7.73 (t, 1H), 7.48 (d, 1H), 7.39-7.30 (m, 2H), 7.02 (t, 1H), 6.93 (s, 1H), 5.07 (t, 1H), 4.86-4.74 (m, 2H), 3.96-3.86 (m, 2H), 3.34-3.22 (m, 1H), 2.95-2.66 (m, 5H), 2.15-2.07 (m, 1H), 1.89-1.80 (m, 1H), 1.75-1.66 (m, 1H), 1.63-1.54 (m, 1H), 1.46-1.37 (m, 1H), 1.10 (d, 3H), 1.06 (d, 3H)

Example 220. (S)-quinuclidin-3-yl (7-(benzo[c][1,2,5]oxadiazol-5-yl)-3,3-dimethylchroman-4-yl)carbamate $^1$H-NMR (400 MHz, $CDCl_3$) δ 7.94-7.85 (m, 2H), 7.66 (d, 1H), 7.36-7.31 (m, 1H), 7.19 (t, 1H), 7.09 (s, 1H), 5.00 (t, 1H), 4.84-4.78 (m, 1H), 4.75 (d, 1H), 3.96-3.86 (m, 2H), 3.34-3.22 (m, 1H), 2.94-2.67 (m, 5H), 2.13-2.06 (m, 1H), 1.90-1.78 (m, 1H), 1.75-1.66 (m, 1H), 1.63-1.54 (m, 1H), 1.47-1.36 (m, 1H), 1.07 (d, 3H), 1.03 (d, 3H)

Example 221. (S)-quinuclidin-3-yl (3,3-dimethyl-7-(5-methylpyridin-3-yl)chroman-4-yl)carbamate $^1$H-NMR (400 MHz, $CDCl_3$) δ 8.55 (s, 1H), 8.40 (s, 1H), 7.63 (s, 1H), 7.35-7.24 (m, 1H), 7.11 (t, 1H), 7.01 (s, 1H), 5.17 (t, 1H), 4.84-4.76 (m, 1H), 4.73 (d, 1H), 3.97-3.80 (m, 2H), 3.35-3.21 (m, 1H), 2.94-2.67 (m, 5H), 2.38 (s, 3H), 2.12-2.05 (m, 1H), 1.89-1.79 (m, 1H), 1.75-1.66 (m, 1H), 1.62-1.54 (m, 1H), 1.45-1.36 (m, 1H), 1.06 (d, 3H), 1.02 (d, 3H)

Example 222. (S)-quinuclidin-3-yl (7-(2-fluoropyridin-3-yl)-3,3-dimethylchroman-4-yl)carbamate $^1$H-NMR (400 MHz, $CDCl_3$) δ 8.18 (d, 1H), 7.85 (t, 1H), 7.35-7.23 (m, 2H), 7.12 (t, 1H), 7.02 (s, 1H), 4.95 (t, 1H), 4.84-4.77 (m, 1H), 4.73 (d, 1H), 3.96-3.81 (m, 2H), 3.33-3.20 (m, 1H), 2.93-2.68 (m, 5H), 2.13-2.05 (m, 1H), 1.87-1.78 (m, 1H), 1.74-1.66 (m, 1H), 1.62-1.55 (m, 1H), 1.45-1.36 (m, 1H), 1.07 (d, 3H), 1.02 (d, 3H)

Example 223. (S)-quinuclidin-3-yl (7-(2-chloro-4-methylphenyl)-3,3-dimethylchroman-4-yl)carbamate $^1$H-NMR (400 MHz, $CDCl_3$) δ 7.30-7.17 (m, 3H), 7.10 (d, 1H), 6.99 (t, 1H), 6.88 (s, 1H), 5.14 (t, 1H), 4.82-4.74 (m, 1H), 4.71 (d, 1H), 3.93-3.79 (m, 2H), 3.30-3.19 (m, 1H), 2.93-2.66 (m, 5H), 2.36 (s, 3H), 2.13-2.05 (m, 1H), 1.88-1.77 (m, 1H), 1.73-1.65 (m, 1H), 1.60-1.52 (m, 1H), 1.44-1.36 (m, 1H), 1.06 (d, 3H), 1.02 (d, 3H)

Example 224. (S)-quinuclidin-3-yl (7-(2-chloro-5-methylphenyl)-3,3-dimethylchroman-4-yl)carbamate $^1$H-NMR (400 MHz, $CDCl_3$) δ 7.33 (d, 1H), 7.28-7.21 (m, 1H), 7.13 (s, 1H), 7.08 (d, 1H), 7.00 (t, 1H), 6.89 (s, 1H), 4.98 (t, 1H), 4.83-4.76 (m, 1H), 4.73 (d, 1H), 3.96-3.79 (m, 2H), 3.31-3.21 (m, 1H), 2.93-2.68 (m, 5H), 2.34 (s, 3H), 2.12-2.07 (m, 1H), 1.89-1.79 (m, 1H), 1.73-1.67 (m, 1H), 1.62-1.54 (m, 1H), 1.45-1.37 (m, 1H), 1.07 (d, 3H), 1.03 (d, 3H)

Example 225. (S)-quinuclidin-3-yl (7-(2-fluoro-4-methylphenyl)-3,3-dimethylchroman-4-yl)carbamate $^1$H-NMR (400 MHz, $CDCl_3$) δ 7.33-7.21 (m, 2H), 7.10 (t, 1H), 7.03-6.90 (m, 3H), 5.02 (t, 1H), 4.83-4.75 (m, 1H), 4.70 (d, 1H), 3.94-3.77 (m, 2H), 3.34-3.16 (m, 1H), 2.95-2.66 (m, 5H), 2.37 (s, 3H), 2.13-2.04 (m, 1H), 1.87-1.77 (m, 1H), 1.73-1.65 (m, 1H), 1.61-1.52 (m, 1H), 1.46-1.34 (m, 1H), 1.06 (d, 3H), 1.02 (d, 3H)

Example 226. (S)-quinuclidin-3-yl (7-(3-chloro-4-methylphenyl)-3,3-dimethylchroman-4-yl)carbamate $^1$H-NMR (400 MHz, $CDCl_3$) δ 7.55 (s, 1H), 7.35 (d, 1H), 7.30-7.22 (m, 2H), 7.12 (t, 1H), 7.01 (s, 1H), 4.80 (t, 1H), 4.82-4.77 (m, 1H), 4.72 (d, 1H), 3.95-3.82 (m, 2H), 3.34-3.22 (m, 1H), 2.94-2.69 (m, 5H), 2.40 (s, 3H), 2.15-2.07 (m, 1H), 1.89-1.80 (m, 1H), 1.75-1.67 (m, 1H), 1.63-1.55 (m, 1H), 1.46-1.36 (m, 1H), 1.06 (d, 3H), 1.02 (d, 3H)

Example 227. (S)-quinuclidin-3-yl (7-(4-fluoro-2-methylphenyl)-3,3-dimethylchroman-4-yl)carbamate $^1$H-NMR (400 MHz, $CDCl_3$) δ 7.29-7.19 (m, 1H), 7.14 (t, 1H), 6.97-6.87 (m, 2H), 6.83 (t, 1H), 6.73 (s, 1H), 5.00 (t, 1H), 4.84-4.77 (m, 1H), 4.73 (d, 1H), 3.94-3.80 (m, 2H), 3.32-3.20 (m, 1H), 2.93-2.67 (m, 5H), 2.26 (s, 3H), 2.13-2.06 (m, 1H), 1.88-1.79 (m, 1H), 1.74-1.65 (m, 1H), 1.62-1.53 (m, 1H), 1.46-1.37 (m, 1H), 1.07 (d, 3H), 1.03 (d, 3H)

Example 228. (S)-quinuclidin-3-yl (7-(3-fluoro-4-methylphenyl)-3,3-dimethylchroman-4-yl)carbamate $^1$H-NMR (400 MHz, $CDCl_3$) δ 7.30-7.18 (m, 4H), 7.12 (t, 1H), 7.01 (s, 1H), 4.94 (t, 1H), 4.82-4.76 (m, 1H), 4.71 (d, 1H), 3.96-3.78 (m, 2H), 3.32-3.21 (m, 1H), 2.94-2.67 (m, 5H), 2.30 (s, 3H), 2.14-2.05 (m, 1H), 1.87-1.79 (m, 1H), 1.75-1.66 (m, 1H), 1.64-1.53 (m, 1H), 1.46-1.36 (m, 1H), 1.06 (d, 3H), 1.02 (d, 3H)

Example 229. (S)-quinuclidin-3-yl (7-(4-fluoro-3-methylphenyl)-3,3-dimethylchroman-4-yl)carbamate $^1$H-NMR (400 MHz, $CDCl_3$) δ 7.39-7.30 (m, 2H), 7.25 (dd, 1H), 7.13-6.99 (m, 2H), 6.98 (s, 1H), 4.94 (t, 1H), 4.83-4.76 (m, 1H), 4.71 (d, 1H), 3.94-3.81 (m, 2H), 3.30-3.21 (m, 1H), 2.92-2.67 (m, 5H), 2.32 (s, 3H), 2.14-2.06 (m, 1H), 1.88-1.79 (m, 1H), 1.73-1.65 (m, 1H), 1.63-1.54 (m, 1H), 1.46-1.36 (m, 1H), 1.06 (d, 3H), 1.02 (d, 3H)

Example 230. (S)-quinuclidin-3-yl (7-(2,4-dichlorophenyl)-3,3-dimethylchroman-4-yl)carbamate $^1$H-NMR (400 MHz, $CDCl_3$) δ 7.46 (s, 1H), 7.31-7.19 (m, 3H), 6.96 (t, 1H), 6.86 (s, 1H), 5.09 (t, 1H), 4.82-4.75 (m, 1H), 4.72 (d, 1H), 3.95-3.78 (m, 2H), 3.30-3.18 (m, 1H), 2.92-2.68 (m, 5H), 2.13-2.05 (m, 1H), 1.88-1.78 (m, 1H), 1.73-1.65 (m, 1H), 1.61-1.52 (m, 1H), 1.44-1.35 (m, 1H), 1.06 (d, 3H), 1.02 (d, 3H)

Example 231. (S)-quinuclidin-3-yl (7-(2-chloro-4-fluorophenyl)-3,3-dimethylchroman-4-yl)carbamate $^1$H-NMR (400 MHz, $CDCl_3$) δ 7.31-7.17 (m, 3H), 7.04-6.93 (m, 2H), 6.85 (s, 1H), 5.15 (t, 1H), 4.82-4.76 (m, 1H), 4.72 (d, 1H), 3.94-3.81 (m, 2H), 3.30-3.18 (m, 1H), 2.91-2.66 (m, 5H), 2.13-2.05 (m, 1H), 1.87-1.77 (m, 1H), 1.73-1.64 (m, 1H), 1.60-1.53 (m, 1H), 1.45-1.36 (m, 1H), 1.06 (d, 3H), 1.02 (d, 3H)

Example 232. (S)-quinuclidin-3-yl (7-(2-chloro-5-fluorophenyl)-3,3-dimethylchroman-4-yl)carbamate $^1$H-NMR (400 MHz, $CDCl_3$) δ 7.40 (dd, 1H), 7.26 (dd, 1H), 7.07-6.94 (m, 3H), 6.88 (s, 1H), 5.08 (t, 1H), 4.83-4.77 (m, 1H), 4.73 (d, 1H), 3.95-3.81 (m, 2H), 3.30-3.21 (m, 1H), 2.93-2.66 (m, 5H), 2.13-2.06 (m, 1H), 1.87-1.78 (m, 1H), 1.74-1.65 (m, 1H), 1.61-1.53 (m, 1H), 1.45-1.35 (m, 1H), 1.07 (d, 3H), 1.03 (d, 3H)

Example 233. (S)-quinuclidin-3-yl (7-(2,4-difluorophenyl)-3,3-dimethylchroman-4-yl)carbamate $^1$H-NMR (400 MHz, $CDCl_3$) δ 7.37 (dd, 1H), 7.26 (dd, 1H), 7.05 (t, 1H), 6.97-6.85 (m, 3H), 5.02 (t, 1H), 4.82-4.76 (m, 1H), 4.71 (d, 1H), 3.93-3.81 (m, 2H), 3.31-3.19 (m, 1H), 2.93-2.68 (m, 5H), 2.13-2.05 (m, 1H), 1.86-1.78 (m, 1H), 1.73-1.65 (m, 1H), 1.62-1.53 (m, 1H), 1.44-1.36 (m, 1H), 1.06 (d, 3H), 1.02 (d, 3H)

Example 234. (S)-quinuclidin-3-yl (7-(2,5-difluorophenyl)-3,3-dimethylchroman-4-yl)carbamate $^1$H-NMR (400 MHz, $CDCl_3$) δ 7.27 (dd, 1H), 7.14-7.05 (m, 3H), 7.02-6.94 (m, 2H), 4.96 (t, 1H), 4.83-4.75 (m, 1H), 4.72 (d, 1H), 3.95-3.81 (m, 2H), 3.32-3.18 (m, 1H), 2.91-2.64 (m, 5H), 2.14-2.02 (m, 1H), 1.88-1.78 (m, 1H), 1.74-1.65 (m, 1H), 1.62-1.54 (m, 1H), 1.46-1.36 (m, 1H), 1.06 (d, 3H), 1.02 (d, 3H)

Example 235. (S)-quinuclidin-3-yl (7-(2,3-dichlorophenyl)-3,3-dimethylchroman-4-yl)carbamate $^1$H-NMR (400 MHz, $CDCl_3$) δ 7.44 (dd, 1H), 7.31-7.15 (m, 3H), 6.96 (dd, 1H), 6.85 (s, 1H), 5.11 (t, 1H), 4.83-4.76 (m, 1H), 4.72 (d, 1H), 3.95-3.80 (m, 2H), 3.31-3.18 (m, 1H), 2.93-2.67 (m, 5H), 2.14-2.06 (m, 1H), 1.87-1.77 (m, 1H), 1.73-1.65 (m, 1H), 1.62-1.53 (m, 1H), 1.45-1.36 (m, 1H), 1.07 (d, 3H), 1.03 (d, 3H)

Example 236. (S)-quinuclidin-3-yl (7-(3-chloro-4-fluorophenyl)-3,3-dimethylchroman-4-yl)carbamate $^1$H-NMR (400 MHz, $CDCl_3$) δ 7.58 (d, 1H), 7.44-7.36 (m, 1H), 7.30-7.22 (m, 1H), 7.18 (t, 1H), 7.11-7.04 (m, 1H), 6.97 (s, 1H), 4.90 (t, 1H), 4.83-4.76 (m, 1H), 4.72 (d, 1H), 3.94-3.82 (m, 2H), 3.32-3.22 (m, 1H), 2.95-2.68 (m, 5H), 2.13-2.06 (m, 1H), 1.89-1.78 (m, 1H), 1.75-1.66 (m, 1H), 1.62-1.55 (m, 1H), 1.46-1.37 (m, 1H), 1.06 (d, 3H), 1.02 (d, 3H)

Example 237. (S)-quinuclidin-3-yl (7-(2-chloro-3-fluorophenyl)-3,3-dimethylchroman-4-yl)carbamate $^1$H-NMR (400 MHz, $CDCl_3$) δ 7.31-7.22 (m, 2H), 7.17-7.08 (m, 2H), 6.99 (t, 1H), 6.89 (s, 1H), 5.08 (t, 1H), 4.83-4.77 (m, 1H), 4.73 (d, 1H), 3.95-3.81 (m, 2H), 3.30-3.21 (m, 1H), 2.93-2.67 (m, 5H), 2.16-2.06 (m, 1H), 1.88-1.78 (m, 1H), 1.74-1.65 (m, 1H), 1.61-1.53 (m, 1H), 1.46-1.36 (m, 1H), 1.07 (d, 3H), 1.03 (d, 3H)

Example 238. (S)-quinuclidin-3-yl (7-(3,4-difluorophenyl)-3,3-dimethylchroman-4-yl)carbamate $^1$H-NMR (400 MHz, $CDCl_3$) δ 7.34 (dd, 1H), 7.30-7.16 (m, 3H), 7.08 (t, 1H), 6.97 (m, 1H), 4.87 (t, 1H), 4.82-4.77 (m, 1H), 4.72 (d, 1H), 3.96-3.81 (m, 2H), 3.34-3.21 (m, 1H), 2.94-2.68 (m, 5H), 2.13-2.05 (m, 1H), 1.87-1.78 (m, 1H), 1.75-1.66 (m, 1H), 1.63-1.54 (m, 1H), 1.46-1.36 (m, 1H), 1.06 (d, 3H), 1.02 (d, 3H)

Example 239. (S)-quinuclidin-3-yl (7-(2,3-difluorophenyl)-3,3-dimethylchroman-4-yl)carbamate $^1$H-NMR (400 MHz, $CDCl_3$) δ 7.27 (dd, 1H), 7.18-7.07 (m, 4H), 6.99 (s, 1H), 5.06 (t, 1H), 4.82-4.75 (m, 1H), 4.72 (d, 1H), 3.95-3.81 (m, 2H), 3.29-3.20 (m, 1H), 2.92-2.68 (m, 5H), 2.13-2.05 (m, 1H), 1.86-1.76 (m, 1H), 1.73-1.64 (m, 1H), 1.62-1.52 (m, 1H), 1.45-1.36 (m, 1H), 1.06 (d, 3H), 1.02 (d, 3H)

Example 240. (S)-quinuclidin-3-yl (7-(3,5-difluorophenyl)-3,3-dimethylchroman-4-yl)carbamate $^1$H-NMR (400 MHz, $CDCl_3$) δ 7.27 (dd, 1H), 7.13-7.03 (m, 3H), 6.99 (s, 1H), 6.77 (t, 1H), 4.98 (t, 1H), 4.84-4.76 (m, 1H), 4.72 (d, 1H), 3.95-3.80 (m, 2H), 3.32-3.20 (m, 1H), 2.93-2.06 (m, 5H), 2.13-2.06 (m, 1H), 1.86-1.78 (m, 1H), 1.74-1.65 (m, 1H), 1.62-1.54 (m, 1H), 1.46-1.37 (m, 1H), 1.06 (d, 3H), 1.01 (d, 3H)

Example 241. (S)-quinuclidin-3-yl (7-(6-methoxypyridin-3-yl)-3,3-dimethylchroman-4-yl)carbamate $^1$H-NMR (400 MHz, $CDCl_3$) δ 8.35 (s, 1H), 7.75 (d, 1H), 7.27 (t, 1H), 7.08 (t, 1H), 6.97 (s, 1H), 6.79 (d, 1H), 4.94 (t, 1H), 4.83-4.75 (m, 1H), 4.71 (d, 1H), 3.97 (s, 3H), 3.93-3.81 (m, 2H), 3.33-3.20 (m, 1H), 2.96-2.65 (m, 5H), 2.13-2.04 (m, 1H), 1.86-1.76 (m, 1H), 1.74-1.66 (m, 1H), 1.61-1.53 (m, 1H), 1.47-1.33 (m, 1H), 1.06 (d, 3H), 1.02 (d, 3H)

Example 242. (S)-quinuclidin-3-yl (7-([1,1'-biphenyl]-4-yl)-3,3-dimethylchroman-4-yl)carbamate $^1$H-NMR (400 MHz, $CDCl_3$) δ 7.69-7.62 (m, 6H), 7.50-7.43 (m, 2H), 7.37 (t, 1H), 7.31 (d, 1H), 7.23 (d, 1H), 7.11 (s, 1H), 4.90-4.88 (m, 1H), 4.85-4.78 (m, 1H), 4.74 (d, 1H), 3.96-3.82 (m, 2H), 3.34-3.24 (m, 1H), 2.95-2.71 (m, 5H), 2.14-2.06 (m, 1H), 1.88-1.79 (m, 1H), 1.75-1.67 (m, 1H), 1.63-1.55 (m, 1H), 1.47-1.37 (m, 1H), 1.07 (s, 3H), 1.03 (s, 3H)

Example 243. (S)-quinuclidin-3-yl (3,3-dimethyl-7-(thiazol-5-yl)chroman-4-yl)carbamate $^1$H-NMR (400 MHz, $CDCl_3$) δ 7.68-7.51 (m, 2H), 7.48-7.39 (m, 1H), 7.33-7.10 (m, sH), 6.96-6.77 (m, 1H), 5.04-4.90 (m, 1H), 4.83-4.74 (m, 1H), 4.73-4.63 (m, 1H), 3.97-3.75 (m, 2H), 3.31-3.18 (m, 1H), 2.93-2.65 (m, 5H), 2.12-2.02 (m, 1H), 1.88-1.76 (m, 1H), 1.73-1.65 (m, 1H), 1.62-1.53 (m, 1H), 1.45-1.35 (m, 1H), 1.09-0.84 (m, 6H)

Example 244. (S)-quinuclidin-3-yl (3,3-dimethyl-7-(3-vinylphenyl)chroman-4-yl)carbamate $^1$H-NMR (400 MHz, $CDCl_3$) δ 7.59 (s, 1H), 7.48-7.43 (m, 1H), 7.41-7.36 (m, 2H), 7.27 (dd, 1H), 7.17 (t, 1H), 7.06 (s, 1H), 6.77 (dd, 1H), 5.80 (d, 1H), 5.30 (d, 1H), 4.99 (t, 1H), 4.83-4.77 (m, 1H), 4.72 (d, 1H), 3.95-3.81 (m, 2H), 3.33-3.20 (m, 1H), 2.93-2.68 (m, 5H), 2.14-2.06 (m, 1H), 1.88-1.79 (m, 1H), 1.75-1.65 (m, 1H), 1.63-1.54 (m, 1H), 1.46-1.36 (m, 1H), 1.07 (d, 3H), 1.03 (d, 3H)

Example 245. (S)-quinuclidin-3-yl (7-(2-methoxypyridin-3-yl)-3,3-dimethylchroman-4-yl)carbamate $^1$H-NMR (400 MHz, $CDCl_3$) δ 8.15 (d, 1H), 7.59 (d, 1H), 7.29-7.21 (m, 1H), 7.13 (t, 1H), 7.03 (s, 1H), 6.96 (dd, 1H), 4.90 (t, 1H), 4.82-4.75 (m, 1H), 4.71 (d, 1H), 3.97 (s, 3H), 3.92-3.80 (m, 2H), 3.33-3.22 (m, 1H), 2.93-2.69 (m, 5H), 2.11-2.03 (m, 1H), 1.89-1.78 (m, 1H), 1.74-1.66 (m, 1H), 1.62-1.54 (m, 1H), 1.45-1.37 (m, 1H), 1.06 (d, 3H), 1.03 (d, 3H)

Example 246. (S)-quinuclidin-3-yl (7-(6-methoxypyridin-2-yl)-3,3-dimethylchroman-4-yl)carbamate $^1$H-NMR (400 MHz, $CDCl_3$) δ 7.64-7.56 (m, 2H), 7.54 (s, 1H), 7.33-7.24 (m, 2H), 6.68 (d, 1H), 4.96 (t, 1H), 4.83-4.76 (m, 1H), 4.72 (d, 1H), 4.01 (s, 3H), 3.95-3.82 (m, 2H), 3.30-3.20 (m, 1H), 2.93-2.68 (m, 5H), 2.14-2.05 (m, 1H), 1.88-1.79 (m, 1H), 1.74-1.65 (m, 1H), 1.61-1.54 (m, 1H), 1.45-1.37 (m, 1H), 1.06 (d, 3H), 1.02 (d, 3H)

Example 247. (S)-quinuclidin-3-yl (7-(4-cyanophenyl)-3,3-dimethylchroman-4-yl)carbamate $^1$H-NMR (400 MHz, $CDCl_3$) δ 7.73-7.60 (m, rH), 7.34-7.25 (m, 1H), 7.14 (t, 1H), 7.03 (s, 1H), 4.98 (t, 1H), 4.83-4.76 (m, 1H), 4.73 (d, 1H), 3.95-3.83 (m, 2H), 3.30-3.20 (m, 1H), 2.91-2.67 (m, 5H), 2.13-2.05 (m, 1H), 1.86-1.78 (m, 1H), 1.73-1.65 (m, 1H), 1.61-1.54 (m, 1H), 1.46-1.37 (m, 1H), 1.06 (d, 3H), 1.02 (d, 3H)

Example 248. (S)-quinuclidin-3-yl (7-(2-fluoro-6-methylpyridin-3-yl)-3,3-dimethylchroman-4-yl)carbamate $^1$H-NMR (400 MHz, $CDCl_3$) δ 7.73 (t, 1H), 7.28 (dd, 1H), 7.15-7.06 (m, 2H), 7.01 (s, 1H), 4.92 (t, 1H), 4.82-4.76 (m, 1H), 4.72 (d, 1H), 3.94-3.81 (m, 2H), 3.32-3.20 (m, 1H), 2.93-2.66 (m, 5H), 2.53 (s, 3H), 2.12-2.04 (m, 1H), 1.86-1.78 (m, 1H), 1.74-1.66 (m, 1H), 1.61-1.53 (m, 1H), 1.45-1.36 (m, 1H), 1.06 (d, 3H), 1.02 (d, 3H)

Example 249. (S)-quinuclidin-3-yl (7-(benzo[d][1,3]dioxol-5-yl)-3,3-dimethylchroman-4-yl)carbamate $^1$H-NMR (400 MHz, $CDCl_3$) δ 7.29-7.19 (m, 1H), 7.12-7.00 (m, 3H), 6.97 (s, 1H), 6.86 (d, 1H), 5.99 (s, 2H), 4.86 (t, 1H), 4.82-4.77 (m, 1H), 4.70 (d, 1H), 3.93-3.80 (m, 2H), 3.32-3.23 (m, 1H), 2.92-2.68 (m, 5H), 2.14-2.04 (m, 1H), 1.86-1.78 (m, 1H), 1.74-1.66 (m, 1H), 1.62-1.54 (m, 1H), 1.45-1.36 (m, 1H), 1.06 (d, 3H), 1.02 (d, 3H)

Example 250. (S)-quinuclidin-3-yl (7-(6-cyclopropylpyridin-3-yl)-3,3-dimethylchroman-4-yl)carbamate $^1$H-NMR (400 MHz, $CDCl_3$) δ 8.63 (s, 1H), 7.69 (d, 1H), 7.28 (dd, 1H), 7.17 (d, 1H), 7.11 (t, 1H), 7.00 (s, 1H), 4.93-4.90 (m, 1H), 4.82-4.76 (m, 1H), 4.72 (d, 1H), 3.96-3.81 (m, 2H), 3.32-3.21 (m, 1H), 2.94-2.67 (m, 5H), 2.13-2.02 (m, 2H), 1.86-1.78 (m, 1H), 1.74-1.66 (m, 1H), 1.62-1.54 (m, 1H), 1.45-1.36 (m, 1H), 1.11-0.95 (m, 10H)

Example 251. (S)-quinuclidin-3-yl (7-(6-(dimethylamino)pyridin-3-yl)-3,3-dimethylchroman-4-yl)carbamate $^1$H-NMR (400 MHz, $CDCl_3$) δ 8.41 (s, 1H), 7.66 (d, 1H), 7.24 (dd, 1H), 7.09 (t, 1H), 6.97 (s, 1H), 6.57 (d, 1H), 4.92-4.85 (m, 1H), 4.83-4.75 (m, 1H), 4.69 (d, 1H), 3.94-3.78 (m, 2H), 3.34-3.21 (m, 1H), 3.13 (s, 6H), 2.93-2.66 (m, 5H), 2.13-2.05 (m, 1H), 1.88-1.77 (m, 1H), 1.74-1.66 (m, 1H), 1.63-1.53 (m, 1H), 1.45-1.35 (m, 1H), 1.06 (d, 3H), 1.02 (d, 3H)

Example 252. (S)-quinuclidin-3-yl (7-(5-fluoro-2-methoxyphenyl)-3,3-dimethylchroman-4-yl)carbamate $^1$H-NMR (400 MHz, $CDCl_3$) δ 7.24 (dd, 1H), 7.12-6.94 (m, 4H), 6.90-6.87 (m, 1H), 4.93 (t, 1H), 4.82-4.75 (m, 1H), 4.70 (d, 1H), 3.94-3.81 (m, 2H), 3.78 (s, 3H), 3.32-3.21 (m, 1H), 2.94-2.66 (m, 5H), 2.15-2.06 (m, 1H), 1.87-1.79 (m, 1H), 1.75-1.66 (m, 1H), 1.62-1.54 (m, 1H), 1.46-1.36 (m, 1H), 1.07 (d, 3H), 1.03 (d, 3H)

Example 253. (S)-quinuclidin-3-yl (7-(6-ethoxypyridin-3-yl)-3,3-dimethylchroman-4-yl)carbamate $^1$H-NMR (400 MHz, $CDCl_3$) δ 8.34 (s, 1H), 7.75 (dd, 1H), 7.27 (dd, 1H), 7.09 (t, 1H), 6.98 (s, 1H), 6.78 (d, 1H), 4.91-4.84 (m, 1H), 4.82-4.77 (m, 1H), 4.72 (d, 1H), 4.39 (q, 2H), 3.94-3.81 (m, 2H), 3.33-3.22 (m, 1H), 2.92-2.68 (m, 5H), 2.13-2.05 (m, 1H), 1.85-1.78 (m, 1H), 1.75-1.66 (m, 1H), 1.62-1.54 (m, 1H), 1.46-1.35 (m, 4H), 1.07 (d, 3H), 1.02 (d, 3H)

Example 254. (S)-quinuclidin-3-yl (7-(6-methoxy-5-methylpyridin-3-yl)-3,3-dimethylchroman-4-yl)carbamate $^1$H-NMR (400 MHz, $CDCl_3$) δ 8.18 (s, 1H), 7.56 (s, 1H), 7.28-7.23 (m, 1H), 7.08 (t, 1H), 6.97 (s, 1H), 4.92 (t, 1H), 4.83-4.75 (m, 1H), 4.70 (d, 1H), 3.99 (s, 3H), 3.94-3.79 (m, 2H), 3.32-3.21 (m, 1H), 2.93-2.67 (m, 5H), 2.23 (s, 3H), 2.13-2.00 (m, 1H), 1.87-1.78 (m, 1H), 1.74-1.65 (m, 1H), 1.62-1.53 (m, 1H), 1.45-1.35 (m, 1H), 1.06 (d, 3H), 1.02 (d, 3H)

Example 255. (S)-quinuclidin-3-yl (7-(4-methoxy-3,5-dimethylphenyl)-3,3-dimethylchroman-4-yl)carbamate $^1$H-NMR (400 MHz, $CDCl_3$) δ 7.28-7.18 (m, 3H), 7.10 (t, 1H), 6.99 (s, 1H), 4.90 (t, 1H), 4.83-4.76 (m, 1H), 4.70 (d, 1H), 3.94-3.81 (m, 2H), 3.75 (s, 3H), 3.33-3.22 (m, 1H), 2.94-2.69 (m, 5H), 2.33 (s, 6H), 2.13-2.06 (m, 1H), 1.89-1.79 (m, 1H), 1.74-1.66 (m, 1H), 1.62-1.53 (m, 1H), 1.46-1.35 (m, 1H), 1.06-(d, 3H), 1.02 (d, 3H)

Example 256. (S)-quinuclidin-3-yl (7-(4-butylphenyl)-3,3-dimethylchroman-4-yl)carbamate $^1$H-NMR (400 MHz, $CDCl_3$) δ 7.49-7.47 (m, 2H), 7.29-7.21 (m, 3H), 7.15 (t, 1H), 7.04 (s, 1H), 4.91 (t, 1H), 4.83-4.77 (m, 1H), 4.71 (d, 1H), 3.94-3.80 (m, 2H), 3.32-3.22 (m, 1H), 2.96-2.70 (m, 5H), 2.65 (t, 2H), 2.13-2.05 (m, 1H), 1.88-1.78 (m, 1H), 1.74-1.54 (m, 4H), 1.46-1.34 (m, 3H), 1.07 (d, 3H), 1.03 (d, 3H), 0.95 (t, 3H)

Example 257. (S)-quinuclidin-3-yl (7-(4-isobutylphenyl)-3,3-dimethylchroman-4-yl)carbamate $^1$H-NMR (400 MHz, $CDCl_3$) δ 7.48-7.47 (m, 2H), 7.28-7.14 (m, 4H), 7.05 (s, 1H), 4.96 (t, 1H), 4.82-4.76 (m, 1H), 4.71 (d, 1H), 3.94-3.79 (m, 2H), 3.32-3.20 (m, 1H), 2.93-2.67 (m, 5H), 2.51 (d, 2H), 2.13-2.04 (m, 1H), 1.94-1.78 (m, 2H), 1.75-1.65 (m, 1H), 1.62-1.54 (m, 1H), 1.46-1.36 (m, 1H), 1.06 (d, 3H), 1.02 (d, 3H), 0.94 (d, 6H)

Example 258. (S)-quinuclidin-3-yl (7-(6-isopropoxypyridin-3-yl)-3,3-dimethylchroman-4-yl)carbamate $^1$H-NMR (400 MHz, $CDCl_3$) δ 8.34 (s, 1H), 7.73 (d, 1H), 7.27 (dd, 1H), 7.09 (t, 1H), 6.97 (s, 1H), 6.73 (d, 1H), 5.37-5.28 (m, 1H), 4.87 (t, 1H), 4.82-4.77 (m, 1H), 4.71 (d, 1H), 3.94-3.80 (m, 2H), 3.32-3.21 (m, 1H), 2.93-2.69 (m, 5H), 2.13-2.05 (m, 1H), 1.89-1.79 (m, 1H), 1.73-1.66 (m, 1H), 1.62-1.53 (m, 1H), 1.47-1.39 (m, 1H), 1.37 (d, 6H), 1.06 (d, 3H), 1.02 (d, 3H)

Example 259. (S)-quinuclidin-3-yl (7-(4-(isoxazol-3-yl)phenyl)-3,3-dimethylchroman-4-yl)carbamate $^1$H-NMR (400 MHz, $CDCl_3$) δ 8.47 (s, 1H), 7.91-7.84 (m, 2H), 7.70-7.61 (m, 2H), 7.29 (dd, 1H), 7.20 (t, 1H), 7.09 (s, 1H), 6.69 (s, 1H), 4.98 (t, 1H), 4.83-4.77 (m, 1H), 4.73 (d, 1H), 3.97-3.81 (m, 2H), 3.33-3.22 (m, 1H), 2.94-2.68 (m, 5H), 2.14-2.05 (m, 1H), 1.88-1.78 (m, 1H), 1.75-1.66 (m, 1H), 1.62-1.54 (m, 1H), 1.47-1.35 (m, 1H), 1.07 (d, 3H), 1.03 (d, 3H)

Example 260. (S)-quinuclidin-3-yl (7-(4-isobutoxy-phenyl)-3,3-dimethylchroman-4-yl)carbamate $^1$H-NMR (400 MHz, $CDCl_3$) δ 7.53-7.42 (m, 2H), 7.25-7.19 (m, 1H), 7.12 (t, 1H), 7.01 (s, 1H), 6.98-6.91 (m, 2H), 4.85 (t, 1H), 4.82-4.76 (m, 1H), 4.70 (d, 1H), 3.95-3.81 (m, 2H), 3.76 (d, 2H), 3.34-3.22 (m, 1H), 2.96-2.67 (m, 5H), 2.16-2.04 (m, 2H), 1.87-1.79 (m, 1H), 1.75-1.66 (m, 1H), 1.62-1.54 (m, 1H), 1.46-1.38 (m, 1H), 1.11-0.92 (m, 12H)

Example 261. (S)-quinuclidin-3-yl (7-(3-fluoro-4-isopropoxyphenyl)-3,3-dimethylchroman-4-yl)carbamate $^1$H-NMR (400 MHz, $CDCl_3$) δ 7.33-7.19 (m, 3H), 7.09 (t, 1H), 7.04-6.96 (m, 2H), 4.95 (t, 1H), 4.83-4.76 (m, 1H), 4.70 (d, 1H), 4.60-4.54 (m, 1H), 3.92-3.81 (m, 2H), 3.31-3.21 (m, 1H), 2.93-2.68 (m, 5H), 2.13-2.05 (m, 1H), 1.87-1.78 (m, 1H), 1.74-1.65 (m, 1H), 1.62-1.53 (m, 1H), 1.45-1.33 (m, 7H), 1.06 (d, 3H), 1.01 (d, 3H)

Example 262. (S)-quinuclidin-3-yl (7-(2-fluoro-4-(trifluoromethyl)phenyl)-3,3-dimethylchroman-4-yl) carbamate $^1$H-NMR (400 MHz, $CDCl_3$) δ 7.54 (t, 1H), 7.47 (d, 1H), 7.41 (d, 1H), 7.35-7.25 (m, 1H), 7.11 (t, 1H), 7.01 (s, 1H), 4.97 (t, 1H), 4.84-4.77 (m, 1H), 4.73 (d, 1H), 3.96-3.81 (m, 2H), 3.32-3.22 (m, 1H), 2.94-2.69 (m, 5H), 2.17-2.05 (m, 1H), 1.88-1.79 (m, 1H), 1.74-1.67 (m, 1H), 1.63-1.54 (m, 1H), 1.46-1.37 (m, 1H), 1.07 (d, 3H), 1.03 (d, 3H)

Example 263. (S)-quinuclidin-3-yl (7-(4-isopropoxy-3,5-dimethylphenyl)-3,3-dimethylchroman-4-yl)carbamate $^1$H-NMR (400 MHz, $CDCl_3$) δ 7.29-7.18 (m, 3H), 7.12 (t, 1H), 7.01 (s, 1H), 4.88 (t, 1H), 4.83-4.76 (m, 1H), 4.70 (d, 1H), 4.20 (m, 1H), 3.94-3.79 (m, 2H), 3.33-3.22 (m, 1H), 2.96-2.69 (m, 5H), 2.31 (s, 6H), 2.14-2.06 (m, 1H), 1.89-1.79 (m, 1H), 1.75-1.66 (m, 1H), 1.63-1.55 (m, 1H), 1.47-1.38 (m, 1H), 1.32 (d, 6H), 1.06 (d, 3H), 1.02 (d, 3H)

Example 264. (S)-quinuclidin-3-yl (3,3-dimethyl-7-phenylchroman-4-yl)carbamate $^1$H-NMR (400 MHz, $CDCl_3$) δ 7.60-7.53 (m, 2H), 7.47-7.39 (m, 2H), 7.36-7.29 (m, 1H), 7.27 (t, 1H), 7.16 (t, 1H), 7.06 (s, 1H), 4.99 (t, 1H), 4.83-4.77 (m, 1H), 4.72 (d, 1H), 3.94-3.82 (m, 2H), 3.33-3.20 (m, 1H), 2.92-2.68 (m, 5H), 2.13-2.06 (m, 1H), 1.87-1.79 (m, 1H), 1.74-1.66 (m, 1H), 1.62-1.54 (m, 1H), 1.45-1.35 (m, 1H), 1.07 (d, 3H), 1.03 (d, 3H)

Example 265. (S)-quinuclidin-3-yl (3,3-dimethyl-7-(pyridin-3-yl)chroman-4-yl)carbamate $^1$H-NMR (400 MHz, $CDCl_3$) δ 8.71 (s, 1H), 8.55 (d, 1H), 7.82 (d, 1H), 7.38-7.23 (m, 2H), 7.11 (t, 1H), 7.01 (s, 1H), 5.30 (t, 1H), 4.83-4.76 (m, 1H), 4.72 (d, 1H), 3.95-3.82 (m, 2H), 3.32-3.20 (m, 1H), 2.92-2.67 (m, 5H), 2.14-2.05 (m, 1H), 1.86-1.77 (m, 1H), 1.74-1.65 (m, 1H), 1.61-1.53 (m, 1H), 1.44-1.36 (m, 1H), 1.06 (d, 3H), 1.02 (d, 3H)

Example 266. (S)-quinuclidin-3-yl (3,3-dimethyl-7-(pyridin-2-yl)chroman-4-yl)carbamate $^1$H-NMR (400 MHz, $CDCl_3$) δ 7.69-7.60 (m, 1H), 7.48-7.40 (m, 1H), 7.23-7.13 (m, 3H), 6.91 (dd, 1H), 6.81 (d, 1H), 4.93 (t, 1H), 4.81-4.74 (m, 1H), 4.67 (d, 1H), 3.90-3.75 (m, 2H), 3.26-3.18 (m, 1H), 2.94-2.66 (m, 5H), 2.11-2.03 (m, 1H), 1.88-1.77 (m, 1H), 1.76-1.65 (m, 1H), 1.61-1.52 (m, 1H), 1.44-1.35 (m, 1H), 1.03 (d, 3H), 0.99 (d, 3H)

Example 267. (S)-quinuclidin-3-yl (7-benzyl-3,3-dimethylchroman-4-yl)carbamate $^1$H-NMR (400 MHz, $CDCl_3$) δ 7.32-7.25 (m, 2H), 7.23-7.16 (m, 3H), 7.13-7.07 (m, 1H), 6.76 (t, 1H), 6.64 (s, 1H), 4.87-4.73 (m, 2H), 4.63 (d, 1H), 3.90 (s, 2H), 3.86-3.73 (m, 2H), 3.31-3.20 (m, 1H), 2.91-2.66 (m, 5H), 2.11-2.02 (m, 1H), 1.87-1.76 (m, 1H), 1.73-1.66 (m, 1H), 1.61-1.53 (m, 1H), 1.45-1.36 (m, 1H), 1.02 (d, 3H), 0.98 (d, 3H)

Example 268. (S)-quinuclidin-3-yl (3,3-dimethyl-7-(m-tolyl)chroman-4-yl)carbamate $^1$H-NMR (400 MHz, $CDCl_3$) δ 7.41-7.21 (m, 4H), 7.19-7.12 (m, 2H), 7.05 (s, 1H), 4.96 (t, 1H), 4.84-4.76 (m, 1H), 4.71 (d, 1H), 3.94-3.80 (m, 2H), 3.33-3.22 (m, 1H), 2.92-2.69 (m, 5H), 2.41 (s, 3H), 2.13-2.05 (m, 1H), 1.88-1.79 (m, 1H), 1.74-1.66 (m, 1H), 1.62-1.54 (m, 1H), 1.46-1.37 (m, 1H), 1.07 (d, 3H), 1.03 (d, 3H)

Example 269. (S)-quinuclidin-3-yl (3,3-dimethyl-7-(p-tolyl)chroman-4-yl)carbamate $^1$H-NMR (400 MHz, $CDCl_3$) δ 7.51-7.39 (m, 2H), 7.30-7.20 (m, 3H), 7.15 (t, 1H), 7.04 (s, 1H), 4.98 (t, 1H), 4.83-4.76 (m, 1H), 4.71 (d, 1H), 3.94-3.80 (m, 2H), 3.32-3.21 (m, 1H), 2.93-2.68 (m, 5H), 2.39 (s, 3H), 2.15-2.05 (m, 1H), 1.87-1.78 (m, 1H), 1.74-1.66 (m, 1H), 1.62-1.53 (m, 1H), 1.45-1.36 (m, 1H), 1.06 (d, 3H), 1.02 (d, 3H)

Example 270. (S)-quinuclidin-3-yl (3,3-dimethyl-7-(o-tolyl)chroman-4-yl)carbamate $^1$H-NMR (400 MHz, $CDCl_3$) δ 7.29-7.16 (m, 5H), 6.88 (t, 1H), 6.78 (s, 1H), 5.05 (t, 1H), 4.83-4.77 (m, 1H), 4.73 (d, 1H), 3.93-3.79 (m, 2H), 3.33-3.20 (m, 1H), 2.94-2.67 (m, 5H), 2.28 (s, 3H), 2.14-2.06 (m, 1H), 1.90-1.78 (m, 1H), 1.75-1.65 (m, 1H), 1.62-1.54 (m, 1H), 1.46-0.135 (m, 1H), 1.07 (d, 3H), 1.03 (d, 3H)

Example 271. (S)-quinuclidin-3-yl (3,3-dimethyl-7-((E)-2-(thiophen-3-yl)vinyl)chroman-4-yl)carbamate $^1$H-NMR (400 MHz, $CDCl_3$) δ 7.36-7.29 (m, 2H), 7.28-7.24 (m, 1H), 7.21-7.14 (m, 1H), 7.08-7.01 (m, 2H), 6.93-6.83 (m, 2H), 4.92 (t, 1H), 4.83-4.73 (m, 1H), 4.67 (d, 1H), 3.92-3.77 (m, 2H), 3.34-3.20 (m, 1H), 2.92-2.67 (m, 5H), 2.14-2.04 (m, 1H), 1.90-1.78 (m, 1H), 1.74-1.65 (m, 1H), 1.62-1.52 (m, 1H), 1.47-1.36 (m, 1H), 1.04 (d, 3H), 1.00 (d, 3H)

Example 272. (S)-quinuclidin-3-yl (3,3-dimethyl-7-(4-vinylphenyl)chroman-4-yl)carbamate $^1$H-NMR (400 MHz, $CDCl_3$) δ 7.57-7.51 (m, 2H), 7.49-7.44 (m, 2H), 7.27 (dd, 1H), 7.17 (t, 1H), 7.06 (s, 1H), 6.75

(dd, 1H), 5.79 (d, 1H), 5.27 (d, 1H), 4.95 (t, 1H), 4.83-4.76 (m, 1H), 4.72 (d, 1H), 3.94-3.81 (m, 2H), 3.32-3.22 (m, 1H), 2.93-2.68 (m, 5H), 2.14-2.06 (m, 1H), 1.87-1.79 (m, 1H), 1.75-1.66 (m, 1H), 1.63-1.54 (m, 1H), 1.47-1.37 (m, 1H), 1.07 (d, 3H), 1.02 (d, 3H)

Example 273. (S)-quinuclidin-3-yl (7-(4-ethylphenyl)-3,3-dimethylchroman-4-yl)carbamate $^1$H-NMR (400 MHz, $CDCl_3$) δ 7.54-7.44 (m, 2H), 7.31-7.23 (m, 3H), 7.16 (t, 1H), 7.04 (s, 1H), 4.89 (t, 1H), 4.84-4.77 (m, 1H), 4.71 (d, 1H), 3.95-3.80 (m, 2H), 3.34-3.21 (m, 1H), 2.94-2.62 (m, 7H), 2.14-2.05 (m, 1H), 1.88-1.79 (m, 1H), 1.75-1.67 (m, 1H), 1.63-1.55 (m, 1H), 1.46-1.38 (m, 1H), 1.28 (t, 3H), 1.07 (d, 3H), 1.03 (d, 3H)

Example 274. (S)-quinuclidin-3-yl (3,3-dimethyl-7-(2-vinylphenyl)chroman-4-yl)carbamate $^1$H-NMR (400 MHz, $CDCl_3$) δ 7.63 (d, 1H), 7.37-7.29 (m, 2H), 7.28-7.19 (m, 2H), 6.90 (t, 1H), 6.81 (s, 1H), 6.74 (dd, 1H), 5.69 (d, 1H), 5.19 (d, 1H), 5.00 (t, 1H), 4.84-4.78 (m, 1H), 4.73 (d, 1H), 3.95-3.80 (m, 2H), 3.33-3.20 (m, 1H), 2.94-2.68 (m, 5H), 2.14-2.06 (m, 1H), 1.89-1.79 (m, 1H), 1.74-1.65 (m, 1H), 1.63-1.54 (m, 1H), 1.46-1.37 (m, 1H), 1.08 (d, 3H), 1.04 (d, 3H)

Example 275. (S)-quinuclidin-3-yl (7-(4-ethoxy-2-methylphenyl)-3,3-dimethylchroman-4-yl)carbamate $^1$H-NMR (400 MHz, $CDCl_3$) δ 7.20 (d, 1H), 7.12 (d, 1H), 6.86 (d, 1H), 6.81-6.73 (m, 3H), 4.98 (t, 1H), 4.83-4.76 (m, 1H), 4.72 (d, 1H), 4.05 (q, 2H), 3.92-3.79 (m, 2H), 3.30-3.21 (m, 1H), 2.95-2.68 (m, 5H), 2.26 (S, 3H), 2.14-2.05 (m, 1H), 1.89-1.80 (m, 1H), 1.74-1.67 (m, 1H), 1.62-1.54 (m, 1H), 1.48-1.36 (m, 4H), 1.07 (d, 3H), 1.03 (d, 3H)

Example 276. (S)-quinuclidin-3-yl (7-(4-(benzyloxy)phenyl)-3,3-dimethylchroman-4-yl)carbamate $^1$H-NMR (400 MHz, $CDCl_3$) δ 7.53-7.44 (m, 4H), 7.42-7.38 (m, 2H), 7.36-7.32 (m, 1H), 7.26-7.20 (m, 1H), 7.15-7.12 (m, 1H), 7.11-7.09 (m, 3H), 5.11 (s, 2H), 4.90 (t, 1H), 4.83-4.77 (m, 1H), 4.71 (d, 1H), 3.95-3.78 (m, 2H), 3.32-3.22 (m, 1H), 2.93-2.70 (m, 5H), 2.14-2.05 (m, 1H), 1.88-1.80 (m, 1H), 1.75-1.66 (m, 1H), 1.62-1.54 (m, 1H), 1.46-1.37 (m, 1H), 1.07 (d, 3H), 1.03 (d, 3H)

Example 277. (S)-quinuclidin-3-yl (7-(3-(benzyloxy)phenyl)-3,3-dimethylchroman-4-yl)carbamate $^1$H-NMR (400 MHz, $CDCl_3$) δ 7.49-7.44 (m, 2H), 7.43-7.38 (m, 2H), 7.36-7.32 (m, 2H), 7.29-7.23 (m, 1H), 7.21-7.11 (m, 3H), 7.05 (s, 1H), 6.96 (d, 1H), 5.12 (S, 2H), 4.90 (t, 1H), 4.84-4.77 (m, 1H), 4.72 (d, 1H), 3.96-3.81 (m, 2H), 3.34-3.22 (m, 1H), 2.94-2.69 (m, 5H), 2.15-2.06 (m, 1H), 1.89-1.79 (m, 1H), 1.76-1.67 (m, 1H), 1.63-1.54 (m, 1H), 1.47-1.38 (m, 1H), 1.07-(d, 3H), 1.03 (d, 3H)

Example 278. (S)-quinuclidin-3-yl (7-(2,6-difluoropyridin-3-yl)-3,3-dimethylchroman-4-yl)carbamate $^1$H-NMR (400 MHz, $CDCl_3$) δ 7.94 (dd, 1H), 7.35-7.23 (m, 2H), 7.15-7.04 (m, 1H), 6.98 (s, 1H), 6.92 (dd, 1H), 4.85 (t, 1H), 4.82-4.78 (m, 1H), 4.74 (d, 1H), 3.91-3.80 (m, 2H), 3.35-3.20 (m, 1H), 2.96-2.69 (m, 5H), 2.14-2.05 (m, 1H), 1.89-1.78 (m, 1H), 1.75-1.66 (m, 1H), 1.62-1.54 (m, 1H), 1.47-1.38 (m, 1H), 1.07 (d, 3H), 1.03 (d, 3H)

Example 279. (S)-quinuclidin-3-yl (7-(2-allylphenyl)-3,3-dimethylchroman-4-yl)carbamate $^1$H-NMR (400 MHz, $CDCl_3$) δ 7.34-7.18 (m, 5H), 6.88 (t, 1H), 6.78 (s, 1H), 5.96-5.84 (m, 1H), 5.03 (d, 1H), 4.99-4.90 (m, 2H), 4.83-4.77 (m, 1H), 4.73 (d, 1H), 3.96-3.79 (m, 2H), 3.35 (d, 2H), 3.29-3.24 (m, 1H), 2.94-2.68 (m, 5H), 2.14-2.06 (m, 1H), 1.88-1.79 (m, 1H), 1.75-1.67 (m, 1H), 1.63-1.54 (m, 1H), 1.47-1.38 (m, 1H), 1.07 (d, 3H), 1.03 (d, 3H)

Example 280. (S)-quinuclidin-3-yl (7-(4-(cyanomethyl)phenyl)-3,3-dimethylchroman-4-yl)carbamate $^1$H-NMR (400 MHz, $CDCl_3$) δ 7.59-7.53 (m, 2H), 7.41-7.35 (m, 2H), 7.27 (dd, 1H), 7.14 (t, 1H), 7.03 (s, 1H), 4.95 (t, 1H), 4.83-4.76 (m, 1H), 4.72 (d, 1H), 3.95-3.82 (m, 2H), 3.78 (s, 2H), 3.32-3.21 (m, 1H), 2.93-2.68 (m, 5H), 2.14-2.06 (m, 1H), 1.88-1.77 (m, 1H), 1.74-1.67 (m, 1H), 1.63-1.54 (m, 1H), 1.48-1.36 (m, 1H), 1.06 (d, 3H), 1.02 (d, 3H)

Example 281. (S)-quinuclidin-3-yl (7-(3-(cyanomethyl)phenyl)-3,3-dimethylchroman-4-yl)carbamate $^1$H-NMR (400 MHz, $CDCl_3$) δ 7.57-7.48 (m, 2H), 7.43 (t, 1H), 7.33-7.23 (m, 2H), 7.14 (t, 1H), 7.03 (s, 1H), 4.93 (t, 1H), 4.84-4.76 (m, 1H), 4.72 (d, 1H), 3.95-3.83 (m, 2H), 3.80 (s, 2H), 3.33-3.21 (m, 1H), 2.94-2.67 (m, 5H), 2.15-2.05 (m, 1H), 1.88-1.78 (m, 1H), 1.74-1.67 (m, 1H), 1.62-1.53 (m, 1H), 1.46-1.37 (m, 1H), 1.07 (d, 3H), 1.02 (d, 3H)

Example 282. (S)-quinuclidin-3-yl (7-((E)-2-([1,1'-diphenyl]-4-yl)vinyl)-3,3-dimethylchroman-4-yl) carbamate $^1$H-NMR (400 MHz, $CDCl_3$) δ 7.68-7.52 (m, 6H), 7.48-7.41 (m, 3H), 7.35 (t, 1H), 7.24-7.16 (m, 1H), 7.14-7.05 (m, 2H), 6.98 (s, 1H), 5.03-4.93 (m, 1H), 4.83-4.75 (m, 1H), 4.69 (d, 1H), 3.93-3.78 (m, 2H), 3.32-3.20 (m, 1H), 2.93-2.67 (m, 5H), 2.14-2.05 (m, 1H), 1.88-1.78 (m, 1H), 1.74-1.65 (m, 1H), 1.62-1.53 (m, 1H), 1.46-1.36 (m, 1H), 1.09-0.95 (m, 6H)

Example 283. (S)-quinuclidin-3-yl (7-(2-cyclopropylpyrimidin-5-yl)-3,3-dimethylchroman-4-yl)carbamate $^1$H-NMR (400 MHz, $CDCl_3$) δ 8.72-7.64 (m, 2H), 7.32 (dd, 1H), 7.07 (t, 1H), 6.96 (s, 1H), 5.10 (dd, 1H), 4.84-4.75 (m, 1H), 4.72 (d, 1H), 3.95-3.80 (m, 2H), 3.30-3.20 (m, 1H), 2.91-2.66 (m, 5H), 2.33-2.24 (m, 1H), 2.11-2.03 (m, 1H), 1.86-1.77 (m, 1H), 1.73-1.65 (m, 1H), 1.61-1.52 (m, 1H), 1.45-1.36 (m, 1H), 1.20-1.09 (m, 4H), 1.06 (d, 3H), 1.01 (d, 3H)

Example 284. (S)-quinuclidin-3-yl (3,3-dimethyl-7-((E)-4-(trifluoromethyl)styryl)chroman-4-yl)carbamate $^1$H-NMR (400 MHz, $CDCl_3$) δ 7.62-7.55 (m, 4H), 7.21 (dd, 1H), 7.14-7.06 (m, 3H), 6.97 (s, 1H), 4.91 (t, 1H), 4.83-4.76 (m, 1H), 4.69 (d, 1H), 3.94-3.80 (m, 2H), 3.32-3.21 (m, 1H), 2.93-2.67 (m, 5H), 2.13-2.06 (m, 1H), 1.88-

1.79 (m, 1H), 1.75-1.67 (m, 1H), 1.63-1.53 (m, 1H), 1.47-1.37 (m, 1H), 1.05 (d, 3H), 1.01 (d, 3H)

Example 285. (S)-quinuclidin-3-yl (7-(2-chloro-3,5-dimethylphenyl)-3,3-dimethylchroman-4-yl)carbamate $^1$H-NMR (400 MHz, $CDCl_3$) δ 7.29-7.19 (m, 1H), 7.04 (s, 1H), 7.01-6.93 (m, 2H), 6.86 (s, 1H), 5.04 (t, 1H), 4.83-4.76 (m, 1H), 4.72 (d, 1H), 3.94-3.79 (m, 2H), 3.31-3.20 (m, 1H), 2.93-2.68 (m, 5H), 2.40 (s, 3H), 2.30 (s, 3H), 2.12-2.05 (m, 1H), 1.8-1.79 (m, 1H), 1.73-1.66 (m, 1H), 1.62-1.54 (m, 1H), 1.46-1.36 (m, 1H), 1.07 (d, 3H), 1.03 (d, 3H)

Example 286. (S)-quinuclidin-3-yl (7-((E)-2,4-difluorostyryl)-3,3-dimethylchroman-4-yl)carbamate $^1$H-NMR (400 MHz, $CDCl_3$) δ 7.54 (dd, 1H), 7.23-7.12 (m, 2H), 7.09-6.98 (m, 2H), 6.95 (s, 1H), 6.91-6.78 (m, 2H), 4.94 (t, 1H), 4.83-4.75 (m, 1H), 4.68 (d, 1H), 3.94-3.79 (m, 2H), 3.35-3.21 (m, 1H), 2.93-2.67 (m, 5H), 2.12-2.05 (m, 1H), 1.88-1.78 (m, 1H), 1.74-1.66 (m, 1H), 1.63-1.54 (m, 1H), 1.46-1.37 (m, 1H), 1.04 (d, 3H), 1.00 (d, 3H)

Example 287. (S)-quinuclidin-3-yl (7-((E)-4-ethylstyryl)-3,3-dimethylchroman-4-yl)carbamate 7.47-7.38 (m, 2H), 7.23-7.14 (m, 3H), 7.11-6.98 (m, 3H), 6.95 (s, 1H), 4.93 (t, 1H), 4.83-4.76 (m, 1H), 4.67 (d, 1H), 3.93-3.77 (m, 2H), 3.32-3.20 (m, 1H), 2.94-2.71 (m, 5H), 2.66 (q, 2H), 2.12-2.04 (m, 1H), 1.87-1.79 (m, 1H), 1.74-1.65 (m, 1H), 1.62-1.53 (m, 1H), 1.45-1.37 (m, 1H), 1.25 (t, 3H), 1.05 (d, 3H), 1.00 (d, 3H)

Example 288. (S)-quinuclidin-3-yl (7-(6-ethoxynaphthalen-2-yl)-3,3-dimethylchroman-4-yl) carbamate $^1$H-NMR (400 MHz, $CDCl_3$) δ 7.94 (s, 1H), 7.81-7.74 (m, 2H), 7.67 (d, 1H), 7.32-7.24 (m, 2H), 7.21-7.11 (m, 3H), 4.95 (t, 1H), 4.84-4.78 (m, 1H), 4.73 (d, 1H), 4.17 (q, 2H), 3.96-3.81 (m, 2H), 3.33-3.23 (m, 1H), 2.93-2.69 (m, 5H), 2.13-2.05 (m, 1H), 1.91-1.76 (m, 1H), 1.75-1.67 (m, 1H), 1.63-1.55 (m, 1H), 1.49 (t, 3H), 1.45-1.37 (m, 1H), 1.08 (d, 3H), 1.04 (d, 3H)

Example 289. (S)-quinuclidin-3-yl (7-((E)-3-fluorostyryl)-3,3-dimethylchroman-4-yl)carbamate $^1$H-NMR (400 MHz, $CDCl_3$) δ 7.34-7.16 (m, 4H), 7.10-7.06 (m, 1H), 7.04-7.00 (m, 2H), 6.98-6.93 (m, 2H), 4.90-4.76 (m, 2H), 4.69 (d, 1H), 3.94-3.80 (m, 2H), 3.32-3.22 (m, 1H), 2.95-2.70 (m, 5H), 2.13-2.06 (m, 1H), 1.86-1.78 (m, 1H), 1.76-1.67 (m, 1H), 1.64-1.55 (m, 1H), 1.46-1.37 (m, 1H), 1.05 (d, 3H), 1.01 (d, 3H)

Example 290. (S)-quinuclidin-3-yl (7-(dibenzo[b,d]furan-4-yl)-3,3-dimethylchroman-4-yl)carbamate $^1$H-NMR (400 MHz, $CDCl_3$) δ 7.99 (d, 1H), 7.94 (d, 1H), 7.64-7.56 (m, 2H), 7.54-7.44 (m, 2H), 7.42-7.32 (m, 4H), 4.96 (t, 1H), 4.85-4.81 (m, 1H), 4.77 (d, 1H), 4.00-3.85 (m, 2H), 3.37-3.23 (m, 1H), 2.96-2.69 (m, 5H), 2.18-2.07 (m, 1H), 1.92-1.80 (m, 1H), 1.77-1.67 (m, 1H), 1.64-1.55 (m, 1H), 1.48-1.37 (m, 1H), 1.11 (d, 3H), 1.07 (d, 3H)

Example 291. (S)-quinuclidin-3-yl (7-(4-cyano-3-fluorophenyl)-3,3-dimethylchroman-4-yl)carbamate $^1$H-NMR (400 MHz, $CDCl_3$) δ 7.65 (t, 1H), 7.44-7.28 (m, 3H), 7.17-7.07 (m, 1H), 7.02 (s, 1H), 4.97 (t, 1H), 4.84-4.77 (m, 1H), 4.73 (d, 1H), 3.98-3.80 (m, 2H), 3.32-3.20 (m, 1H), 2.93-2.67 (m, 5H), 2.12-2.05 (m, 1H), 1.88-1.78 (m, 1H), 1.75-1.66 (m, 1H), 1.63-1.54 (m, 1H), 1.47-1.37 (m, 1H), 1.06 (d, 3H), 1.02 (d, 3H)

Example 292. (S)-quinuclidin-3-yl (7-(1-benzyl-6-oxo-1,6-dihydropyridin-3-yl)-3,3-dimethylchroman-4-yl)carbamate $^1$H-NMR (400 MHz, $CDCl_3$) δ 7.54 (d, 1H), 7.43 (s, 1H), 7.37-7.25 (m, 5H), 7.20 (dd, 1H), 6.88 (t, 1H), 6.76 (s, 1H), 6.64 (d, 1H), 5.17 (s, 2H), 5.07 (q, 1H), 4.82-4.74 (m, 1H), 4.66 (d, 1H), 3.90-3.79 (m, 2H), 3.31-3.18 (m, 1H), 2.90-2.63 (m, 5H), 2.11-2.04 (m, 1H), 1.87-1.76 (m, 1H), 1.73-1.65 (m, 1H), 1.61-1.52 (m, 1H), 1.45-1.35 (m, 1H), 1.03 (d, 3H), 0.99 (d, 3H)

Example 293. (S)-quinuclidin-3-yl (7-((E)-4-fluorostyryl)-3,3-dimethylchroman-4-yl)carbamate $^1$H-NMR (400 MHz, $CDCl_3$) δ 7.66 (dd, 1H), 7.51-7.40 (m, 2H), 7.30-7.13 (m, 2H), 7.10-6.99 (m, 2H), 6.96-6.79 (m, 2H), 4.89 (t, 1H), 4.82-4.74 (m, 1H), 4.68 (d, 1H), 3.97-3.76 (m, 2H), 3.32-3.65 (m, 1H), 2.93-2.65 (m, 5H), 2.14-2.04 (m, 1H), 1.87-1.78 (m, 1H), 1.73-1.65 (m, 1H), 1.62-1.53 (m, 1H), 1.46-1.35 (m, 1H), 1.09 (d, 3H), 0.92 (d, 3H)

Example 294. (S)-quinuclidin-3-yl (6-(3-fluorophenyl)-2,2-dimethylchroman-4-yl)carbamate The titled compound was prepared in accordance with the same procedures as in Example 1, using (S)-quinuclidin-3-yl (6-bromo-2,2-dimethylchroman-4-yl)carbamate Preparation 6 and 3-fluorophenylboronic acid.

$^1$H-NMR (400 MHz, $CDCl_3$) δ 7.52-7.48 (d, 1H), 7.41-7.21 (m, 4H), 7.02-6.98 (t, 1H), 6.89-6.87 (d, 1H), 5.06-5.04 (m, 1H), 4.97-4.95 (m, 1H), 4.81 (m, 1H), 3.30-3.25 (m, 1H), 2.87-2.72 (m, 5H), 2.31-2.27 (m, 1H), 2.13-2.06 (m, 1H), 1.93-1.69 (m, 3H), 1.64 (m, 1H), 1.47 (s, 3H), 1.47-1.37 (m, 1H), 1.34 (s, 3H)

Examples 295 and 296

The titled compounds of Examples 295 and 296 were prepared in accordance with the same procedures as in Example 1, using (S)-quinuclidin-3-yl (7-bromo-2,2-dimethylchroman-4-yl)carbamate prepared in Preparation 5; and the corresponding substituted-boronic acids, respectively.

Example 295. (S)-quinuclidin-3-yl (2,2-dimethyl-7-(3-(trifluoromethyl)phenyl)chroman-4-yl)carbamate $^1$H-NMR (400 MHz, $CDCl_3$) δ 7.81 (s, 1H), 7.51-7.32 (d, 1H), 7.60-7.58 (d, 1H), 7.55-7.51 (t, 1H), 7.41-7.36 (m, 1H), 7.16-7.12 (t, 1H), 7.05 (s, 1H), 5.06-5.03 (m, 2H), 4.82-4.80 (m, 1H), 3.26 (m, 1H), 2.89-2.71 (m, 5H), 2.27-2.25 (m, 1H), 2.14-2.05 (m, 2H), 1.80-1.69 (m, 3H), 1.60-1.59 (m, 1H), 1.47 (s, 3H), 1.44-1.41 (m, 1H), 1.37 (s, 3H)

Example 296. (S)-quinuclidin-3-yl (2,2-dimethyl-7-(3-(trifluoromethoxy)phenyl)chroman-4-yl)carbamate $^1$H-NMR (400 MHz, $CDCl_3$) δ 7.50-7.48 (d, 1H), 7.44-7.34 (m, 3H), 7.19-7.17 (d, 1H), 7.13-7.09 (t, 1H), 7.02 (s, 1H), 5.10-5.02 (m, 2H), 4.81-4.79 (m, 1H), 3.28-3.24 (m, 1H), 2.88-2.70 (m, 5H), 2.38 (m, 1H), 2.28-2.24 (m, 1H), 2.11-2.05 (m, 1H), 1.79-1.68 (m, 3H), 1.59-1.58 (m, 1H), 1.46 (s, 3H), 1.44-1.40 (m, 1H), 1.36 (s, 3H)

Examples 297 to 311

The titled compounds of Examples 297 to 311 were prepared in accordance with the same procedures as in Example 1, using (S)-quinuclidin-3-yl (7-bromo-4-methylchroman-4-yl)carbamate prepared in Preparation 7; and the corresponding substituted-boronic acids, respectively.

Example 297. (S)-quinuclidin-3-yl (7-(3-chlorophenyl)-4-methylchroman-4-yl)carbamate $^1$H-NMR (400 MHz, $CDCl_3$) δ 7.53 (s, 1H), 7.48-7.40 (m, 2H), 7.38-7.28 (m, 2H), 7.13 (d, 1H), 7.03 (s, 1H), 5.07-5.06 (m, 1H), 4.71-4.60 (m, 1H), 4.37-4.18 (m, 2H), 3.28-3.13 (m, 1H), 2.92-2.58 (m, 6H), 2.07-1.92 (m, 2H), 1.86-1.59 (m, 5H), 1.57-1.46 (m, 1H), 1.40-1.30 (m, 1H)

Example 298. (S)-quinuclidin-3-yl (7-(3-fluorophenyl)-4-methylchroman-4-yl)carbamate $^1$H-NMR (400 MHz, $CDCl_3$) δ 7.45 (d, 1H), 7.41-7.31 (m, 2H), 7.26-7.23 (m, 1H), 7.14 (d, 1H), 7.07-6.99 (m, 2H), 5.07 (s, 1H), 4.71-4.62 (m, 1H), 4.36-4.18 (m, 2H), 3.28-3.12 (m, 1H), 2.94-2.58 (m, 6H), 2.08-1.91 (m, 2H), 1.86-1.59 (m, 5H), 1.56-1.46 (m, 1H), 1.41-1.30 (m, 1H)

Example 299. (S)-quinuclidin-3-yl (7-(3-methoxyphenyl)-4-methylchroman-4-yl)carbamate $^1$H-NMR (400 MHz, $CDCl_3$) δ 7.47-7.40 (m, 1H), 7.34 (t, 1H), 7.20-7.12 (m, 2H), 7.10-7.03 (m, 2H), 6.89 (d, 1H), 5.14-5.04 (m, 1H), 4.72-4.61 (m, 1H), 4.34-4.20 (m, 2H), 3.85 (s, 3H), 3.26-3.15 (m, 1H), 2.89-2.59 (m, 6H), 2.09-1.91 (m, 2H), 1.84-1.60 (m, 5H), 1.56-1.47 (m, 1H), 1.40-1.30 (m, 1H)

Example 300. (S)-quinuclidin-3-yl (7-(3-isopropylphenyl)-4-methylchroman-4-yl)carbamate $^1$H-NMR (400 MHz, $CDCl_3$) δ 7.48-7.32 (m, 4H), 7.23 (d, 1H), 7.17 (d, 1H), 7.07 (s, 1H), 5.15-5.07 (m, 1H), 4.72-4.63 (m, 1H), 4.35-4.19 (m, 2H), 3.27-3.13 (m, 1H), 3.02-2.92 (m, 1H), 2.89-2.60 (m, 6H), 2.09-1.91 (m, 2H), 1.85-1.60 (m, 5H), 1.57-1.45 (m, 1H), 1.41-1.33 (m, 1H), 1.31-1.29 (d, 6H)

Example 301. (S)-quinuclidin-3-yl (7-(2-chloro-5-methoxyphenyl)-4-methylchroman-4-yl)carbamate $^1$H-NMR (400 MHz, $CDCl_3$) δ 7.47-7.39 (m, 1H), 7.34 (d, 1H), 7.03 (d, 1H), 6.92 (s, 1H), 6.87-6.79 (m, 2H), 5.12 (s, 1H), 4.72-4.62 (m, 1H), 4.36-4.17 (m, 2H), 3.80 (s, 3H), 3.28-3.13 (m, 1H), 2.90-2.57 (m, 6H), 2.11-1.92 (m, 2H), 1.87-1.62 (m, 5H), 1.57-1.47 (m, 1H), 1.41-1.29 (m, 1H)

Example 302. (S)-quinuclidin-3-yl (7-(4-ethoxyphenyl)-4-methylchroman-4-yl)carbamate $^1$H-NMR (400 MHz, $CDCl_3$) δ 7.51-7.45 (m, 2H), 7.44-7.37 (m, 1H), 7.13 (d, 1H), 7.02 (s, 1H), 6.98-6.90 (m, 2H), 5.13-5.05 (m, 1H), 4.71-4.63 (m, 1H), 4.33-4.18 (m, 2H), 4.07 (q, 2H), 3.25-3.13 (m, 1H), 2.91-2.59 (m, 6H), 2.08-1.92 (m, 2H), 1.85-1.60 (m, 5H), 1.56-1.48 (m, 1H), 1.45-1.44 (m, 1H), 1.38 (t, 3H)

Example 303. (S)-quinuclidin-3-yl (7-(3-(dimethylamino)phenyl)-4-methylchroman-4-yl)carbamate $^1$H-NMR (400 MHz, $CDCl_3$) δ 7.49-7.39 (m, 1H), 7.30 (d, 1H), 7.18 (d, 1H), 7.08 (s, 1H), 6.95-6.85 (m, 2H), 6.74 (d, 1H), 5.16-5.05 (m, 1H), 4.72-4.63 (m, 1H), 4.34-4.19 (m, 2H), 3.27-3.12 (m, 1H), 3.00 (s, 6H), 2.89-2.58 (m, 6H), 2.10-1.93 (m, 2H), 1.86-1.59 (m, 5H), 1.56-1.46 (m, 1H), 1.42-1.31 (m, 1H)

Example 304. (S)-quinuclidin-3-yl (7-(benzofuran-3-yl)-4-methylchroman-4-yl)carbamate $^1$H-NMR (400 MHz, $CDCl_3$) δ 7.84 (d, 1H), 7.78 (s, 1H), 7.55 (d, 1H), 7.47 (d, 1H), 7.39-7.28 (m, 2H), 7.22 (d, 1H), 7.14 (s, 1H), 5.14-5.07 (m, 1H), 4.72-4.65 (m, 1H), 4.36-4.20 (m, 2H), 3.28-3.14 (m, 1H), 2.91-2.59 (m, 6H), 2.10-1.91 (m, 2H), 1.87-1.62 (m, 5H), 1.57-1.47 (m, 1H), 1.41-1.30 (m, 1H)

Example 305. (S)-quinuclidin-3-yl (4-methyl-7-(3-(trifluoromethyl)phenyl)chroman-4-yl)carbamate $^1$H-NMR (400 MHz, $CDCl_3$) δ 7.79 (s, 1H), 7.72 (d, 1H), 7.60 (d, 1H), 7.54 (t, 1H), 7.47 (d, 1H), 7.16 (d, 1H), 7.06 (s, 1H), 5.16-5.04 (m, 1H), 4.70-4.62 (m, 1H), 4.36-4.20 (m, 2H), 3.26-3.13 (m, 1H), 2.91-2.56 (m, 6H), 2.07-1.90 (m, 2H), 1.85-1.60 (m, 5H), 1.56-1.44 (m, 1H), 1.40-1.30 (m, 1H)

Example 306. (S)-quinuclidin-3-yl (4-methyl-7-(3-(trifluoromethoxy)phenyl)chroman-4-yl)carbamate $^1$H-NMR (400 MHz, $CDCl_3$) δ 7.51-7.36 (m, 4H), 7.19 (d, 1H), 7.13 (d, 1H), 7.04 (s, 1H), 5.11 (s, 1H), 4.70-4.61 (m, 1H), 4.34-4.21 (m, 2H), 3.26-3.13 (m, 1H), 2.91-2.59 (m, 6H), 2.08-1.89 (m, 2H), 1.85-1.59 (m, 5H), 1.56-1.46 (m, 1H), 1.41-1.29 (m, 1H)

Example 307. (S)-quinuclidin-3-yl (7-(2,2-difluorobenzo[d][1,3]dioxol-5-yl)-4-methylchroman-4-yl) carbamate $^1$H-NMR (400 MHz, $CDCl_3$) δ 7.44 (d, 1H), 7.29-7.19 (m, 2H), 7.13-7.03 (m, 2H), 6.97 (s, 1H), 5.10 (s, 1H), 4.72-4.61 (m, 1H), 4.35-4.19 (m, 2H), 3.25-3.13 (m, 1H), 2.90-2.56 (m, 6H), 2.06-1.90 (m, 2H), 1.83-1.59 (m, 5H), 1.56-1.46 (m, 1H), 1.41-1.19 (m, 1H)

Example 308. (S)-quinuclidin-3-yl (7-(4-ethoxy-3,5-dimethylphenyl)-4-methylchroman-4-yl)carbamate $^1$H-NMR (400 MHz, $CDCl_3$) δ 7.45-7.37 (m, 1H), 7.22-7.16 (m, 2H), 7.11 (d, 1H), 7.01 (s, 1H), 5.11-5.04 (m, 1H), 4.72-4.60 (m, 1H), 4.31-4.16 (m, 2H), 3.88 (q, 2H), 3.27-

3.13 (m, 1H), 2.92-2.56 (m, 6H), 2.32 (s, 6H), 2.06-1.90 (m, 2H), 1.83-1.59 (m, 5H), 1.56-1.46 (m, 1H), 1.44 (t, 3H), 1.41-1.19 (m, 1H)

Example 309. (S)-quinuclidin-3-yl (7-(2-cyanophenyl)-4-methylchroman-4-yl)carbamate $^1$H-NMR (400 MHz, $CDCl_3$) δ 7.76 (d, 1H), 7.63 (t, 1H), 7.52-7.41 (m, 3H), 7.15 (d, 1H), 7.00 (s, 1H), 5.08 (s, 1H), 4.72-4.63 (m, 1H), 4.35-4.17 (m, 2H), 3.26-3.15 (m, 1H), 2.91-2.58 (m, 6H), 2.16-1.92 (m, 2H), 1.88-1.61 (m, 5H), 1.58-1.48 (m, 1H), 1.42-1.31 (m, 1H)

Example 310. (S)-quinuclidin-3-yl (7-(3-(tert-butyl)phenyl)-4-methylchroman-4-yl)carbamate $^1$H-NMR (400 MHz, $CDCl_3$) δ 7.57 (s, 1H), 7.48-7.33 (m, 4H), 7.17 (d, 1H), 7.07 (s, 1H), 5.11 (s, 1H), 4.72-4.63 (m, 1H), 4.35-4.20 (m, 2H), 3.27-3.12 (m, 1H), 2.91-2.59 (m, 6H), 2.10-1.92 (m, 2H), 1.86-1.60 (m, 5H), 1.57-1.47 (m, 1H), 1.41-1.28 (m, 10H)

Example 311. (S)-quinuclidin-3-yl (4-methyl-7-(4-methylthiophen-3-yl)chroman-4-yl)carbamate $^1$H-NMR (400 MHz, $CDCl_3$) δ 7.45-7.35 (m, 1H), 7.18 (d, 1H), 7.04-6.93 (m, 2H), 6.87 (s, 1H), 5.09 (s, 1H), 4.70-4.62 (m, 1H), 4.34-4.17 (m, 2H), 3.27-3.12 (m, 1H), 2.91-2.58 (m, 6H), 2.28 (s, 3H), 2.09-1.91 (m, 2H), 1.87-1.60 (m, 5H), 1.56-1.47 (m, 1H), 1.41-1.29 (m, 1H)

Examples 312 and 313

The titled compounds of Examples 312 and 313 were prepared in accordance with the same procedures as in Example 1, using (S)-quinuclidin-3-yl (7-bromoisochroman-4-yl)carbamate prepared in Preparation 8; and the corresponding substituted-boronic acids, respectively.

Example 312. (S)-quinuclidin-3-yl (7-(3-(tert-butyl)phenyl)isochroman-4-yl)carbamate $^1$H-NMR (400 MHz, $CDCl_3$) δ 7.55 (s, 1H), 7.52-7.46 (m, 2H), 7.43-7.33 (m, 3H), 7.22 (s, 1H), 5.42-5.33 (m, 1H), 4.93-4.71 (m, 4H), 4.17-4.07 (m, 1H), 3.98-3.87 (m, 1H), 3.32-3.19 (m, 1H), 2.92-2.65 (m, 5H), 2.08-1.98 (m, 1H), 1.85-1.75 (m, 1H), 1.73-1.64 (m, 1H), 1.62-1.52 (m, 1H), 1.43-1.21 (m, 10H)

Example 313. (S)-quinuclidin-3-yl (7-(3-isopropylphenyl)isochroman-4-yl)carbamate $^1$H-NMR (400 MHz, $CDCl_3$) δ 7.52-7.46 (m, 2H), 7.41-7.33 (m, 3H), 7.26-7.19 (m, 2H), 5.42-5.35 (m, 1H), 4.92-4.72 (m, 4H), 4.16-4.08 (m, 1H), 3.98-3.88 (m, 1H), 3.32-3.20 (m, 1H), 3.03-2.93 (m, 1H), 2.90-2.67 (m, 5H), 2.07-1.99 (m, 1H), 1.84-1.75 (m, 1H), 1.72-1.65 (m, 1H), 1.61-1.53 (m, 1H), 1.42-1.34 (m, 1H), 1.31 (d, 6H)

Examples 314 and 315

The titled compounds of Examples 314 and 315 were prepared in accordance with the same procedures as in Example 1, using (S)-quinuclidin-3-yl (7-bromo-1-methyl-1,2,3,4-tetrahydroquinolin-4-yl)carbamate prepared in Preparation 9; and the corresponding substituted-boronic acids, respectively.

Example 314. (S)-quinuclidin-3-yl (7-(3-(tert-butyl)phenyl)-1-methyl-1,2,3,4-tetrahydroquinolin-4-yl)carbamate $^1$H-NMR (400 MHz, $CDCl_3$) δ 7.58 (s, 1H), 7.43-7.34 (m, 3H), 7.27 (t, 1H), 6.90 (t, 1H), 6.81 (s, 1H), 5.07 (d, 1H), 4.92-4.84 (m, 1H), 4.81-4.72 (m, 1H), 3.34-3.19 (m, 3H), 2.99 (s, 3H), 2.92-2.66 (m, 5H), 2.18-2.09 (m, 2H), 2.07-2.00 (m, 1H), 1.87-1.76 (m, 1H), 1.73-1.65 (m, 1H), 1.62-1.52 (m, 1H), 1.45-1.31 (m, 10H)

Example 315. (S)-quinuclidin-3-yl (7-(benzofuran-3-yl)-1-methyl-1,2,3,4-tetrahydroquinolin-4-yl)carbamate $^1$H-NMR (400 MHz, $CDCl_3$) δ 7.84 (d, 1H), 7.78 (s, 1H), 7.55 (d, 1H), 7.39-7.24 (m, 3H), 6.95 (t, 1H), 6.88 (s, 1H), 5.08 (d, 1H), 4.93-4.85 (m, 1H), 4.82-4.73 (m, 1H), 3.34-3.19 (m, 3H), 2.99 (s, 3H), 2.94-2.66 (m, 5H), 2.18-2.09 (m, 2H), 2.08-2.00 (m, 1H), 1.85-1.76 (m, 1H), 1.73-1.65 (m, 1H), 1.61-1.53 (m, 1H), 1.43-1.34 (m, 1H)

Example 316. (S)-quinuclidin-3-yl (6-(4-chlorophenyl)thiochroman-4-yl)carbamate

The titled compound was prepared in accordance with the same procedures as in Example 1, using (S)-quinuclidin-3-yl (6-bromothiochroman-4-yl)carbamate prepared in Preparation 10 and 4-chlorophenylboronic acid.

$^1$H-NMR (400 MHz, $CDCl_3$) δ 7.52-7.44 (m, 3H), 7.43-7.34 (m, 3H), 7.20 (d, 1H), 5.09 (br, 1H), 4.99 (br, 1H), 4.77 (br, 1H), 3.32-3.11 (m, 2H), 3.09-2.97 (m, 1H), 2.90-2.68 (m, 5H), 2.53-2.38 (m, 1H), 2.21-1.97 (m, 2H), 1.89-1.77 (m, 1H), 1.70 (br, 2H), 1.64-1.50 (m, 1H), 1.44-1.34 (m, 1H)

Examples 317 to 328

The titled compounds of Examples 317 to 328 were prepared in accordance with the same procedures as in Example 1, using (S)-quinuclidin-3-yl (7-bromothiochroman-4-yl)carbamate prepared in Preparation 11; and the corresponding substituted-boronic acids, respectively.

Example 317. (S)-quinuclidin-3-yl (7-(3-fluorophenyl)thiochroman-4-yl)carbamate $^1$H-NMR (400 MHz, $CD_3OD$) δ 7.61-7.58 (m, 1H), 7.56-7.51 (m, 1H), 7.45 (s, 1H), 7.34 (s, 3H), 7.27 (d, 1H), 4.84-4.76 (m, 2H), 3.29-3.11 (m, 2H), 3.07 (d, 1H), 2.89-2.72 (m, 6H), 2.37-2.26 (m, 1H), 2.26-2.14 (m, 1H), 2.09-2.06 (m, 1H), 1.99-1.89 (m, 1H), 1.79-1.77 (m, 1H), 1.66 (m, 1H), 1.51-1.49 (m, 1H)

Example 318. (S)-quinuclidin-3-yl (7-(3-chlorophenyl)thiochroman-4-yl)carbamate $^1$H-NMR (400 MHz, $CD_3OD$) δ 7.58 (brs, 1H), 7.52-7.49 (m, 1H), 7.44-7.29 (m, 5H), 4.84-4.75 (m, 2H), 3.29-3.11 (m, 3H), 3.07-3.04 (m, 1H), 2.89-2.71 (m, 5H), 2.28 (brs, 1H), 2.19 (dd, 1H), 2.09-2.05 (m, 1H), 1.96-1.93 (m, 1H), 1.80-1.75 (m, 1H), 1.68-1.64 (m, 1H), 1.50 (brs, 1H)

Example 319. (S)-quinuclidin-3-yl (7-(3-(trifluoromethyl)phenyl)thiochroman-4-yl)carbamate $^1$H-NMR (400 MHz, $CD_3OD$) δ 7.86-7.82 (m, 2H), 7.66-7.63 (m, 2H), 7.41-7.34 (m, 3H), 4.85-4.76 (m, 2H), 3.30-3.11 (m, 2H), 3.09-3.06 (m, 1H), 2.93-2.67 (m, 6H), 2.31-2.28 (m, 1H), 2.21-2.19 (m, 1H), 2.10-2.06 (m, 1H), 1.95 (s, 1H), 1.80-1.76 (m, 1H), 1.68-1.64 (m, 1H), 1.52-1.48 (m, 1H)

Example 320. (S)-quinuclidin-3-yl (7-(3-(trifluoromethoxy)phenyl)thiochroman-4-yl)carbamate $^1$H-NMR (400 MHz, $CD_3OD$) δ 7.61-7.58 (m, 1H), 7.56-7.51 (m, 1H), 7.45 (s, 1H), 7.34 (s, 3H), 7.27 (d, 1H), 4.84-4.76 (m, 2H), 3.29-3.11 (m, 2H), 3.07 (d, 1H), 2.89-2.72 (m, 6H), 2.37-2.26 (m, 1H), 2.26-2.14 (m, 1H), 2.09-2.06 (m, 1H), 1.99-1.89 (m, 1H), 1.79-1.77 (m, 1H), 1.66 (dd, 1H), 1.51-1.49 (m, 1H)

Example 321. (S)-quinuclidin-3-yl (7-(3-(methoxymethoxy)phenyl)thiochroman-4-yl)carbamate $^1$H-NMR (400 MHz, $CDCl_3$) δ 7.38-7.32 (m, 3H), 7.29-7.25 (m, 1H), 7.22-7.17 (m, 2H), 7.04 (d, 1H), 5.31 (brd, 1H), 5.22 (s, 2H), 4.98-4.94 (m, 1H), 4.79-4.74 (m, 1H), 3.77-3.73 (m, 1H), 3.50 (s, 3H), 3.24 (dd, 1H), 3.15-3.10 (m, 1H), 3.01 (ddd, 1H), 2.86-2.67 (m, 5H), 2.46-2.41 (m, 1H), 2.23-2.14 (m, 1H), 1.82-1.76 (m, 1H), 1.70-1.66 (m, 1H), 1.60-1.55 (m, 1H), 1.38 (d, 1H)

Example 322. (S)-quinuclidin-3-yl (7-(3-(tert-butyl)phenyl)thiochroman-4-yl)carbamate $^1$H-NMR (400 MHz, $CDCl_3$) δ 7.54 (s, 1H), 7.42-7.28 (m, 5H), 6.99 (s, 1H), 5.13-4.88 (m, 2H), 4.77 (br, 1H), 3.33-3.09 (m, 2H), 3.03 (m, 1H), 2.93-2.68 (m, 5H), 2.57-2.36 (m, 1H), 2.23-2.09 (m, 1H), 2.05-2.01 (m, 1H), 1.98-1.89 (m, 1H), 1.84-1.75 (m, 1H), 1.74-1.65 (m, 1H), 1.63-1.50 (m, 1H), 1.37 (s, 9H)

Example 323. (S)-quinuclidin-3-yl (7-(2,5-dichlorophenyl)thiochroman-4-yl)carbamate $^1$H-NMR (400 MHz, $CDCl_3$) δ 7.43-7.33 (m, 1H), 7.33-7.21 (m, 2H), 7.19-7.04 (m, 2H), 7.01-6.93 (m, 1H), 5.17 (br, 1H), 5.10-4.90 (m, 1H), 4.76 (br, 1H), 3.26 (br, 1H), 3.18-2.96 (m, 2H), 2.91-2.68 (m, 4H), 2.53-2.40 (m, 1H), 2.21-2.12 (m, 1H), 2.12-2.00 (m, 1H), 1.94-1.89 (m, 1H), 1.83-1.76 (m, 1H), 1.70 (qd, 1H), 1.62-1.50 (m, 1H), 1.42-1.34 (m, 1H)

Example 324. (S)-quinuclidin-3-yl (7-(3-ethoxyphenyl)thiochroman-4-yl)carbamate $^1$H-NMR (400 MHz, $CDCl_3$) δ 7.39-7.28 (m, 3H), 7.12 (d, 1H), 7.07 (s, 1H), 6.99 (s, 1H), 6.89 (m, 1H), 5.16-5.01 (m, 1H), 5.00-4.87 (m, 1H), 4.87-4.69 (m, 1H), 4.14-4.02 (m, 2H), 3.34-3.21 (m, 1H), 3.20-3.09 (m, 1H), 3.07-2.96 (m, 1H), 2.92-2.68 (m, 5H), 2.56-2.38 (m, 1H), 2.23-2.09 (m, 1H), 2.06-2.00 (m, 1H), 1.94-1.86 (m, 1H), 1.83-1.75 (m, 1H), 1.74-1.66 (m, 1H), 1.63-1.51 (m, 1H), 1.44 (m, 3H)

Example 325. (S)-quinuclidin-3-yl (7-(3-(methylthio)phenyl)thiochroman-4-yl)carbamate $^1$H-NMR (400 MHz, $CDCl_3$) δ 7.42-7.22 (m, 6H), 6.99 (s, 1H), 5.16-5.01 (m, 1H), 5.01-4.88 (m, 1H), 4.88-4.69 (m, 1H), 3.30-3.10 (m, 2H), 3.03 (m, 1H), 2.92-2.68 (m, 5H), 2.53 (s, 3H), 2.50-2.39 (m, 1H), 2.23-2.09 (m, 1H), 2.03 (br, 1H), 1.83-1.65 (m, 2H), 1.62-1.52 (m, 1H), 1.42-1.35 (m, 1H)

Example 326. (S)-quinuclidin-3-yl (7-(3-(dimethylamino)phenyl)thiochroman-4-yl)carbamate $^1$H-NMR (400 MHz, $CDCl_3$) δ 7.37-7.27 (m, 3H), 6.99 (s, 1H), 6.93-6.84 (m, 2H), 6.76 (s, 1H), 5.17-5.01 (m, 1H), 5.00-4.87 (m, 1H), 4.77 (br, 1H), 3.33-3.21 (m, 1H), 3.21-3.08 (m, 1H), 3.08-3.02 (m, 1H), 3.02-2.98 (m, 6H), 2.95-2.68 (m, 5H), 2.57-2.39 (m, 1H), 2.23-2.09 (m, 1H), 2.03 (br, 1H), 1.83-1.74 (m, 1H), 1.70 (m, 1H), 1.58-1.49 (m, 1H), 1.43-1.38 (m, 1H)

Example 327. (S)-quinuclidin-3-yl (7-(2,2-difluorobenzo[d][1,3]dioxol-5-yl)thiochroman-4-yl)carbamate $^1$H-NMR (400 MHz, $CDCl_3$) δ 7.44-7.31 (m, 1H), 7.27-7.17 (m, 3H), 7.11 (d, 1H), 6.99 (s, 1H), 5.13-5.01 (m, 1H), 4.98 (d, 1H), 4.87-4.69 (m, 1H), 3.26 (m, 1H), 3.19-3.08 (m, 1H), 3.08-2.99 (m, 1H), 2.92-2.68 (m, 4H), 2.56-2.38 (m, 1H), 2.23-2.09 (m, 1H), 2.04 (d, 1H), 1.94-1.88 (m, 1H), 1.84-1.74 (m, 1H), 1.70 (qd, 1H), 1.63-1.50 (m, 1H), 1.42-1.35 (m, 1H)

Example 328. (S)-quinuclidin-3-yl (7-(benzofuran-3-yl)thiochroman-4-yl)carbamate $^1$H-NMR (400 MHz, $CDCl_3$) δ 7.85-7.74 (m, 2H), 7.55 (d, 1H), 7.44-7.30 (m, 4H), 6.99 (s, 1H), 5.11 (br d, 1H), 5.06-4.89 (m, 1H), 4.89-4.70 (m, 1H), 3.49-3.21 (m, 1H), 3.15 (br m, 1H), 3.05 (m, 1H), 2.93-2.82 (m, 2H), 2.82-2.69 (m, 3H), 2.56-2.36 (m, 1H), 2.23-2.11 (m, 1H), 2.10-1.96 (m, 1H), 1.81 (m, 1H), 1.69 (m, 1H), 1.63-1.52 (m, 1H), 1.42-1.39 (m, 1H)

Example 329. (S)-quinuclidin-3-yl (3,3-dimethyl-6-(4-(trifluoromethyl)phenyl)thiochroman-4-yl)carbamate The titled compound was prepared in accordance with the same procedures as in Example 1, using (S)-quinuclidin-3-yl (6-bromo-3,3-dimethylthiochroman-4-yl)carbamate prepared in Preparation 12 and 4-(trifluoromethyl)phenylboronic acid.

$^1$H-NMR (400 MHz, $CDCl_3$) δ 7.45-7.32 (m, 2H), 7.29 (d, 1H), 7.21-7.15 (m, 2H), 7.15-7.09 (m, 1H), 6.97 (s, 1H), 4.90-4.84 (m, 1H), 4.75-4.70 (m, 1H), 4.60 (d, 1H), 3.30-3.16 (m, 1H), 3.01-2.92 (m, 1H), 2.90-2.64 (m, 6H), 2.04-1.97 (m, 1H), 1.72-1.61 (m, 2H), 1.58-1.49 (m, 1H), 1.40-1.30 (m, 1H), 1.17 (d, 3H), 1.11-1.08 (m, 3H)

Examples 330 to 348

The titled compounds of Examples 330 to 348 were prepared in accordance with the same procedures as in Example 1, using (S)-quinuclidin-3-yl (7-bromo-6-fluoro-3,3-dimethylchroman-4-yl)carbamate prepared in Preparation 13; and the corresponding substituted-boronic acids, respectively.

Example 330. (S)-quinuclidin-3-yl (6-fluoro-7-(3-fluorophenyl)-3,3-dimethylchroman-4-yl)carbamate $^1$H-NMR (400 MHz, $CDCl_3$) δ 7.39 (dd, 1H), 7.33-7.21 (m, 2H), 7.10-6.97 (m, 2H), 6.87 (d, 1H), 4.92-4.85 (m, 1H), 4.83-4.78 (m, 1H), 4.73 (d, 1H), 3.95-3.80 (m, 2H), 3.35-3.23 (m, 1H), 2.97-2.68 (m, 5H), 2.17-2.07 (m, 1H), 1.89-1.78 (m, 1H), 1.76-1.67 (m, 1H), 1.64-1.55 (m, 1H), 1.49-1.39 (m, 1H), 1.06 (d, 3H), 1.02 (d, 3H)

Example 331. (S)-quinuclidin-3-yl (6-fluoro-7-(4-fluorophenyl)-3,3-dimethylchroman-4-yl)carbamate $^1$H-NMR (400 MHz, $CDCl_3$) δ 7.54-7.45 (m, 2H), 7.16-7.08 (m, 2H), 7.00 (dd, 1H), 6.84 (d, 1H), 4.91-4.78 (m, 2H), 4.72 (d, 1H), 3.93-3.81 (m, 2H), 3.34-3.23 (m, 1H), 2.96-2.70 (m, 5H), 2.14-2.06 (m, 1H), 1.88-1.78 (m, 1H), 1.76-1.67 (m, 1H), 1.64-1.55 (m, 1H), 1.48-1.38 (m, 1H), 1.06 (d, 3H), 1.02 (d, 3H)

Example 332. (S)-quinuclidin-3-yl (6-fluoro-7-(3-chlorophenyl)-3,3-dimethylchroman-4-yl)carbamate $^1$H-NMR (400 MHz, $CDCl_3$) δ 7.52 (s, 1H), 7.43-7.31 (m, 3H), 7.02 (dd, 1H), 6.86 (d, 1H), 4.89-4.78 (m, 2H), 4.73 (d, 1H), 3.94-3.79 (m, 2H), 3.35-3.23 (m, 1H), 2.98-2.69 (m, 5H), 2.16-2.06 (m, 1H), 1.89-1.79 (m, 1H), 1.76-1.67 (m, 1H), 1.64-1.56 (m, 1H), 1.49-1.39 (m, 1H), 1.06 (d, 3H), 1.02 (d, 3H)

Example 333. (S)-quinuclidin-3-yl (7-(3-ethylphenyl)-6-fluoro-3,3-dimethylchroman-4-yl)carbamate $^1$H-NMR (400 MHz, $CDCl_3$) δ 7.39-7.31 (m, 3H), 7.24-7.18 (m, 1H), 7.00 (dd, 1H), 6.89 (d, 1H), 4.89-4.78 (m, 2H), 4.73 (d, 1H), 3.94-3.79 (m, 2H), 3.35-3.23 (m, 1H), 2.97-2.66 (m, 7H), 2.16-2.06 (m, 1H), 1.90-1.80 (m, 1H), 1.76-1.67 (m, 1H), 1.64-1.56 (m, 1H), 1.48-1.38 (m, 1H), 1.28 (t, 3H), 1.07 (d, 3H), 1.03 (d, 3H)

Example 334. (S)-quinuclidin-3-yl (7-(4-ethylphenyl)-6-fluoro-3,3-dimethylchroman-4-yl)carbamate $^1$H-NMR (400 MHz, $CDCl_3$) δ 7.49-7.40 (m, 2H), 7.31-7.22 (m, 2H), 6.99 (dd, 1H), 6.88 (d, 1H), 4.92-4.76 (m, 2H), 4.72 (d, 1H), 3.93-3.78 (m, 2H), 3.36-3.21 (m, 1H), 2.98-2.64 (m, 7H), 2.16-2.06 (m, 1H), 1.91-1.79 (m, 1H), 1.76-1.67 (m, 1H), 1.63-1.55 (m, 1H), 1.48-1.38 (m, 1H), 1.28 (t, 3H), 1.06 (d, 3H), 1.02 (d, 3H)

Example 335. (S)-quinuclidin-3-yl (6-fluoro-7-(3-methoxyphenyl)-3,3-dimethylchroman-4-yl)carbamate $^1$H-NMR (400 MHz, $CDCl_3$) δ 7.34 (t, 1H), 7.11 (d, 1H), 7.06 (s, 1H), 7.00 (dd, 1H), 6.94-6.86 (m, 2H), 4.91-4.77 (m, 2H), 4.72 (d, 1H), 3.95-3.79 (m, 5H), 3.34-3.24 (m, 1H), 2.96-2.69 (m, 5H), 2.14-2.07 (m, 1H), 1.88-1.79 (m, 1H), 1.76-1.67 (m, 1H), 1.64-1.55 (m, 1H), 1.47-1.38 (m, 1H), 1.07 (d, 3H), 1.02 (d, 3H)

Example 336. (S)-quinuclidin-3-yl (6-fluoro-7-(4-methoxyphenyl)-3,3-dimethylchroman-4-yl)carbamate $^1$H-NMR (400 MHz, $CDCl_3$) δ 7.50-7.43 (m, 2H), 7.02-6.93 (m, 3H), 6.86 (d, 1H), 4.90-4.77 (m, 2H), 4.72 (d, 1H), 3.93-3.78 (m, 5H), 3.35-3.23 (m, 1H), 2.96-2.69 (m, 5H), 2.15-2.07 (m, 1H), 1.89-1.80 (m, 1H), 1.75-1.68 (m, 1H), 1.64-1.55 (m, 1H), 1.48-1.39 (m, 1H), 1.06 (d, 3H), 1.02 (d, 3H)

Example 337. (S)-quinuclidin-3-yl (7-(4-ethoxyphenyl)-6-fluoro-3,3-dimethylchroman-4-yl)carbamate $^1$H-NMR (400 MHz, $CDCl_3$) δ 7.49-7.40 (m, 2H), 7.03-6.92 (m, 3H), 6.86 (d, 1H), 4.90-4.78 (m, 2H), 4.71 (d, 1H), 4.08 (q, 2H), 3.93-3.78 (m, 2H), 3.34-3.23 (m, 1H), 2.97-2.70 (m, 5H), 2.15-2.07 (m, 1H), 1.89-1.79 (m, 1H), 1.76-1.67 (m, 1H), 1.64-1.54 (m, 1H), 1.49-1.38 (m, 4H), 1.06 (d, 3H), 1.02 (d, 3H)

Example 338. (S)-quinuclidin-3-yl (6-fluoro-3,3-dimethyl-7-(thiophen-3-yl)chroman-4-yl)carbamate $^1$H-NMR (400 MHz, $CDCl_3$) δ 7.60 (s, 1H), 7.42-7.35 (m, 2H), 7.05-6.93 (m, 2H), 4.91-4.76 (m, 2H), 4.71 (d, 1H), 3.95-3.79 (m, 2H), 3.35-3.23 (m, 1H), 2.96-2.69 (m, 5H), 2.16-2.07 (m, 1H), 1.89-1.78 (m, 1H), 1.75-1.67 (m, 1H), 1.63-1.56 (m, 1H), 1.47-1.38 (m, 1H), 1.06 (d, 3H), 1.01 (d, 3H)

Example 339. (S)-quinuclidin-3-yl (6-fluoro-7-(3-isopropylphenyl)-3,3-dimethylchroman-4-yl)carbamate $^1$H-NMR (400 MHz, $CDCl_3$) δ 7.39-7.32 (m, 3H), 7.26-7.21 (m, 1H), 7.00 (dd, 1H), 6.90 (d, 1H), 4.91-4.78 (m, 2H), 4.72 (d, 1H), 3.93-3.80 (m, 2H), 3.35-3.24 (m, 1H), 3.00-2.70 (m, 6H), 2.16-2.06 (m, 1H), 1.89-1.80 (m, 1H), 1.76-1.68 (m, 1H), 1.64-1.56 (m, 1H), 1.49-1.39 (m, 1H), 1.29 (d, 6H), 1.07 (d, 3H), 1.03 (d, 3H)

Example 340. (S)-quinuclidin-3-yl (7-(2-chloro-5-methoxyphenyl)-6-fluoro-3,3-dimethylchroman-4-yl)carbamate $^1$H-NMR (400 MHz, $CDCl_3$) δ 7.36 (d, 1H), 7.00 (dd, 1H), 6.87 (dd, 1H), 6.84 (s, 1H), 6.75 (d, 1H), 5.03-4.93 (m, 1H), 4.84-4.78 (m, 1H), 4.74 (d, 1H), 3.94-3.76 (m, 5H), 3.32-3.22 (m, 1H), 2.95-2.69 (m, 5H), 2.14-2.06 (m, 1H), 1.89-1.78 (m, 1H), 1.75-1.67 (m, 1H), 1.62-1.55 (m, 1H), 1.47-1.39 (m, 1H), 1.07 (d, 3H), 1.03 (d, 3H)

Example 341. (S)-quinuclidin-3-yl (6-fluoro-7-(2-fluoro-4-methoxyphenyl)-3,3-dimethylchroman-4-yl)carbamate $^1$H-NMR (400 MHz, $CDCl_3$) δ 7.30-7.22 (m, 2H), 7.00 (dd, 1H), 6.81 (d, 1H), 6.74 (dd, 1H), 4.91-4.85 (m, 1H), 4.83-4.78 (m, 1H), 4.72 (d, 1H), 3.93-3.79 (m, 5H), 3.34-3.22 (m, 1H), 2.94-2.70 (m, 5H), 2.14-2.06 (m, 1H), 1.87-1.79 (m, 1H), 1.75-1.67 (m, 1H), 1.63-1.55 (m, 1H), 1.47-1.38 (m, 1H), 1.06 (d, 3H), 1.02 (d, 3H)

Example 342. (S)-quinuclidin-3-yl (6-fluoro-7-(4-methoxy-2-methylphenyl)-3,3-dimethylchroman-4-yl)carbamate $^1$H-NMR (400 MHz, $CDCl_3$) δ 7.11 (d, 1H), 6.96 (dd, 1H), 6.82 (s, 1H), 6.79 (d, 1H), 6.68 (d, 1H), 4.91-4.85 (m, 1H), 4.83-4.78 (m, 1H), 4.73 (d, 1H), 3.93-3.78 (m, 5H), 3.34-3.23 (m, 1H), 2.93-2.69 (m, 5H), 2.20 (s, 3H), 2.14-2.07 (m, 1H), 1.89-1.80 (m, 1H), 1.75-1.67 (m, 1H), 1.64-1.55 (m, 1H), 1.48-1.39 (m, 1H), 1.07 (d, 3H), 1.03 (d, 3H)

Example 343. (S)-quinuclidin-3-yl (7-(4-butylphenyl)-6-fluoro-3,3-dimethylchroman-4-yl)carbamate $^1$H-NMR (400 MHz, $CDCl_3$) δ 7.47-7.41 (m, 2H), 7.28-7.20 (m, 2H), 6.99 (dd, 1H), 6.88 (d, 1H), 4.91-4.85 (m, 1H), 4.83-4.78 (m, 1H), 4.72 (d, 1H), 3.92-3.79 (m, 2H), 3.33-3.24 (m, 1H), 2.96-2.71 (m, 5H), 2.65 (t, 2H), 2.14-2.07 (m, 1H), 1.89-1.79 (m, 1H), 1.76-1.68 (m, 1H), 1.67-1.55 (m, 3H), 1.47-1.35 (m, 3H), 1.06 (d, 3H), 1.02 (d, 3H), 0.95 (t, 3H)

Example 344. (S)-quinuclidin-3-yl (7-(3-chloro-4-isopropoxyphenyl)-6-fluoro-3,3-dimethylchroman-4-yl)carbamate $^1$H-NMR (400 MHz, $CDCl_3$) δ 7.55 (s, 1H), 7.36 (d, 1H), 7.03-6.94 (m, 2H), 6.84 (d, 1H), 4.90-4.77 (m, 2H), 4.71 (d, 1H), 4.63-4.57 (m, 1H), 3.93-3.79 (m, 2H), 3.33-3.23 (m, 1H), 2.96-2.69 (m, 5H), 2.15-2.07 (m, 1H), 1.88-1.79 (m, 1H), 1.76-1.67 (m, 1H), 1.64-1.55 (m, 1H), 1.47-1.37 (m, 7H), 1.06 (d, 3H), 1.01 (d, 3H)

Example 345. (S)-quinuclidin-3-yl (7-(4-(tert-butyl)phenyl)-6-fluoro-3,3-dimethylchroman-4-yl)carbamate $^1$H-NMR (400 MHz, $CDCl_3$) δ 7.50-7.43 (m, 4H), 7.00 (dd, 1H), 6.89 (d, 1H), 4.89-4.77 (m, 2H), 4.72 (d, 1H), 3.94-3.79 (m, 2H), 3.35-3.23 (m, 1H), 2.97-2.70 (m, 5H), 2.16-2.07 (m, 1H), 1.90-1.79 (m, 1H), 1.75-1.67 (m, 1H), 1.64-1.55 (m, 1H), 1.47-1.39 (m, 1H), 1.36 (s, 9H), 1.06 (d, 3H), 1.02 (d, 3H)

Example 346. (S)-quinuclidin-3-yl (6-fluoro-7-(4-methoxy-3,5-dimethylphenyl)-3,3-dimethylchroman-4-yl)carbamate $^1$H-NMR (400 MHz, $CDCl_3$) δ 7.20-7.13 (m, 2H), 6.97 (dd, 1H), 6.84 (d, 1H), 4.90-4.78 (m, 2H), 4.71 (d, 1H), 3.93-3.80 (m, 2H), 3.76 (s, 3H), 3.35-3.24 (m, 1H), 2.96-2.70 (m, 5H), 2.33 (s, 6H), 2.15-2.07 (m, 1H), 1.91-1.80 (m, 1H), 1.76-1.66 (m, 1H), 1.64-1.54 (m, 1H), 1.48-1.39 (m, 1H), 1.06 (d, 3H), 1.02 (d, 3H)

Example 347. (S)-quinuclidin-3-yl (6-fluoro-7-(4-isobutoxyphenyl)-3,3-dimethylchroman-4-yl)carbamate $^1$H-NMR (400 MHz, $CDCl_3$) δ 7.48-7.41 (m, 2H), 7.02-6.92 (m, 3H), 6.86 (d, 1H), 4.86-4.77 (m, 2H), 4.71 (d, 1H), 3.92-3.80 (m, 2H), 3.76 (d, 2H), 3.35-3.24 (m, 1H), 2.95-2.69 (m, 5H), 2.16-2.06 (m, 2H), 1.89-1.79 (m, 1H), 1.75-1.67 (m, 1H), 1.64-1.55 (m, 1H), 1.47-1.38 (m, 1H), 1.09-0.96 (m, 12H)

Example 348. (S)-quinuclidin-3-yl (6-fluoro-7-(6-isopropoxypyridin-3-yl)-3,3-dimethylchroman-4-yl)carbamate $^1$H-NMR (400 MHz, $CDCl_3$) δ 8.29 (s, 1H), 7.72 (d, 1H), 7.01 (dd, 1H), 6.84 (d, 1H), 6.74 (d, 1H), 5.37-5.31 (m, 1H), 4.90-4.77 (m, 2H), 4.72 (d, 1H), 3.94-3.79 (m, 2H), 3.33-3.22 (m, 1H), 2.95-2.70 (m, 5H), 2.14-2.07 (m, 1H), 1.87-1.78 (m, 1H), 1.74-1.67 (m, 1H), 1.64-1.55 (m, 1H), 1.48-1.41 (m, 1H), 1.38 (d, 6H), 1.06 (d, 3H), 1.02 (d, 3H)

Examples 349 to 367

The titled compounds of Examples 349 to 367 were prepared in accordance with the same procedures as in Example 1, using (S)-quinuclidin-3-yl (7-bromo-6-methoxy-3,3-dimethylchroman-4-yl)carbamate prepared in Preparation 14; and the corresponding substituted-boronic acids, respectively.

Example 349. (S)-quinuclidin-3-yl (7-(3-fluorophenyl)-6-methoxy-3,3-dimethylchroman-4-yl)carbamate $^1$H-NMR (400 MHz, $CDCl_3$) δ 7.35 (dd, 1H), 7.30-7.21 (m, 2H), 7.02 (t, 1H), 6.83-6.75 (m, 2H), 4.92-4.78 (m, 2H), 4.69 (d, 1H), 3.89-3.70 (m, 5H), 3.36-3.23 (m, 1H), 2.95-2.70 (m, 5H), 2.15-2.07 (m, 1H), 1.89-1.79 (m, 1H), 1.76-1.67 (m, 1H), 1.64-1.56 (m, 1H), 1.47-1.38 (m, 1H), 1.07 (d, 3H), 1.04 (d, 3H)

Example 350. (S)-quinuclidin-3-yl (7-(4-fluorophenyl)-6-methoxy-3,3-dimethylchroman-4-yl)carbamate $^1$H-NMR (400 MHz, $CDCl_3$) δ 7.51-7.43 (m, 2H), 7.13-7.03 (m, 2H), 6.82-6.72 (m, 2H), 4.91-4.78 (m, 2H), 4.68 (d, 1H), 3.89-3.68 (m, 5H), 3.36-3.23 (m, 1H), 2.93-2.70 (m, 5H), 2.14-2.07 (m, 1H), 1.87-1.79 (m, 1H), 1.75-1.67 (m, 1H), 1.63-1.55 (m, 1H), 1.46-1.38 (m, 1H), 1.07 (d, 3H), 1.04 (d, 3H)

Example 351. (S)-quinuclidin-3-yl (7-(3-chlorophenyl)-6-methoxy-3,3-dimethylchroman-4-yl)carbamate $^1$H-NMR (400 MHz, $CDCl_3$) δ 7.50 (s, 1H), 7.40-7.24 (m, 3H), 6.82-6.74 (m, 2H), 4.92-4.78 (m, 2H), 4.69 (d, 1H), 3.88-3.68 (m, 5H), 3.35-3.24 (m, 1H), 2.94-2.70 (m, 5H), 2.14-2.07 (m, 1H), 1.89-1.79 (m, 1H), 1.75-1.68 (m, 1H), 1.64-1.55 (m, 1H), 1.47-1.38 (m, 1H), 1.07 (d, 3H), 1.03 (d, 3H)

Example 352. (S)-quinuclidin-3-yl (7-(3-ethylphenyl)-6-methoxy-3,3-dimethylchroman-4-yl)carbamate $^1$H-NMR (400 MHz, $CDCl_3$) δ 7.36-7.29 (m, 3H), 7.17 (d, 1H), 6.84-6.74 (m, 2H), 4.91-4.77 (m, 2H), 4.68 (d, 1H), 3.88-3.68 (m, 5H), 3.34-3.23 (m, 1H), 2.94-2.65 (m, 7H), 2.14-2.06 (m, 1H), 1.88-1.79 (m, 1H), 1.75-1.67 (m, 1H), 1.63-1.55 (m, 1H), 1.46-1.37 (m, 1H), 1.27 (t, 3H), 1.08 (d, 3H), 1.04 (d, 3H)

Example 353. (S)-quinuclidin-3-yl (7-(4-ethylphenyl)-6-methoxy-3,3-dimethylchroman-4-yl)carbamate $^1$H-NMR (400 MHz, $CDCl_3$) δ 7.46-7.40 (m, 2H), 7.28-7.20 (m, 2H), 6.81 (s, 1H), 6.77 (d, 1H), 4.93-4.86 (m, 1H), 4.83-4.77 (m, 1H), 4.67 (d, 1H), 3.87-3.68 (m, 5H), 3.35-3.22 (m, 1H), 2.94-2.64 (m, 7H), 2.14-2.06 (m, 1H), 1.88-1.79 (m, 1H), 1.76-1.67 (m, 1H), 1.64-1.55 (m, 1H), 1.47-1.37 (m, 1H), 1.28 (t, 3H), 1.07 (d, 3H), 1.04 (d, 3H)

Example 354. (S)-quinuclidin-3-yl (6-methoxy-7-(3-methoxyphenyl)-3,3-dimethylchroman-4-yl)carbamate $^1$H-NMR (400 MHz, $CDCl_3$) δ 7.31 (t, 1H), 7.11-7.04 (m, 2H), 6.88 (dd, 1H), 6.82 (s, 1H), 6.79 (d, 1H), 4.91-4.77 (m, 2H), 4.68 (d, 1H), 3.89-3.76 (m, 5H), 3.73 (d, 3H), 3.35-3.23 (m, 1H), 2.96-2.70 (m, 5H), 2.15-2.06 (m, 1H), 1.91-1.79

(m, 1H), 1.76-1.67 (m, 1H), 1.64-1.55 (m, 1H), 1.46-1.37 (m, 1H), 1.08 (d, 3H), 1.04 (d, 3H)

Example 355. (S)-quinuclidin-3-yl (6-methoxy-7-(4-methoxyphenyl)-3,3-dimethylchroman-4-yl)carbamate $^1$H-NMR (400 MHz, $CDCl_3$) δ 7.49-7.40 (m, 2H), 6.97-6.90 (m, 2H), 6.82-6.73 (m, 2H), 4.92-4.77 (m, 2H), 4.67 (d, 1H), 3.88-3.76 (m, 5H), 3.72 (d, 3H), 3.36-3.23 (m, 1H), 2.94-2.69 (m, 5H), 2.15-2.07 (m, 1H), 1.89-1.78 (m, 1H), 1.75-1.67 (m, 1H), 1.63-1.55 (m, 1H), 1.46-1.38 (m, 1H), 1.07 (d, 3H), 1.03 (d, 3H)

Example 356. (S)-quinuclidin-3-yl (7-(4-ethoxyphenyl)-6-methoxy-3,3-dimethylchroman-4-yl)carbamate $^1$H-NMR (400 MHz, $CDCl_3$) δ 7.47-7.41 (m, 2H), 6.95-6.89 (m, 2H), 6.81-6.72 (m, 2H), 4.90-4.77 (m, 2H), 4.67 (d, 1H), 4.07 (q, 2H), 3.87-3.75 (m, 2H), 3.72 (d, 3H), 3.34-3.23 (m, 1H), 2.94-2.69 (m, 5H), 2.13-2.06 (m, 1H), 1.88-1.79 (m, 1H), 1.75-1.67 (m, 1H), 1.64-1.55 (m, 1H), 1.47-1.38 (m, 4H), 1.07 (d, 3H), 1.03 (d, 3H)

Example 357. (S)-quinuclidin-3-yl (6-methoxy-3,3-dimethyl-7-(thiophen-3-yl)chroman-4-yl)carbamate $^1$H-NMR (400 MHz, $CDCl_3$) δ 7.61 (s, 1H), 7.41 (d, 1H), 7.34 (d, 1H), 6.98 (s, 1H), 6.78 (d, 1H), 4.90-4.78 (m, 2H), 4.67 (d, 1H), 3.90-3.73 (m, 5H), 3.37-3.24 (m, 1H), 2.96-2.70 (m, 5H), 2.14-2.07 (m, 1H), 1.89-1.80 (m, 1H), 1.76-1.68 (m, 1H), 1.65-1.55 (m, 1H), 1.47-1.38 (m, 1H), 1.07 (d, 3H), 1.03 (d, 3H)

Example 358. (S)-quinuclidin-3-yl (7-(3-isopropylphenyl)-6-methoxy-3,3-dimethylchroman-4-yl)carbamate $^1$H-NMR (400 MHz, $CDCl_3$) δ 7.38-7.30 (m, 3H), 7.20 (d, 1H), 6.83 (s, 1H), 6.81-6.74 (m, 1H), 4.91-4.76 (m, 2H), 4.68 (d, 1H), 3.88-3.69 (m, 5H), 3.36-3.23 (m, 1H), 2.99-2.70 (m, 6H), 2.15-2.06 (m, 1H), 1.87-1.79 (m, 1H), 1.75-1.67 (m, 1H), 1.63-1.55 (m, 1H), 1.46-1.37 (m, 1H), 1.28 (d, 6H), 1.08 (d, 3H), 1.04 (d, 3H)

Example 359. (S)-quinuclidin-3-yl (7-(2-chloro-5-methoxyphenyl)-6-methoxy-3,3-dimethylchroman-4-yl)carbamate $^1$H-NMR (400 MHz, $CDCl_3$) δ 7.32 (d, 1H), 6.87-6.73 (m, 3H), 6.69 (s, 1H), 5.05-4.94 (m, 1H), 4.83-4.78 (m, 1H), 4.70 (d, 1H), 3.90-3.76 (m, 5H), 3.71 (d, 3H), 3.35-3.22 (m, 1H), 2.94-2.69 (m, 5H), 2.14-2.06 (m, 1H), 1.89-1.79 (m, 1H), 1.75-1.67 (m, 1H), 1.63-1.54 (m, 1H), 1.46-1.37 (m, 1H), 1.08 (d, 3H), 1.04 (d, 3H)

Example 360. (S)-quinuclidin-3-yl (7-(2-fluoro-4-methoxyphenyl)-6-methoxy-3,3-dimethylchroman-4-yl)carbamate $^1$H-NMR (400 MHz, $CDCl_3$) δ 7.23 (t, 1H), 6.81-6.72 (m, 3H), 6.68 (d, 1H), 4.93-4.87 (m, 1H), 4.83-4.77 (m, 1H), 4.68 (d, 1H), 3.87-3.76 (m, 5H), 3.72 (d, 3H), 3.35-3.22 (m, 1H), 2.92-2.68 (m, 5H), 2.13-2.07 (m, 1H), 1.87-1.79 (m, 1H), 1.75-1.67 (m, 1H), 1.63-1.56 (m, 1H), 1.46-1.37 (m, 1H), 1.07 (d, 3H), 1.03 (d, 3H)

Example 361. (S)-quinuclidin-3-yl (6-methoxy-7-(4-methoxy-2-methylphenyl)-3,3-dimethylchroman-4-yl)carbamate $^1$H-NMR (400 MHz, $CDCl_3$) δ 7.07 (d, 1H), 6.79 (s, 1H), 6.78-6.71 (m, 2H), 6.62 (s, 1H), 4.97-4.88 (m, 1H), 4.84-4.78 (m, 1H), 4.69 (d, 1H), 3.88-3.73 (m, 5H), 3.67 (d, 3H), 3.35-3.22 (m, 1H), 2.94-2.69 (m, 5H), 2.13 (s, 3H), 2.12-2.07 (m, 1H), 1.88-1.80 (m, 1H), 1.75-1.67 (m, 1H), 1.63-1.55 (m, 1H), 1.46-1.37 (m, 1H), 1.08 (d, 3H), 1.04 (d, 3H)

Example 362. (S)-quinuclidin-3-yl (7-(4-butylphenyl)-6-methoxy-3,3-dimethylchroman-4-yl)carbamate $^1$H-NMR (400 MHz, $CDCl_3$) δ 7.45-7.38 (m, 2H), 7.24-7.18 (m, 2H), 6.81 (s, 1H), 6.77 (d, 1H), 4.91-4.86 (m, 1H), 4.84-4.78 (m, 1H), 4.68 (d, 1H), 3.87-3.76 (m, 2H), 3.72 (d, 3H), 3.35-3.23 (m, 1H), 2.94-2.70 (m, 5H), 2.64 (t, 2H), 2.13-2.06 (m, 1H), 1.90-1.78 (m, 1H), 1.75-1.68 (m, 1H), 1.67-1.54 (m, 3H), 1.46-1.35 (m, 3H), 1.07 (d, 3H), 1.03 (d, 3H), 0.95 (t, 3H)

Example 363. (S)-quinuclidin-3-yl (7-(3-chloro-4-isopropoxyphenyl)-6-methoxy-3,3-dimethylchroman-4-yl)carbamate $^1$H-NMR (400 MHz, $CDCl_3$) δ 7.54 (s, 1H), 7.34 (d, 1H), 6.96 (d, 1H), 6.80-6.72 (m, 2H), 4.91-4.84 (m, 1H), 4.83-4.77 (m, 1H), 4.67 (d, 1H), 4.61-4.54 (m, 1H), 3.87-3.77 (m, 2H), 3.73 (d, 3H), 3.35-3.22 (m, 1H), 2.93-2.68 (m, 5H), 2.14-2.06 (m, 1H), 1.87-1.79 (m, 1H), 1.74-1.67 (m, 1H), 1.63-1.54 (m, 1H), 1.46-1.36 (m, 7H), 1.07 (d, 3H), 1.03 (d, 3H)

Example 364. (S)-quinuclidin-3-yl (7-(4-(tert-butyl)phenyl)-6-methoxy-3,3-dimethylchroman-4-yl)carbamate $^1$H-NMR (400 MHz, $CDCl_3$) δ 7.49-7.39 (m, 4H), 6.83 (s, 1H), 6.77 (d, 1H), 4.93-4.86 (m, 1H), 4.84-4.78 (m, 1H), 4.68 (d, 1H), 3.87-3.78 (m, 2H), 3.73 (d, 3H), 3.37-3.22 (m, 1H), 2.96-2.69 (m, 5H), 2.14-2.06 (m, 1H), 1.91-1.79 (m, 1H), 1.75-1.67 (m, 1H), 1.64-1.54 (m, 1H), 1.47-1.40 (m, 1H), 1.36 (s, 9H), 1.07 (d, 3H), 1.04 (d, 3H)

Example 365. (S)-quinuclidin-3-yl (6-methoxy-7-(4-methoxy-3,5-dimethylphenyl)-3,3-dimethylchroman-4-yl)carbamate $^1$H-NMR (400 MHz, $CDCl_3$) δ 7.19-7.11 (m, 2H), 6.80-6.71 (m, 2H), 4.93-4.85 (m, 1H), 4.83-4.78 (m, 1H), 4.67 (d, 1H), 3.87-3.69 (m, 8H), 3.35-3.22 (m, 1H), 2.94-2.70 (m, 5H), 2.31 (s, 6H), 2.14-2.06 (m, 1H), 1.88-1.78 (m, 1H), 1.76-1.66 (m, 1H), 1.64-1.54 (m, 1H), 1.47-1.36 (m, 1H), 1.07 (d, 3H), 1.03 (d, 3H)

Example 366. (S)-quinuclidin-3-yl (7-(4-isobutoxyphenyl)-6-methoxy-3,3-dimethylchroman-4-yl)carbamate $^1$H-NMR (400 MHz, $CDCl_3$) δ 7.48-7.39 (m, 2H), 6.96-6.89 (m, 2H), 6.82-6.72 (m, 2H), 4.91-4.84 (m, 1H), 4.83-4.78 (m, 1H), 4.67 (d, 1H), 3.87-3.67 (m, 7H), 3.35-3.22 (m, 1H), 2.93-2.69 (m, 5H), 2.16-2.06 (m, 2H), 1.89-1.79 (m, 1H), 1.76-1.67 (m, 1H), 1.64-1.55 (m, 1H), 1.45-1.37 (m, 1H), 1.12-0.97 (m, 12H)

Example 367. (S)-quinuclidin-3-yl (7-(6-isopropoxypyridin-3-yl)-6-methoxy-3,3-dimethylchroman-4-yl)carbamate $^{1}$H-NMR (400 MHz, $CDCl_3$) δ 8.27 (s, 1H), 7.23 (d, 1H), 6.81-6.74 (m, 2H), 6.70 (d, 1H), 5.38-5.29 (m, 1H), 4.93-4.85 (m, 1H), 4.83-4.77 (m, 1H), 4.68 (d, 1H), 3.88-3.77 (m, 2H), 3.73 (d, 3H), 3.34-3.23 (m, 1H), 2.94-2.69 (m, 5H), 2.13-2.06 (m, 1H), 1.87-1.77 (m, 1H), 1.74-1.67 (m, 1H), 1.62-1.55 (m, 1H), 1.46-1.40 (m, 1H), 1.37 (d, 6H), 1.07 (d, 3H), 1.03 (d, 3H)

Experimental Example 1: Evaluation of Inhibitory Activities Against GCS

The inhibitory activities of the compounds of the present invention against GCS were evaluated, as follows, according to the method described in the known literature (Hayashi Y et al., A sensitive and reproducible assay to measure the activity of glucosylceramide synthase and lactosylceramide synthase using HPLC and fluorescent substrates, *Analytical Biochemistry* 345 (2005) 181-186). Ibiglustat, known as a GCS inhibitor, was used as a control.

(1) Materials

A549 cells (ATCC, CCL-185)
NBD C6-ceramide (Thermo Fisher, N1154)
UDP-glucose (Sigma, U4625)
Potassium chloride (Sigma, P9333)
UltraPure™ 0.5 M EDTA (Invitrogen, 15575-038)
BCA protein assay kit (Thermo Fisher, 23227)
Ibiglustat (Shanghai Systeam Biochem Co., ltd, Genz-682452)
HEPES (sigma, H3375)
Protease/phosphatase inhibitor cocktail (CST, 5872s)
DMEM (GIBCO, 11995-065)
FBS (GIBCO, 16000-044)
Antibiotic-Antimycotic (100X) (GIBCO, 15240-112)
200 mM L-glutamine (GIBCO, 25030081)
PBS (GIBCO, 10010-023)
0.25% Trypsin-EDTA (GIBCO, 25200-056)
Dimethyl sulfoxide (Sigma, 34869)
2-propanol, HPLC grade (Burdick & Jackson, AH323-4)
Hexane, HPLC grade (Burdick & Jackson, AH216-4)
Chloroform (Sigma, C2432)
Methanol (Merck, 1.06009.1011)

(2) Protocol

<1> Preparation of Cell Lysates

A549 cells (ATCC, CCL-185) were cultured in a DMEM medium supplemented with 10% fetal bovine serum (FBS), 1× antibiotic-antimycotic, and 1× L-glutamine, in an incubator at 37° C. and 5% $CO_2$. After the cells attached to the culture dish were washed with phosphate buffered saline (PBS), the cells were scraped off with a cell scraper and then centrifuged (4000 rpm, 3 min, 4° C.) to collect the cells in a 50 ml tube. The cell pellets were suspended in a lysis buffer (50 mM HEPES, pH 7.3, containing 1× the protease/phosphatase inhibitor cocktail), lysed by sonication, and then the lysate was centrifuged (13000 rpm, 10 min, 4° C.). The obtained supernatant was used for the quantitative analysis of proteins. The amount of proteins was measured using the BCA protein assay kit, using bovine serum albumin as a standard.

<2> GCS Enzyme Reaction

Enzymatic reactions were initiated by sequentially adding the following reaction materials to a 96 deep-well plate. Thereafter, the enzymatic reactions were performed at 37° C. for 90 minutes.

| Enzyme reaction mix (Total 50 ul) | | | |
|---|---|---|---|
| | Stock Con. | Final Con. | Volume (ul) |
| 1 | | | |
| Cpd. Mix | Cpd. 500~0.003 uM (DMSO) | 10000~0.056 nM | 1 |
| | Total | | 1 |
| 2 | | | |
| Sub Mix | 20 mM UDP-Glc | 500 uM | 1.25 |
| | 25 mM EDTA | 1 mM | 2 |
| | 500 uM NBD-Cer/BSA | 5 uM | 0.5 |
| | D.W | | 35.25 |
| | Total | | 39 |
| 3 | | | |
| Enzyme Mix | 3.135 ug/ul A549 cell lysate | 0.627 ug/ul(31.35 ug) | 10 |
| | Total | | 10 |

<3> Lipid Extraction

The enzymatic reactions were stopped by adding 100 µl of chloroform/methanol (2:1, v/v). After vortexing for 15 seconds, each mixture was centrifuged (4000 rpm, 10 min, 18° C.). The lower layer (50 µl) was transferred to a new 96 deep-well plate and dried with a reduced concentrator.

<4> HPLC Analysis

Lipids were dissolved in 100 µl of isopropyl alcohol/n-hexane/$H_2O$ (55:44:1, v/v/v) and then transferred to a glass vial for HPLC (Agilent, 8004-HP-H/i3u). The sample (100 µl) was automatically loaded onto a normal-phase column (Intersil SIL 150A-5, 4.6×250 mm, GL Sciences, Japan) and then eluted at a flow rate of 2.0 ml/min with isopropyl alcohol/n-hexane/$H_2O$ (55:44:1, v/v/v). The fluorescence thereof was measured with a fluorescence detector (Agilent, 1260 FLD Spectra), using 470 nm and 530 nm as excitation and emission wavelengths, respectively.

<5> Data Analysis

Data analysis was performed by the following equations.

$$\% \text{ Area(Sample)} = \text{Area(GlcCer)}/[\text{Area(Cer)}+\text{Area(GlcCer)}]\times 100$$

$$\% \text{ GCS activity} = [\text{Area(Sample)}-\text{Area(ibiglustat)}]/[\text{Area(DMSO)}-\text{Area(ibiglustat)}]\times 100$$

The obtained % GCS activity data was analyzed with the software GraphPad Prism (Ver 5.01) to calculate the $IC_{50}$ values. The results are shown in Tables 1 to 4 below.

TABLE 1

| Example | $IC_{50}$ (nM) |
|---|---|
| 1 | 2.6 |
| 2 | 0.7 |
| 3 | 0.7 |
| 4 | 0.7 |
| 5 | 3.71 |
| 6 | 0.67 |
| 7 | 3.28 |
| 8 | 0.48 |

TABLE 1-continued

| Example | $IC_{50}$ (nM) |
|---|---|
| 9 | 1.81 |
| 10 | 2.02 |
| 11 | 10.44 |
| 12 | 4.28 |
| 13 | 8.54 |
| 14 | 9.67 |
| 15 | 11.75 |
| 16 | 9.40 |
| 17 | 1.41 |
| 18 | 1.54 |
| 19 | 8.32 |
| 20 | 2.86 |
| 21 | 0.67 |
| 22 | 4.00 |
| 23 | 0.48 |
| 24 | 4.88 |
| 25 | 0.65 |
| 26 | 10.18 |
| 27 | 0.75 |
| 28 | 5.19 |
| 29 | 2.28 |
| 30 | 3.92 |
| 31 | 3.26 |
| 32 | 3.34 |
| 33 | 1.43 |
| 34 | 1.97 |
| 35 | 2.77 |
| 36 | 1.53 |
| 37 | 1.40 |
| 38 | 3.02 |
| 39 | 1.82 |
| 40 | 3.78 |
| 41 | 0.52 |
| 42 | 14.01 |
| 43 | 0.58 |
| 44 | 9.17 |
| 45 | 4.13 |
| 46 | 4.08 |
| 47 | 2.55 |
| 48 | 6.27 |
| 49 | 3.80 |
| 50 | 3.98 |
| 51 | 1.02 |
| 52 | 7.06 |
| 53 | 1.77 |
| 54 | 2.14 |
| 55 | 3.58 |
| 56 | 1.38 |
| 57 | 3.52 |
| 58 | 2.00 |
| 59 | 0.30 |
| 60 | 2.39 |
| 61 | 1.36 |
| 62 | 1.03 |
| 63 | 1.33 |
| 64 | 1.32 |
| 65 | 0.22 |
| 66 | 1.75 |
| 67 | 0.93 |
| 68 | 3.65 |
| 69 | 1.91 |
| 70 | 0.59 |
| 71 | 5.30 |
| 72 | 0.92 |
| 73 | 1.47 |
| 74 | 5.03 |
| 75 | 2.44 |
| 76 | 1.94 |
| 77 | 3.33 |
| 78 | 1.26 |
| 79 | 2.57 |
| 80 | 5.75 |
| 81 | 0.94 |
| 82 | 2.86 |
| 83 | 3.93 |
| 84 | 2.79 |
| 85 | 9.67 |
| 86 | 9.68 |

TABLE 1-continued

| Example | $IC_{50}$ (nM) |
|---|---|
| 87 | 3.57 |
| 88 | 9.41 |
| 89 | 6.63 |
| 90 | 4.27 |
| 91 | 5.38 |
| 92 | 29.59 |
| 93 | 4.25 |
| 94 | 8.13 |
| 95 | 19.75 |
| 96 | 8.55 |
| 97 | 11.49 |
| 98 | 14.95 |
| 99 | 19.18 |
| 100 | 7.1 |
| 101 | 9.2 |
| 102 | 0.8 |
| 103 | 1 |
| 104 | 1 |
| 105 | 1.11 |
| 106 | 1.17 |
| 107 | 1.17 |
| 108 | 0.69 |
| 109 | 2.14 |
| 110 | 1.30 |
| 111 | 1.93 |
| 112 | 0.53 |
| 113 | 2.92 |
| 114 | 0.75 |
| 115 | 1.88 |
| 116 | 1.39 |
| 117 | 1.66 |
| 118 | 1.63 |
| 119 | 0.65 |
| 120 | 0.71 |

TABLE 2

| Example | $IC_{50}$ (nM) |
|---|---|
| 121 | 2.67 |
| 122 | 0.96 |
| 123 | 0.79 |
| 124 | 0.75 |
| 125 | 0.86 |
| 126 | 0.58 |
| 127 | 2.11 |
| 128 | 2.84 |
| 129 | 1.15 |
| 130 | 0.71 |
| 131 | 1.02 |
| 132 | 1.55 |
| 133 | 1.35 |
| 134 | 2.83 |
| 135 | 0.44 |
| 136 | 0.61 |
| 137 | 0.62 |
| 138 | 0.63 |
| 139 | 0.62 |
| 140 | 0.88 |
| 141 | 0.19 |
| 142 | 0.67 |
| 143 | 0.78 |
| 144 | 0.17 |
| 145 | 0.69 |
| 146 | 0.98 |
| 147 | 0.40 |
| 148 | 0.74 |
| 149 | 0.41 |
| 150 | 0.72 |
| 151 | 0.53 |
| 152 | 0.91 |
| 153 | 0.48 |
| 154 | 0.74 |
| 155 | 0.60 |
| 156 | 0.29 |

TABLE 2-continued

| Example | $IC_{50}$ (nM) |
|---|---|
| 157 | 0.48 |
| 158 | 0.42 |
| 159 | 0.57 |
| 160 | 0.52 |
| 161 | 0.38 |
| 162 | 0.52 |
| 163 | 0.59 |
| 164 | 1.59 |
| 165 | 0.82 |
| 166 | 0.31 |
| 167 | 0.71 |
| 168 | 1.40 |
| 169 | 0.37 |
| 170 | 0.42 |
| 171 | 0.79 |
| 172 | 0.37 |
| 173 | 1.17 |
| 174 | 0.35 |
| 175 | 0.71 |
| 176 | 0.59 |
| 177 | 1.39 |
| 178 | 1.14 |
| 179 | 1.31 |
| 180 | 0.44 |
| 181 | 0.50 |
| 182 | 0.25 |
| 183 | 1.22 |
| 184 | 0.91 |
| 185 | 0.67 |
| 186 | 0.38 |
| 187 | 0.32 |
| 188 | 0.75 |
| 189 | 0.36 |
| 190 | 0.29 |
| 191 | 0.63 |
| 192 | 0.92 |
| 193 | 0.51 |
| 194 | 0.60 |
| 195 | 1.14 |
| 196 | 1.25 |
| 197 | 0.90 |
| 198 | 0.66 |
| 199 | 0.51 |
| 200 | 0.49 |
| 201 | 0.41 |
| 202 | 0.28 |
| 203 | 0.72 |
| 204 | 0.52 |
| 205 | 0.65 |
| 206 | 0.50 |
| 207 | 1.12 |
| 208 | 1.41 |
| 209 | 0.34 |
| 210 | 1.57 |
| 211 | 0.71 |
| 212 | 0.87 |
| 213 | 0.78 |
| 214 | 0.55 |
| 215 | 1.57 |
| 216 | 1.51 |
| 217 | 0.55 |
| 218 | 0.40 |
| 219 | 2.26 |
| 220 | 0.80 |
| 221 | 0.74 |
| 222 | 0.79 |
| 223 | 1.58 |
| 224 | 0.62 |
| 225 | 0.45 |
| 226 | 0.71 |
| 227 | 0.56 |
| 228 | 0.55 |
| 229 | 0.71 |
| 230 | 0.86 |
| 231 | 0.62 |
| 232 | 0.41 |
| 233 | 0.49 |
| 234 | 0.40 |

TABLE 2-continued

| Example | $IC_{50}$ (nM) |
|---|---|
| 235 | 0.75 |
| 236 | 0.75 |
| 237 | 0.63 |
| 238 | 0.47 |
| 239 | 0.47 |
| 240 | 0.92 |

TABLE 3

| Example | $IC_{50}$ (nM) |
|---|---|
| 241 | 0.81 |
| 242 | 0.53 |
| 243 | 1.90 |
| 244 | 0.42 |
| 245 | 0.95 |
| 246 | 0.75 |
| 247 | 0.58 |
| 248 | 0.86 |
| 249 | 0.39 |
| 250 | 0.35 |
| 251 | 1.64 |
| 252 | 0.54 |
| 253 | 0.76 |
| 254 | 1.70 |
| 255 | 1.20 |
| 256 | 0.39 |
| 257 | 0.36 |
| 258 | 0.45 |
| 259 | 1.14 |
| 260 | 0.51 |
| 261 | 0.65 |
| 262 | 0.52 |
| 263 | 1.44 |
| 264 | 0.35 |
| 265 | 2.03 |
| 266 | 4.07 |
| 267 | 1.48 |
| 268 | 0.62 |
| 269 | 0.66 |
| 270 | 0.78 |
| 271 | 1.26 |
| 272 | 0.89 |
| 273 | 0.46 |
| 274 | 0.58 |
| 275 | 0.84 |
| 276 | 0.54 |
| 277 | 0.65 |
| 278 | 2.19 |
| 279 | 0.73 |
| 280 | 0.62 |
| 281 | 0.65 |
| 282 | 1.64 |
| 283 | 2.20 |
| 284 | 0.91 |
| 285 | 1.96 |
| 286 | 0.93 |
| 287 | 0.79 |
| 288 | 1.11 |
| 289 | 0.61 |
| 290 | 1.54 |
| 291 | 1.03 |
| 292 | 1.38 |
| 293 | 1.23 |
| 294 | 144.6 |
| 295 | 18.1 |
| 296 | 11.4 |
| 297 | 0.80 |
| 298 | 0.70 |
| 299 | 0.60 |
| 300 | 0.23 |
| 301 | 0.80 |
| 302 | 0.80 |
| 303 | 0.50 |
| 304 | 0.38 |

TABLE 3-continued

| Example | $IC_{50}$ (nM) |
|---|---|
| 305 | 0.70 |
| 306 | 0.50 |
| 307 | 1.07 |
| 308 | 1.06 |
| 309 | 5.77 |
| 310 | 0.23 |
| 311 | 0.17 |
| 312 | 5.62 |
| 313 | 3.89 |
| 314 | 6.47 |
| 315 | 14.70 |
| 316 | 36.45 |
| 317 | 2.94 |
| 318 | 1.29 |
| 319 | 1.07 |
| 320 | 1.5 |
| 321 | 1.00 |
| 322 | 1.78 |
| 323 | 0.63 |
| 324 | 1.25 |
| 325 | 0.58 |
| 326 | 0.64 |
| 327 | 2.70 |
| 328 | 1.18 |
| 329 | 14.93 |
| 330 | 0.28 |
| 331 | 0.36 |
| 332 | 0.39 |
| 333 | 0.45 |
| 334 | 0.33 |
| 335 | 0.35 |
| 336 | 0.27 |
| 337 | 0.23 |
| 338 | 0.19 |
| 339 | 0.61 |
| 340 | 0.48 |
| 341 | 0.17 |
| 342 | 0.45 |
| 343 | 0.12 |
| 344 | 0.58 |
| 345 | 0.37 |
| 346 | 1.18 |
| 347 | 0.23 |
| 348 | 0.24 |
| 349 | 0.32 |
| 350 | 0.47 |
| 351 | 0.45 |
| 352 | 0.38 |
| 353 | 0.33 |
| 354 | 0.63 |
| 355 | 0.58 |
| 356 | 0.48 |
| 357 | 0.45 |
| 358 | 0.61 |
| 359 | 0.62 |
| 360 | 0.55 |

TABLE 4

| Example | $IC_{50}$ (nM) |
|---|---|
| 361 | 0.99 |
| 362 | 0.11 |
| 363 | 0.75 |
| 364 | 0.43 |
| 365 | 1.20 |
| 366 | 0.19 |
| 367 | 0.22 |

From the results of Tables 1 to 4, it can be seen that the compounds of the present invention exhibit excellent inhibitory activity against GCS.

Experimental Example 2: Evaluation of Inhibitory Activities Against GM1 Production GM1, which is the final product of sphingolipid metabolism, is expressed on the cell membrane and thus the detection thereof is easy. In addition, the amount of GM1 represents the conversion of ceramide to glucosylceramide. Therefore, the inhibitory activities of the compounds of the present invention against GM1 production were evaluated, as follows, according to the method described in the known literature (Dijkhuis et al., Gangliosides do not affect ABC transporter function in human neuroblastoma cells. *The Journal of Lipid Research* 47 (2006). 1187-1195). Ibiglustat, known as a GCS inhibitor, was used as a control.

(1) Materials

Jurkat cells, Clone E6-1 (ATCC, TIB-152)

Cholera toxin subunit B (CTB), FITC (Sigma, C1655)

Ibiglustat (Shanghai Systeam Biochem Co., ltd, Genz-682452)

DMSO (Sigma, D2650)

Fixation buffer (BD, 554655)

RPMI 1640 (Gibco, A1049101)

FBS (Gibco, 16000-044)

Antibiotic-Antimycotic (100X) (Gibco, 15240-122)

FACS Sheath Fluid (BD, 342003)

Jurkat cells were cultured in RPMI 1640 medium supplemented with 10% FBS and 1× Antibiotic-Antimycotic. A washing solution was prepared by adding 10 ml of FBS to 490 ml of FACS Sheath Fluid. The CTB-FITC solution was prepared by diluting the CTB-FITC stock solution (10 mg/ml) with the washing solution to a final concentration of 2 μg/ml.

(2) Protocol

A cell suspension ($1\times10^5$ cells/ml) was prepared with the culture medium (RPMI 1640 medium supplemented with 10% FBS and 1× Antibiotic-Antimycotic). The cell suspension (200 μl) was added to each well of a 96-well plate (20,000 cells/well) and then the compounds were treated thereto in a final concentration of 0.05 to 3000 nM (3 fold, 11 points) per well. Each mixture was incubated in a $CO_2$ incubator at 37° C. for 72 hours. After centrifuging at 1500 rpm for 3 minutes to remove the medium, the cells were resuspended in 200 μl of the washing solution per well. After centrifuging at 1500 rpm for 3 minutes to remove the washing solution, the cells were resuspended in 200 μl of the 2 μg/ml CTB-FITC solution. The obtained suspension was incubated at 4° C. for 60 minutes, while not being exposed to light. After centrifuging at 1500 rpm for 3 minutes to remove the CTB-FITC solution, the cells were washed with 200 μl of the washing solution. The washing process was additionally repeated twice. The washed plate was centrifuged at 1500 rpm for 3 minutes to remove the washing solution and then the cells were completely resuspended in 200 μl of the fixation buffer. $IC_{50}$ was determined from the values obtained by quantifying FITC fluorescences with Guava™ easyCyte 5HT (Merck Milipore, 0500-4005).

Data analysis was performed by the following equations.

% MFI (median fluorescence intensity)=(fluorescence value of drug-treated group/fluorescence value of DMSO-treated group)×100

% Cells=(cell concentration in the well/cell concentration in the DMSO-treated group)×100

% MFI and % cell data were analyzed with the software GraphPad Prism (Ver 5.01) to calculate $IC_{50}$ values. The results are shown in Tables 5 to 8 below.

TABLE 5

| Example | $IC_{50}$ (nM) |
|---|---|
| 1 | 1.686 |
| 2 | 3.474 |
| 3 | 2.127 |
| 4 | 1.084 |
| 5 | 29.21 |
| 6 | 7.18 |
| 7 | 34.13 |
| 8 | 3.59 |
| 9 | 2.83 |
| 10 | 7.23 |
| 11 | 18.22 |
| 12 | 3.28 |
| 13 | 42.76 |
| 14 | 42.11 |
| 15 | 38.94 |
| 16 | 27.80 |
| 17 | 5.50 |
| 18 | 6.98 |
| 19 | 30.49 |
| 20 | 19.10 |
| 21 | 4.56 |
| 22 | 34.24 |
| 23 | 0.57 |
| 24 | 10.69 |
| 25 | 1.07 |
| 26 | 23.26 |
| 27 | 0.54 |
| 28 | 24.07 |
| 29 | 12.40 |
| 30 | 48.23 |
| 31 | 27.63 |
| 32 | 48.65 |
| 33 | 10.75 |
| 34 | 5.97 |
| 35 | 5.44 |
| 36 | 11.07 |
| 37 | 9.47 |
| 38 | 14.49 |
| 39 | 7.73 |
| 40 | 19.71 |
| 41 | 0.45 |
| 42 | 34.06 |
| 43 | 0.02 |
| 44 | 15.59 |
| 45 | 26.23 |
| 46 | 20.46 |
| 47 | 10.54 |
| 48 | 42.03 |
| 49 | 12.32 |
| 50 | 25.93 |
| 51 | 4.99 |
| 52 | 24.77 |
| 53 | 2.66 |
| 54 | 14.06 |
| 55 | 22.34 |
| 56 | 6.03 |
| 57 | 36.60 |
| 58 | 21.17 |
| 59 | 2.22 |
| 60 | 16.49 |
| 61 | 40.07 |
| 62 | 21.20 |
| 63 | 27.02 |
| 64 | 19.20 |
| 65 | 1.18 |
| 66 | 11.35 |
| 67 | 11.30 |
| 68 | 28.29 |
| 69 | 8.93 |
| 70 | 5.78 |
| 71 | 38.79 |
| 72 | 12.84 |
| 73 | 28.20 |
| 74 | 44.27 |
| 75 | 23.60 |
| 76 | 29.18 |
| 77 | 28.68 |
| 78 | 27.27 |

TABLE 5-continued

| Example | $IC_{50}$ (nM) |
|---|---|
| 79 | 33.42 |
| 80 | 44.16 |
| 81 | 14.79 |
| 82 | 7.00 |
| 83 | 19.61 |
| 84 | 7.18 |
| 85 | 222 |
| 86 | 181.4 |
| 87 | 98.71 |
| 88 | 159.6 |
| 89 | 216.5 |
| 90 | 140.9 |
| 91 | 171.2 |
| 92 | 494.6 |
| 93 | 79.77 |
| 94 | 407.5 |
| 95 | 513 |
| 96 | 78.93 |
| 97 | 502.4 |
| 98 | 525.1 |
| 99 | 322.3 |
| 100 | 289.3 |
| 101 | 65.94 |
| 102 | 2.812 |
| 103 | 1.434 |
| 104 | 1.024 |
| 105 | 1.409 |
| 106 | 0.22 |
| 107 | 0.10 |
| 108 | 0.46 |
| 109 | 2.00 |
| 110 | 0.12 |
| 111 | 1.27 |
| 112 | 0.55 |
| 113 | 13.01 |
| 114 | 2.81 |
| 115 | 3.72 |
| 116 | 1.16 |
| 117 | 4.43 |
| 118 | 3.63 |
| 119 | 1.25 |
| 120 | 6.41 |

TABLE 6

| Example | $IC_{50}$ (nM) |
|---|---|
| 121 | 15.92 |
| 122 | 3.75 |
| 123 | 4.24 |
| 124 | 4.47 |
| 125 | 3.85 |
| 126 | 0.85 |
| 127 | 14.18 |
| 128 | 23.16 |
| 129 | 4.56 |
| 130 | 1.40 |
| 131 | 1.21 |
| 132 | 8.95 |
| 133 | 0.10 |
| 134 | 12.66 |
| 135 | 3.46 |
| 136 | 2.73 |
| 137 | 0.11 |
| 138 | 1.57 |
| 139 | 0.30 |
| 140 | 0.15 |
| 141 | 0.20 |
| 142 | 0.19 |
| 143 | 1.46 |
| 144 | 1.20 |
| 145 | 0.08 |
| 146 | 2.35 |
| 147 | 1.00 |
| 148 | 0.03 |

TABLE 6-continued

| Example | $IC_{50}$ (nM) |
|---|---|
| 149 | 0.03 |
| 150 | 0.40 |
| 151 | 0.31 |
| 152 | 0.22 |
| 153 | 0.06 |
| 154 | 0.41 |
| 155 | 0.77 |
| 156 | 0.27 |
| 157 | 0.12 |
| 158 | 1.50 |
| 159 | 0.55 |
| 160 | 0.54 |
| 161 | 0.18 |
| 162 | 0.02 |
| 163 | 0.50 |
| 164 | 3.22 |
| 165 | 0.66 |
| 166 | 0.07 |
| 167 | 3.28 |
| 168 | 2.05 |
| 169 | 0.25 |
| 170 | 5.83 |
| 171 | 5.23 |
| 172 | 1.92 |
| 173 | 2.95 |
| 174 | 1.37 |
| 175 | 2.20 |
| 176 | 3.20 |
| 177 | 9.73 |
| 178 | 4.36 |
| 179 | 4.42 |
| 180 | 3.42 |
| 181 | 5.55 |
| 182 | 0.79 |
| 183 | 6.43 |
| 184 | 4.16 |
| 185 | 0.98 |
| 186 | 2.81 |
| 187 | 2.06 |
| 188 | 4.59 |
| 189 | 0.04 |
| 190 | 0.03 |
| 191 | 0.31 |
| 192 | 1.35 |
| 193 | 0.46 |
| 194 | 1.81 |
| 195 | 1.39 |
| 196 | 6.13 |
| 197 | 1.99 |
| 198 | 1.83 |
| 199 | 3.63 |
| 200 | 1.94 |
| 201 | 1.12 |
| 202 | 0.47 |
| 203 | 8.03 |
| 204 | 0.31 |
| 205 | 0.25 |
| 206 | 0.01 |
| 207 | 1.06 |
| 208 | 2.47 |
| 209 | 0.01 |
| 210 | 17.99 |
| 211 | 1.41 |
| 212 | 2.45 |
| 213 | 0.03 |
| 214 | 1.81 |
| 215 | 2.51 |
| 216 | 8.58 |
| 217 | 7.35 |
| 218 | 2.69 |
| 219 | 7.58 |
| 220 | 2.42 |
| 221 | 2.80 |
| 222 | 6.59 |
| 223 | 1.60 |
| 224 | 0.60 |
| 225 | 1.70 |
| 226 | 1.30 |

TABLE 6-continued

| Example | $IC_{50}$ (nM) |
|---|---|
| 227 | 4.50 |
| 228 | 1.30 |
| 229 | 2.10 |
| 230 | 0.80 |
| 231 | 1.50 |
| 232 | 0.30 |
| 233 | 3.00 |
| 234 | 1.10 |
| 235 | 7.10 |
| 236 | 3.60 |
| 237 | 5.10 |
| 238 | 5.90 |
| 239 | 4.80 |
| 240 | 5.00 |

TABLE 7

| Example | $IC_{50}$ (nM) |
|---|---|
| 241 | 24.10 |
| 242 | 3.80 |
| 243 | 24.10 |
| 244 | 0.60 |
| 245 | 4.70 |
| 246 | 1.30 |
| 247 | 10.70 |
| 248 | 29.60 |
| 249 | 4.00 |
| 250 | 5.40 |
| 251 | 17.50 |
| 252 | 1.40 |
| 253 | 6.40 |
| 254 | 17.40 |
| 255 | 5.10 |
| 256 | 0.20 |
| 257 | 0.70 |
| 258 | 1.00 |
| 259 | 6.90 |
| 260 | 0.30 |
| 261 | 2.60 |
| 262 | 3.70 |
| 263 | 4.00 |
| 264 | 0.70 |
| 265 | 38.70 |
| 266 | 26.90 |
| 267 | 9.10 |
| 268 | 1.40 |
| 269 | 1.90 |
| 270 | 1.00 |
| 271 | 9.00 |
| 272 | 4.40 |
| 273 | 2.90 |
| 274 | 1.70 |
| 275 | 2.60 |
| 276 | 1.30 |
| 277 | 0.90 |
| 278 | 12.40 |
| 279 | 6.20 |
| 280 | 9.30 |
| 281 | 6.90 |
| 282 | 2.00 |
| 283 | 25.60 |
| 284 | 0.50 |
| 285 | 9.70 |
| 286 | 3.30 |
| 287 | 1.00 |
| 288 | 0.70 |
| 289 | 1.40 |
| 290 | 0.90 |
| 291 | 8.90 |
| 292 | 30.20 |
| 293 | 3.00 |
| 295 | 11.16 |
| 296 | 1.256 |
| 297 | 5.60 |

TABLE 7-continued

| Example | $IC_{50}$ (nM) |
|---|---|
| 298 | 5.50 |
| 299 | 9.70 |
| 300 | 0.90 |
| 301 | 17.50 |
| 302 | 2.60 |
| 303 | 3.20 |
| 304 | 2.10 |
| 305 | 5.40 |
| 306 | 3.00 |
| 307 | 3.10 |
| 308 | 4.10 |
| 309 | 37.20 |
| 310 | 0.20 |
| 311 | 0.70 |
| 312 | 28.8 |
| 313 | 34.5 |
| 314 | 56.30 |
| 315 | 58.10 |
| 316 | 251.1 |
| 317 | 13.83 |
| 318 | 27.24 |
| 319 | 6.703 |
| 320 | 13.77 |
| 321 | 3.64 |
| 322 | 5.88 |
| 323 | 26.34 |
| 324 | 14.44 |
| 325 | 6.13 |
| 326 | 10.28 |
| 327 | 37.62 |
| 328 | 13.76 |
| 329 | 33.76 |
| 330 | 1.8 |
| 331 | 3.7 |
| 332 | 0.9 |
| 333 | 0.8 |
| 334 | 0.4 |
| 335 | 2.0 |
| 336 | 3.5 |
| 337 | 1.2 |
| 338 | 3.3 |
| 339 | 0.2 |
| 340 | 2.4 |
| 341 | 4.1 |
| 342 | 3.5 |
| 343 | 0.1 |
| 344 | 7.3 |
| 345 | 1.6 |
| 346 | 9.5 |
| 347 | 0.02 |
| 348 | 0.5 |
| 349 | 3.2 |
| 350 | 7.5 |
| 351 | 1.7 |
| 352 | 2 |
| 353 | 2.3 |
| 354 | 3.1 |
| 355 | 5.8 |
| 356 | 3.4 |
| 357 | 4 |
| 358 | 2 |
| 359 | 2.4 |
| 360 | 10 |
| 361 | 8.5 |

TABLE 8

| Example | $IC_{50}$ (nM) |
|---|---|
| 362 | 0.7 |
| 363 | 8.7 |
| 364 | 2 |
| 365 | 14.5 |
| 366 | 0.7 |
| 367 | 3.2 |

From the results of Tables 5 to 8, it can be seen that the compounds of the present invention exhibit excellent inhibitory activity against GM1 production.

The invention claimed is:

1. A compound of Formula 1 or pharmaceutically acceptable salt thereof:

<Formula 1>

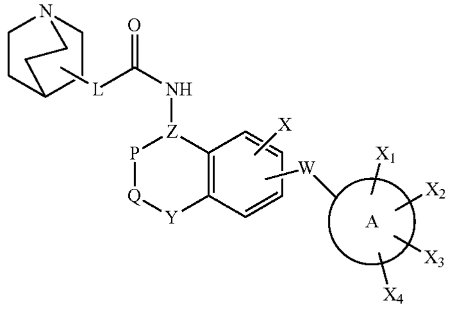

wherein,

L is —O—, —CO—, —$CR_1R_2$—, or —$NR_3$—,

X is hydrogen; halogen; $C_1$-$C_6$ alkyl; $C_1$-$C_6$ alkyl substituted with 1 to 3 halogens; $C_1$-$C_6$ alkoxy; or $C_1$-$C_6$ alkoxy substituted with 1 to 3 halogens, Y is —$NR_3$—; —O—; or —S—, P is —$CR_4R_5$—, Q is —O— or —$CR_4R_5$—, Z is —$CR_6$—, $R_1$ and $R_2$ are, independently of each other, hydrogen; halogen; $C_1$-$C_6$ alkyl; $C_3$-$C_{10}$ cycloalkyl; 3- to 12-membered heterocyclic; or $C_1$-$C_6$ alkoxy; or $R_1$ and $R_2$ form $C_3$-$C_{10}$ cycloalkyl together with the carbon atom to which they are attached, $R_3$ is $C_1$-$C_6$ alkyl, $R_4$ and $R_5$ are, independently of each other, hydrogen; halogen; $C_1$-$C_6$ alkyl; $C_3$-$C_{10}$ cycloalkyl; 3- to 12-membered heterocyclic; or $C_1$-$C_6$ alkoxy; or $R_4$ and $R_5$ form $C_3$-$C_{10}$ cycloalkyl together with the carbon atom of P or Q to which they are attached, $R_6$ is hydrogen; or $C_1$-$C_6$ alkyl;

W is a bond, —$CH_2$—, —O—, —NH—, —$CH_2CH_2$—, —CH═CH—, or —C≡C—,

A ring is phenyl, biphenyl, thiophenyl, pyrazolyl, thiazolyl, naphthalenyl, benzothiadiazolyl, benzodioxolyl, 2,3-dihydrobenzodioxinyl, benzofuranyl, 2,3-dihydrobenzofuranyl, 1,3-dihydroisobenzofuranyl, 3,4-dihydro-1,4-benzoxazinyl, 3-oxo-3,4-dihydro-1,4-benzoxazinyl, benzothiophenyl, indolyl, indazolyl, isoquinolinyl, quinolinyl, 3,4-dihydro-benzodioxepinyl, benzo[c][1,2-5]oxadiazolyl, pyridinyl, 6-oxo-1,6-dihydropyridinyl, chromanyl, dibenzofuranyl, or pyrimidinyl, and $X_1$, $X_2$, $X_3$, and $X_4$ are, independently of each other, hydrogen; cyano; halogen; $C_1$-$C_6$ alkyl; $C_1$-$C_6$ alkyl substituted with 1 to 3 halogens; $C_1$-$C_6$ alkyl substituted with cyano or $C_1$-$C_6$ alkoxy; $C_3$-$C_{10}$ cycloalkyl; $C_1$-$C_6$ alkenyl; $C_1$-$C_6$ alkoxy; $C_1$-$C_6$ alkoxy-$C_1$-$C_6$ alkoxy; $C_1$-$C_6$ alkoxy substituted with 1 to 3 halogens; $C_1$-$C_6$ alkoxy substituted with $C_3$-$C_{10}$ cycloalkyl or benzyl; morpholinyl; mono- or di-$C_1$-$C_6$ alkylamino; pyrrolidinyl-sulfonyl; benzyl; tetrahydropyranyl; $C_1$-$C_6$ alkylthio; or isoxazolyl.

2. The compound or pharmaceutically acceptable salt thereof as claimed in claim 1, wherein L is —O—.

3. The compound or pharmaceutically acceptable salt thereof as claimed in claim 1, wherein X is hydrogen; halogen; or $C_1$-$C_6$ alkoxy.

4. The compound or pharmaceutically acceptable salt thereof as claimed in claim 1, wherein $R_4$, $R_5$, and $R_6$ are, independently of each other, hydrogen or $C_1$-$C_6$ alkyl.

5. The compound or pharmaceutically acceptable salt thereof as claimed in claim 1, wherein Y is —O—.

6. The compound or pharmaceutically acceptable salt thereof as claimed in claim 1, wherein Q is —O—.

7. The compound or pharmaceutically acceptable salt thereof as claimed in claim 1, wherein Y is —S—.

8. The compound or pharmaceutically acceptable salt thereof as claimed in claim 1, wherein Y is —$NR_3$—.

9. The compound or pharmaceutically acceptable salt thereof as claimed in claim 1, wherein W is a bond, —$CH_2$—, or —CH═CH—.

10. The compound or pharmaceutically acceptable salt thereof as claimed in claim 1, wherein L is —O—, X is hydrogen; halogen; or $C_1$-$C_6$ alkoxy, Y is —$NR_3$—; —O—; or —S—, P is —$CR_4R_5$—, Q is —O— or —$CR_4R_5$—, Z is —$CR_6$—, $R_3$ is $C_1$-$C_6$ alkyl, $R_4$, $R_5$, and $R_6$ are, independently of each other, hydrogen or $C_1$-$C_6$ alkyl, W is a bond, —$CH_2$—, -or —CH═CH—, A ring is phenyl, biphenyl, thiophenyl, pyrazolyl, thiazolyl, naphthalenyl, benzothiadiazolyl, benzodioxolyl, 2,3-dihydrobenzodioxinyl, benzofuranyl, 2,3-dihydrobenzofuranyl, 1,3-dihydroisobenzofuranyl, 3,4-dihydro-1,4-benzoxazinyl, 3-oxo-3,4-dihydro-1,4-benzoxazinyl, benzothiophenyl, indolyl, indazolyl, isoquinolinyl, quinolinyl, 3,4-dihydro-benzodioxepinyl, benzo[c][1,2-5]oxadiazolyl, pyridinyl, 6-oxo-1,6-dihydropyridinyl, chromanyl, dibenzofuranyl, or pyrimidinyl, and $X_1$, $X_2$, $X_3$, and $X_4$ is, independently of each other, hydrogen; cyano; halogen; $C_1$-$C_6$ alkyl; $C_1$-$C_6$ alkyl substituted with 1 to 3 halogens; $C_1$-$C_6$ alkyl substituted with cyano or $C_1$-$C_6$ alkoxy; $C_3$-$C_{10}$ cycloalkyl; $C_1$-$C_6$ alkenyl; $C_1$-$C_6$ alkoxy; $C_1$-$C_6$ alkoxy-$C_1$-$C_6$ alkoxy; $C_1$-$C_6$ alkoxy substituted with 1 to 3 halogens; $C_1$-$C_6$ alkoxy substituted with $C_3$-$C_{10}$ cycloalkyl or benzyl; morpholinyl; mono- or di-$C_1$-$C_6$ alkylamino; pyrrolidinyl-sulfonyl; benzyl; tetrahydropyranyl; $C_1$-$C_6$ alkylthio; or isoxazolyl.

11. A compound or pharmaceutically acceptable salt thereof, which is selected from the group consisting of:

(S)-quinuclidin-3-yl (7-(3-fluorophenyl)chroman-4-yl)carbamate;

(S)-quinuclidin-3-yl (7-(3-chlorophenyl)chroman-4-yl)carbamate;

(S)-quinuclidin-3-yl (7-(3-(trifluoromethyl)phenyl)chroman-4-yl)carbamate;

(S)-quinuclidin-3-yl (7-(3-(trifluoromethoxy)phenyl)chroman-4-yl)carbamate;

(S)-quinuclidin-3-yl (7-(2-(methoxymethoxy)phenyl)chroman-4-yl)carbamate;

(S)-quinuclidin-3-yl (7-(3-(methoxymethoxy)phenyl)chroman-4-yl)carbamate;

(S)-quinuclidin-3-yl (7-(2-(2-methoxyethoxy)phenyl)chroman-4-yl)carbamate;

(S)-quinuclidin-3-yl (7-(3-(2-methoxyethoxy)phenyl)chroman-4-yl)carbamate;

(S)-quinuclidin-3-yl (7-(2-fluorophenyl)chroman-4-yl)carbamate;

(S)-quinuclidin-3-yl (7-(2-chlorophenyl)chroman-4-yl)carbamate;

(S)-quinuclidin-3-yl (7-(2-(trifluoromethyl)phenyl)chroman-4-yl)carbamate;

(S)-quinuclidin-3-yl (7-(2-(trifluoromethoxy)phenyl)chroman-4-yl)carbamate;

(S)-quinuclidin-3-yl (7-(4-fluorophenyl)chroman-4-yl)carbamate;

(S)-quinuclidin-3-yl (7-(4-chlorophenyl)chroman-4-yl)carbamate;

(S)-quinuclidin-3-yl (7-(4-(trifluoromethyl)phenyl)chroman-4-yl)carbamate;

(S)-quinuclidin-3-yl (7-(4-(trifluoromethoxy)phenyl)chroman-4-yl)carbamate;

(S)-quinuclidin-3-yl (7-(2-methoxyphenyl)chroman-4-yl)carbamate;

(S)-quinuclidin-3-yl (7-(3-methoxyphenyl)chroman-4-yl)carbamate;

(S)-quinuclidin-3-yl (7-(4-methoxyphenyl)chroman-4-yl)carbamate;

(S)-quinuclidin-3-yl (7-(2-ethoxyphenyl)chroman-4-yl)carbamate;

(S)-quinuclidin-3-yl (7-(3-ethoxyphenyl)chroman-4-yl)carbamate;

(S)-quinuclidin-3-yl (7-(4-ethoxyphenyl)chroman-4-yl)carbamate;

(S)-quinuclidin-3-yl (7-(3-isopropylphenyl)chroman-4-yl)carbamate;

(S)-quinuclidin-3-yl (7-(4-isopropylphenyl)chroman-4-yl)carbamate;

(S)-quinuclidin-3-yl (7-(3-(tert-butyl)phenyl)chroman-4-yl)carbamate;

(S)-quinuclidin-3-yl (7-(4-(tert-butyl)phenyl)chroman-4-yl)carbamate;

(S)-quinuclidin-3-yl (7-(2,5-dichlorophenyl)chroman-4-yl)carbamate;

(S)-quinuclidin-3-yl (7-(3,4-dichlorophenyl)chroman-4-yl)carbamate;

(S)-quinuclidin-3-yl (7-(3,5-dichlorophenyl)chroman-4-yl)carbamate;

(S)-quinuclidin-3-yl (7-(2,3,4-trifluorophenyl)chroman-4-yl)carbamate;

(S)-quinuclidin-3-yl (7-(2,4,5-trifluorophenyl)chroman-4-yl)carbamate;

(S)-quinuclidin-3-yl (7-(4-(difluoromethoxy)phenyl)chroman-4-yl)carbamate;

(S)-quinuclidin-3-yl (7-(4-fluoro-3-(trifluoromethyl)phenyl)chroman-4-yl)carbamate;

(S)-quinuclidin-3-yl (7-(3-chloro-5-(trifluoromethyl)phenyl)chroman-4-yl)carbamate;

(S)-quinuclidin-3-yl (7-(4-cyclopropylphenyl)chroman-4-yl)carbamate;

(S)-quinuclidin-3-yl (7-(2,2-difluorobenzo[d][1,3]dioxol-5-yl)chroman-4-yl)carbamate;

(S)-quinuclidin-3-yl (7-(2,3-dihydrobenzo[b][1,4]dioxin-6-yl)chroman-4-yl)carbamate;

(S)-quinuclidin-3-yl (7-(2,3-dihydrofuran-5-yl)chroman-4-yl)carbamate;

(S)-quinuclidin-3-yl (7-(3-cyanophenyl)chroman-4-yl)carbamate;

(S)-quinuclidin-3-yl (7-(2-cyanophenyl)chroman-4-yl)carbamate;

(S)-quinuclidin-3-yl (7-(3-(dimethylamino)phenyl)chroman-4-yl)carbamate;
(S)-quinuclidin-3-yl (7-(benzo[b]thiophen-2-yl)chroman-4-yl)carbamate;
(S)-quinuclidin-3-yl (7-(benzofuran-3-yl)chroman-4-yl)carbamate;
(S)-quinuclidin-3-yl (7-(benzofuran-2-yl)chroman-4-yl)carbamate;
(S)-quinuclidin-3-yl (7-(1H-indol-6-yl)chroman-4-yl)carbamate;
(S)-quinuclidin-3-yl (7-(1H-indol-3-yl)chroman-4-yl)carbamate;
(S)-quinuclidin-3-yl (7-(1H-indol-7-yl)chroman-4-yl)carbamate;
(S)-quinuclidin-3-yl (7-(1H-indazol-4-yl)chroman-4-yl)carbamate;
(S)-quinuclidin-3-yl (7-(1H-indazol-7-yl)chroman-4-yl)carbamate;
(S)-quinuclidin-3-yl (7-(1-methyl-1H-indazol-6-yl)chroman-4-yl)carbamate;
(S)-quinuclidin-3-yl (7-(1-methyl-1H-indazol-4-yl)chroman-4-yl)carbamate;
(S)-quinuclidin-3-yl (7-(1-methyl-1H-indol-2-yl)chroman-4-yl)carbamate;
(S)-quinuclidin-3-yl (7-(isoquinolin-4-yl)chroman-4-yl)carbamate;
(S)-quinuclidin-3-yl (7-(isoquinolin-5-yl)chroman-4-yl)carbamate;
(S)-quinuclidin-3-yl (7-(quinolin-3-yl)chroman-4-yl)carbamate;
(S)-quinuclidin-3-yl (7-(quinolin-8-yl)chroman-4-yl)carbamate;
(S)-quinuclidin-3-yl (7-(isoquinolin-7-yl)chroman-4-yl)carbamate;
(S)-quinuclidin-3-yl (7-(3,4-dihydro-2H-benzo[b][1,4]dioxepin-7-yl)chroman-4-yl)carbamate;
(S)-quinuclidin-3-yl (7-([1,1'-biphenyl]-3-yl)chroman-4-yl)carbamate;
(S)-quinuclidin-3-yl (7-(3-(pyrrolidin-1-ylsulfonyl)phenyl)chroman-4-yl)carbamate;
(S)-quinuclidin-3-yl (7-(1,3-dihydroisobenzofuran-5-yl)chroman-4-yl)carbamate;
(S)-quinuclidin-3-yl (7-(benzo[c][1,2,5]thiadiazol-5-yl)chroman-4-yl)carbamate;
(S)-quinuclidin-3-yl (7-(4-methyl-3,4-dihydro-2H-benzo[b][1,4]oxazin-7-yl)chroman-4-yl)carbamate;
(S)-quinuclidin-3-yl (7-(thiophen-3-yl)chroman-4-yl)carbamate;
(S)-quinuclidin-3-yl (7-(2-chloro-5-methoxyphenyl)chroman-4-yl)carbamate;
(S)-quinuclidin-3-yl (7-(4-chloro-3-methoxyphenyl)chroman-4-yl)carbamate;
(S)-quinuclidin-3-yl (7-(2-chloro-3-methoxyphenyl)chroman-4-yl)carbamate;
(S)-quinuclidin-3-yl (7-(2-methoxypyridin-4-yl)chroman-4-yl)carbamate;
(S)-quinuclidin-3-yl (7-(3-(dimethylamino)-4-fluorophenyl)chroman-4-yl)carbamate;
(S)-quinuclidin-3-yl [6,7'-bichroman]-4'-ylcarbamate;
(S)-quinuclidin-3-yl (7-(6-methoxy-5-(trifluoromethyl)pyridin-3-yl)chroman-4-yl)carbamate;
(S)-quinuclidin-3-yl (7-(1-benzyl-1H-pyrazol-4-yl)chroman-4-yl)carbamate;
(S)-quinuclidin-3-yl (7-(4-(tetrahydro-2H-pyran-4-yl)phenyl)chroman-4-yl)carbamate;
(S)-quinuclidin-3-yl (7-(4-methyl-3-oxo-3,4-dihydro-2H-benzo[b][1,4]oxazin-6-yl)chroman-4-yl)carbamate;
(S)-quinuclidin-3-yl (7-(3-methyl-4-morpholinophenyl)chroman-4-yl)carbamate;
(S)-quinuclidin-3-yl (7-(3-chloro-4-morpholinophenyl)chroman-4-yl)carbamate;
(S)-quinuclidin-3-yl (7-(3-fluoro-4-morpholinophenyl)chroman-4-yl)carbamate;
(S)-quinuclidin-3-yl (7-(3-cyano-4-methylphenyl)chroman-4-yl)carbamate;
(S)-quinuclidin-3-yl (7-(5-methoxypyridin-3-yl)chroman-4-yl)carbamate;
(S)-quinuclidin-3-yl (7-(5-chloro-6-methoxypyridin-3-yl)chroman-4-yl)carbamate;
(S)-quinuclidin-3-yl (7-(6-(cyclopropylmethoxy)pyridin-3-yl)chroman-4-yl)carbamate;
(S)-quinuclidin-3-yl (7-(3-chloro-4-isopropoxyphenyl)chroman-4-yl)carbamate;
(S)-quinuclidin-3-yl (7-(4-methoxy-3-(trifluoromethyl)phenyl)chroman-4-yl)carbamate;
(S)-quinuclidin-3-yl (7-(2,6-dimethoxyphenyl)chroman-4-yl)carbamate;
(S)-quinuclidin-3-yl (6-(4-fluorophenyl)chroman-4-yl)carbamate;
(S)-quinuclidin-3-yl (6-(3-fluorophenyl)chroman-4-yl)carbamate;
(S)-quinuclidin-3-yl (6-(2-fluorophenyl)chroman-4-yl)carbamate;
(S)-quinuclidin-3-yl (6-(4-chlorophenyl)chroman-4-yl)carbamate;
(S)-quinuclidin-3-yl (6-(3-chlorophenyl)chroman-4-yl)carbamate;
(S)-quinuclidin-3-yl (6-(2-chlorophenyl)chroman-4-yl)carbamate;
(S)-quinuclidin-3-yl (6-(4-(trifluoromethyl)phenyl)chroman-4-yl)carbamate;
(S)-quinuclidin-3-yl (6-(3-(trifluoromethyl)phenyl)chroman-4-yl)carbamate;
(S)-quinuclidin-3-yl (6-(2-(trifluoromethyl)phenyl)chroman-4-yl)carbamate;
(S)-quinuclidin-3-yl (6-(4-(trifluoromethoxy)phenyl)chroman-4-yl)carbamate;
(S)-quinuclidin-3-yl (6-(3-(trifluoromethoxy)phenyl)chroman-4-yl)carbamate;
(S)-quinuclidin-3-yl (6-(2-(trifluoromethoxy)phenyl)chroman-4-yl)carbamate;
(S)-quinuclidin-3-yl (6-(4-(methylthio)phenyl)chroman-4-yl)carbamate;
(S)-quinuclidin-3-yl (6-(3-(methylthio)phenyl)chroman-4-yl)carbamate;
(S)-quinuclidin-3-yl (6-(p-tolyl)chroman-4-yl)carbamate;
(S)-quinuclidin-3-yl (6-(4-cyanophenyl)chroman-4-yl)carbamate;
(S)-quinuclidin-3-yl (6-(3-fluorophenyl)-3,3-dimethylchroman-4-yl)carbamate;
(S)-quinuclidin-3-yl (7-(3-fluorophenyl)-3,3-dimethylchroman-4-yl)carbamate;
(S)-quinuclidin-3-yl (7-(3-chlorophenyl)-3,3-dimethylchroman-4-yl)carbamate;
(S)-quinuclidin-3-yl (3,3-dimethyl-7-(3-(trifluoromethyl)phenyl)chroman-4-yl)carbamate;
(S)-quinuclidin-3-yl (3,3-dimethyl-7-(3-(trifluoromethoxy)phenyl)chroman-4-yl)carbamate;
(S)-quinuclidin-3-yl (7-(2-(methoxymethoxy)phenyl)-3,3-dimethylchroman-4-yl)carbamate;
(S)-quinuclidin-3-yl (7-(3-(methoxymethoxy)phenyl)-3,3-dimethylchroman-4-yl)carbamate;
(S)-quinuclidin-3-yl (7-(4-(methoxymethoxy)phenyl)-3,3-dimethylchroman-4-yl)carbamate;

(S)-quinuclidin-3-yl (7-(2-(2-methoxyethoxy)phenyl)-3,3-dimethylchroman-4-yl)carbamate;
(S)-quinuclidin-3-yl (7-(3-(2-methoxyethoxy)phenyl)-3,3-dimethylchroman-4-yl)carbamate;
(S)-quinuclidin-3-yl (7-(4-(2-methoxyethoxy)phenyl)-3,3-dimethylchroman-4-yl)carbamate;
(S)-quinuclidin-3-yl (7-(3-(difluoromethyl)phenyl)-3,3-dimethylchroman-4-yl)carbamate;
(S)-quinuclidin-3-yl (3,3-dimethyl-7-(8-methylquinolin-5-yl)chroman-4-yl)carbamate;
(S)-quinuclidin-3-yl (7-(3,5-dimethoxyphenyl)-3,3-dimethylchroman-4-yl)carbamate;
(S)-quinuclidin-3-yl (7-(4-methoxy-3-methylphenyl)-3,3-dimethylchroman-4-yl)carbamate;
(S)-quinuclidin-3-yl (7-(4-methoxy-2-methylphenyl)-3,3-dimethylchroman-4-yl)carbamate;
(S)-quinuclidin-3-yl (7-(3-chloro-4-methoxyphenyl)-3,3-dimethylchroman-4-yl)carbamate;
(S)-quinuclidin-3-yl (7-(3-fluoro-4-methoxyphenyl)-3,3-dimethylchroman-4-yl)carbamate;
(S)-quinuclidin-3-yl (7-(2-chloro-4-methoxyphenyl)-3,3-dimethylchroman-4-yl)carbamate;
(S)-quinuclidin-3-yl (7-(4-fluoro-2-methoxyphenyl)-3,3-dimethylchroman-4-yl)carbamate;
(S)-quinuclidin-3-yl (7-(2-chloro-6-methoxyphenyl)-3,3-dimethylchroman-4-yl)carbamate;
(S)-quinuclidin-3-yl (7-(2-fluoro-6-methoxyphenyl)-3,3-dimethylchroman-4-yl)carbamate;
(S)-quinuclidin-3-yl (7-(2,5-difluoro-4-methoxyphenyl)-3,3-dimethylchroman-4-yl)carbamate;
(S)-quinuclidin-3-yl (7-(4-ethoxy-3-fluorophenyl)-3,3-dimethylchroman-4-yl)carbamate;
(S)-quinuclidin-3-yl (7-(2,4-dimethoxyphenyl)-3,3-dimethylchroman-4-yl)carbamate;
(S)-quinuclidin-3-yl (7-(2,5-dimethoxyphenyl)-3,3-dimethylchroman-4-yl)carbamate;
(S)-quinuclidin-3-yl (7-(2,3-dimethoxyphenyl)-3,3-dimethylchroman-4-yl)carbamate;
(S)-quinuclidin-3-yl (7-(3,4-dimethoxyphenyl)-3,3-dimethylchroman-4-yl)carbamate;
(S)-quinuclidin-3-yl (7-(2,6-dimethoxypyridin-3-yl)-3,3-dimethylchroman-4-yl)carbamate;
(S)-quinuclidin-3-yl (3,3-dimethyl-7-(naphthalen-2-yl)chroman-4-yl)carbamate;
(S)-quinuclidin-3-yl (3,3-dimethyl-7-(naphthalen-1-yl)chroman-4-yl)carbamate;
(S)-quinuclidin-3-yl (3,3-dimethyl-7-(quinolin-6-yl)chroman-4-yl)carbamate;
(S)-quinuclidin-3-yl (7-(4-ethoxy-3,5-dimethylphenyl)-3,3-dimethylchroman-4-yl)carbamate;
(S)-quinuclidin-3-yl (7-(2,4-dichloro-5-ethoxyphenyl)-3,3-dimethylchroman-4-yl)carbamate;
(S)-quinuclidin-3-yl (7-(2-fluoro-5-isopropoxyphenyl)-3,3-dimethylchroman-4-yl)carbamate;
(S)-quinuclidin-3-yl (7-(3-fluoro-5-isopropoxyphenyl)-3,3-dimethylchroman-4-yl)carbamate;
(S)-quinuclidin-3-yl (7-(2-chloro-4-(trifluoromethyl)phenyl)-3,3-dimethylchroman-4-yl)carbamate;
(S)-quinuclidin-3-yl (7-(2-chloro-3-(trifluoromethyl)phenyl)-3,3-dimethylchroman-4-yl)carbamate;
(S)-quinuclidin-3-yl (7-(2-chloro-5-(trifluoromethyl)phenyl)-3,3-dimethylchroman-4-yl)carbamate;
(S)-quinuclidin-3-yl (7-(3,5-dimethyl-4-propoxyphenyl)-3,3-dimethylchroman-4-yl)carbamate;
(S)-quinuclidin-3-yl (7-(4-(tert-butoxymethyl)phenyl)-3,3-dimethylchroman-4-yl)carbamate;
(S)-quinuclidin-3-yl (7-(2-chloro-5-(trifluoromethoxy)phenyl)-3,3-dimethylchroman-4-yl)carbamate;
(S)-quinuclidin-3-yl (7-(2-butoxy-6-fluorophenyl)-3,3-dimethylchroman-4-yl)carbamate;
(S)-quinuclidin-3-yl (3,3-dimethyl-7-(6-(2,2,2-trifluoroethoxy)pyridin-3-yl)chroman-4-yl)carbamate;
(S)-quinuclidin-3-yl (7-(6-methoxynaphthalen-2-yl)-3,3-dimethylchroman-4-yl)carbamate;
(S)-quinuclidin-3-yl (7-(4-ethoxy-3-(trifluoromethyl)phenyl)-3,3-dimethylchroman-4-yl)carbamate;
(S)-quinuclidin-3-yl (7-(benzofuran-3-yl)-3,3-dimethylchroman-4-yl)carbamate;
(S)-quinuclidin-3-yl (7-(3-(dimethylamino)phenyl)-3,3-dimethylchroman-4-yl)carbamate;
(S)-quinuclidin-3-yl (7-(2,2-difluorobenzo[d][1,3]dioxol-5-yl)-3,3-dimethylchroman-4-yl)carbamate;
(S)-quinuclidin-3-yl (7-(2,5-dichlorophenyl)-3,3-dimethylchroman-4-yl)carbamate;
(S)-quinuclidin-3-yl (7-(3-isopropylphenyl)-3,3-dimethylchroman-4-yl)carbamate;
(S)-quinuclidin-3-yl (7-(3-(tert-butyl)phenyl)-3,3-dimethylchroman-4-yl)carbamate;
(S)-quinuclidin-3-yl (7-(2-chloro-5-methoxyphenyl)-3,3-dimethylchroman-4-yl)carbamate;
(S)-quinuclidin-3-yl (7-([1,1'-biphenyl]-3-yl)-3,3-dimethylchroman-4-yl)carbamate;
(S)-quinuclidin-3-yl (7-(isoquinolin-4-yl)-3,3-dimethylchroman-4-yl)carbamate;
(S)-quinuclidin-3-yl (7-(2-fluorophenyl)-3,3-dimethylchroman-4-yl)carbamate;
(S)-quinuclidin-3-yl (3,3-dimethyl-7-(2-(trifluoromethoxy)phenyl)chroman-4-yl)carbamate;
(S)-quinuclidin-3-yl (7-(3-ethoxyphenyl)-3,3-dimethylchroman-4-yl)carbamate;
(S)-quinuclidin-3-yl (3,3-dimethyl-7-(1-methyl-1H-indazol-4-yl)chroman-4-yl)carbamate;
(S)-quinuclidin-3-yl (7-(isoquinolin-8-yl)-3,3-dimethylchroman-4-yl)carbamate;
(S)-quinuclidin-3-yl (7-(4-cyclopropylphenyl)-3,3-dimethylchroman-4-yl)carbamate;
(S)-quinuclidin-3-yl (7-(2-methoxyphenyl)-3,3-dimethylchroman-4-yl)carbamate;
(S)-quinuclidin-3-yl (3',3'-dimethyl-[6,7'-bichroman]-4'-yl)carbamate;
(S)-quinuclidin-3-yl (7-(3-chloro-5-(trifluoromethyl)phenyl)-3,3-dimethylchroman-4-yl)carbamate;
(S)-quinuclidin-3-yl (3,3-dimethyl-7-(quinolin-8-yl)chroman-4-yl)carbamate;
(S)-quinuclidin-3-yl (7-(3-methoxyphenyl)-3,3-dimethylchroman-4-yl)carbamate;
(S)-quinuclidin-3-yl (7-(3-chloro-4-isopropoxyphenyl)-3,3-dimethylchroman-4-yl)carbamate;
(S)-quinuclidin-3-yl (7-(2,6-dimethoxyphenyl)-3,3-dimethylchroman-4-yl)carbamate;
(S)-quinuclidin-3-yl (7-(2-chlorophenyl)-3,3-dimethylchroman-4-yl)carbamate;
(S)-quinuclidin-3-yl (7-(3-cyanophenyl)-3,3-dimethylchroman-4-yl)carbamate;
(S)-quinuclidin-3-yl (7-(3-(dimethylamino)-4-fluorophenyl)-3,3-dimethylchroman-4-yl)carbamate;
(S)-quinuclidin-3-yl (7-(2,3-dihydrobenzo[b][1,4]dioxin-6-yl)-3,3-dimethylchroman-4-yl)carbamate;
(S)-quinuclidin-3-yl (7-(1H-indol-7-yl)-3,3-dimethylchroman-4-yl)carbamate;
(S)-quinuclidin-3-yl (7-(4-isopropylphenyl)-3,3-dimethylchroman-4-yl)carbamate;

(S)-quinuclidin-3-yl (7-(4-fluoro-3-(trifluoromethyl)phenyl)-3,3-dimethylchroman-4-yl)carbamate;
(S)-quinuclidin-3-yl (7-(2-chloro-3-methoxyphenyl)-3,3-dimethylchroman-4-yl)carbamate;
(S)-quinuclidin-3-yl (7-(4-chloro-3-methoxyphenyl)-3,3-dimethylchroman-4-yl)carbamate;
(S)-quinuclidin-3-yl (7-(1H-indazol-7-yl)-3,3-dimethylchroman-4-yl)carbamate;
(S)-quinuclidin-3-yl (7-(3,5-dichlorophenyl)-3,3-dimethylchroman-4-yl)carbamate;
(S)-quinuclidin-3-yl (7-(1-benzyl-1H-pyrazol-4-yl)-3,3-dimethylchroman-4-yl)carbamate;
(S)-quinuclidin-3-yl (7-(2,3-dihydrobenzofuran-5-yl)-3,3-dimethylchroman-4-yl)carbamate;
(S)-quinuclidin-3-yl (7-(6-(cyclopropylmethoxy)pyridin-3-yl)-3,3-dimethylchroman-4-yl)carbamate;
(S)-quinuclidin-3-yl (7-(benzofuran-2-yl)-3,3-dimethylchroman-4-yl)carbamate;
(S)-quinuclidin-3-yl (3,3-dimethyl-7-(3-(pyrrolidin-1-ylsulfonyl)phenyl)chroman-4-yl)carbamate;
(S)-quinuclidin-3-yl (3,3-dimethyl-7-(2-(trifluoromethyl)phenyl)chroman-4-yl)carbamate;
(S)-quinuclidin-3-yl (7-(2-ethoxyphenyl)-3,3-dimethylchroman-4-yl)carbamate;
(S)-quinuclidin-3-yl (3,3-dimethyl-7-(thiophen-3-yl)chroman-4-yl)carbamate;
(S)-quinuclidin-3-yl (7-(4-methoxy-3-(trifluoromethyl)phenyl)-3,3-dimethylchroman-4-yl)carbamate;
(S)-quinuclidin-3-yl (7-(2-cyanophenyl)-3,3-dimethylchroman-4-yl)carbamate;
(S)-quinuclidin-3-yl (7-(3,4-dihydro-2H-benzo[b][1,4]dioxepin-7-yl)-3,3-dimethylchroman-4-yl)carbamate;
(S)-quinuclidin-3-yl (7-(benzo[c][1,2,5]thiadiazol-5-yl)-3,3-dimethylchroman-4-yl)carbamate;
(S)-quinuclidin-3-yl (7-(isoquinolin-4-yl)-3,3-dimethylchroman-4-yl)carbamate;
(S)-quinuclidin-3-yl (7-(4-(tert-butyl)phenyl)-3,3-dimethylchroman-4-yl)carbamate;
(S)-quinuclidin-3-yl (3,3-dimethyl-7-(3-methyl-4-morpholinophenyl)chroman-4-yl)carbamate;
(S)-quinuclidin-3-yl (7-(3,4-dichlorophenyl)-3,3-dimethylchroman-4-yl)carbamate;
(S)-quinuclidin-3-yl (3,3-dimethyl-7-(1-methyl-1H-indazol-6-yl)chroman-4-yl)carbamate;
(S)-quinuclidin-3-yl (7-(1H-indol-6-yl)-3,3-dimethylchroman-4-yl)carbamate;
(S)-quinuclidin-3-yl (3,3-dimethyl-7-(4-methyl-3,4-dihydro-2H-benzo[b][1,4]oxazin-7-yl)chroman-4-yl)carbamate;
(S)-quinuclidin-3-yl (7-(3-cyano-4-methylphenyl)-3,3-dimethylchroman-4-yl)carbamate;
(S)-quinuclidin-3-yl (3,3-dimethyl-7-(2,4,5-trifluorophenyl)chroman-4-yl)carbamate;
(S)-quinuclidin-3-yl (3,3-dimethyl-7-(4-(trifluoromethoxy)phenyl)chroman-4-yl)carbamate;
(S)-quinuclidin-3-yl (3,3-dimethyl-7-(4-(tetrahydro-2H-pyran-4-yl)phenyl)chroman-4-yl)carbamate;
(S)-quinuclidin-3-yl (7-(2-methoxypyridin-4-yl)-3,3-dimethylchroman-4-yl)carbamate;
(S)-quinuclidin-3-yl (7-(3-fluoro-4-morpholinophenyl)-3,3-dimethylchroman-4-yl)carbamate;
(S)-quinuclidin-3-yl (7-(3-chloro-4-morpholinophenyl)-3,3-dimethylchroman-4-yl)carbamate;
(S)-quinuclidin-3-yl (7-(4-methoxyphenyl)-3,3-dimethylchroman-4-yl)carbamate;
(S)-quinuclidin-3-yl (7-(5-methoxypyridin-3-yl)-3,3-dimethylchroman-4-yl)carbamate;
(S)-quinuclidin-3-yl (7-(benzo[b]thiophen-2-yl)-3,3-dimethylchroman-4-yl)carbamate;
(S)-quinuclidin-3-yl (7-(4-ethoxyphenyl)-3,3-dimethylchroman-4-yl)carbamate;
(S)-quinuclidin-3-yl (7-(4-methoxy-3-(trifluoromethyl)phenyl)-3,3-dimethylchroman-4-yl)carbamate;
(S)-quinuclidin-3-yl (3,3-dimethyl-7-(4-(trifluoromethyl)phenyl)chroman-4-yl)carbamate;
(S)-quinuclidin-3-yl (7-(1H-indazol-4-yl)-3,3-dimethylchroman-4-yl)carbamate;
(S)-quinuclidin-3-yl (7-(4-chlorophenyl)-3,3-dimethylchroman-4-yl)carbamate;
(S)-quinuclidin-3-yl (7-(4-fluorophenyl)-3,3-dimethylchroman-4-yl)carbamate;
(S)-quinuclidin-3-yl (7-(5-chloro-6-methoxypyridin-3-yl)-3,3-dimethylchroman-4-yl)carbamate;
(S)-quinuclidin-3-yl (3,3-dimethyl-7-(4-methyl-3-oxo-3,4-dihydro-2H-benzo[b][1,4]oxazin-6-yl)chroman-4-yl)carbamate;
(S)-quinuclidin-3-yl (3,3-dimethyl-7-(2,3,4-trifluorophenyl)chroman-4-yl)carbamate;
(S)-quinuclidin-3-yl (7-(4-(difluoromethoxy)phenyl)-3,3-dimethylchroman-4-yl)carbamate;
(S)-quinuclidin-3-yl (3,3-dimethyl-7-(quinolin-5-yl)chroman-4-yl)carbamate;
(S)-quinuclidin-3-yl (7-(benzo[c][1,2,5]oxadiazol-5-yl)-3,3-dimethylchroman-4-yl)carbamate;
(S)-quinuclidin-3-yl (3,3-dimethyl-7-(5-methylpyridin-3-yl)chroman-4-yl)carbamate;
(S)-quinuclidin-3-yl (7-(2-fluoropyridin-3-yl)-3,3-dimethylchroman-4-yl)carbamate;
(S)-quinuclidin-3-yl (7-(2-chloro-4-methylphenyl)-3,3-dimethylchroman-4-yl)carbamate;
(S)-quinuclidin-3-yl (7-(2-chloro-5-methylphenyl)-3,3-dimethylchroman-4-yl)carbamate;
(S)-quinuclidin-3-yl (7-(2-fluoro-4-methylphenyl)-3,3-dimethylchroman-4-yl)carbamate;
(S)-quinuclidin-3-yl (7-(3-chloro-4-methylphenyl)-3,3-dimethylchroman-4-yl)carbamate;
(S)-quinuclidin-3-yl (7-(4-fluoro-2-methylphenyl)-3,3-dimethylchroman-4-yl)carbamate;
(S)-quinuclidin-3-yl (7-(3-fluoro-4-methylphenyl)-3,3-dimethylchroman-4-yl)carbamate;
(S)-quinuclidin-3-yl (7-(4-fluoro-3-methylphenyl)-3,3-dimethylchroman-4-yl)carbamate;
(S)-quinuclidin-3-yl (7-(2,4-dichlorophenyl)-3,3-dimethylchroman-4-yl)carbamate;
(S)-quinuclidin-3-yl (7-(2-chloro-4-fluorophenyl)-3,3-dimethylchroman-4-yl)carbamate;
(S)-quinuclidin-3-yl (7-(2-chloro-5-fluorophenyl)-3,3-dimethylchroman-4-yl)carbamate;
(S)-quinuclidin-3-yl (7-(2,4-difluorophenyl)-3,3-dimethylchroman-4-yl)carbamate;
(S)-quinuclidin-3-yl (7-(2,5-difluorophenyl)-3,3-dimethylchroman-4-yl)carbamate;
(S)-quinuclidin-3-yl (7-(2,3-dichlorophenyl)-3,3-dimethylchroman-4-yl)carbamate;
(S)-quinuclidin-3-yl (7-(3-chloro-4-fluorophenyl)-3,3-dimethylchroman-4-yl)carbamate;
(S)-quinuclidin-3-yl (7-(2-chloro-3-fluorophenyl)-3,3-dimethylchroman-4-yl)carbamate;
(S)-quinuclidin-3-yl (7-(3,4-difluorophenyl)-3,3-dimethylchroman-4-yl)carbamate;
(S)-quinuclidin-3-yl (7-(2,3-difluorophenyl)-3,3-dimethylchroman-4-yl)carbamate;
(S)-quinuclidin-3-yl (7-(3,5-difluorophenyl)-3,3-dimethylchroman-4-yl)carbamate;

(S)-quinuclidin-3-yl (7-(6-methoxypyridin-3-yl)-3,3-dimethylchroman-4-yl)carbamate;
(S)-quinuclidin-3-yl (7-([1,1'-biphenyl]-4-yl)-3,3-dimethylchroman-4-yl)carbamate;
(S)-quinuclidin-3-yl (3,3-dimethyl-7-(thiazol-5-yl)chroman-4-yl)carbamate;
(S)-quinuclidin-3-yl (3,3-dimethyl-7-(3-vinylphenyl)chroman-4-yl)carbamate;
(S)-quinuclidin-3-yl (7-(2-methoxypyridin-3-yl)-3,3-dimethylchroman-4-yl)carbamate;
(S)-quinuclidin-3-yl (7-(6-methoxypyridin-2-yl)-3,3-dimethylchroman-4-yl)carbamate;
(S)-quinuclidin-3-yl (7-(4-cyanophenyl)-3,3-dimethylchroman-4-yl)carbamate;
(S)-quinuclidin-3-yl (7-(2-fluoro-6-methylpyridin-3-yl)-3,3-dimethylchroman-4-yl)carbamate;
(S)-quinuclidin-3-yl (7-(benzo[d][1,3]dioxol-5-yl)-3,3-dimethylchroman-4-yl)carbamate;
(S)-quinuclidin-3-yl (7-(6-cyclopropylpyridin-3-yl)-3,3-dimethylchroman-4-yl)carbamate;
(S)-quinuclidin-3-yl (7-(6-(dimethylamino)pyridin-3-yl)-3,3-dimethylchroman-4-yl)carbamate;
(S)-quinuclidin-3-yl (7-(5-fluoro-2-methoxyphenyl)-3,3-dimethylchroman-4-yl)carbamate;
(S)-quinuclidin-3-yl (7-(6-ethoxypyridin-3-yl)-3,3-dimethylchroman-4-yl)carbamate;
(S)-quinuclidin-3-yl (7-(6-methoxy-5-methylpyridin-3-yl)-3,3-dimethylchroman-4-yl)carbamate;
(S)-quinuclidin-3-yl (7-(4-methoxy-3,5-dimethylphenyl)-3,3-dimethylchroman-4-yl)carbamate;
(S)-quinuclidin-3-yl (7-(4-butylphenyl)-3,3-dimethylchroman-4-yl)carbamate;
(S)-quinuclidin-3-yl (7-(4-isobutylphenyl)-3,3-dimethylchroman-4-yl)carbamate;
(S)-quinuclidin-3-yl (7-(6-isopropoxypyridin-3-yl)-3,3-dimethylchroman-4-yl)carbamate;
(S)-quinuclidin-3-yl (7-(4-(isoxazol-3-yl)phenyl)-3,3-dimethylchroman-4-yl)carbamate;
(S)-quinuclidin-3-yl (7-(4-isobutoxyphenyl)-3,3-dimethylchroman-4-yl)carbamate;
(S)-quinuclidin-3-yl (7-(3-fluoro-4-isopropoxyphenyl)-3,3-dimethylchroman-4-yl)carbamate;
(S)-quinuclidin-3-yl (7-(2-fluoro-4-(trifluoromethyl)phenyl)-3,3-dimethylchroman-4-yl)carbamate;
(S)-quinuclidin-3-yl (7-(4-isopropoxy-3,5-dimethylphenyl)-3,3-dimethylchroman-4-yl)carbamate;
(S)-quinuclidin-3-yl (3,3-dimethyl-7-phenylchroman-4-yl)carbamate;
(S)-quinuclidin-3-yl (3,3-dimethyl-7-(pyridin-3-yl)chroman-4-yl)carbamate;
(S)-quinuclidin-3-yl (3,3-dimethyl-7-(pyridin-2-yl)chroman-4-yl)carbamate;
(S)-quinuclidin-3-yl (7-benzyl-3,3-dimethylchroman-4-yl)carbamate;
(S)-quinuclidin-3-yl (3,3-dimethyl-7-(m-tolyl)chroman-4-yl)carbamate;
(S)-quinuclidin-3-yl (3,3-dimethyl-7-(p-tolyl)chroman-4-yl)carbamate;
(S)-quinuclidin-3-yl (3,3-dimethyl-7-(o-tolyl)chroman-4-yl)carbamate;
(S)-quinuclidin-3-yl (3,3-dimethyl-7-((E)-2-(thiophen-3-yl)vinyl)chroman-4-yl)carbamate;
(S)-quinuclidin-3-yl (3,3-dimethyl-7-(4-vinylphenyl)chroman-4-yl)carbamate;
(S)-quinuclidin-3-yl (7-(4-ethylphenyl)-3,3-dimethylchroman-4-yl)carbamate;
(S)-quinuclidin-3-yl (3,3-dimethyl-7-(2-vinylphenyl)chroman-4-yl)carbamate;
(S)-quinuclidin-3-yl (7-(4-ethoxy-2-methylphenyl)-3,3-dimethylchroman-4-yl)carbamate;
(S)-quinuclidin-3-yl (7-(4-(benzyloxy)phenyl)-3,3-dimethylchroman-4-yl)carbamate;
(S)-quinuclidin-3-yl (7-(3-(benzyloxy)phenyl)-3,3-dimethylchroman-4-yl)carbamate;
(S)-quinuclidin-3-yl (7-(2,6-difluoropyridin-3-yl)-3,3-dimethylchroman-4-yl)carbamate;
(S)-quinuclidin-3-yl (7-(2-allylphenyl)-3,3-dimethylchroman-4-yl)carbamate;
(S)-quinuclidin-3-yl (7-(4-(cyanomethyl)phenyl)-3,3-dimethylchroman-4-yl)carbamate;
(S)-quinuclidin-3-yl (7-(3-(cyanomethyl)phenyl)-3,3-dimethylchroman-4-yl)carbamate;
(S)-quinuclidin-3-yl (7-((E)-2-([1,1'-diphenyl]-4-yl)vinyl)-3,3-dimethylchroman-4-yl)carbamate;
(S)-quinuclidin-3-yl (7-(2-cyclopropylpyrimidin-5-yl)-3,3-dimethylchroman-4-yl)carbamate;
(S)-quinuclidin-3-yl (3,3-dimethyl-7-((E)-4-(trifluoromethyl)styryl)chroman-4-yl)carbamate;
(S)-quinuclidin-3-yl (7-(2-chloro-3,5-dimethylphenyl)-3,3-dimethylchroman-4-yl)carbamate;
(S)-quinuclidin-3-yl (7-((E)-2,4-difluorostyryl)-3,3-dimethylchroman-4-yl)carbamate;
(S)-quinuclidin-3-yl (7-((E)-4-ethylstyryl)-3,3-dimethylchroman-4-yl)carbamate;
(S)-quinuclidin-3-yl (7-(6-ethoxynaphthalen-2-yl)-3,3-dimethylchroman-4-yl)carbamate;
(S)-quinuclidin-3-yl (7-((E)-3-fluorostyryl)-3,3-dimethylchroman-4-yl)carbamate;
(S)-quinuclidin-3-yl (7-(dibenzo[b,d]furan-4-yl)-3,3-dimethylchroman-4-yl)carbamate;
(S)-quinuclidin-3-yl (7-(4-cyano-3-fluorophenyl)-3,3-dimethylchroman-4-yl)carbamate;
(S)-quinuclidin-3-yl (7-(1-benzyl-6-oxo-1,6-dihydropyridin-3-yl)-3,3-dimethylchroman-4-yl)carbamate;
(S)-quinuclidin-3-yl (7-((E)-4-fluorostyryl)-3,3-dimethylchroman-4-yl)carbamate;
(S)-quinuclidin-3-yl (6-(3-fluorophenyl)-2,2-dimethylchroman-4-yl)carbamate;
(S)-quinuclidin-3-yl (2,2-dimethyl-7-(3-(trifluoromethyl)phenyl)chroman-4-yl)carbamate;
(S)-quinuclidin-3-yl (2,2-dimethyl-7-(3-(trifluoromethoxy)phenyl)chroman-4-yl)carbamate;
(S)-quinuclidin-3-yl (7-(3-chlorophenyl)-4-methylchroman-4-yl)carbamate;
(S)-quinuclidin-3-yl (7-(3-fluorophenyl)-4-methylchroman-4-yl)carbamate;
(S)-quinuclidin-3-yl (7-(3-methoxyphenyl)-4-methylchroman-4-yl)carbamate;
(S)-quinuclidin-3-yl (7-(3-isopropylphenyl)-4-methylchroman-4-yl)carbamate;
(S)-quinuclidin-3-yl (7-(2-chloro-5-methoxyphenyl)-4-methylchroman-4-yl)carbamate;
(S)-quinuclidin-3-yl (7-(4-ethoxyphenyl)-4-methylchroman-4-yl)carbamate;
(S)-quinuclidin-3-yl (7-(3-(dimethylamino)phenyl)-4-methylchroman-4-yl)carbamate;
(S)-quinuclidin-3-yl (7-(benzofuran-3-yl)-4-methylchroman-4-yl)carbamate;
(S)-quinuclidin-3-yl (4-methyl-7-(3-(trifluoromethyl)phenyl)chroman-4-yl)carbamate;
(S)-quinuclidin-3-yl (4-methyl-7-(3-(trifluoromethoxy)phenyl)chroman-4-yl)carbamate;

(S)-quinuclidin-3-yl (7-(2,2-difluorobenzo[d][1,3]dioxol-5-yl)-4-methylchroman-4-yl)carbamate;
(S)-quinuclidin-3-yl (7-(4-ethoxy-3,5-dimethylphenyl)-4-methylchroman-4-yl)carbamate;
(S)-quinuclidin-3-yl (7-(2-cyanophenyl)-4-methylchroman-4-yl)carbamate;
(S)-quinuclidin-3-yl (7-(3-(tert-butyl)phenyl)-4-methylchroman-4-yl)carbamate;
(S)-quinuclidin-3-yl (4-methyl-7-(4-methylthiophen-3-yl)chroman-4-yl)carbamate;
(S)-quinuclidin-3-yl (7-(3-(tert-butyl)phenyl)isochroman-4-yl)carbamate;
(S)-quinuclidin-3-yl (7-(3-isopropylphenyl)isochroman-4-yl)carbamate;
(S)-quinuclidin-3-yl (7-(3-(tert-butyl)phenyl)-1-methyl-1,2,3,4-tetrahydroquinolin-4-yl)carbamate;
(S)-quinuclidin-3-yl (7-(benzofuran-3-yl)-1-methyl-1,2,3,4-tetrahydroquinolin-4-yl)carbamate;
(S)-quinuclidin-3-yl (6-(4-chlorophenyl)thiochroman-4-yl)carbamate;
(S)-quinuclidin-3-yl (7-(3-fluorophenyl)thiochroman-4-yl)carbamate;
(S)-quinuclidin-3-yl (7-(3-chlorophenyl)thiochroman-4-yl)carbamate;
(S)-quinuclidin-3-yl (7-(3-(trifluoromethyl)phenyl)thiochroman-4-yl)carbamate;
(S)-quinuclidin-3-yl (7-(3-(trifluoromethoxy)phenyl)thiochroman-4-yl)carbamate;
(S)-quinuclidin-3-yl (7-(3-(methoxymethoxy)phenyl)thiochroman-4-yl)carbamate;
(S)-quinuclidin-3-yl (7-(3-(tert-butyl)phenyl)thiochroman-4-yl)carbamate;
(S)-quinuclidin-3-yl (7-(2,5-dichlorophenyl)thiochroman-4-yl)carbamate;
(S)-quinuclidin-3-yl (7-(3-ethoxyphenyl)thiochroman-4-yl)carbamate;
(S)-quinuclidin-3-yl (7-(3-(methylthio)phenyl)thiochroman-4-yl)carbamate;
(S)-quinuclidin-3-yl (7-(3-(dimethylamino)phenyl)thiochroman-4-yl)carbamate;
(S)-quinuclidin-3-yl (7-(2,2-difluorobenzo[d][1,3]dioxol-5-yl)thiochroman-4-yl)carbamate;
(S)-quinuclidin-3-yl (7-(benzofuran-3-yl)thiochroman-4-yl)carbamate;
(S)-quinuclidin-3-yl (3,3-dimethyl-6-(4-(trifluoromethyl)phenyl)thiochroman-4-yl)carbamate;
(S)-quinuclidin-3-yl (6-fluoro-7-(3-fluorophenyl)-3,3-dimethylchroman-4-yl)carbamate;
(S)-quinuclidin-3-yl (6-fluoro-7-(4-fluorophenyl)-3,3-dimethylchroman-4-yl)carbamate;
(S)-quinuclidin-3-yl (6-fluoro-7-(3-chlorophenyl)-3,3-dimethylchroman-4-yl)carbamate;
(S)-quinuclidin-3-yl (7-(3-ethylphenyl)-6-fluoro-3,3-dimethylchroman-4-yl)carbamate;
(S)-quinuclidin-3-yl (7-(4-ethylphenyl)-6-fluoro-3,3-dimethylchroman-4-yl)carbamate;
(S)-quinuclidin-3-yl (6-fluoro-7-(3-methoxyphenyl)-3,3-dimethylchroman-4-yl)carbamate;
(S)-quinuclidin-3-yl (6-fluoro-7-(4-methoxyphenyl)-3,3-dimethylchroman-4-yl)carbamate;
(S)-quinuclidin-3-yl (7-(4-ethoxyphenyl)-6-fluoro-3,3-dimethylchroman-4-yl)carbamate;
(S)-quinuclidin-3-yl (6-fluoro-3,3-dimethyl-7-(thiophen-3-yl)chroman-4-yl)carbamate;
(S)-quinuclidin-3-yl (6-fluoro-7-(3-isopropylphenyl)-3,3-dimethylchroman-4-yl)carbamate;
(S)-quinuclidin-3-yl (7-(2-chloro-5-methoxyphenyl)-6-fluoro-3,3-dimethylchroman-4-yl)carbamate;
(S)-quinuclidin-3-yl (6-fluoro-7-(2-fluoro-4-methoxyphenyl)-3,3-dimethylchroman-4-yl)carbamate;
(S)-quinuclidin-3-yl (6-fluoro-7-(4-methoxy-2-methylphenyl)-3,3-dimethylchroman-4-yl)carbamate;
(S)-quinuclidin-3-yl (7-(4-butylphenyl)-6-fluoro-3,3-dimethylchroman-4-yl)carbamate;
(S)-quinuclidin-3-yl (7-(3-chloro-4-isopropoxyphenyl)-6-fluoro-3,3-dimethylchroman-4-yl)carbamate;
(S)-quinuclidin-3-yl (7-(4-(tert-butyl)phenyl)-6-fluoro-3,3-dimethylchroman-4-yl)carbamate;
(S)-quinuclidin-3-yl (6-fluoro-7-(4-methoxy-3,5-dimethylphenyl)-3,3-dimethylchroman-4-yl)carbamate;
(S)-quinuclidin-3-yl (6-fluoro-7-(4-isobutoxyphenyl)-3,3-dimethylchroman-4-yl)carbamate;
(S)-quinuclidin-3-yl (6-fluoro-7-(6-isopropoxypyridin-3-yl)-3,3-dimethylchroman-4-yl)carbamate;
(S)-quinuclidin-3-yl (7-(3-fluorophenyl)-6-methoxy-3,3-dimethylchroman-4-yl)carbamate;
(S)-quinuclidin-3-yl (7-(4-fluorophenyl)-6-methoxy-3,3-dimethylchroman-4-yl)carbamate;
(S)-quinuclidin-3-yl (7-(3-chlorophenyl)-6-methoxy-3,3-dimethylchroman-4-yl)carbamate;
(S)-quinuclidin-3-yl (7-(3-ethylphenyl)-6-methoxy-3,3-dimethylchroman-4-yl)carbamate;
(S)-quinuclidin-3-yl (7-(4-ethylphenyl)-6-methoxy-3,3-dimethylchroman-4-yl)carbamate;
(S)-quinuclidin-3-yl (6-methoxy-7-(3-methoxyphenyl)-3,3-dimethylchroman-4-yl)carbamate;
(S)-quinuclidin-3-yl (6-methoxy-7-(4-methoxyphenyl)-3,3-dimethylchroman-4-yl)carbamate;
(S)-quinuclidin-3-yl (7-(4-ethoxyphenyl)-6-methoxy-3,3-dimethylchroman-4-yl)carbamate;
(S)-quinuclidin-3-yl (6-methoxy-3,3-dimethyl-7-(thiophen-3-yl)chroman-4-yl)carbamate;
(S)-quinuclidin-3-yl (7-(3-isopropylphenyl)-6-methoxy-3,3-dimethylchroman-4-yl)carbamate;
(S)-quinuclidin-3-yl (7-(2-chloro-5-methoxyphenyl)-6-methoxy-3,3-dimethylchroman-4-yl)carbamate;
(S)-quinuclidin-3-yl (7-(2-fluoro-4-methoxyphenyl)-6-methoxy-3,3-dimethylchroman-4-yl)carbamate;
(S)-quinuclidin-3-yl (6-methoxy-7-(4-methoxy-2-methylphenyl)-3,3-dimethylchroman-4-yl)carbamate;
(S)-quinuclidin-3-yl (7-(4-butylphenyl)-6-methoxy-3,3-dimethylchroman-4-yl)carbamate;
(S)-quinuclidin-3-yl (7-(3-chloro-4-isopropoxyphenyl)-6-methoxy-3,3-dimethylchroman-4-yl)carbamate;
(S)-quinuclidin-3-yl (7-(4-(tert-butyl)phenyl)-6-methoxy-3,3-dimethylchroman-4-yl)carbamate;
(S)-quinuclidin-3-yl (6-methoxy-7-(4-methoxy-3,5-dimethylphenyl)-3,3-dimethylchroman-4-yl)carbamate;
(S)-quinuclidin-3-yl (7-(4-isobutoxyphenyl)-6-methoxy-3,3-dimethylchroman-4-yl)carbamate; and
(S)-quinuclidin-3-yl (7-(6-isopropoxypyridin-3-yl)-6-methoxy-3,3-dimethylchroman-4-yl)carbamate.

12. A pharmaceutical composition for inhibiting glucosylceramide synthase comprising the compound or pharmaceutically acceptable salt thereof as claimed in claim 1 as an active ingredient.

13. A pharmaceutical composition as claimed in claim 12, for treating Gaucher disease, Fabry disease, Tay-Sachs disease, or Parkinson's disease.

14. A method for inhibiting glucosylceramide synthase in a mammal in need thereof, which comprises administering a therapeutically effective amount of the compound or pharmaceutically acceptable salt thereof as claimed in claim 1 to the mammal.

15. The compound or pharmaceutically acceptable salt thereof as claimed in claim 1, which is selected from the group consisting of:

(S)-quinuclidin-3-yl (7-(3-methoxyphenyl)chroman-4-yl) carbamate;

(S)-quinuclidin-3-yl (7-(2-methoxypyridin-4-yl)chroman-4-yl)carbamate;

(S)-quinuclidin-3-yl (7-(4-ethoxy-3,5-dimethylphenyl)-3,3-dimethylchroman-4-yl)carbamate;

(S)-quinuclidin-3-yl (7-(3,5-dimethyl-4-propoxyphenyl)-3,3-dimethylchroman-4-yl)carbamate;

(S)-quinuclidin-3-yl (7-(4-(tert-butoxymethyl)phenyl)-3,3-dimethylchroman-4-yl)carbamate;

(S)-quinuclidin-3-yl (7-(3-methoxyphenyl)-3,3-dimethylchroman-4-yl)carbamate;

(S)-quinuclidin-3-yl (7-(4-(tert-butyl)phenyl)-3,3-dimethylchroman-4-yl)carbamate;

(S)-quinuclidin-3-yl (7-(2-chloro-5-methylphenyl)-3,3-dimethylchroman-4-yl)carbamate;

(S)-quinuclidin-3-yl (7-(4-methoxy-3,5-dimethylphenyl)-3,3-dimethylchroman-4-yl)carbamate;

(S)-quinuclidin-3-yl (7-(6-isopropoxypyridin-3-yl)-3,3-dimethylchroman-4-yl)carbamate; and (S)-quinuclidin-3-yl (7-(4-isobutoxyphenyl)-3,3-dimethylchroman-4-yl)carbamate.

16. A compound, which is (S)-quinuclidin-3-yl (7-(3,5-dimethyl-4-propoxyphenyl)-3,3-dimethylchroman-4-yl)carbamate.

17. A compound, which is (S)-quinuclidin-3-yl (7-(3-methoxyphenyl)-3,3-dimethylchroman-4-yl)carbamate.

18. A compound, which is (S)-quinuclidin-3-yl (7-(4-(tert-butyl)phenyl)-3,3-dimethylchroman-4-yl)carbamate.

19. A compound, which is (S)-quinuclidin-3-yl (7-(6-isopropoxypyridin-3-yl)-3,3-dimethylchroman-4-yl)carbamate.

20. A compound, which is (S)-quinuclidin-3-yl (7-(4-isobutoxyphenyl)-3,3-dimethylchroman-4-yl)carbamate.

* * * * *